United States Patent
Bandaru et al.

(10) Patent No.: US 7,256,010 B2
(45) Date of Patent: Aug. 14, 2007

(54) NUCLEIC ACID SEQUENCES ENCODING MELANOMA ASSOCIATED ANTIGEN MOLECULES, AMINOTRANSFERASE MOLECULES, ATPASE MOLECULES, ACYLTRANSFERASE MOLECULES, PYRIDOXAL-PHOSPHATE DEPENDANT ENZYME MOLECULES AND USES THEREFOR

(75) Inventors: Rajasekhar Bandaru, Watertown, MA (US); Maria Alexandra Glucksmann, Lexington, MA (US); Rachel E. Meyers, Newton, MA (US); Laura A. Rudolph-Owen, Jamaica Plain, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/245,400

(22) Filed: Oct. 6, 2005

(65) Prior Publication Data

US 2006/0040357 A1 Feb. 23, 2006

Related U.S. Application Data

(60) Division of application No. 10/164,966, filed on Jun. 7, 2002, now Pat. No. 7,078,205, which is a continuation-in-part of application No. 10/034,864, filed on Dec. 27, 2001, now abandoned, and a continuation-in-part of application No. 09/996,194, filed on Nov. 28, 2001, now abandoned, and a continuation-in-part of application No. 09/908,928, filed on Jul. 19, 2001, now abandoned, and a continuation-in-part of application No. 09/908,180, filed on Jul. 18, 2001, now abandoned, and a continuation-in-part of application No. 09/887,389, filed on Jun. 22, 2001, now abandoned, and a continuation-in-part of application No. 09/789,300, filed on Feb. 20, 2001, now Pat. No. 6,458,576.

(60) Provisional application No. 60/258,517, filed on Dec. 28, 2000, provisional application No. 60/250,438, filed on Nov. 30, 2000, provisional application No. 60/250,073, filed on Nov. 30, 2000, provisional application No. 60/253,878, filed on Nov. 29, 2000, provisional application No. 60/253,338, filed on Nov. 30, 2000, provisional application No. 60/220,465, filed on Jul. 20, 2000, provisional application No. 60/219,740, filed on Jul. 20, 2000, provisional application No. 60/214,138, filed on Jun. 26, 2000, provisional application No. 60/183,208, filed on Feb. 17, 2000.

(51) Int. Cl.
*C12Q 11/48* (2006.01)
*C12N 9/10* (2006.01)
*C07H 21/04* (2006.01)
*C07K 1/00* (2006.01)

(52) U.S. Cl. .................. 435/15; 435/193; 536/23.2; 536/23.4; 536/23.5; 530/350

(58) Field of Classification Search ............. 435/193, 435/15; 536/23.2, 23.4, 23.5; 530/350
See application file for complete search history.

(56) References Cited

FOREIGN PATENT DOCUMENTS

| WO | WO 00/55320 A1 | 9/2000 |
|----|----------------|--------|
| WO | WO 00/58473 A2 | 10/2000 |
| WO | WO 01/55314 A2 | 8/2001 |
| WO | WO 01/77288 A2 | 10/2001 |
| WO | WO 02/40715 A2 | 5/2002 |

OTHER PUBLICATIONS

DOE Joint Genome Institute, Stanford Human Genome Center and Los Alamos National Laboratory, "*Homo sapiens* chromosome 16 clone RP11-169E6," Mar. 14, 2003 (sequence) GenBank [online] Bethesda, MD, USA. Retrieved from the Internet: URL: http://www.ncbi.nlm.nih.gov, GenBank Accession No. AC018845.

DOE Joint Genome Institute, Stanford Human Genome Center and Los Alamos National Laboratory, "*Homo sapiens* chromosome 16 clone RP11-283C7," Mar. 27, 2003 (sequence) GenBank [online] Bethesda, MD, USA. Retrieved from the internet: URL: http://www.ncbi.nlm.nih.gov, GenBank Accession No. AC007338.

GenBank Report for Accession No. AAB01685, Direct Submission on Jul. 20, 1995.

GenBank Report for Accession No. AAC51155, Direct Submission on Sep. 13, 1996.

GenBank Report for Accession No. AAF87015, Direct Submission on Jul. 18, 1998.

GenBank Report for Accession No. AI356291, Direct Submission 1997.

GenBank Report for Accession No. AI609152, Direct Submission 1997.

GenBank Report for Accession No. AI818924, Direct Submission 1997.

(Continued)

*Primary Examiner*—Rebecca E. Prouty
*Assistant Examiner*—Malgorzata A. Walicka

(57) ABSTRACT

The invention provides isolated nucleic acids molecules that encode novel polypeptides. The invention also provides antisense nucleic acid molecules, recombinant expression vectors containing the nucleic acid molecules of the invention, host cells into which the expression vectors have been introduced, and nonhuman transgenic animals in which a sequence of the invention has been introduced or disrupted. The invention still further provides isolated proteins, fusion proteins, antigenic peptides and antibodies. Diagnostic methods utilizing compositions of the invention are also provided.

15 Claims, 42 Drawing Sheets

OTHER PUBLICATIONS

GenBank Report for Accession No. AR073849, Direct Submission on Sep. 14, 1999.
GenBank Report for Accession No. BAA01185, Direct Submission on Jan. 27, 1992.
GenBank Report for Accession No. BAA01186, Direct Submission on Jan. 27, 1992.
GenBank Report for Accession No. BE296746, Direct Submission 1999.
GenBank Report for Accession No. D10354, Direct Submission on Jan. 27, 1992.
GenBank Report for Accession No. D10355, Direct Submission on Jan. 27, 1992.
GenBank Report for Accession No. EO4413, Direct Submission on Mar. 23, 1993.
GenBank Report for Accession No. EO4414, Direct Submission on Mar. 23, 1993.
GenBank Report for Accession No. EI5521, Direct Submission on Mar. 24, 1998.
GenBank Report for Accession No. EI6553, Direct Submission on Jul. 28, 1998.
GenBank Report for Accession No. P25409, Direct Submission Mar. 1994.
GenBank Report for Accession No. U70732, Direct Submission on Sep. 13, 1996.

Transmembrane Segments Predicted by MEMSAT

Analysis of 22406

| Start | End | Orient | Score |
|-------|-----|--------|-------|
| 176 | 197 | ins→out | 2.6 |
| 308 | 326 | out→ins | 0.4 |

>22406
MCAQYCISFADVEKAHINIRDSIHLTPVLTSSILNQLTGRNLFFKCELFQKTGSFKIRGA
LNAVRSLVPDALERKPKAVVTHSSGNHGQALTYAAKLEGIPAYIVVPQTAPDCKKLAIQA
YGASIVYCEPSDESRENVAKRVTEETEGIMVHPNQEPAVIAGQGTIALEVLNQVPLVDAL
VVPVGGGHLAGIAITVKALKPSVKVYAAEPSNADDCYQSKLKGLMPNLYPPETIADGV
KSSIGLNTVPIIRDLVDDIFTVTEDEIKCATQLVWERMKLLIEPTAGVGVAAVLSQHFQT
VSPEVKNICIVLSGGNVDLTSSITVVKQAERPASYQSVSV

Prosite Pattern Matches for 22406
Prosite version: Release 12.2 of February 1995

>PS00004/PDOC00004/CAMP_PHOSPHO_SITE cAMP- and cGMP-dependent protein kinase phosphorylation site.

Query: 140    KRVT    143

>PS00005/PDOC00005/PKC_PHOSPHO_SITE Protein kinase C phosphorylation site.

Query: 38     TGR     40
Query: 54     SFK     56
Query: 196    TVK     198
Query: 203    SVK     205

>PS00006/PDOC00006/CK2_PHOSPHO_SITE Casein kinase II phosphorylation site.

Query: 8      SFAD    11
Query: 109    TAPD    112
Query: 212    SNAD    215
Query: 235    TIAD    238
Query: 261    TVTE    264

>PS00008/PDOC00008/MYRISTYL N-myristoylation site.

Query: 59     GALNAV  64
Query: 88     GQALTY  93
Query: 187    GGHLAG  192
Query: 239    GVKSSI  244
Query: 287    GVGVAA  292

>PS00165/PDOC00149/DEHYDRATASE_SER_THR Serine/threonine dehydratases pyridoxal-phosphate attachment site.

Query: 47     ELFQKTGSFKIRGA   60

FIG. 3

PSORT Prediction of Protein Localization

MITDISC: discrimination of mitochondrial targeting seq
    R content:    0    Hyd Moment (75):  6.24
    Hyd Moment (95):  3.23    G content:    0
    D/E content:    2    S/T content:    1
    Score: -7.07

Gavel: prediction of cleavage sites for mitochondrial preseq
    cleavage site motif not found NUCDISC: discrimination of nuclear localization signals
    pat4: RKPK (4) at 74
    pat7: none
    bipartite: none
    content of basic residues: 9.1%
    NLS Score: -0.22

Final Results (k = 9/23):

34.8%: nuclear
    21.7%: mitochondrial
    21.7%: cytoplasmic
    8.7%: vesicles of secretory system
    4.3%: vacuolar
    4.3%: peroxisomal
    4.3%: endoplasmic reticulum prediction for 22406 is nuc (k=23)

| Start | End | Feature | Seq |
|---|---|---|---|
| 280 | 281 | Dileucine motif in the tail | LL |

FIG. 5

Protein Family / Domain Matches, HMMer version 2
Searching for complete domains in PFAM
hmmpfam - search a single seq against HMM database
HMMER 2.1.1 (Dec 1998)
Copyright (c) 1992-1998 Washington University School of Medicine
HMMER is freely distributed under the GNU General Public License (GPL).

```
HMM file:              /prod/ddm/seqanal/PFAM/pfam4.4/Pfam
Sequence file:         /prod/ddm/wspace/orfanal/oa-script.20753.seq
```

Query:    22406

Scores for sequence family classification (score includes all domains):

| Model | Description | Score | E-value | N |
|---|---|---|---|---|
| S_T_dehydratase | Pyridoxal-phosphate dependent enzyme | 220.9 | 1.8e-62 | 1 |

Parsed for domains:

| Model | Domain | seq-f | seq-t | hmm-f | hmm-t | score | E-value |
|---|---|---|---|---|---|---|---|
| S_T_dehydratase | 1/1 | 19 | 315 .. | 1 | 378 [] | 220.9 | 1.8e-62 |

Alignments of top-scoring domains:
S_T_dehydratase: domain 1 of 1, from 19 to 315: score 220.9, E = 1.8e-62

```
              *->vtelignTPLvr2nr2skelgeglganaaveiy1K1EdlnGPtGSfK
                 +++  1  TP+ ++  1       +g     ++++K+E+++  tGSfK
   22406   19  IRDSIHLTPVLTSSILN----QLTGR----NLFFKCELFQ-KTGSFK  56

DRglalnmil....lAeklgkkggivpgtvqveskttiiEptsGNtGial
              +Rg aln++++   ++A +   k++++ +          sGN+G+al
   22406   57  IRG-ALNAVRslvpDALERKPKAVVTHS-------------SGNHGQAL  91

AlaaallGlkctivMPatdtsreKraqlralGAelvvvpvagGgsddlad
              +aa+l G++++iv+P t ++  K+ ++ a+GA +v +++++        s
   22406   92  TYAAKLEGIPAYIVVPQT-APDCKKLAIQAYGASIVYCEPSD-ESRE--- 136 aiakAeelaeenpenayllnqaaGpfdnPanpeiaggktigpEIweQlgg
              +ak + ee++  +++++   +  Pa+++  gq+ti+++E++  Q++
   22406  137  NVAK--RVTEETE--GIMVHP----NQEPAVIA--GQGTIALEVLNQVP- 175 keislgrlpDavvapvGgGGtitGiarylKelnpdgkIdvlelpvkvigV
                        l+Da+v+pvGgGG  ++Gia   K  l+p+       vkv+++
   22406  176  -------LVDALVVPVGGGGMLAGIAITVKALKPS---------VKVYAA 209

EPegsavlsgslkatltlagkpGplhgrdskyllQDepvtlpetksigiG
              EP +++  ++s       +G+l +           l+++ +i++G
   22406  210  EPSNADDCYQSKL--------KGKLMP------------NLYPPETIADG 239 lgvprvgefvppildelldrrqgidevvtvtdeealeaarlLarEGilv
              +   +g  ++pi++ l+d      ++ tvt++e+ a++l+++++++++1+
   22406  240  VKSS-IGLNTWPIIRDLVD------DIFTVTEDEIKCATQLVWERMKLLI 282 gpssgaavaaalklakegkkplnkgktiVvilsgg<-*
              +p  g+ vaa+l+  ++ +   ++ l+o ++lsgg
   22406  283  EPTAGVGVAAVLSQHFQTV--SPEVKNICIVLSGG  315
```

FROM FIG. 6A

```
//
Searching for complete domains in SMART
hmmpfam - search a single seq against HMM database
HMMER 2.1.1 (Dec 1998).
Copyright (C) 1992-1998 Washington University School of Medicine
HMMER is freely distributed under the GNU General Public License (GPL).
-------------------------------------------------------------------------
HMM file:          /ddm/robison/smart/smart/smart.all.hmms
Sequence file:     /prod/ddm/wspace/orfanal/oa-script.20753.seq
-------------------------------------------------------------------------
   Query:  22406
Scores for sequence family classification (score includes all domains):
Model    Description                                    Score    E-value  N
-------  -----------                                    -----    -------  ---
        (no hits above thresholds)

Parsed for domains:
Model    Domain  seq-f seq-t    hmm-f hmm-t      score  E-value
-------  ------  ----- -----    ----- -----      -----  -------
        (no hits above thresholds)

Alignments of top-scoring domains:
        (no hits above thresholds)
//
```

FIG. 6B

| ProdomId | Start | End | Description | Score |
|---|---|---|---|---|
| View Prodom 206 | 19 | 316 | p99.2(175) TRPB(29) CYSK(16) THRC(15)//LYASE SYNTHASE PYRIDOXAL PHOSPHATE BIOSYNTHESIS TRYPTOPHAN CYSTEINE THREONINE BETA CHAIN | 103 |

| ProdomId | Start | End | Description | Score |
|---|---|---|---|---|

View Prodom 206
06 p99.2 (175) TRPB(29) CYSK(16) THRC(15) //LYASE SNYTHASE PYRIDOXAL PHOSPHATE BIOSYNTHESIS TRYPTOPHAN CYSTEINE THREONINE BETA CHAIN
    Length = 374
    Score = 103 (41.3 bits), Expect = 0.0046, Sum P(2) = 0.0046
    Identities = 41/141 (29%), Positives = 69/141 (48%)

```
Query:  19 IRDSIHLTPVLTSSILNQLTGRN--LFFKCE-LFQKTGS---FKIRGALNAVRSLVPDALE 73
             + + I  TP++  + L++  G    ++ K E L  TGS    +k RGA + +     + L
Sbjct:  10 VTELIGNTPLVRLNNLSERLGCKAAIYLKKEELMNPTGSGSYKDRGAYSMISEAEEEGLI 69

Query:  74 R--KPKAVVTHSSGNHGQ-ALTYAAKLEGIPAYIVVPQT-APDCKKLA-IQAYGASIVYC 128
             +   K   +V +SGN G  AL    A   G+   IV+P++ + +  K+++  ++AYGA IV
Sbjct:  70 KPGKKSVIVESTSGNTGAVALAMVAARLGLKCVIVMPESMSQEQKRVSMLRAYGAEIVLT 129

Query: 129 EPSD--ESRENVAKRVTEETE 147
             + S   E   +N     E E
Sbjct: 130 PTSGVVEGSKNYVDAANEAME 150
```

Score = 81 (33.6 bits), Expect = 1.5, P = 0.78
    Identities = 31/101 (30%), Positives = 49/101 (48%)

```
Query: 127 YCEPSDESREN-VAKRVTEETE-GIMVHPNQEPAVIAG----QGTIALEVLNQV------ 174
              Y + ++E+ E+ V+      T  +   G V+P+Q P       G    Q T+  E    Q+
Sbjct: 141 YVDAANEAMEDVVSNEETPNSALGTYVNPHQFPNPANGKAHYQTTVPEEVKEQMGEEKEG 200

Query: 175 PLVDALVVPVGGGGMLAGIAITVKAL-KPSVKVYAAEPSNA 214
              VD +V  VG GG +AG+A  +K    P+VK+   EP +
Sbjct: 201 KKVDVIVASVGTGGTIAGVARYLKLEDNPNVKLVGVEPEGS 241
```

Score = 40 (19.1 bits), Expect = 0.0046, Sum P(2) = 0.0046
    Identities = 26/132 (19%), Positives = 53/132 (40%)

```
Query: 190 LAGIAITVKALKPSVKVYAAEPSNADDCYQSKLKGKLMPN-LYPPETIADGVKSSI-GLN 247
              L G+    +   ++   ++   E    A   + +    GK+ P+ +    T+A        G
Sbjct: 233 LVGVEPEGGVIETPKRLAGVEAGGAGSLHGALKSGKMQPHKIQGVGTVAVPANLDYPGEV 292

Query: 248 TVPIIRDLVD--DIFTVTEDEIKCATQLVVERMKLLIEPTAGVGVAAVLSQHFQTVSPEV 305
             +I+  D  + +V+++E   A  :+ E   ++  EP +     +AA              +
Sbjct: 293 VDEVIQVSSDRAEEAVSVSDEEALEAGLLLGESEGIVPEPASAAAIAAAKKLAENEGKKDQ 352

Query: 306 KNICIVL-SGGN 316
              I +V+  SGG+
Sbjct: 353 GEIVVVIPSGGD 364
```

FIG. 7

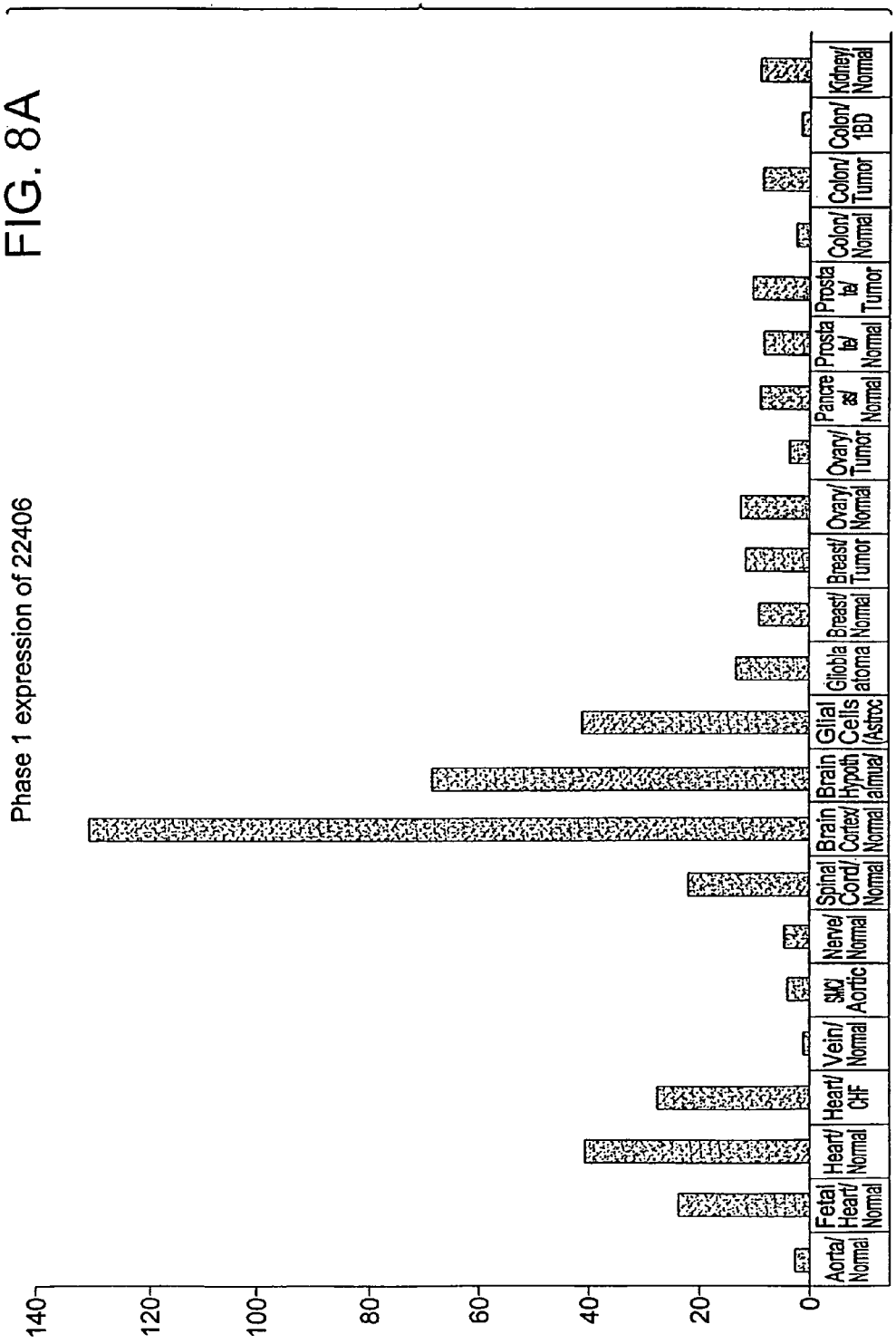

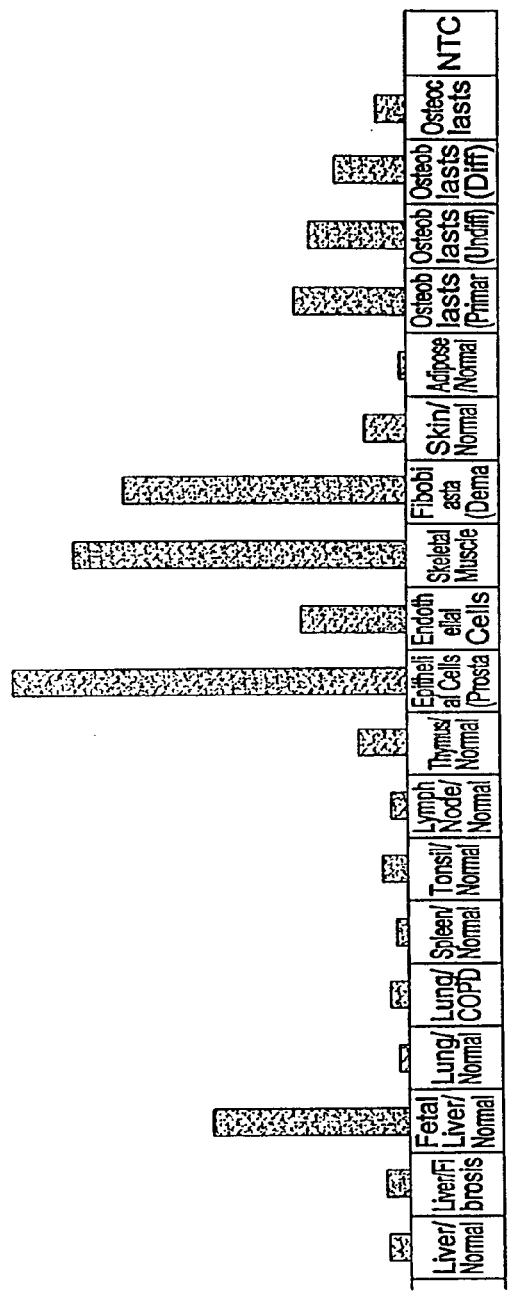

Acyltransferase: domain 1 of 1, from 131 to 317: score 4.3, E = 0.0024

```
           *->lenlpkkgpaivvsNHrSylDilvlsaalprrgpwlvrrlvfiakke
              ++ p + p+ v++ H++  D++   +a ++         ++ e
NoLabel 131   KIASPLEAPVFVAAPHSTFFDGIACVVAGLPS----------IVSRNE   168 llkvPllFGwlmrlagaifidRnnrakdalaaadelvrvlellrkgrs..
           +++vPl +G l+r    + + R +   ++ +++e  ++          g++++
NoLabel 169  NAQVPL-IGRLLRAVQPVLVSRVDPD-SRKNTINEIIKRTT--SGGEWpq   214 vllFPEGTRsrsgellppfkKGiaafrlAlkagvpivPvvivsgteel..
           +l+FPEGT++         l    fK G++      gvp++Pv  ++  +l++
NoLabel 215  ILVFPEGTCTNRSCLIT-FKPGAF-----IPGVPVQPVLL-RYPNKLdt   256

......epkneagkllrlarkkgpvtvrvlppipld...pedikela
                 ++ ++ ++       ++L +   ++++v v+p  + +++++d ++ +a
NoLabel 257  vtwtwqgytFIQL----CMLTFCQLFTKVEVEFMPVQVPNdeeKNDPVLFA  303 erlrdilvqaalee1<-*
           + r ++++a l+
NoLabel 304  NKVRNLMAEALGIP     317
```

FIG. 10

```
Protein Family / Domain Matches, HMMer version 2

AAA:  domain 1 of 2, from 236 to 421: score 262.7, E = 4.8e-75
                *->gvLLyGPPGtGKTlLAkavAkelgvpfisisgselvskyv.Gesekr
                   gvLL GPPG+GKT L++avA+e+g++++ +s+ ++++ ++Ge+e++
       7716  236  GVLLAGPPGVGKTQLVQAVAREAGAELLAVSA-PALQGSRpGETEEN 281 vralfelArkslkkaaPspiiFIDEiDalapkRgdegdvservvnqLLte
                vr +f++Ar+    +Ps  +F+DE+Dal+p+Rg +f +++rvv+q Lt
       7716  282 VRRVFQRAREL-ASRGPS-LLFLDEMDALCPQRG-SRAPESRVVAQVLTL 328 mDLerigfekhylrvsdvvDlsgviviaaTNrpdlldpaLlrpGRfdrri
                +D    g ++            ++v+v++aTNrpd ldpaL+rpGRfdr++
       7716  329 LD----GASG----------DREVVVVGATNRPDALDPALRRPGRFDREV 364 evplPdeeerlel lkihlkkmplalcqerselakdvdldelakelArrtp
                +++P+ ++r+e]l++++++kmp++         + vdl      lA+++t
       7716  365 VIGTPTLKQRKEILQVITSKMPIS---------SHVDLGL----LAEMTV 401 gfsgadlaalcreAalralr<-*
                g++gadl+alcreAa+ al
       7716  402 GYVGADLTALCREAAMHALL   421

AAA:  domain 2 of 2, from 500 to 705: score 249.8, E = 3.8e-71
                *->gvLLyGPPGtGKTlLAkavAkelgvpfisisgselvskyvGesekrv
                   gvLLyGPPG+ KT+L++a+A+ + ++f+s+sg++l+s +vG+sek +
       7716  500  GVLLYGPPGCAKTTLVRALATSCHCSFVSVSGADLFSPFVGDSEKVL 546 ralfelArkslkkaaPspiiFIDEiDalapkRgd...egdvservvnqLL
                ++f++Ar+s     P  i+F+DE+iD++ ++R+ ++++ dv erv+++LL
       7716  547 SQIFRQARAS----TPA-ILFLEIDSILGARSAsktGCDVQERVLSVLL 591 temDLerigfekhylr.v.s.....dv..vDlsgviviaaTNrpdlldpa
                +e+D    g++ +++++++s+++++++++v ++ v++iaaTNrpd ld a
       7716  592 NELD----GVGLKTIErRgSkssqqEFqeVFNRSVMIIAATNRPDVLDTA 637

LlrpGRfdrrievplPdeeerlel lkihlkkmplalcqerselakdvdld
                LlrpGR+d++i++p Pd ++rl llk+++k mp++       +dv+l+
       7716  638 LLRPGRLDKIIYIPPPDHKGRLSILKVCTKTMPIG--------PDVSLE 678 elakelArrtpgfsgadlaalcreAalralr<-*
                +    lA+ t  fsgadl++lc+eAal al
       7716  679 N----LAAETCFFSGADLRNLCTEAALLALQ   705
```

FIG. 12

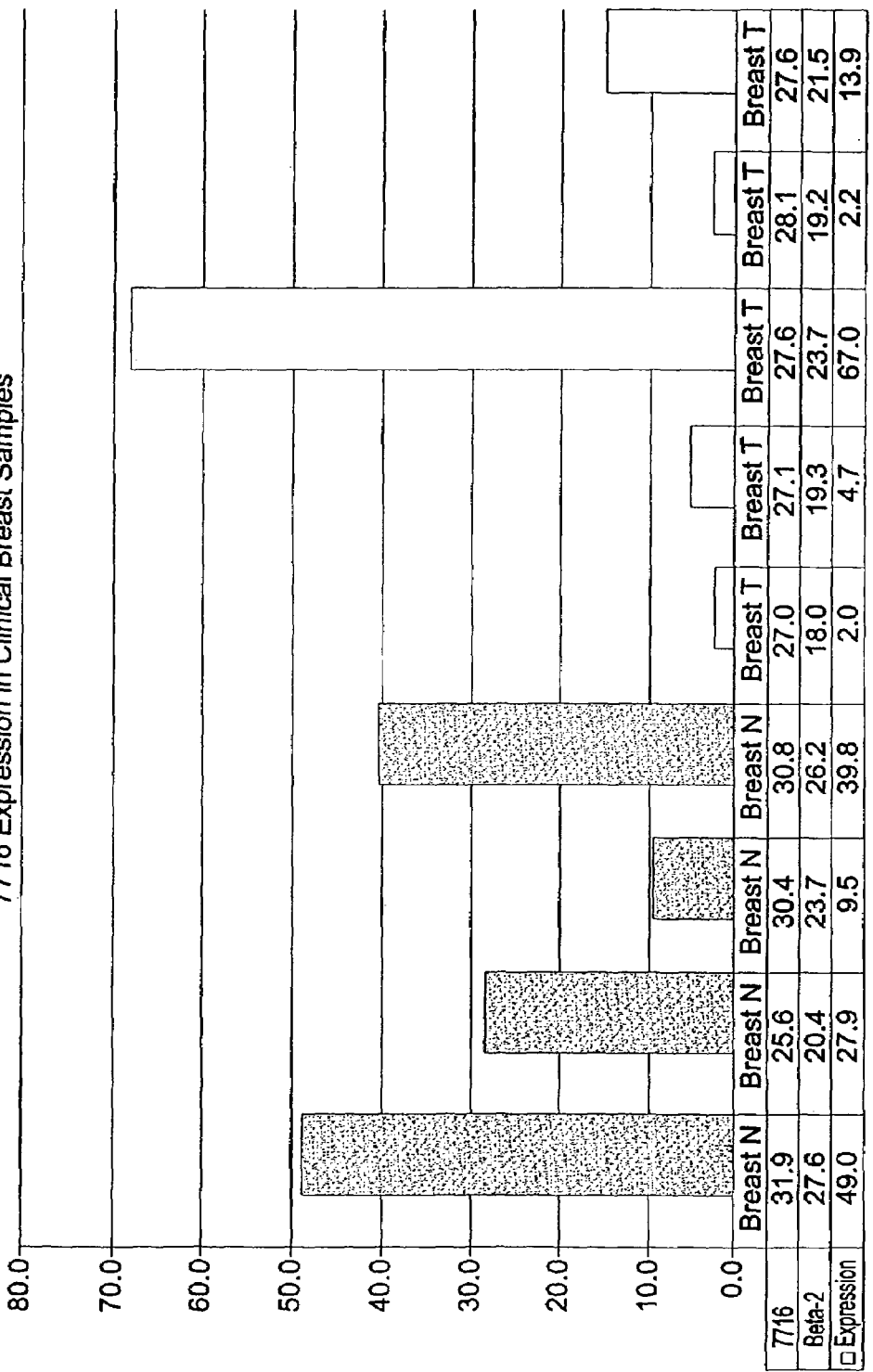

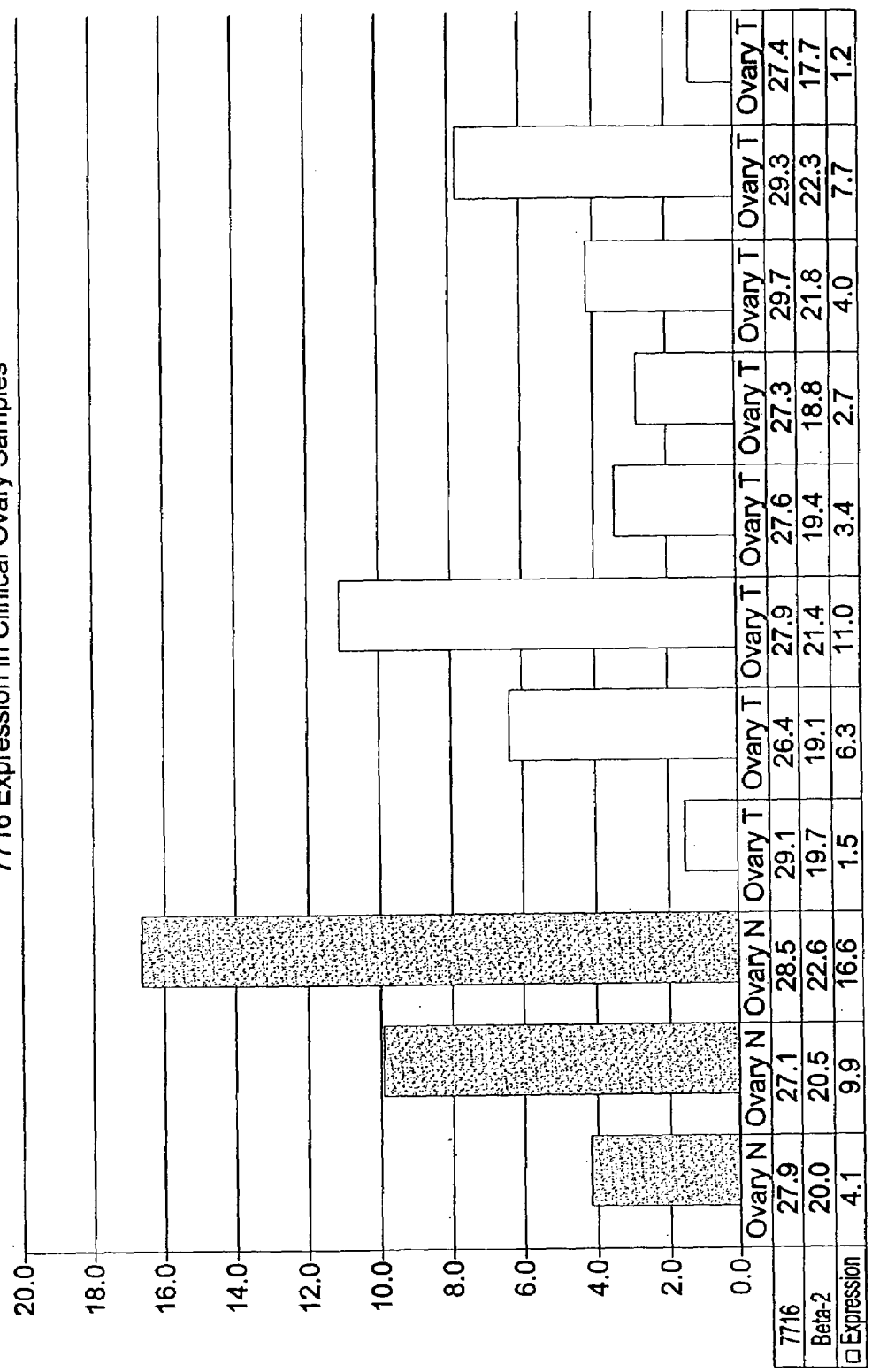

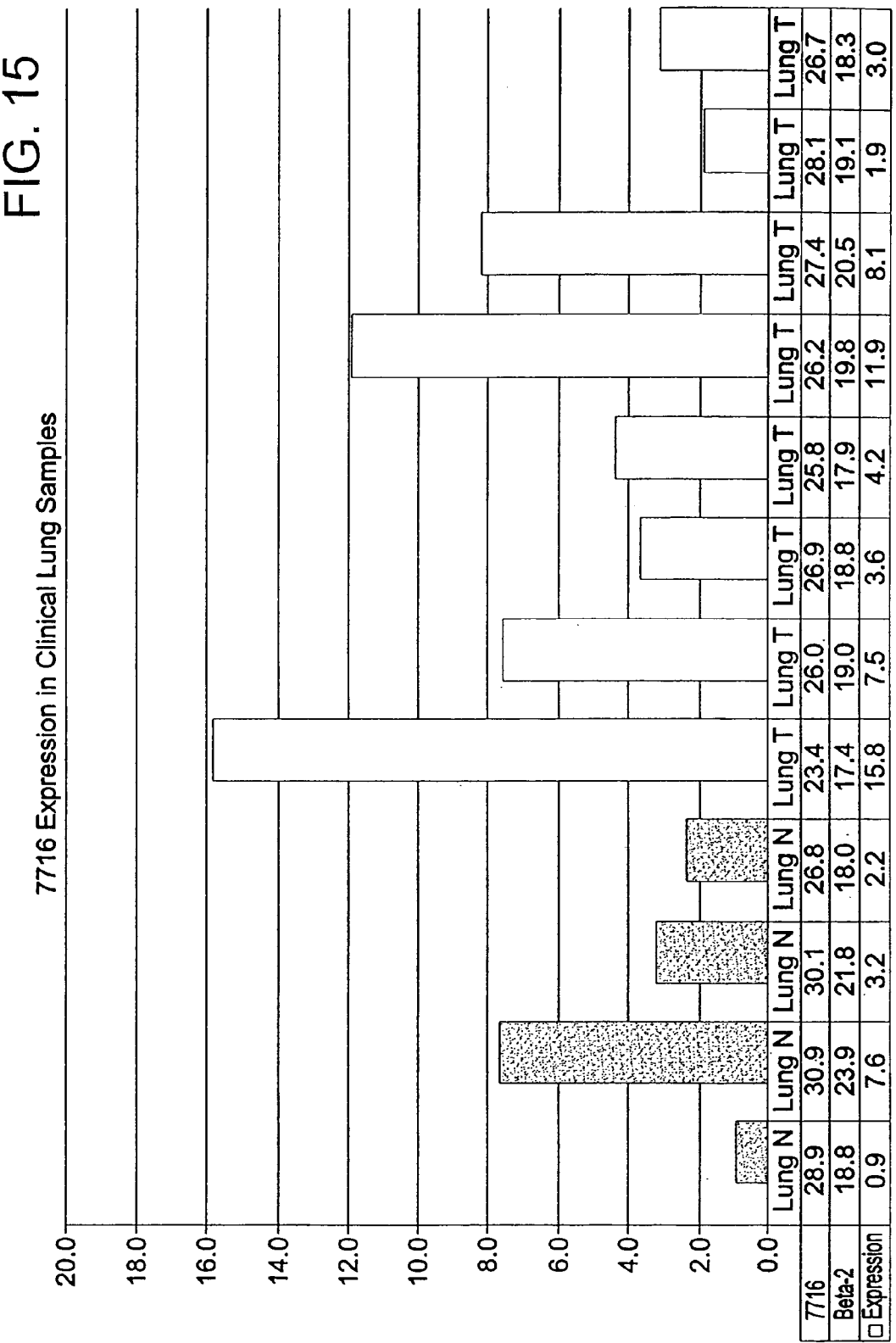

```
aminotran_1:  domain 1 of 1, from 83 to 517:  score 10.6, E = 2e-10
              *->lssmaanvshgpgdpilgvweafkedprpgkdNpnGvigvGayepql
                 ++++ v ++     g ++a      p +      v  + y +l
     25233   83 IKKPFTEVIRANI----GDAQAMGQQPITFLRQ---VMALCTYPNLL  122 gkdlvlpavkkaekrlaldregniefreikeYlPihGlpefreaiAkllf
              + +  +++ kk+++r++   +gn    +  +Y  + G+ +  re +A+++
     25233  123 DSPSFPEDAKKRARRILQACGGN----SLGSYSASQGVNCIREDVAAYIT  168 garspklkfkrvrvvqtlGGtgAlrlaadflanpgdgsrgrevlvPtPtw
              +  r++++   +++++ ++G++ ++   +++    l   g  +s ++v +P P +
     25233  169 R-RDGGVPADPDNIYLTTGASDGISTILKILVSGGGKS-RTGVMIPIPQY  216 pnykrdifwaaGvevivpyhyyKdennfgldfeaLeaaiekApekNiktk
              p  y    i ++  ++v   y+ +  en +  l  +  L +a+++A+     k
     25233  217 PLYSAVISELDAIQVN--YYLD-EENCWALNVNELRRAVQEAKDHC-DPK  262 vllhnnPhNPTGtdptreqlkkiadvvkekninlllsDeaYqgfvfgslde
              vl + nP NPTG + +r     ++++ ++ e  +++ll De+Yq+ v++ +d
     25233  263 VLCIINPGNPTGQVQSRKCIEDVIHFAWEEKLFLLADEVYQDNVYS-PDC  311 daasvaefaeevkeem.ec..ngdellvvqSfSK.nfGLyGwRvGaiyvv
              ++ s+ ++ e      m+++  +  el + S SK+ +G  G R G+ + v
     25233  312 RFHSFKKVLYE----MgPEysSNVELASFHSTSKgYMGECGYRGGYMEVI  357 nprigdavisaaakmssagrvssqlqalaramySnpdfppdhgae·····
              n    ++++    k++s +++ +   ++a    + np     p  g+e+ ++
     25233  358 N--LHPEIKGQLVKLLSVRLCPPVSGQAAMDIVVNP---PVAGEEsfeqf 402

·····ivarilerrdlftswleevkGmacripngrlylwmdL.rkllke
              +++++++   + ++++l   +  +++v+G+  c   +g++y ++++  + + +
     25233  403 srekesVLGNLAKKAKLTEDLFNQVPGIHCNPLQGAMYAFPRIFIPAKAV  452 eddwshiieqegmFsftWlLneeqVnvspgseFhiye.pgwgRislAgls
              e+   +h  +  ++ +++ lL+e ++ v+pgs F+  e++ ++R + l +   +
     25233  453 EAAQAHQMAPDMFYCMK-LLEETGICVVPGSGFGQREgTYHFRMTIL-PP  500 eanveeaaerIrafvkr<-*
              +++++ ++++ ++f +
     25233  501 VEKLKTVLQKVKDFHIN    517
```

FIG. 19

Transmembrane Segments Predicted by MEMSAT

| Start | End | Orient | Score |
|---|---|---|---|
| 181 | 199 | out-->ins | 0.1 |

>25233

Prosite Pattern Matches for 25233

Prosite version: Release 16.0 of July 1999.

>PS00002/PDOC00002/GLYCOSAMINOGLYCAN Glycosaminoglycan attachment site.
RU   Additional rules:
RU   There must be at least two acidic amino acids (Glu or Asp) from -2 to
RU   -4 relative to the serine.

Query: 200    SGGG    203
Query: 482    SGFG    485

>PS00005/PDOC00005/PDC_PHOSPHO_SITE Protein kinase C phosphorylation site.

Query: 42     SRR     44
Query: 168    TRR     170
Query: 278    SRK     280
Query: 315    SFK     317
Query: 339    TSK     341
Query: 372    SVR     374

>PS00006/PDOC00006/CK2_PHOSPHO_SITE Casein kinase II phosphorylation site.

Query: 42     SRRE    45
Query: 126    SFPE    129
Query: 168    TRRD    171
Query: 224    SELD    227
Query: 329    SNVE    332

>PS00008/PDOC00008/MYRISTYL N-myristoylation site.

Query: 144    GNSLGS  149
Query: 172    GGVPAD  177
Query: 186    GASDGI  191
Query: 201    GGGKSR  206
Query: 270    GNPTGQ  275
Query: 437    GAMYAF  442
Query: 481    GSGFGQ  486

FIG. 20

FROM FIG. 21A

Analysis of 8035 (433 aa)

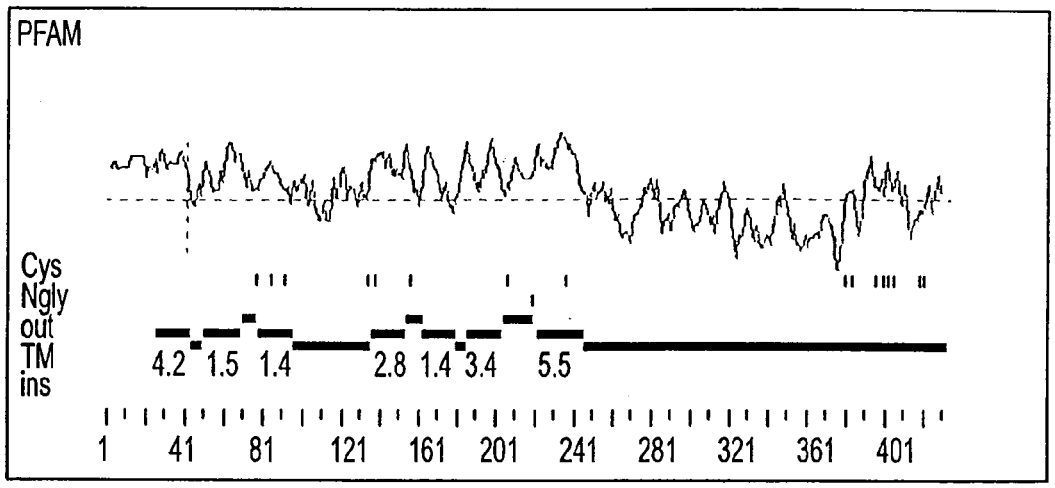

>8035
MEAVYLVVNGLGLVLDVLTLVLDLNFLLVSSLLASLAWLLAFVYNLPHTVLTSLLHLGRG
VLLSLLALIEAVVRFTCGGLQALCTLLYSCCSGLESLKLLGHLASHGALRSREILHRGVL
NVVSSGHALLRQACDICAIAMSLVAYVINSLVNICLIGTQNLFSLVLALWDAVTGPLWRM
TDVVAAFLAHISSSAVAMAILLWTPCQLALELLASAARLLASFVLVNLTGLVLLACVLAV
TVTVLHPDFTLRLATQALSQLHARPSYHRLREDVMRLSRLALGSEAWRRVWSRSLQLASW
PNRGGAPGAPQGDPMRVFSVRTRRQDTLPEAGRRSEAEEEEARTIRVTPVRGRERLNEEE
PPGGQDPWKLLKEQEERKKCVICQDQSKTVLLLPCRHLCLCQACTEILMRHPVYHRNCPL
CRRGILQTLNVYL

FIG. 25

Analysis of 84242 (403 aa)

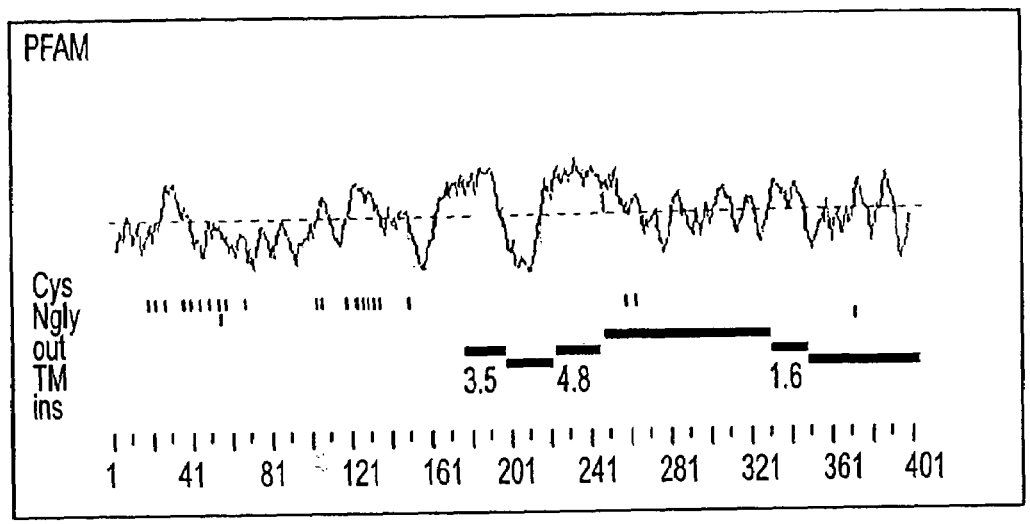

>84242
MHKYEEFMLRRYLASDPDCRWCPAPDCGYAVIAYGCASCPKLTCEREGCQTEFCYHCKQI
WHPNQTCDMARQQRAQTLRVRTKHTSGLSYGQESGPDDIKPCPRCSAYIIKMNDGSCNHM
TCAVCGCEFCWLCMKEISDLHYLSPSGCTFWGKKPWSRKKKILWQLGTLIGAPVGISLID
GIAIPAMVIGIPVYVGRKIHSRYEGRKTSKHKRNLAITGGVTLSVIASPVIAAVSVGIGV
PIMLAYVYGVVPISLCRGGGCGVSTANGKGVKIEFDEDDGPITVADAWRALKNPSIGESS
IEGLTSVLSTSGSPTDGLSVMQGPYSETASFAALSGGTLSGGILSSGKGKYSRLEVQADV
QKEIFPKDTASLGAISDNASTRAMAGSIISSYNPQDRFSMIHA

FIG. 26

```
Protein Family/Domain Matches, HMMer version 2
Searching for complete domains in PFAM
hmmpfam - search a single seq against HMM database
HMMER 2.1.1 (Dec. 1998)
Copyright (C) 1992-1998 Washington University School of Medicine
HMMER is freely distributed under the GNU General Public License (GPL).
- - - - - - - - - - - - - - - - - - - - - - - - - - - - - - - - - -
HMM file:              /prod/ddm/seqanal/PFAM/pfam5.5/Pfam
Sequence file:         /prod/ddm/wspace/orfanal/oa-script.11497.seq
- - - - - - - - - - - - - - - - - - - - - - - - - - - - - - - - - -
Query: 8035
Scores for sequence family classification (score includes all domains):
Model      Description                                   Score    E-value   N
-------    -----------                                   -----    -------   ---
zf-C3HC4   Zinc finger, C3HC4 type (RING finger)         17.1     0.00059   1

Parsed for domains:
Model      Domain   seq-f  seq-t   hmm-f  hmm-t     score    E-value
--------   ------   -----  -----   -----  -----     -----    -------
zf-C3HC4   1/1      380    421 ..    1     54 [ ]   17.1     0.00059

Alignments of top-scoring domains:
zf-C3HC4: domain 1 of 1, from 380 to 421 : score 17.1, E = 0.00059
              *->CpICltTFdldepkpfkepvllpCgHsF.CskCivellrlsqnsknn
                 C IC   +d     k+ +llpC+H++ C +C e+l      ++
    8035  380    CVIC-----QDQ---SKTVLLLPCRHLClCQACT-EILM------RH  411 svy..kCPlC<-*
              +vy++ CPlC
    8035  412  PVYhrNCPLC    421
```

FIG. 27

```
Protein Family/Domain Matches, HMMer version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
HMM file:            /prod/ddm/seqanal/PFAM/pfam5.5/Pfam
Sequence file:       /prod/ddm/wspace/orfanal/oa-script.11462.seq
Query:   84242
Scores for sequence family classification (score includes all domains):
Model    Description                                          Score    E-value   N
IBR      IBR domain                                           93.0     6.1e-24   1
Parsed for domains:
Model    Domain   seq-f   seq-t    hmm-f  hmm-t       score   E-value
IBR       1/1       2      67 ..      1     72 [ ]     93.0    6.1e-24
Alignments of top-scoring domains:
IBR: domain 1 of 1, from 2 to 67: score 93.0, E = 6.1e-24
                 *->eKYekfmvrsyveknpdlkwCPgpdCsyavrltevssstelaepprV
                    KYe fm+r+y+ ++pd +wCP+pdC+yav + +    +a++p
         84242  2   HKYEEFMLRRYLASDPDCRWCPAPDCGYAVIAYG------CASCPKL 42 eCkkPaCgtsFCfkCgaeWHapvsC<-*
                 +C++ +C t+FC++C++ WH++++C
         84242 43 TCEREGCQTEFCYHCKQIWHPNQTC        67
```

FIG. 28

```
Protein Family/Domain Matches, HMMer version 2
Searching for complete domains in PFAM
hmmpfam - search a single seq against HMM database
HMMER 2.1.1 (Dec 1998)
Copyright (C) 1992-1998 Washington University School of Medicine
HMMER is freely distributed under the GNU General Public License (GPL).
HMM file:            /prod/ddm/seqanal/PFAM/pfam5.5/Pfam
Sequence file:       /prod/ddm/wspace/orfanal/oa-script.11651.seq
Query:  52999
Scores for sequence family classification (score includes all domains):
Model        Description                              Score    E-value  N
--------     -----------                              -----    -------  ---
Peptidase_M8 Leishmanolysin                            78.1    3.4e-22  4
Dishevelled  Dishevelled specific domain              -6.3     6.1      1

Parsed for domains:
Model          Domain  seq-f seq-t   hmm-f hmm-t     score  E-value
--------       ------- ----- -----   ----- -----     -----  -------
Peptidase_M8   1/4      180   192 ..   198   210 ..    1.7    4.6
Peptidase_M8   2/4      230   290 ..   221   285 ..   44.4    2e-12
Dishevelled    1/1      312   376 ..     1    74 []   -6.3    6.1
Peptidase_M8   3/4      354   409 ..   373   427 ..   28.1    1e-07
Peptidase_M8   4/4      520   554 ..   587   623 ..    3.6    1.4

Alignments of top-scoring domains:
Peptidase_M8: domain 1 of 4, from 180 to 192: score 1.7, E = 4.6
                   *->GeGvsntDFVLYV<-*
                      G Gv ntDF LYV
      52999   180    GPGVQNTDFLLYV    192
Peptidase_M8: domain 2 of 4, from 230 to 290: score 44.4, E = 2e-12
                   *->PgvLAWAttCQvfsDfgrPaVGViNIpAanitsrnhYdqlvtrvVtH
                      P+v A+A+ CQ  s +rP +G i +A ++ts+   + ++ ++ H
      52999   230    PSVIAYAACCQLDSE-DRPLAGTIVYCAQHLTSPSLSHSDIVMATLH    275

EiaHALGFSvGLYtfFee<-*
                      E +HALGFS+     F++
      52999   276    ELLHALGFSG---QLFKK    290
Dishevelled: domain 1 of 1, from 312 to 376: score -6.3, E = 6.1
                   *->rRdrprrlarteqasvlnglkamGarrrqpggrydssssllsSEles
                      r+d ++l  t  a  l+ k +G +   +g + + ++ lLsS  e+
      52999   312    RQDEWGQLLLTTPAVSLSLAKHLGVSGASLGVPLEEEEGLLSSHWEA    358 tsffDsdeddtldRfSssTeqSSvSRL<-*
                      + + +s            +  + ++R
      52999   359    RLLQGSL---------MTATFDGAQRT    376
Peptidase_M8: domain 3 of 4, from 354 to 409: score 28.1, E = 1e-07
                   *->SHwkkRnAkdElMAgaagsdaGyYsaL...TmAvFeDlGFYkAdfsk
                      SHw++R + lM+ +     ++ ++L++ T+A+F D G+Y+ + s
      52999   354    SHWEARLLQGSLMTATFD--GAQRTRLdpiTLAAFKDSGWYQVNHSA    398

AEdMpWGknaG<-*
                      AE++ WG ++G
      52999   399    AEELLWGQGSG    409
Peptidase_M8: domain 4 of 4, from 520 to 554: score 3.6, E = 1.4
                   *->aalCanVkCd.tatrtysVqvygssgyypCtpGlrvel<-*
                      ++ C+ ++C+++++   y Vqv g s ++pC pG+ +++
      52999   520    MGRCYLHQCTgRGA--YKVQVEG-SPWVPCLPGKVIQI    554
```

FIG. 31

>21999
MALAALMIALGSLGLHTWQAQAVPTILPLGLAPDTFDDTYVGCAEEMEEKAAPLLKEEMA
HHALLRESWEAAQETWEDKRRGLTLPPGFKAQNGIAIMVYTNSSNTLYWELNQAVRTGGG
SRELYMRHFPFKALHFYLIRALQLLRGSGGCSRGPGEVVFRGVGSLRFEPKRLGDSVRLG
QFASSSLDKAVAHRFGNATLFSLTTCFGAPIQAFSVFPKEREVLIPPHEVFLVTRFSQDG
AQSLVTLWSYNQTCSHFNCAYLGGEKRRGCVSAPGALGTGDLHMTKRHLQQP

```
Alignments of top-scoring domains:
ART:  domain 1 of 1, from 3 to 271:   score 490.4, E = 1.4e-143
               *->mpalhfvLllSVglllstqalssaiqqkdglvkelvLDMApnsFDDq
                  + al+  L+              l  +++ q   p +l+L +Ap++FDD
     21999    3  LAALMIALGS----------LGLHTWQAQAVPTILPLGLAPDTFDDT   39

YlGCvdrMeakYlpqLlkeEFaanevlavgWesAkakWqerkargsvwgs
                 Y+GC+++Me+k +  LlkeE+a +++l ++We A++ W     +       +
     21999   40  YVGCAEEMEEK-AAPLLKEEMAHHALLRESWEAAQETWEDKRR----GLT   84 lpyPSPPmgFkdeHGiALlAYTasSqEqtplyreFNeAVReaGrSRedYl
                 lp     P gFK++ GiA+++YT+sS    ++ly+e+N+AVR++G+SRe+Y+
     21999   85  LP----P-GFKAQNGIAIMVYTNSS---NTLYWELNQAVRTGGGSRELYM  126 hhFhFKaLHFyLTRALQLLrssGGcqpgpChvVYRGvrglRFrpqgggas
                 +hF+FKaLHFyL RALQLLr+sGGc++gp++vV+RGv++lRF+p+++g+s
     21999  127  RHFPFKALHFYLIRALQLLRGSGGCSRGPGEVVFRGVGSLRFEPKRLGDS  176

VRFGqFTSsSLkkkvAqSseFffGqdTfFsikTClGvpIkafSfFPsEeE
                 VR+GqF+SsSL+k vA      +fG++T+Fs+ TC+G+pI+afS+FP E+E
     21999  177  VRLGQFASSSLDKAVAH----RFGNATLFSLTTCFGAPIQAFSVFPKERE  222

VLIPPfEVFqVintsrptagsaiiillsskgKcStYNCeYlkgkktenCi<
                 VLIPP+EVF+V+++s+++a+s ++l s++++cS++NC+Yl+g+k    C+
     21999  223  VLIPPHEVFLVTRFSQDGAQSLVTLWSYNQTCSHFNCAYLGGEKRRGCV   271
                  -*

```
Query: 52020

Scores for sequence family classification (score includes all domains) :
Model    Description                                        Score    E-value  N
-------  -----------                                        -----    -------  ---
MAGE     MAGE Family                                        127.0    3.5e-34  1

Parsed for domains:
Model    Domain  seq-f  seq-t    hmm-f  hmm-t    score    E-value
-------  ------  -----  -----    -----  -----    -----    -------
MAGE      1/1      1     208 [.    1     260 []   127.0    3.5e-34
Alignments of top-scoring domains:
MAGE: domain 1 of 1, from 1 to 208: score 127.0, E = 3.5e-34
                   *->rgQkSqlckrEerlqargetqgglvgaqapaaeeqqeeassSSplqsp
                      + Qk   + r+ ++++r+ +  +  +  + a+ + +       ++
          52020   1  MLQKPRNRGRSGGQAERDRDW-SHSGNPGASRAGE-----DAR----   37 vslgvsedeaLvlgtleevpaAggspspPqsPQgsPPeSPlasstisava
                                vl++ +       +                + +++s
          52020  38  -----------VLRDGFA-----E----------------EAPSTSRGP   54 aktswtqsdEGssSqvvLqeEEgpstSqaltstesl frdaLdeKvaeLVq
                     +q + G s q      g++ qa +    + ++ +L  Kv+eLVq
          52020  55  G---GSQGSQGPSPQ--------GARRAQAAPAVGPRSQKQLELKVSELVQ  94

FLLlKYqmKePvTKAEMLksViKnYKdhFPeIFrKASeflelVFGidLKE
                   FLL K+q+K P+ +A++Lk Vi+ YKd FP++F++A e+l+ VFG  L E
          52020  95  FLLIKDQKKIPIKRADILKHVIGDYKDIFPPDLFKRAAERLQYVFGYKLVE  144 vDPtgHSYvLVtkLgLsydGlLsd.nqgmPktGLLiivLgvIFmkGncAp
                   P +++Y+L+++L + +++      +++qg P tGLL+ivLg+IFmkGn +
          52020 145  LEPKSNTYILINTLEPVEEDAEMRgDQGTPTTGLLMIVLGLIFMKGNTIK  194

EEeIWEvLsvlGVY<-*
                   E e W++L+ 1GVY
          52020 195  ETEAWDFLRRLGVY      208
//
```

FIG. 35

:# NUCLEIC ACID SEQUENCES ENCODING MELANOMA ASSOCIATED ANTIGEN MOLECULES, AMINOTRANSFERASE MOLECULES, ATPASE MOLECULES, ACYLTRANSFERASE MOLECULES, PYRIDOXAL-PHOSPHATE DEPENDANT ENZYME MOLECULES AND USES THEREFOR

CROSS-REFERENCE TO RELATED APPLICATIONS

This application is a divisional of U.S. patent application Ser. No. 10/164,966, filed Jun. 7, 2002 (pending), published as U.S. Patent Application Publication No. 2003-0064439 A1 on Apr. 3, 2003, which is:

a continuation-in-part of Ser. No. 10/034,864, filed Dec. 27, 2001, which claims the benefit of U.S. Provisional Application No. 60/258,517, filed Dec. 28, 2000;

and a continuation-in-part of Ser. No. 09/996,194, filed Nov. 28, 2001, which claims the benefit of U.S. Provisional Application No. 60/250,348, filed Nov. 30, 2000, U.S. Provisional Application No. 60/250,073, filed Nov. 30, 2000, U.S. Provisional Application No. 60/253,878, filed Nov. 29, 2000, and U.S. Provisional Application No. 60/250,338, filed Nov. 30, 2000;

and a continuation-in-part of Ser. No. 09/908,928, filed Jul. 19, 2001, which claims the benefit of U.S. Provisional Application No. 60/220,465, filed Jul. 20, 2000;

and a continuation-in-part of Ser. No. 09/908,180, filed Jul. 18, 2001, which claims the benefit of U.S. Provisional Application No. 60/219,740, filed Jul. 20, 2000;

and a continuation-in-part of Ser. No. 09/887,389, filed Jun. 22, 2001, which claims the benefit of U.S. Provisional Application No. 60/214,138, filed Jun. 26, 2000;

and a continuation-in-part of Ser. No. 09/789,300, filed Feb. 20, 2001, which claims the benefit of U.S. Provisional Application No. 60/183,208, filed Feb. 17, 2000;

all of which are hereby incorporated herein in their entirety by reference.

The contents of the Sequence Listing are submitted herewith on compact disc in duplicate. Each duplicate disc has a copy of the file "sequence listing.txt" which is incorporated herein by this reference. This file is 188 kilobytes and is a copy of the sequence listing filed in U.S. patent application Ser. No. 10/164,966, filed Jun. 7, 2002. This file was copied onto compact disc on Oct. 5, 2005.

FIELD OF THE INVENTION

The invention relates to novel nucleic acid sequences and polypeptides. Also provided are vectors, host cells, and recombinant methods for making and using the novel molecules.

TABLE OF CONTENTS

Chapter 1 22406, A Novel Human Pyridoxal-Phosphate Dependent Enzyme Family Member and Uses Therefor
i) SEQ ID NOS: 1–5
ii) FIGS. 1–8
iii) Continuation-In-Part of Ser. No. 09/789,300, filed Feb. 20, 2001, which claims the benefit of U.S. Provisional Application No. 60/183,208, filed Feb. 17, 2000

Chapter 2 32447, A Novel Human Acyltransferase and Uses Thereof
i) SEQ-ID NOS: 6–9
ii) FIGS. 9–10
iii) Continuation-In-Part of Ser. No. 09/887,389, filed Jun. 22, 2001, which claims the benefit of U.S. Provisional Application No. 60/214,138, filed Jun. 26, 2000

Chapter 3 7716, A Novel Human ATPase and Uses Therefor
i) SEQ ID NOS: 10–13
ii) FIGS. 11–17
iii) Continuation-In-Part of Ser. No. 09/908,180, filed Jul. 18, 2001, which claims the benefit of U.S. Provisional Application No. 60/219,740, filed Jul. 20, 2000

Chapter 4 25233, A Novel Human Aminotransferase and Uses Therefor
i) SEQ ID NOS: 14–17
ii) FIGS. 18–24
iii) Continuation-In-Part of Ser. No. 09/908,928, filed Jul. 19, 2001, which claims the benefit of U.S. Provisional Application No. 60/220,465, filed Jul. 20, 2000

Chapter 5 8035, 84242, 55304, 52999, AND 21999, Novel Human Proteins and Methods of Use Thereof
i) SEQ ID NOS:18–39
ii) FIGS. 25–33
iii) Continuation-In-Part of Ser. No. 09/996,194, filed Nov. 28, 2001, which claims the benefit of U.S. Provisional Application No. 60/250,073, filed Nov. 30, 2000, and U.S. Provisional Application No. 60/253,878, filed Nov. 29, 2000, and U.S. Provisional Application No. 60/250,338, filed Nov. 30, 2000

Chapter 6 52020, A Novel Human Melanoma Associated Antigen and Uses Therefor
i) SEQ ID NOS:40–43
ii) FIGS. 34–35
iii) Continuation-In-Part of Ser. No. 10/034,864, filed Dec. 27, 2001, which claims the benefit of U.S. Provisional Application No. 60/258,517, filed Dec. 28, 2000

Chapter 7 22406, acyltransferase, 7716, 25233, 8035, 84242, 55304, 52999, 21999, and 52020 Combined Specification

BRIEF DESCRIPTION OF THE DRAWINGS

FIG. 3 shows transmembrane segments predicted by MEMSAT and Prosite matches for the 22406 open reading frame for amino acids corresponding to specific functional sites. For the cAMP- and cGMP-dependent protein kinase phosphorylation site, the actual modified residue is the last amino acid. For the protein kinase C phosphorylation sites, the actual modified residue is the first amino acid. For the casein kinase II phosphorylation sites, the actual modified residue is the first amino acid. For the N-myristoylation site, the actual modified residue is the first amino acid. In addition, Prosite matches the protein of the invention to a serine/threonine dehydratase pyridoxal-phosphate attachment site at about amino acids 47–60.

FIG. 5 shows the PSORT prediction of protein localization.

FIGS. 6A–6B depict an alignment of the pyridoxal-phosphate dependent enzyme family member domain (PALP) of human 22406 with a consensus amino acid sequence derived from a hidden Markov model. The upper sequence is the consensus amino acid sequence (SEQ ID NO:4), while the lower amino acid sequence corresponds to amino acids 19 to 315 of SEQ ID NO:2.

FIG. 7 displays the ProDom matches for 22406.

FIGS. 8A–8B display the expression levels of 22406 in various tissues determined by quantitative PCR. The highest level of expression is observed in brain cortex. The tissue types are as follows from left to right: Aorta/Normal, Fetal Heart/Normal, Heart/Normal, Heart/CHF, Vein/Normal, SMC/Aortic, Nerve/Normal, Spinal Cord/Normal, Brain Cord/Normal, Brain Cortex/Normal, Brain Hypothalmus/Normal, Glial Cells (Astrocytes), Glioblastoma, Breast/Normal, Breast/Tumor, Ovary/Normal, Ovary/Tumor, Pancreas/Normal, Prostate/Normal, Prostate/Tumor, Colon/Normal, Colon/Tumor, Colon/IBD, Kidney/Normal, Liver/Normal, Liver/Fibrosis, Fetal Liver/Normal, Lung/Normal, Lung/COPD, Spleen/Normal, Tonsil/Normal, Lymph Node/Normal, Thymus/Normal, Epithelial Cells (Prostate), Endothelial Cells (Aortic), Skeletal Muscle/Normal, Fibroblasts (Dermal), Skin/Normal, Adipose/Normal, Osteoblasts (Primary), Osteoblasts (Undiff), Osteoblasts (Diff), Osteoclasts, NTC.

FIG. 10 depicts an alignment of the acyltransferase domain of human acyltransferase with a consensus amino acid sequence derived from a hidden Markov model. The upper sequence is the consensus amino acid sequence (SEQ ID NO:9), while the lower amino acid sequence corresponds to amino acids 131 to 317 of SEQ ID NO:7.

FIG. 12 depicts an alignment of two ATPase domains of human 7716 with a consensus amino acid sequences derived from a hidden Markov model. The upper sequence is the consensus amino acid sequence (SEQ ID NO:13), while the lower amino acid sequence corresponds to amino acids 236–421 of SEQ ID NO: 11 for the domain 1 alignment and amino acids 500–705 of SEQ ID NO: 11 for the domain 2 alignment.

FIG. 13 shows the expression of 7716 in clinical samples from normal human breast tissue (columns 1–4) and human breast tumor tissue (columns 5–9). Expression levels for 7716 were determined by quantitative RT-PCR (Reverse Transcriptase Polymerase Chain Reaction; Taqman® brand PCR kit, Applied Biosystems). The quantitative RT-PCR reactions were performed according to the kit manufacturer's instructions.

FIG. 14 shows the expression of 7716 in clinical samples from normal human ovary tissue (columns 1–3) and human ovary tumor tissue (columns 4–11). Expression levels for 7716 were determined as described in the legend for FIG. 13.

FIG. 15 shows the expression of 7716 in clinical samples from normal human lung tissue (columns 1–4), and human lung tumor tissue (columns 5–12). Expression levels for 7716 were determined as described in the legend for FIG. 13.

FIG. 19 depicts an alignment of the aminotransferase domain of human 25233 with a consensus amino acid sequence derived from a hidden Markov model. The upper sequence is the consensus amino acid sequence (SEQ ID NO:17), while the lower amino acid sequence corresponds to amino acids 83 to 517 of SEQ ID NO:15.

FIG. 20 shows an analysis of the 25233 open reading frame for amino acid residues corresponding to specific functional sites. A transmembrane region is predicted at amino acid residues 181–199 of SEQ ID NO:15. A glycosaminoglycan attachment site is found from about amino acid residues 200–203 and 482–485 of SEQ ID NO:15; a protein kinase C phosphorylation site from about amino acid residues 42–44, 168–170, 278–280, 315–317, 339–341, and 372–374 of SEQ ID NO:15; a casein kinase II phosphorylation site from about amino acid residues 42–45, 126–129, 168–171, 224–227, and 329–332 of SEQ ID NO:15; and a N-myristoylation site from about amino acid residues 144–149, 172–177, 186–191, 201–206, 270–275, 437–442, and 481–486 of SEQ ID NO:15.

FIG. 22A: Breast N (Normal) (Columns 1–4); Breast T (Tumor) (Columns 5–12). FIG. 22B: Ovary N (Columns 14); Ovary T (Columns 5–12). FIG. 22C: Lung N (Columns 1–4); Lung T (Columns 5–12). FIG. 22D depicts a time course study of 25233 expression levels in the human cancer cell line H460 with and without p16: 24 hr H460 −P16 (Column 1); 48 hr H460−P16 (Column 2); 72 hr H460 −P16 (Column 3); 96 hr H460−P16 (Column 4); 48 hr H460+P16 (Column 5); 72 hr H460+P16 (Column 6); And 96 hr H 460+P16 (Column 7). Expression levels were determined as in FIG. 21.

FIG. 23A: Colon N (Normal) (Columns 1–4); Colon T (Tumor) (Columns 5–11); Liver M (Metastases) (Columns 12–15); Liver N (Columns 16–17). FIG. 23B: Brain N (Columns 1–4); Astrocytes (Column 5); Brain T (Columns 6–10); HMVEC-Arresting (Column 11); HMVEC-Proliferating (Column 12); Placenta (Column 13); Fetal Adrenal (Columns 14–15); Fetal Liver (Columns 16–17). Expression levels were determined as in FIG. 21.

FIG. 25 depicts a hydropathy plot of human 8035. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:19) of human 8035 are indicated. Polypeptides of the invention include fragments that include: all or a part of a hydrophobic sequence (a sequence above the dashed line); or all or part of a hydrophilic fragment (a sequence below the dashed line). Other fragments include a cysteine residue or an N-glycosylation site.

FIG. 26 depicts a hydropathy plot of human 84242. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:23) of human 84242 are indicated. Polypeptides of the invention include fragments that include: all or a part of a hydrophobic sequence (a sequence above the dashed line); or all or part of a hydrophilic fragment (a sequence below the dashed line). Other fragments include a cysteine residue or an N-glycosylation site.

FIG. 27 depicts an alignment of the RING finger protein domain (C3HC4 type) of human 8035 with a consensus amino acid sequence derived from a hidden Markov model. The upper sequence is the consensus amino acid sequence (SEQ ID NO:21), while the lower amino acid sequence corresponds to amino acids 380 to 421 of SEQ ID NO:19.

FIG. 28 depicts an alignment of the IBR (In Between RING Fingers) protein domain of human 84242 with a consensus amino acid sequence derived from a hidden Markov model. The upper sequence is the consensus amino acid sequence (SEQ ID NO:25), while the lower amino acid sequence corresponds to amino acids 2 to 67 of SEQ ID NO:23.

FIG. 31 depicts an alignment of portions of the metallopeptidase domain of human 52999 with consensus amino acid sequences derived from hidden Markov models. The upper sequences are the consensus amino acid sequences for the Peptidase_M8 family of zinc metallopeptidases and the lower amino acid sequences correspond to amino acids of human 52999. The upper sequence of domain 1 of 4 is SEQ ID NO:32 and the lower amino acid sequence corresponds to amino acids 180 to 192 of SEQ ID NO:30. The upper sequence of domain 2 of 4 is SEQ ID NO:33 and the lower amino acid sequence corresponds to amino acids 230 to 290 of SEQ ID NO:30. The upper sequence of domain 3 of 4 is SEQ ID NO:34 and the lower amino acid sequence corresponds to amino acids 354 to 409 of SEQ ID NO:30. The upper sequence of domain 4 of 4 is SEQ ID NO:35 and the lower amino acid sequence corresponds to amino acids 520 to 554 of SEQ ID NO:30.

FIG. 33 depicts an alignment of the human ADP-ribosyltransferase polypeptiode with a consensus amino acid sequence derived from a hidden Markov model. The upper sequence is the consensus amino acid sequence (SEQ ID NO:39), while the lower amino acid sequence corresponds to amino acid 3 to amino acid 271 of SEQ ID NO:37.

FIG. 35 depicts an alignment of the MAGE domain of human 52020 with a consensus amino acid sequence derived from a hidden Markov model. The upper sequence is the consensus amino acid sequence (SEQ ID NO:43), while the lower amino acid sequence corresponds to amino acids 1 to 208 of SEQ ID NO:41.

CHAPTER 1

Figure 1:
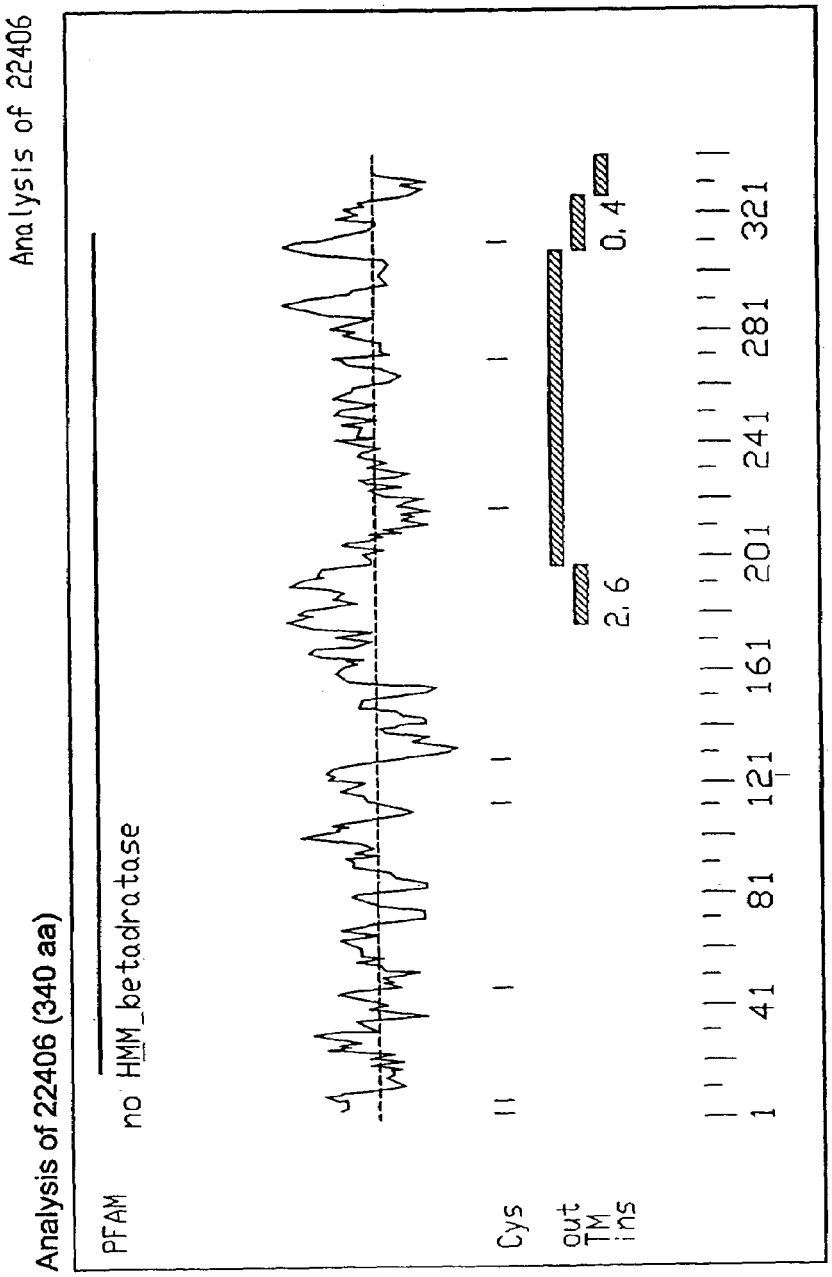
FIG. 1 depicts a hydropathy plot of human 22406. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human 22406 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site. Predicted transmembrane domains (TM) are also depicted.
Figure 2:
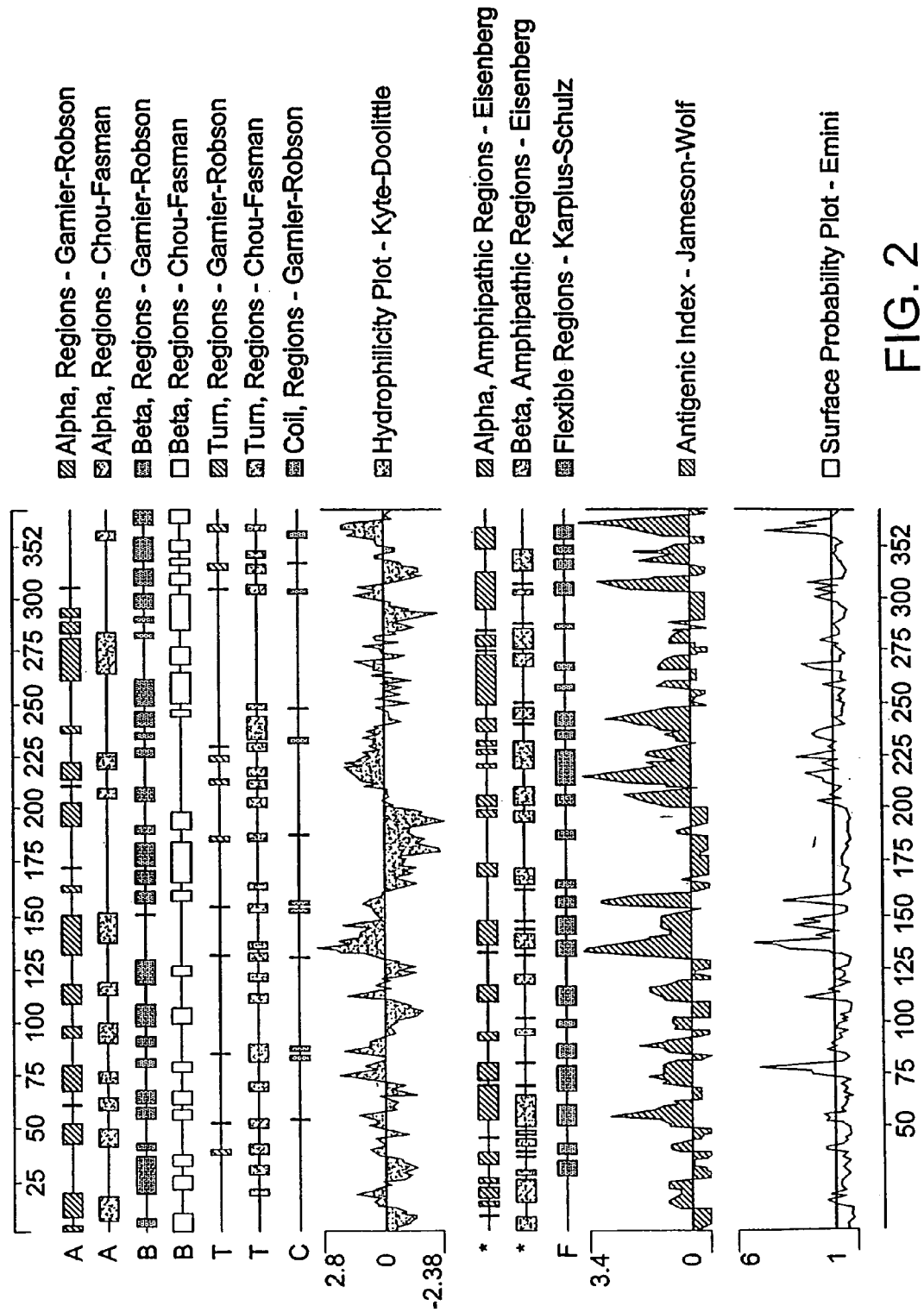
FIG. 2 shows an analysis of the 22406 amino acid sequence: αβturn and coil regions; hydrophilicity; amphipathic regions; flexible regions; antigenic index; and surface probability plot.

22406, A NOVEL HUMAN PYRIDOXAL-PHOSPHATE DEPENDENT ENZYME FAMILY MEMBER AND USES THEREFOR

BACKGROUND OF THE INVENTION

The pyridoxal-phosphate dependent family of enzymes require the co-factor, pyridoxal-5'-phosphate (pyridoxal-phosphate), for catalytic activity. Pyridoxal-phosphate dependent enzymes (B6 enzymes) catalyze manifold reactions in the metabolism of amino acids. L- and D-serine dehydratase, threonine dehydratase, and serine racemase are a few of the members of this family of enzymes. In all of the members of the family, the pyridoxal-phosphate group is attached to a lysine residue. The sequence around this residue is sufficiently conserved to allow the derivation of a pattern specific to pyridoxal-phosphate dependent enzymes.

The pyridoxal-phosphate dependent family member, serine racemase, has been shown to catalyze the direct racemization of L-serine to D-serine with a requirement for pyridoxal 5'-phosphate (Wolosker et al. (1999) *PNAS* 96:721–725). The properties of this enzyme resemble those of bacterial racemases, suggesting that the biosynthetic pathway for D-amino acids is conserved from bacteria to mammalian brain.

It has been demonstrated that D-serine is the endogenous ligand for the glycine site of the glutamate N-methyl-D-aspartate (NMDA) receptor (Mothet et al. (2000) *PNAS* 97:4926–4931). The amino acid D-serine is synthesized and stored in glia rather than in neurons. Released glutamate acts on receptors on the protoplasmic astrocytes closely opposed to the synapse to release D-serine, which co-activates post-synaptic NMDA receptors together with glutamate. As D-serine is formed by serine racemase, inhibitors of this enzyme can be expected to reduce NMDA neurotransmission.

D-serine has been shown to modify behavioral changes associated with learning, memory, convulsion, anxiety, psychotomimetic induced abnormal behavior, cerebellar ataxia, and neurodengeneration. Inhibitors of serine racemase can be expected to quell anxiety and epilepsy and to prevent damage from stroke and certain neurodegenerative conditions including Alzheimer's disease. On the other hand, stimulating serine racemase might improve schizophrenia symptoms, which are partly caused by depressed NMDA receptor function.

Accordingly, members of the pyridoxal-phosphate dependent enzyme class are a major target for drug action and development. Therefore, it is valuable to the field of pharmaceutical development to identify and characterize previously unknown serine racemases. The present invention advances the state of the art by providing a previously unidentified human pyridoxal-phosphate dependent serine racemace.

SUMMARY OF THE INVENTION

The present invention is based, in part, on the discovery of a novel human pyridoxal-phosphate dependent enzyme family member, referred to herein as "22406". The nucleotide sequence of a cDNA encoding 22406 is shown in SEQ ID NO:1, and the amino acid sequence of a 22406 polypeptide is shown in SEQ ID NO:2. In addition, the nucleotide sequence of the coding region is depicted in SEQ ID NO:3.

Accordingly, in one aspect the invention features a nucleic acid molecule which encodes a 22406 protein or polypeptide, e.g., a biologically active portion of the 22406 protein. In a preferred embodiment, the isolated nucleic acid molecule encodes a polypeptide having the amino acid sequence of SEQ ID NO:2. In other embodiments, the invention provides an isolated 22406 nucleic acid molecule having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 22406 protein or an active fragment thereof.

In a related aspect, the invention further provides nucleic acid constructs which include a 22406 nucleic acid molecule described herein. In certain embodiments, the nucleic acid molecules of the invention are operatively linked to native or heterologous regulatory sequences. Also included, are vectors and host cells containing the 22406 nucleic acid molecules of the invention e.g., vectors and host cells suitable for producing 22406 nucleic acid molecules and polypeptides.

In another related aspect, the invention provides nucleic acid fragments suitable as primers or hybridization probes for the detection of 22406-encoding nucleic acids.

In still another related aspect, isolated nucleic acid molecules that are antisense to a 22406 encoding nucleic acid molecule are provided.

In another aspect, the invention features 22406 polypeptides, and biologically active or antigenic fragments thereof that are useful, e.g., as reagents or targets in assays applicable to treatment and diagnosis of 22406-mediated or -related disorders. In another embodiment, the invention provides 22406 polypeptides having a 22406 activity. Preferred polypeptides are 22406 proteins including at least one pyridoxal-phosphate dependent enzyme family member domain, and, preferably, having a 22406 activity, e.g., a 22406 activity as described herein.

In other embodiments, the invention provides 22406 polypeptides, e.g., a 22406 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1, SEQ ID NO:3, wherein the nucleic acid encodes a full length 22406 protein or an active fragment thereof.

In a related aspect, the invention further provides nucleic acid constructs which include a 22406 nucleic acid molecule described herein.

In a related aspect, the invention provides 22406 polypeptides or fragments operatively linked to non-22406 polypeptides to form fusion proteins.

In another aspect, the invention features antibodies and antigen-binding fragments thereof, that react with, or more preferably specifically bind 22406 polypeptides.

In another aspect, the invention provides methods of screening for compounds that modulate the expression or activity of the 22406 polypeptides or nucleic acids.

In still another aspect, the invention provides a process for modulating 22406 polypeptide or nucleic acid expression or activity, e.g. using the screened compounds. In certain embodiments, the methods involve treatment of conditions related to aberrant activity or expression of the 22406 polypeptides or nucleic acids, such as conditions involving neurological disorders.

The invention also provides assays for determining the activity of or the presence or absence of 22406 polypeptides or nucleic acid molecules in a biological sample, including for disease diagnosis.

In further aspect the invention provides assays for determining the presence or absence of a genetic alteration in a 22406 polypeptide or nucleic acid molecule, including for disease diagnosis.

Other features and advantages of the invention will be apparent from the following detailed description, Chapter 7, Examples and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Human 22406

The human 22406 sequence (SEQ ID NO:1), which is approximately 1770 nucleotides long including untranslated regions, contains a predicted methionine-initiated coding sequence of about 1020 nucleotides (nucleotides 69–1088 of SEQ ID NO:1; SEQ ID NO:3), not including the terminal codon. The coding sequence encodes a 340 amino acid protein (SEQ ID NO:2). Chromosome mapping localized the gene to human chromosome 17 between D17S849 and D17S796 (0.6–14 cM).

Human 22406 contains a predicted pyridoxal-phosphate dependent enzyme family member domain (PALP) (PFAM Accession PF00291) located at about amino acid residues 19–315 of SEQ ID NO:2 (FIG. 6). The annotation "S_T_dehydratase" in the PFAM alignment of FIG. 6 reflects a change in nomenclature of the Pfam identifier for this class of enzyme domain. Human 22406 is also predicted to contain two transmembrane domains which extend from about amino acid residues 176–197 and 308–326 of SEQ ID NO:2 (FIG. 3).

The results of a BLASTX search reveal that the amino acid sequence of 22406 shares about 90% sequence identity and about 96% sequence similarity with a murine serine racemase (Accession No. AF148321). Similar results of a BLASTN search reveal that the nucleotide sequence of 22406 shares about 88% sequence identity with this murine serine racemase (Accession No. AAF08701). This serine racemase is a member of the pyridoxal-phosphate dependent family of enzymes with the Pfam identifier, PALP, (Wolosker et al. (1999) *PNAS* 96:13409–13414).

Members of the pyridoxal-phosphate dependent enzymes frequently have the pyridoxal-phosphate group attached via a lysine residue. The sequence around this residue is sufficiently conserved to allow the derivation of a pattern specific to pyridoxal-phosphate dependent enzymes. This pyridoxal-phosphate attachment site consensus pattern (SEQ ID NO:5) is as follows:

[DESH]-x(4,5)-[STVG]-x-[AS]-[FYI]-K-[DLIFSA]-[RVMF]-[GA]-[LIVMGA]

In this sequence the "x" can represent any amino acid and the brackets indicate that any of the amino acids contained within are allowed at that position. The "K" is the lysine pyridoxal-phosphate attachment site. The 22406 polypeptide contains such a consensus pattern at amino acid residues 47–60 (FIG. 3). The annotation "Dehydratase_Ser_Thr" rather than "PALP" in this figure reflects the fact that the Pfam identifier for this class of enzyme domain has been recently been updated from Dehydratase_Ser_Thr to PALP.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

The 22406 protein contains a significant number of structural characteristics in common with members of the pyridoxal-phosphate dependent enzyme family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "pyridoxal-phosphate dependent enzyme family member" refers to a protein or polypeptide which is capable of metabolism of amino acids. As referred to herein, pyridoxal-phosphate dependent family members preferably include a catalytic domain of about 100–340 amino acid residues in length, preferably about 200–320 amino acid residues in length, or more preferably about 250–310 amino acid residues in length. A pyridoxal-phosphate dependent enzyme family member typically includes at least one of block of homology known as a pyridoxal-phosphate attachment site characterized by the following motif and described above: [DESH]-x(4,5)-[STVG]-x-[AS]-[FYI]-K-[DLIFSA]-[RVMF]-[GA]-[LIVMGA] (SEQ ID NO:5). Specificity of a pyridoxal-phosphate dependent enzyme family member for catalysis of a particular amino acid metabolic reaction is determined by sequence identity to such a particular sub-class of pyridoxal-phosphate dependent enzyme family members.

For example, the 22406 nucleotide and amino acid sequences of the invention contain high sequence identity to the serine racemase class of pyridoxal-phosphate dependent enzymes as described above and found in Wolosker et al. (1999) *PNAS* 96:13409–13414, herein incorporated by reference in its entirety. Based on this sequence similarity, the 22406 molecules of the present invention are predicted to have similar biological activities as pyridoxal-phosphate dependent serine racemase enzyme family members.

Typically, pyridoxal-phosphate dependent enzyme family members play a role in diverse cellular processes. For example, the metabolism of amino acids involves specific reactions catalyzed by various pyridoxal-phosphate dependent enzyme family members. The pyridoxal-phosphate dependent serine racemase enzymes catalyze the formation of D-serine from L-serine. This reaction is important as D-serine is the endogenous ligand for the glycine site of the glutamate N-methyl-D-aspartate (NMDA) receptor (Mothet et al. (2000) *PNAS* 97:4926–4931). In the brain D-serine co-activates post-synaptic NMDA receptors together with glutamate. NMDA receptor function has been shown to be a mediator of behavioral changes associated with a variety of neurological disorders. Thus, the molecules of the present invention may be involved in one or more of: 1) catalyzation of the formation of D-serine from L-serine; 2) the activation of NMDA receptors; 3) learning; 4) memory; 5) convulsion; 6) anxiety; 7) psychotomimetic induced abnormal behavior; 8) cerebellar ataxia; and 9) neurodengeneration.

A 22406 polypeptide can include a "pyridoxal-phosphate dependent enzyme family member domain" or regions homologous with an "pyridoxal-phosphate dependent enzyme family member domain".

As used herein, the term "pyridoxal-phosphate dependent enzyme family member domain" includes an amino acid sequence of about 100–340 amino acid residues in length and having a bit score for the alignment of the sequence to the pyridoxal-phosphate dependent enzyme family member domain (HMM) of at least 8. Preferably, an pyridoxal-phosphate dependent enzyme family member domain includes at least about 200–320 amino acids, more preferably about 250–310 amino acid residues, or about 290–300 amino acids and has a bit score for the alignment of the sequence to the pyridoxal-phosphate dependent enzyme family member domain (HMM) of at least 16 or greater. The pyridoxal-phosphate dependent enzyme family member domain (HMM) has been assigned the PFAM Accession PF00291 (found at the Pfam website, pfam.wustl.edu). An alignment of the pyridoxal-phosphate dependent enzyme family member domain (amino acids 19 to 315 of SEQ ID NO:2) of human 22406 with a consensus amino acid sequence derived from a hidden Markov model is depicted in FIG. 6.

In a preferred embodiment 22406 polypeptide or protein has a "pyridoxal-phosphate dependent enzyme family member domain (PALP)" or a region which includes at least about 200–320, more preferably about 250–310 or 290–300 amino acid residues and has at least about 60%, 70%, 80%, 90%, 95%, 99%, or 100% homology with a "PALP domain," e.g., the pyridoxal-phosphate dependent enzyme family member domain of human 22406 (e.g., amino acid residues 19–315 of SEQ ID NO:2).

To identify the presence of an "pyridoxal-phosphate dependent enzyme family member" domain in a 22406 protein sequence, and make the determination that a polypeptide or protein of interest has a particular profile, the amino acid sequence of the protein can be searched against a database of HMMs (e.g., the Pfam database, release 2.1)

using the default parameters (sanger.ac.uk/Software/Pfam). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, a 22406 protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In one embodiment, a 22406 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 22406 (e.g., amino acid residues 176–197 and 308–326 of SEQ ID NO:2).

In one embodiment, a 22406 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 22406 protein, or 22406-like protein.

In one embodiment a 22406 polypeptide or protein has at least one "non-transmembrane domain" or a region which includes at least about 1–175 acid residues, and has at least about 60%, 70% 80% 90% 95%, 99% or 100% homology with a "non-transmembrane domain", e.g., a non-transmembrane domain of human 22406 (e.g., residues 1–175, 198–307, and 327–340 of SEQ ID NO:2). Preferably, a non-transmembrane domain is capable of catalytic activity (e.g., catalyzing a serine racemazation reaction).

As the 22406 polypeptides of the invention may modulate 22406-mediated activities, they may be useful as of for developing novel diagnostic and therapeutic agents for 22406-mediated or related disorders, as described below.

As used herein, a "22406 activity", "biological activity of 22406" or "functional activity of 22406", refers to an activity exerted by a 22406 protein, polypeptide or nucleic acid molecule on e.g., a 22406-responsive cell or on a 22406 substrate, e.g., an amino acid substrate, as determined in vivo or in vitro. In one embodiment, a 22406 activity is a direct activity, such as an association with a 22406 target molecule. A "target molecule" or "binding partner" is a molecule with which a 22406 protein binds or interacts in nature, e.g., an amino acid such as L-serine or D-serine. A 22406 activity can also be an indirect activity, e.g., a cellular signaling activity mediated by interaction of the D-serine product of 22406 catalysis with a D-serine "receptor", "target molecule" or "binding partner". A D-serine "receptor", "target molecule" or "binding partner" is herein defined as a molecule with which D-serine binds or interacts in nature, and these terms are herein used interchangeably. For example, the 22406 proteins of the present invention can have one or more of the following activities: 1) catalyzation of the formation of D-serine from L-serine; 2) activation of the NMDA receptor; 3) mediation of learning; 4) mediation of memory; 5) mediation of convulsion; 6) mediation of anxiety; 7) mediation of psychotomimetic induced abnormal behavior; 8) mediation of cerebellar ataxia; 9) mediation of neurodengeneration and 10) the ability to modulate, competitively or non-competitively, any of 1–10. "Modulate" is herein defined as increasing or decreasing an activity or process by any mechanism, including but not limited to, inhibition or antagonism by competitive or non-competitive binding.

Accordingly, 22406 protein may mediate various disorders, particularly brain disorders, including but not limited to, behavioral changes associated with learning, memory, convulsion, anxiety, psychotomimetic induced abnormal behavior, cerebellar ataxia, and neurodengeneration. Inhibitors of 22406 protein can be expected to quell anxiety and epilepsy and to prevent damage from stroke and certain neurodegenerative conditions including Alzheimer's disease. On the other hand, stimulating 22406 protein might improve schizophrenia symptoms, which are partly caused by depressed NMDA receptor function.

Figure 4:
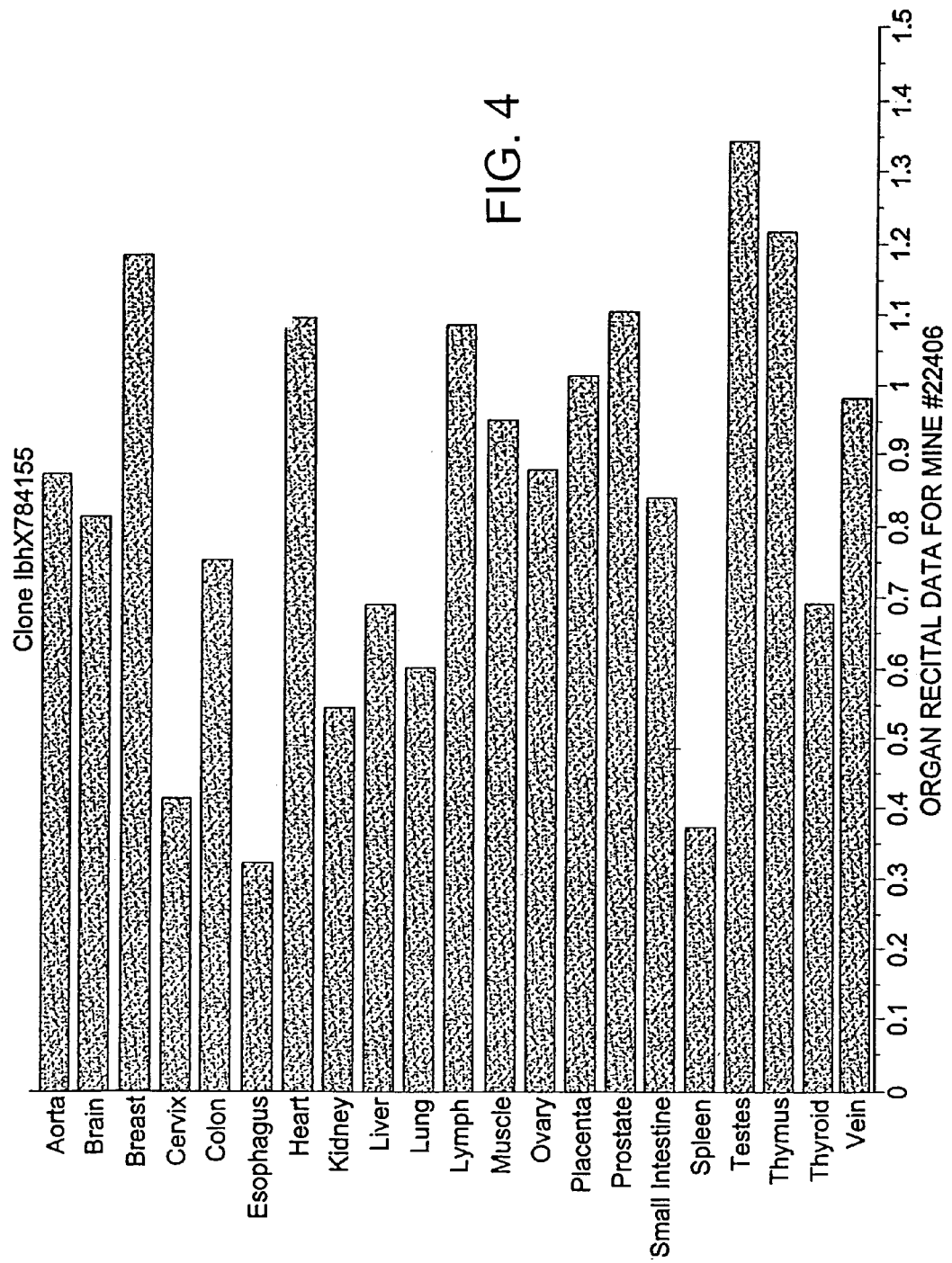
FIG. 4 shows expression of the 22406 protein in various normal human tissues.
Figure 9:
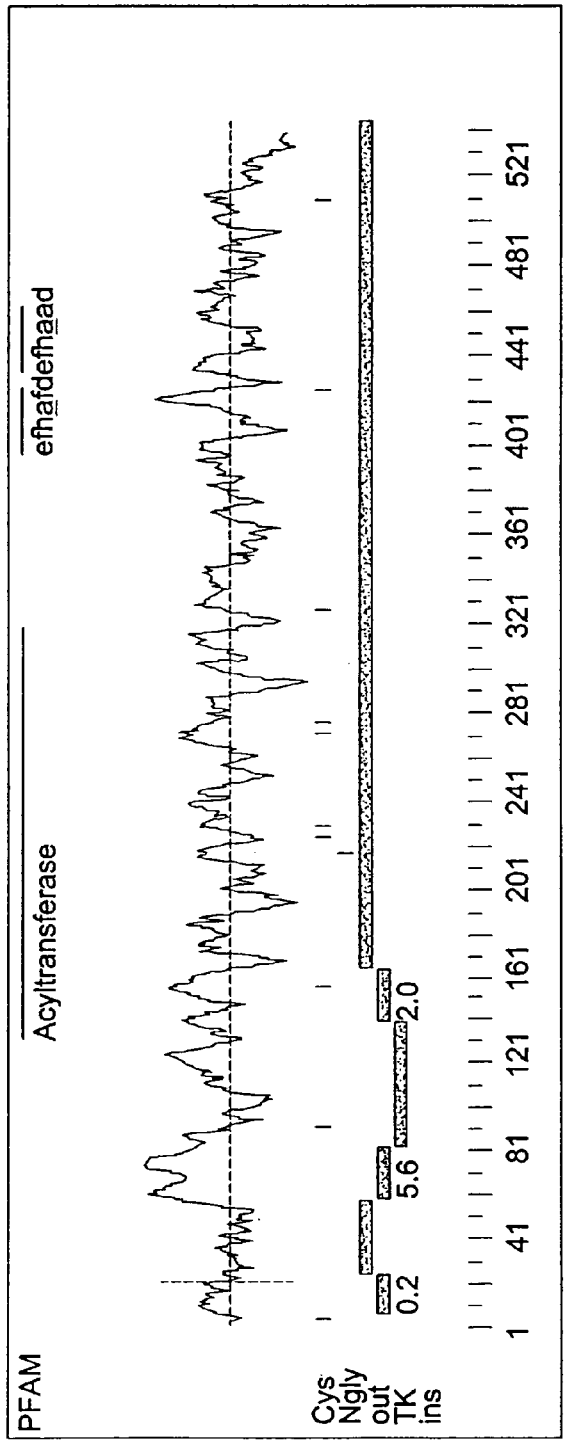
FIG. 9 depicts a hydropathy plot of human acyltransferase. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence of human acyltransferase are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.
Figure 11:
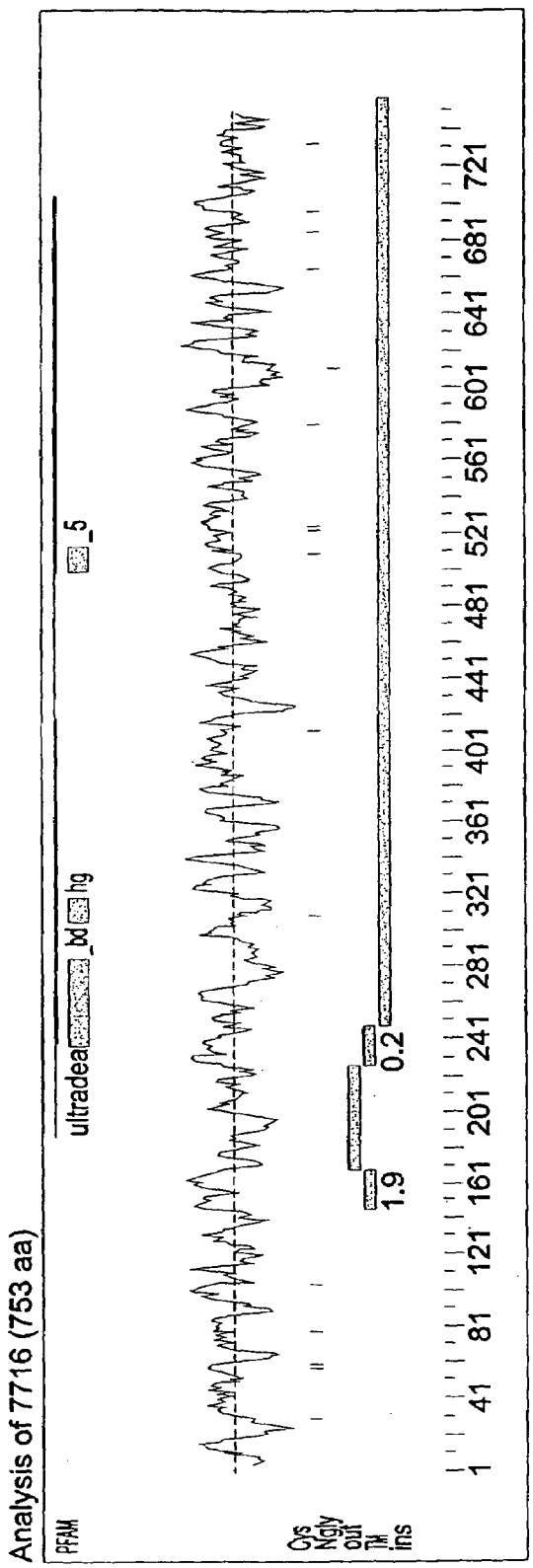
FIG. 11 depicts a hydropathy plot of human 7716. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence of human 7716 (shown in SEQ ID NO:11) are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 16:
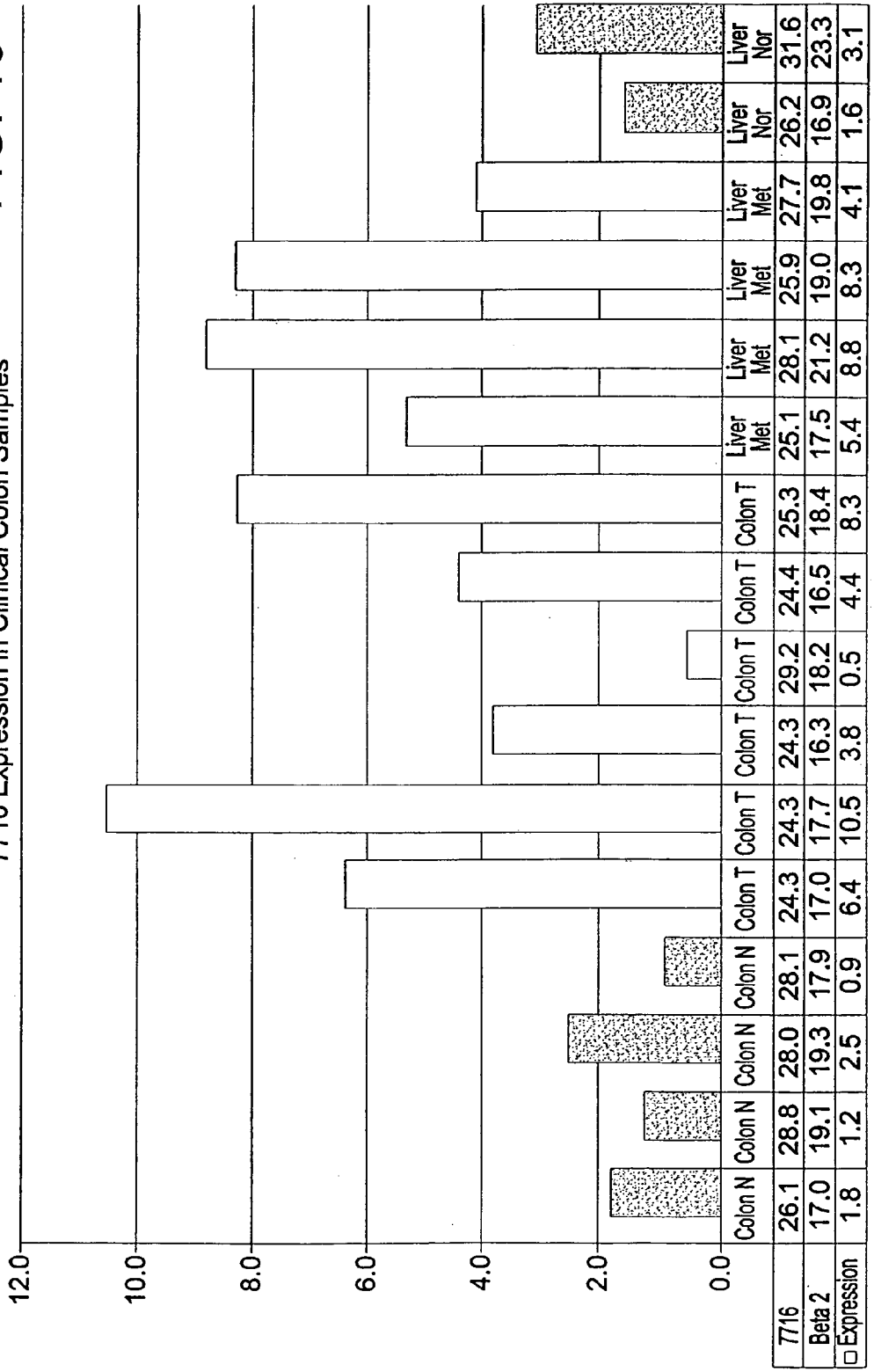
FIG. 16 shows the expression of 7716 in clinical samples from normal human colon tissue (columns 1–4), human colon tumor tissue (columns 5–10), human colon cancer liver metastases tissue (columns 11–14); and normal human liver tissue (columns 15 and 16). Expression levels of 7716 were determined as described in the legend for FIG. 13.
Figure 17:
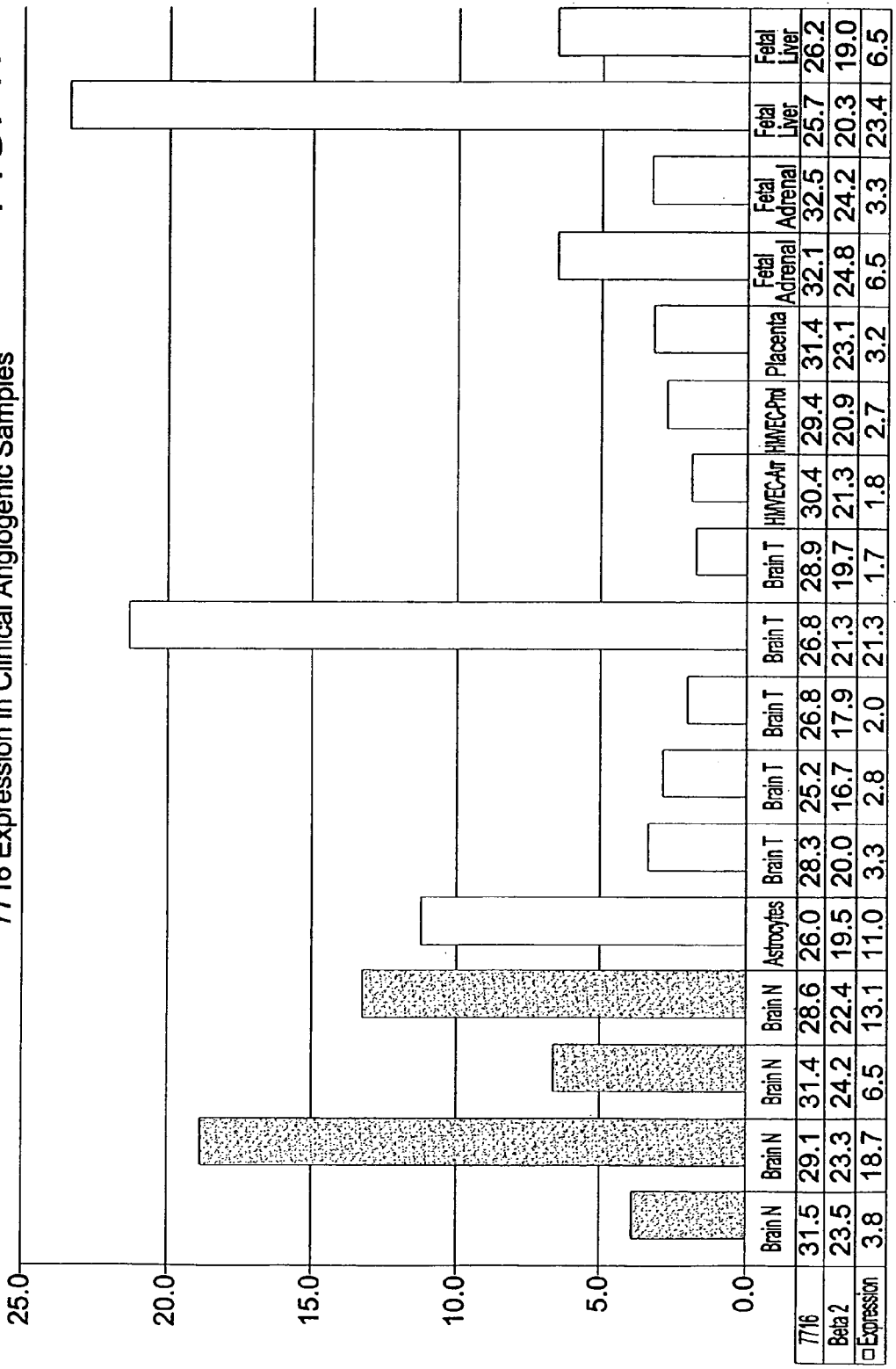
FIG. 17 shows the expression of 7716 in clinical samples from normal human brain tissue (columns 1–4), normal human astrocytes (column 5), human brain tumor tissue (columns 6–10); arresting human microvascular endothelial cells (column 11), proliferating human microvascular endothelial cells (column 12), placenta (column 13), fetal adrenal tissue (columns 14 and 15), and fetal liver (columns 16 and 17). Expression levels of 7716 were determined as described in the legend for FIG. 13.
Figure 18:
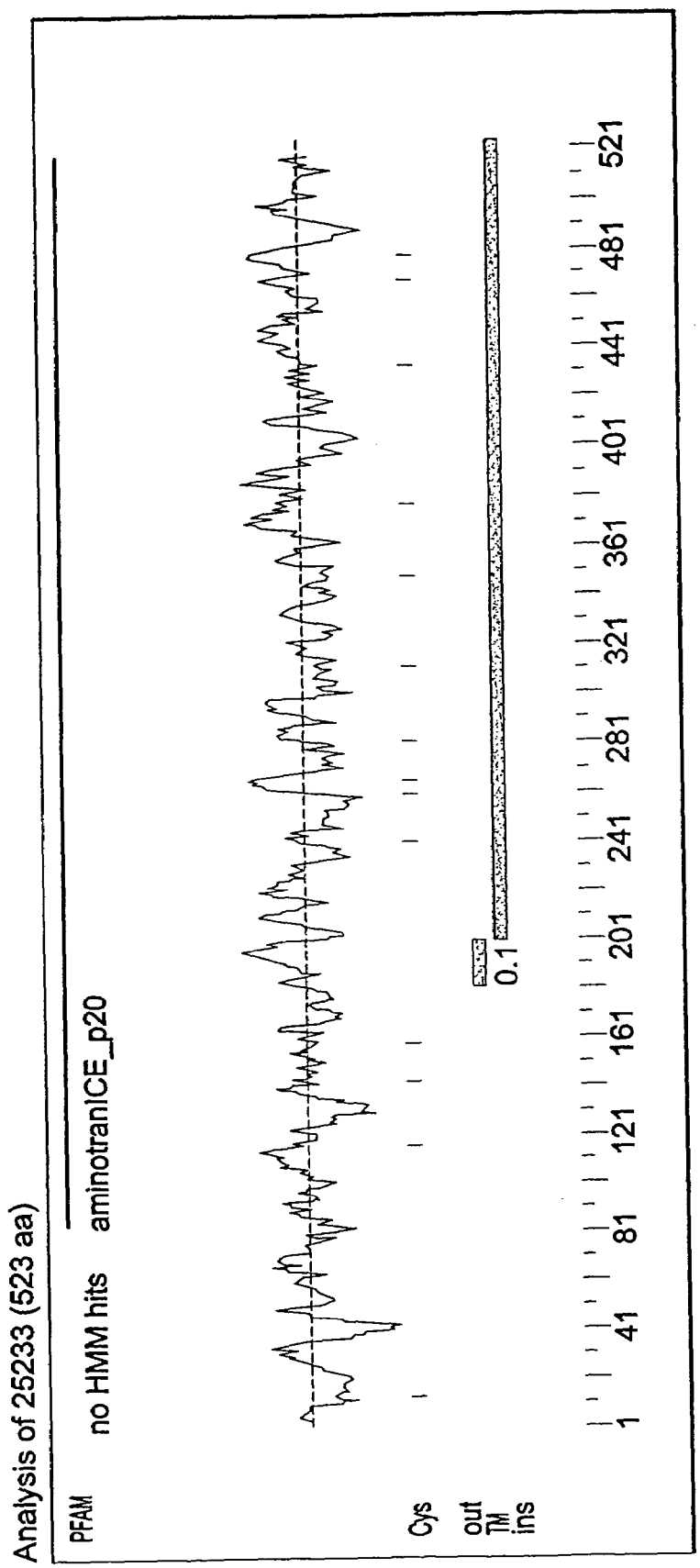
FIG. 18 depicts a hydropathy plot of human 25233. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence of human 25233 (shown in SEQ ID NO:15) are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.
Figure 21A:
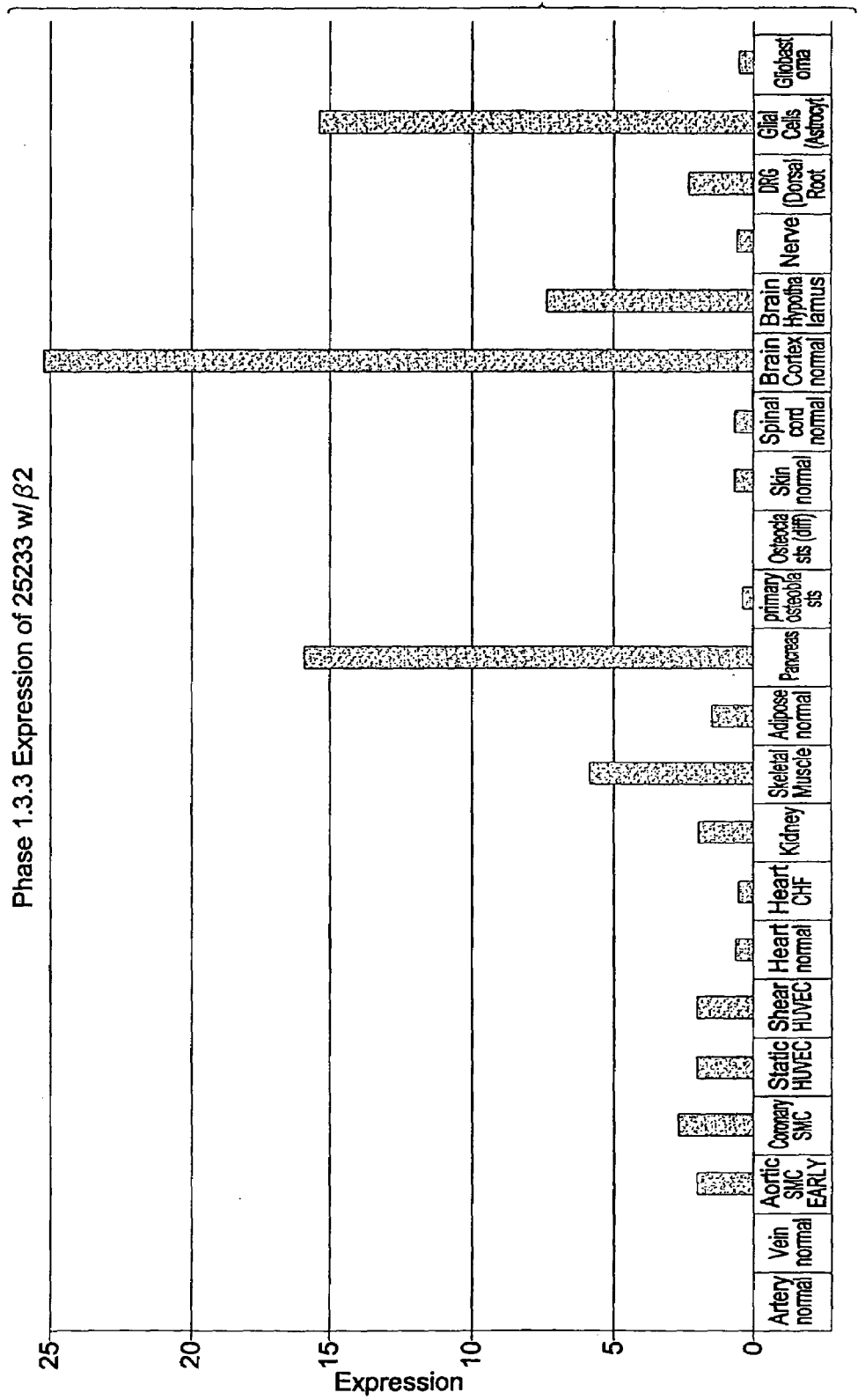
FIGS. 21A–21B show the expression of 25233 in the following human tissues and cell lines: Artery Normal (Column 1); Vein Normal (Column 2); Aortic SMC (Smooth Muscle Cell) EARLY (Column 3); Coronary SMC (Column 4); Static HUVEC (Human Umbilical Vein Endothelial Cells) (Column 5); Shear HUVEC (Column 6); Heart Normal (Column 7); Heart CHF (Congestive Heart Failure) (Column 8); Kidney (Column 9); Skeletal Muscle (Column 10); Adipose Normal (Column 11); Pancreas (Column 12); Primary Osteoblasts (Column 13); Osteoclasts (Differentiated); (Column 14); Skin Normal (Column 15); Spinal Cord Normal (Column 16); Brain Cortex Normal (Column 17); Brain Hypothalamus Normal (Column 18); Nerve (Column 19); DRG (Dorsal Root Ganglion); (Column 20); Glial Cells (Astrocytes); (Column 21); Glioblastoma (Column 22); Breast Normal (Column 23); Breast Tumor (Column 24); Ovary Normal (Column 25); Ovary Tumor (Column 26); Prostate Normal (Column 27); Prostate Tumor (Column 28); Epithelial Cells (Prostate); (Column 29); Colon Normal (Column 30); Colon Tumor (Column 31); Lung Normal (Column 32); Lung Tumor (Column 33); Lung COPD (Chronic Obstructive Pulmonary Disease) (Column 34); Colon IBD (Inflammatory Bowel Disease) (Column 35); Liver Normal (Column 36); Liver Fibrosis (Column 37); Dermal Cells-Fibroblasts (Column 38); Spleen Normal (Column 39); Tonsil Normal (Column 40); Lymph Node (Column 41); Small Intestine (Column 42); Skin-Decubitus (Column 43); Synovium (Column 44); BM-MNC (Bone Marrow Mononuclear Cells); (Column 45); and Activated PBMC (Peripheral Blood Mononuclear Cells) (Column 46). Expression levels were determined by reverse transcriptase (RT) quantitative PCR (Taqman® brand quantitative PCR kit, Applied Biosystems). The quantitative PCR reactions were performed according to the kit manufacturer's instructions.
Figure 21B:
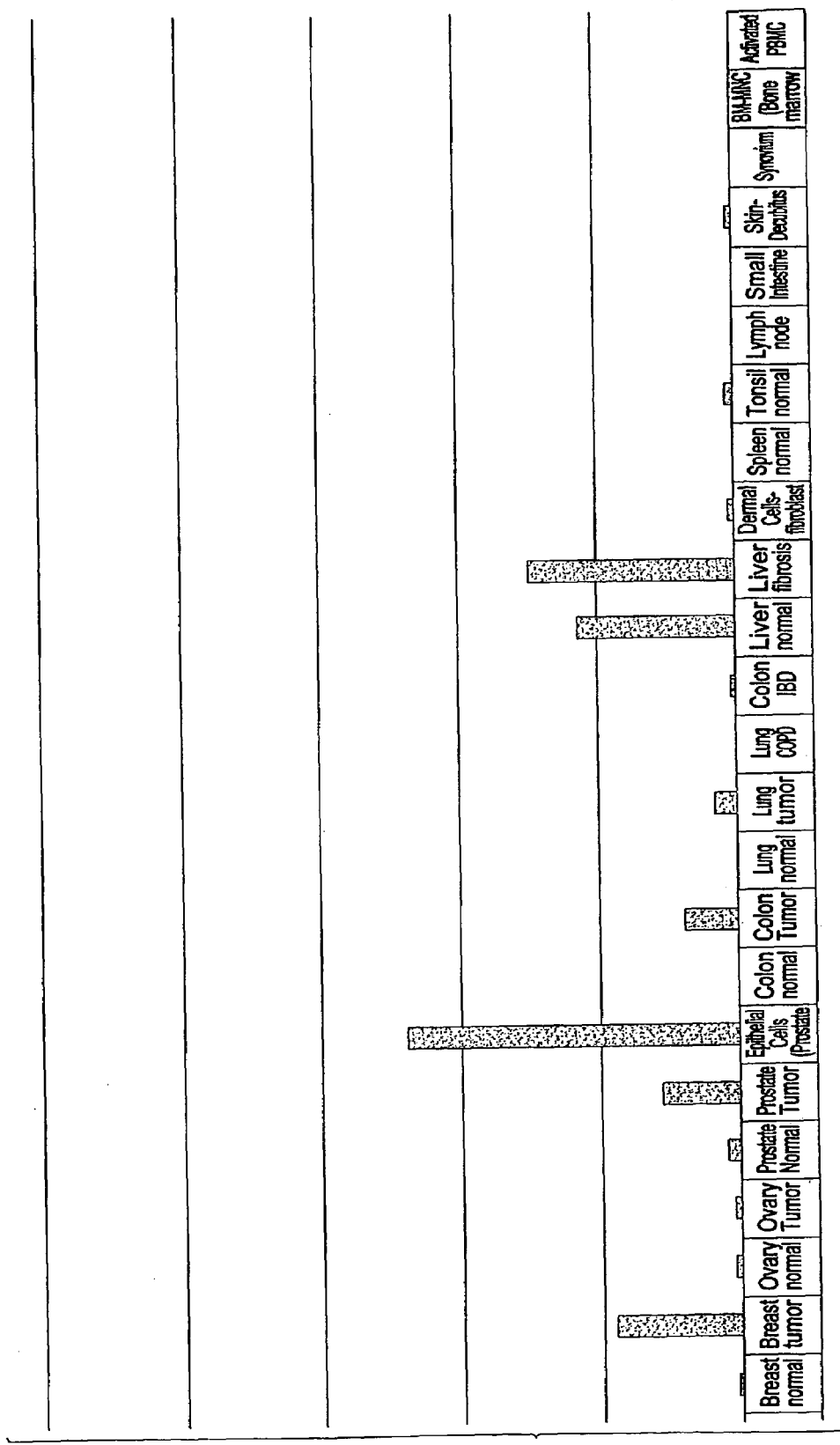
Figure 22A:
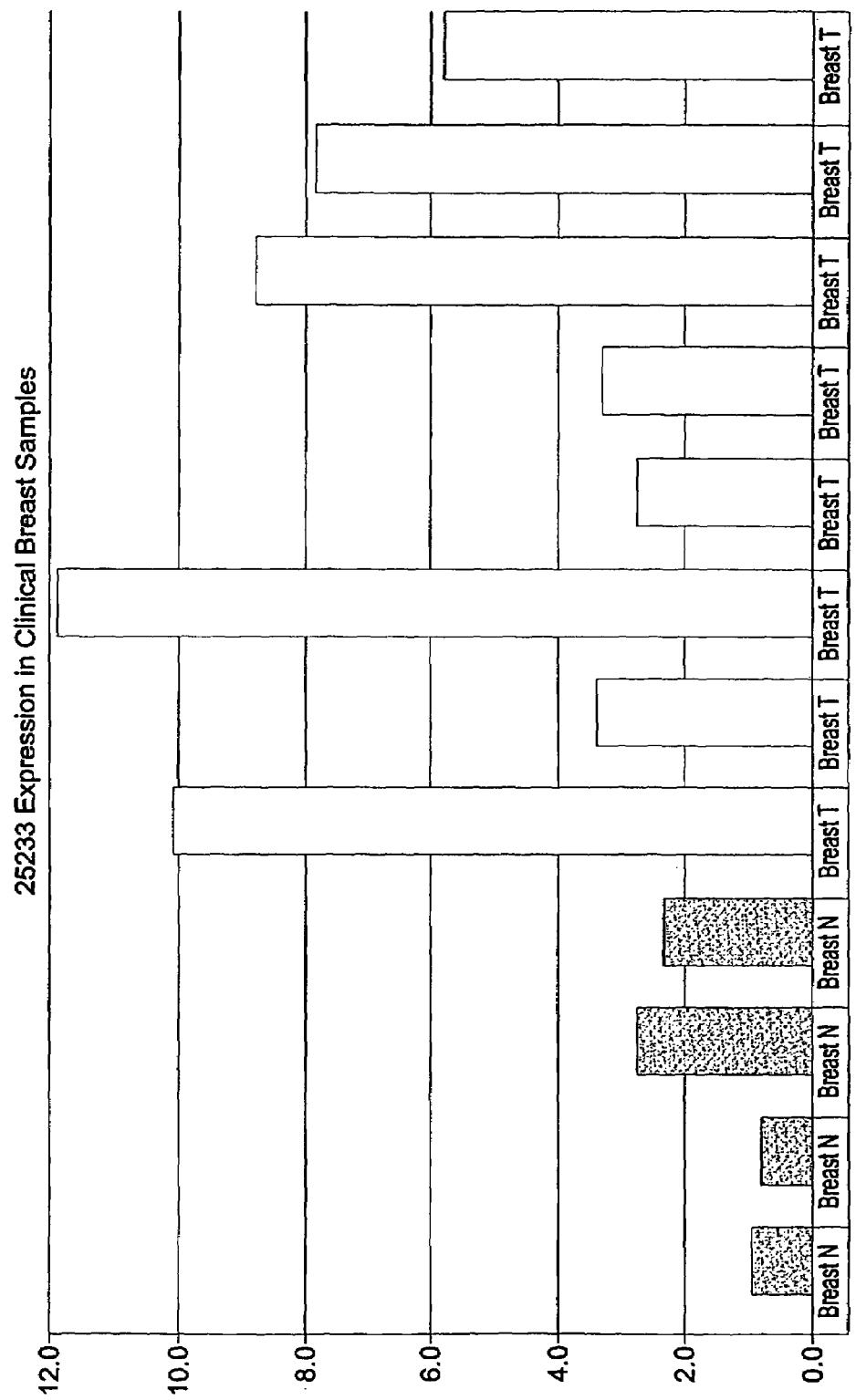
FIGS. 22A–22D show the expression of 25233 in human tissues and cell lines, as follows.
Figure 22B:
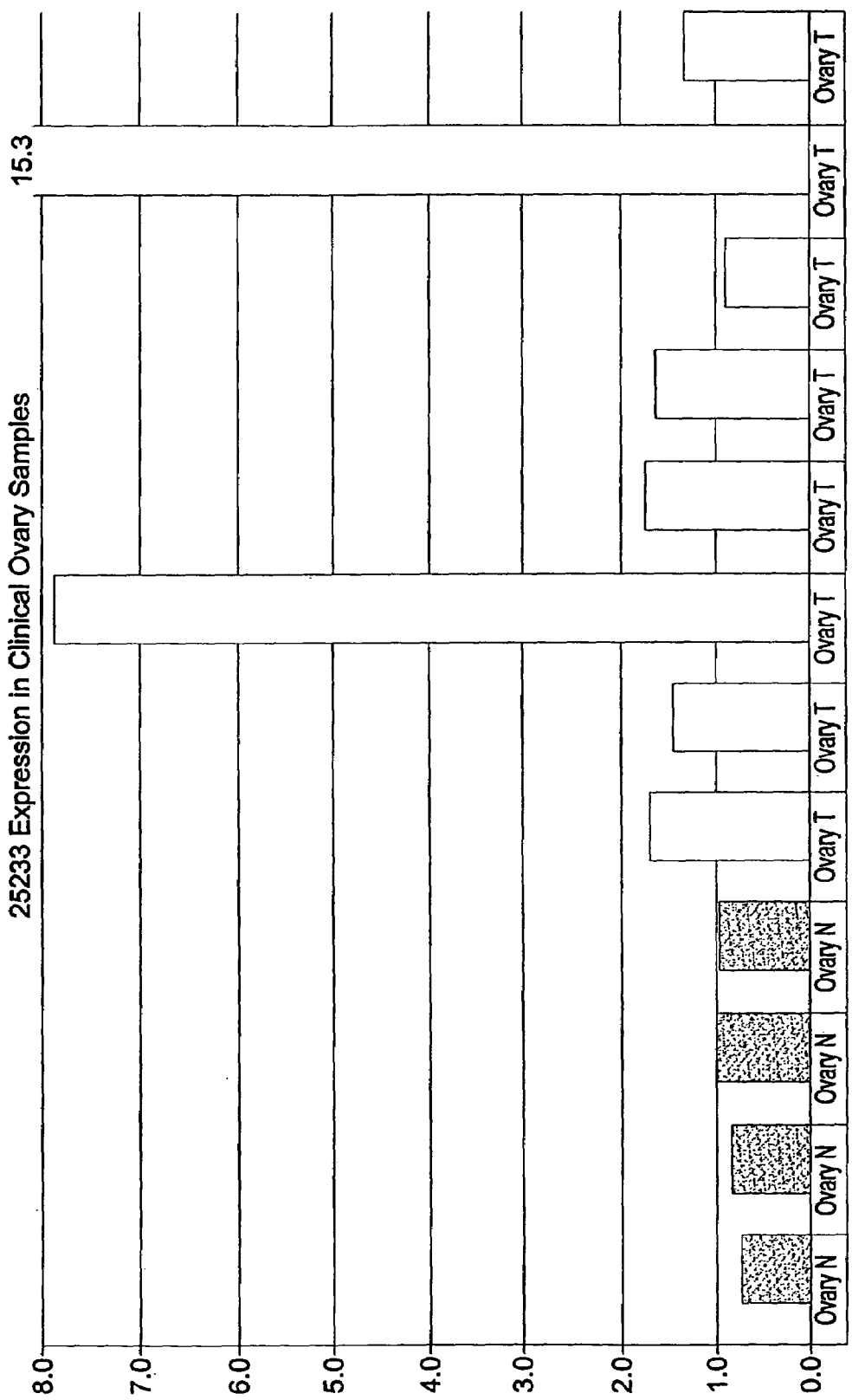
Figure 22C:
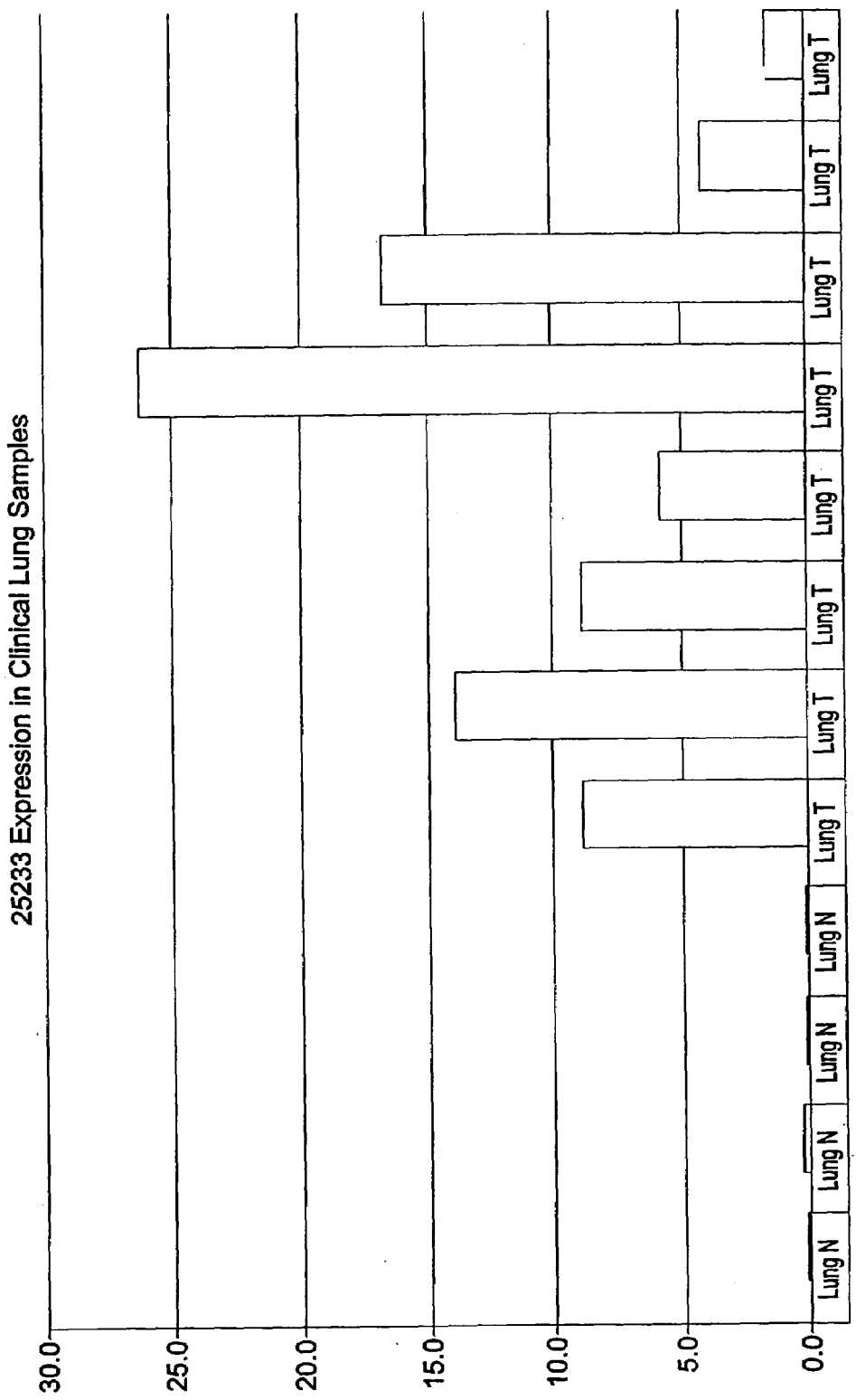
Figure 22D:
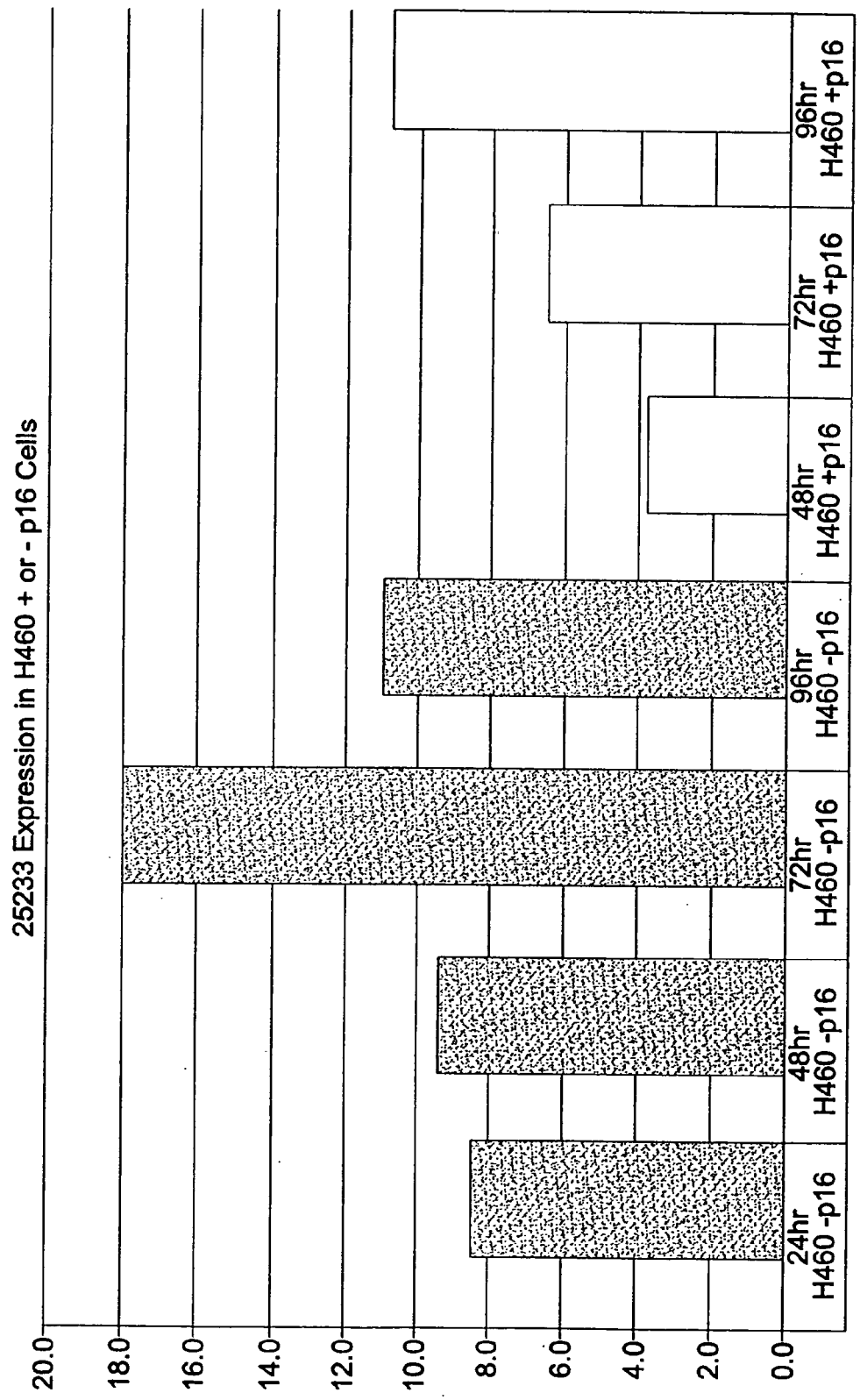

In addition, 22406 protein can be expected to be involved in various disorders of the tissues in which it is expressed. FIGS. 4 and 8 show expression of the 22406 protein in various normal human tissues with highest expression in brain, heart, liver, skeletal muscle, lymph node, prostate, dermal fibroblast, testes, and thymus. Significant expression is also found in various other tissues. In addition to the tissues shown in the Figures, expression has also been observed in adrenal gland, bone, endothelial cells, total fetal tissue, hypothalamus, keratinocytes, natural killer cells, osteoblasts, pituitary, skin, spinal cord, T-cells, colon to liver metastases and lymphoma.

Expression was also observed in two separate lung tumor cDNA libraries while libraries of normal lung and bronchial epithelia sequenced to equal depths yielded no sequences for the 22406 protein. Additionally, PCR analysis on panels containing normal and tumor lung cDNAs showed that the gene may be expressed at higher levels in lung tumor samples. Expression was also observed in colonic tumor cDNA libraries.

Thus, 22406 can be also be expected to be involved in disorders including heart disorders, liver disorders, lung disorders, prostrate disorders, colon disorders, skeletal muscle disorders, dermal fibroblast disorders, lymph node disorders, and blood vessel disorders.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephalopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system-carcinomas, testicular carcinomas, breast carcinomas, prostatic carcinomas, endocrine system carcinomas, and melanomas. Exemplary carcinomas include those forming from tissue of the lung, prostate, and colon. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the prostate include, but are not limited to, inflammations, benign enlargement, for example, nodular hyperplasia (benign prostatic hypertrophy or hyperplasia), and tumors such as carcinoma.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sézary syndrome, peripheral T-cell lymphoma, unspecified, angioimmunoblastic T-cell lymphoma, angiocentric lymphoma (NK/T-cell lymphoma$^{4a}$), intestinal T-cell lymphoma, adult T-cell leukemia/lymphoma, and anaplastic large cell lymphoma.

Disorders involving the skeletal muscle include tumors such as rhabdomyosarcoma.

CHAPTER 2

32447, A NOVEL HUMAN ACYLTRANSFERASE AND USES THEREOF

BACKGROUND OF THE INVENTION

Glycerophospholipids, which include phopholipids and triacylglycerol, are ubiquitous and critically important molecules. Phospholipids are the predominant component of biomembranes, and determine such properties as membrane permeability and the activity of membrane proteins. Triacylglycerol is the major storage form of energy in animals. In the de novo biosynthesis of glycerophospholipids in most tissues, glycerol-3-phosphate is esterified with a fatty acyl-CoA in the sn-1 position by glycerol-3-phosphate acyltransferase to form 1-acylglycerol-3-phsophate (lysophosphatidic acid). Lysophosphatidic acid is esterified in the sn-2 position with a fatty acyl-CoA by 1-acylglycerol-3-phophate acyltransferase to form 1,2-diacylglycerol-3-phosphate (phosphatidic acid) (Dircks et al. (1999) *Progress in Lipid Research* 38:461–479). Phosphatidic acid can be converted to CDP-diacylglycerol and ultimately to phosphatidylinositol, phosphatidylglycerol, and cardiolipin.

Glycerol-3-phophate acyltransferase (E.C. 2.3.1.15) is the first committed and presumed to be a rate-limiting step in glycerophospholipid biosynthesis. It catalyzes the esterification of glycerol-3-phosphate in the sn-1 position with a fatty acyl-CoA to form 1-acylglycerol-3-phosphate (lysophosphatidic acid). Two isoforms of the enzyme have been detected, a mitochondrial form and an endoplasmic reticulum isoform. The two forms of the enzyme can be differentiated by their differential sensitivity to the sulfhydryl modifying agent N-ethylmaleimide (NEM) (Haldar, D. et al. (1979) *J. Biol. Chem.* 254(11):4502–9).

Glycerol-3-phosphate acyltransferase is found in most tissues including liver, adipose, heart, lung, kidney, adrenal, muscle, lactating mammary, intestinal mucosa, brain and in various cultured cell lines. In most tissues the mitochondrial isoform comprises 10% of the total activity. The mitochondrial isoform is the isoform under nutritional and hormonal regulation that occurs in lipogenic tissues such as liver and adipose tissue. The mitochondrial isoform of the enzyme is regulated by hormonal and nutritional fluctuations while the endoplasmic reticulum isoform is unaffected (Dircks et al. (1999) *Progress in Lipid Research* 38:461–479).

Lysophophatidic acid is catalyzed in the sn-2 position by 1-acylglycerol-3-phosphate acyltransferase (E.C. 2.3.1.51). also called lysophosphatidic acid acyltransferase to form 1,2-diacylglycerol-phosphate (phosphatidic acid). This enzyme has been cloned from many organisms, including several species of bacteria and plants, yeast, human, and mouse. It has been demonstrated that this acyltransferase increases several fold when preadipocytes differentiate into adipocytes (Coleman et al. (1978) *J. Biol. Chem.* 253: 7256–61).

The final acylation step in triacylglycerol biosynthesis is the esterification of fatty acyl-CoA in the sn-3 position by diacylglycerol acyltransferase (E.C. 2.3.1.20) which occurs after dephosphorylation of phosphatidic acid by phosphatide phosphohydrolase. This acyltransferase is the only enzyme which is specific to triacylglycerol synthesis and may play an important role in triacylglycerol synthesis. This enzyme is localized in the endoplasmic reticulum membrane. At present, very little information is reported about this acyltransferase or its regulation.

Accordingly, acyltransferases are a major target for drug action and development. Thus, it is valuable to the field of pharmaceutical development to identify and characterize novel acyltransferases and tissues and disorders in which these enzymes are differentially expressed. The present invention advances the state of the art by providing novel human acyltransferase molecules and the uses thereof.

SUMMARY OF THE INVENTION

The present invention is based, in part, on the discovery of a novel human enzyme, referred to herein as "acyltransferase". The nucleotide sequence of a cDNA encoding acyltransferase is shown in SEQ ID NO:6, and the amino acid sequence of an acyltransferase polypeptide is shown in SEQ ID NO:7 Accordingly, in one aspect, the invention features a nucleic acid molecule which encodes an acyltransferase protein or polypeptide, e.g., a biologically active portion of the acyltransferase protein. In a preferred embodiment, the isolated nucleic acid molecule encodes a polypeptide having the amino acid sequence of SEQ ID NO:7. In other embodiments, the invention provides an isolated acyltransferase nucleic acid molecule having the nucleotide sequence shown in SEQ ID NO:6. In still other embodiments, the invention provides nucleic acid molecules that are substantially identical (e.g., naturally occurring allelic variants) to the nucleotide sequence shown in SEQ ID NO:6. In other embodiments, the invention provides a nucleic acid molecule which hybridizes under stringent hybridization conditions to a nucleic acid molecule comprising the nucleotide sequence of SEQ ID NO:6, wherein the nucleic acid encodes a full length acyltransferase protein or an active fragment thereof.

In a related aspect, the invention further provides nucleic acid constructs which include an acyltransferase nucleic acid molecule described herein. In certain embodiments, the nucleic acid molecules of the invention are operatively linked to native or heterologous regulatory sequences. Also included, are vectors and host cells containing the acyltransferase nucleic acid molecules of the invention e.g., vectors and host cells suitable for producing acyltransferase nucleic acid molecules and polypeptides.

In another related aspect, the invention provides nucleic acid fragments suitable as primers or hybridization probes for the detection of acyltransferase-encoding nucleic acids.

In still another related aspect, isolated nucleic acid molecules that are antisense to an acyltransferase encoding nucleic acid molecule are provided.

In another aspect, the invention features, acyltransferase polypeptides, and biologically active or antigenic fragments thereof that are useful, e.g., as reagents or targets in assays applicable to treatment and diagnosis of acyltransferase-mediated or -related disorders. In another embodiment, the invention provides acyltransferase polypeptides having acyltransferase activity. Preferred polypeptides are proteins including at least domain or active site involved in the transfer of an acyl group from acyl-CoA onto a substrate (e.g., transfer of an acyl group onto sn-glycerol-3-phosphate from Acyl-CoA to yield 1-acylglycerol-3-phosphate(lysophosphatidate)).

In other embodiments, the invention provides acyltransferase polypeptides, e.g., an acyltransferase polypeptide having the amino acid sequence shown in SEQ ID NO:7; an amino acid sequence that is substantially identical to the amino acid sequence shown in SEQ ID NO:7; or an amino acid sequence encoded by a nucleic acid molecule having a nucleotide sequence which hybridizes under stringent hybridization conditions to a nucleic acid molecule comprising the nucleotide sequence of SEQ ID NO:6, wherein the nucleic acid encodes a full length acyltransferase protein or an active fragment thereof.

In a related aspect, the invention further provides nucleic acid constructs which include an acyltransferase nucleic acid molecule described herein.

In a related aspect, the invention provides acyltransferase polypeptides or fragments operatively linked to non-acyl-transferase polypeptides to form fusion proteins.

In another aspect, the invention features antibodies and antigen-binding fragments thereof, that react with, or more preferably specifically bind acyltransferase polypeptides.

In another aspect, the invention provides methods of screening for compounds that modulate the expression or activity of the acyltransferase polypeptides or nucleic acids.

In still another aspect, the invention provides a process for modulating acyltransferase polypeptide or nucleic acid expression or activity, e.g. using the screened compounds. In certain embodiments, the methods involve treatment of conditions related to aberrant activity or expression of the acyltransferase polypeptides or nucleic acids, such as conditions involving aberrant or deficient cellular proliferation or differentiation.

The invention also provides assays for determining the activity of or the presence or absence of acyltransferase polypeptides or nucleic acid molecules in a biological sample, including for disease diagnosis.

In further aspect the invention provides assays for determining the presence or absence of a genetic alteration in an acyltransferase polypeptide or nucleic acid molecule, including for disease diagnosis.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Human Acyltransferase

The human acyltransferase sequence (SEQ ID NO:6), which is approximately 2299 nucleotides long including untranslated regions, contains a predicted methionine-initiated coding sequence of about 1632 nucleotides (SEQ ID NO:6) not including the terminal codon. The coding sequence encodes a 544 amino acid protein (SEQ ID NO:7).

This mature protein form is approximately 544 amino acid residues in length. Human acyltransferase contains the following regions or other structural features: MEMSAT predicted transmembrane domains which extend from about amino acid residue 7 to 24, aa 58 to 81, and aa 140 to 164; a predicted signal peptide from aa 1–20; and presumed mature peptide transmembrane segments numbered from about aa 38 to 61, 90 to 108, and 120 to 144 of the cleaved polypeptide, that is, numbered from the N-terminus of the polypeptide resulting from the cleavage of the aa 1–20 signal sequence.

The acyltransferase protein (SEQ ID NO:7) also includes the following domains: cAMP- and cGMP-dependent protein kinase phosphorylation sites at aa 104 to 107, aa 195 to 198, aa 204 to 207; N-glycosylation site at aa 225 to 228; protein kinase C phosphorylation sites at aa 52 to 54, aa 194 to 196, aa 224 to 226, aa 231 to 233, aa 350 to 352, a a 373 to 375 526 to 528, and aa 539 to 541; casein kinase II phosphorylation sites at aa 134 to 137, aa 148 to 151, aa 165 to 168, aa 188 to 191, aa 198 to 201, aa 208 to 211, aa 279 to 282, aa 322 to 325, aa 427 to 430, aa 449 to 452, aa 482 to 485, aa 502 to 505, and 537 to 540; N-myristoylation sites at aa 16 to 21, aa 221 to 226, aa 315 to 320, aa 376 to 381; and an EF-hand calcium binding domain at aa 404 to 416, and aa 441 to 453.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

As used herein, the term "acyltransferase" refers to a protein or polypeptide which is capable of transferring an "acyl group" from Acyl-CoA onto a substrate. All three known and described acyltransferases (glycerol-3-phosphate acyltransferase (GPAT); 1-acylglycerol 3-phosphate acyltransferase(AGPAT); and diacylglycerol acyltransferase) all act to transfer acyl groups. Assays for acyltransferases have been previously described (Dircks et al. (1999) *Progress in Lipid Research* 38:461–479).

Typically, acyltransferases play a role in diverse cellular processes. For example, the glycerophospholipids are predominant components of biomembranes and triacylglycerol is a major storage form of energy in animals.

As used herein, the term "acyltransferase domain" includes an amino acid sequence of about 80–300 amino acid residues in length. Preferably, an acyltransferase domain includes at least about 100–250 amino acids, more preferably about 130–200 amino acid residues, or about 160–200 amino acids. The acyltransferase domain (HMM) has been assigned the PFAM Accession PF01553 (at the Pfam website, pfam.wustl.edu). An alignment of the acyltransferase domain (amino acids 131 to 317 of SEQ ID NO:7) of human acyltransferase with a consensus amino acid sequence derived from a hidden Markov model is depicted in FIG. 10.

In a preferred embodiment acyltransferase polypeptide or protein has an "acyltransferase domain" or a region which includes at least about 100–250 more preferably about 130–200 or 160–200 amino acid residues and has at least about 60%, 70%, 80%, 90%, 95%, 99%, or 100% sequence identity with an "acyltransferase domain," e.g., the acyltransferase domain of human acyltransferase (e.g., amino acid residues 131–317 of SEQ ID NO:7).

To identify the presence of an acyltransferase domain in an acyltransferase protein sequence and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the HMMER package of search programs, is a family specific default program for MIL-PAT0063. A description of the Pfam database can be found in Sonhammer et al., (1997) *Proteins* 28(3):405–420 and a detailed description of HMMs can be found, for example, in Gribskov et al., (1990) *Meth. Enzymol.* 183:146–159; Gribskov et al., (1987) *Proc. Natl. Acad. Sci. USA* 84:4355–4358; Krogh et al., (1994) *J. Mol. Biol.* 235: 1501–1531; and Stultz et al., (1993) *Protein Sci.* 2:305–314, the contents of which are incorporated herein by reference.

In one embodiment, an acyltransferase protein includes at least one transmembrane domain. As used herein, the term "transmembrane domain" includes an amino acid sequence of at least 15 amino acid residues in length that spans a phospholipid membrane. More preferably, a transmembrane domain includes about at least 18, 20, 22, 24, or 25 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al., (1996) *Annual Rev. Neuronsci.* 19: 235–63, the contents of which are incorporated herein by reference.

In a preferred embodiment, an acyltransferase polypeptide or protein has at least one transmembrane domain or a region which includes at least 16, 18, 20, 22, 24, or 25 amino acid residues and has at least about 60%, 70% 80% 90% 95%, 99%, or 100% homology with a "transmembrane domain," e.g., at least one transmembrane domain of human acyltransferase (e.g., amino acid residues 7 to 24, 58 to 81, and 140 to 164 of SEQ ID NO:7).

In another embodiment, an acyltransferase protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring acyltransferase protein.

In a preferred embodiment, an acyltransferase protein has a "non-transmembrane domain" or a region which includes at least about 1–7, about 1–34, about 1–59, and about 1–381 amino acid residues, and has at least about 60%, 70% 80% 90% 95%, 99% or 100% sequence identity with a "non-transmembrane domain", e.g., a non-transmembrane domain of human 32447 (e.g., residues 1–6, 25–57, 82–139, and 165–544 of SEQ ID NO:7). Preferably, a non-transmembrane domain is capable of catalytic activity (e.g., acyltransferase activity).

A non-transmembrane domain located at the N-terminus of an acyltransferase protein or polypeptide is referred to herein as an "N-terminal non-transmembrane domain." As used herein, an "N-terminal non-transmembrane domain" includes an amino acid sequence having about 1–350, preferably about 30–325, more preferably about 50–320, or even more preferably about 80–310 amino acid residues in length and is located outside the boundaries of a membrane. For example, an N-terminal non-transmembrane domain is located at about amino acid residues 1–6 of SEQ ID NO:7.

Similarly, a non-transmembrane domain located at the C-terminus of an acyltransferase protein or polypeptide is referred to herein as a "C-terminal non-transmembrane domain." As used herein, a "C-terminal non-transmembrane domain" includes an amino acid sequence having about 1–300, preferably about 15–290, preferably about 20–270, more preferably about 25–255 amino acid residues in length and is located outside the boundaries of a membrane. For example, an C-terminal non-transmembrane domain is located at about amino acid residues 165–544 of SEQ ID NO:7.

An acyltransferase polypeptide or protein can further include a signal sequence. As used herein, a "signal sequence" refers to a peptide of about 20–80 amino acid residues in length which occurs at the N-terminus of secretory and integral membrane proteins and which contains a majority of hydrophobic amino acid residues. For example, a signal sequence contains at least about 12–25 amino acid residues, preferably about 30–70 amino acid residues, more preferably about 20 amino acid residues, and has at least about 40–70%, preferably about 50–65%, and more preferably about 55–60% hydrophobic amino acid residues (e.g., alanine, valine, leucine, isoleucine, phenylalanine, tyrosine, tryptophan, or proline). Such a "signal sequence", also referred to in the art as a "signal peptide", serves to direct a protein containing such a sequence to a lipid bilayer. For example, in one embodiment, an acyltransferase protein contains a signal sequence of about amino acids 1–20 of SEQ ID NO:7. The "signal sequence" is cleaved during processing of the mature protein. The mature acyltransferase protein corresponds to amino acids 21–544 of SEQ ID NO:7.

As the acyltransferase polypeptides of the invention may modulate acyltransferase-mediated activities, they may be useful for developing novel diagnostic and therapeutic agents for acyltransferase-mediated or related disorders, and for treatment of those disorders, as described below.

As used herein, a "acyltransferase activity", "biological activity of acyltransferase" or "functional activity of acyltransferase", refers to an activity exerted by an acyltransferase protein, polypeptide or nucleic acid molecule on e.g., an acyltransferase-responsive cell or on an acyltransferase substrates, e.g., glycerol-3-phosphate and fatty acyl CoA, or as determined in vivo or in vitro. In one embodiment, an acyltransferase activity is a direct activity, such as an association with an acyltransferase target molecule. A "target molecule" or "binding partner" is a molecule with which an acyltransferase protein binds or interacts in nature.

Accordingly, acyltransferase protein may mediate various disorders, including cellular proliferative and/or differentiative disorders, brain disorders, heart disorders, blood vessel disorders, and platelet disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The acyltransferase nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

By "variants" is intended proteins or polypeptides having an amino acid sequence that is at least about 60%, 65%, preferably about 75%, 85%, 95%, 96%, 97%, 98%, or 99% identical to the amino acid sequence of SEQ ID NO:7. Variants also include polypeptides encoded by a nucleic acid molecule that hybridizes to the nucleic acid molecule of SEQ ID NO:6 or 3, or a complement thereof, under stringent conditions. In another embodiment, a variant of an isolated polypeptide of the present invention differs, by at least 1, but less than 5, 10, 20, 50, or 100 amino acid residues from the sequence shown in SEQ ID NO:7. If alignment is needed for this comparison the sequences should be aligned for maximum identity. "Looped" out sequences from deletions or insertions, or mismatches, are considered differences. Such variants generally retain the functional activity of the acyltransferase proteins of the invention. Variants include polypeptides that differ in amino acid sequence due to natural allelic variation or mutagenesis.

CHAPTER 3

7716, A NOVEL HUMAN ATPase AND USES THEREFOR

BACKGROUND OF THE INVENTION

The AAA (ATPases Associated with a variety of cellular Activities) family of proteins is a group of proteins linked by common ancestry (reviewed by Beyer (1997) *Protein Sci.* 6:2043–2058). This $Mg^{2}$-dependent ATPase family is characterized by the presence of one (type I) or two (type II) copies of the AAA cassette, a conserved region of 220–250 amino acids that includes the Walker signature sequences of P-loop ATPases as well as other regions of similarity unique to AAA ATPases (reviewed by Patel et al. (1998) *Trends Cell Biol.* 8:65–71). AAA ATPases play essential roles in a number of cellular processes including the biogenesis of organelles, the regulation of proteasome function, and the quality control and regulated degradation of membrane proteins.

One of the best-characterized AAA ATPases is the NSF (N-ethylmaleimide-sensitive factor), which is involved in the docking/fusion step of all cellular fusion events, ranging from the secretory pathway to synaptic transmission. Another example of an AAA protein involved in membrane fusion events is Cdc48, which is required for the ATP-dependent fusion of endoplasmic reticular membranes. cdc48-1 was originally identified as a yeast cell-cycle mutant that arrests in mitosis with an undivided nucleus. At least two mammalian orthologs of Cdc48 have been identified, and have been demonstrated to participate in Golgi membrane fusion events (reviewed by Patel et al. (1998) *Trends Cell Biol.* 8:65–71). The AAA ATPases PEX1 and PEX6 are required for peroxisome biogenesis, and mutations in these genes are the most common cause of the lethal neurologic disorders Zellweger syndrome, neonatal adrenoleukodystrophy, and infantile Refsum disease (Dodt et al. (1995) *Nat. Genet.* 9:115–124).

AAA ATPases also play a role in the 26S proteasome-mediated proteolytic degradation of proteins via the ubiquitin pathway. The regulatory component of the 26 S proteasome, which is responsible for the recognition, binding, and unfolding of ubiquinated molecules, contains at least six AAA ATPases (Sug1p, Sug2p, Yta1p, Yta3p, and Yta5p). Evidence suggests that these subunits are functionally distinct, with proteolysis of different cellular substrates requiring specific AAA ATPase subunit activities (reviewed by Patel et al. (1998) *Trends Cell Biol.* 8:65–71).

The proteolytic degradation of mitochondrial membrane proteins also requires the activity of several integral membrane AAA ATPases. These AAA ATPases combine proteolytic and chaperone-like activities to form a membrane-integrated quality control system (reviewed by Langer (2000) *Trends Biochem. Sci.* 25:247–251). AAA ATPase membrane proteases involved in the degradation of membrane proteins include Yta10p (Afg3p), Yta12p (Rca1p), and Yme1p.

The critical role that AAA ATPases play in numerous biological processes and diseases make them important targets for therapeutic intervention. It is consequently important to identify novel genes encoding members of this enzyme family.

SUMMARY OF THE INVENTION

The present invention is based, in part, on the discovery of a novel human ATPase, referred to herein as "7716". The nucleotide sequence of a cDNA encoding 7716 is shown in SEQ ID NO:10, and the amino acid sequence of a 7716 polypeptide is shown in SEQ ID NO:11. In addition, the nucleotide sequence of the coding region is depicted in SEQ ID NO:12.

Accordingly, in one aspect the invention features a nucleic acid molecule which encodes a 7716 protein or polypeptide, e.g., a biologically active portion of the 7716 protein. In a preferred embodiment, the isolated nucleic acid molecule encodes a polypeptide having the amino acid sequence of SEQ ID NO:11. In other embodiments, the invention provides an isolated 7716 nucleic acid molecule having the nucleotide sequence shown in SEQ ID NO:10 or SEQ ID NO:12. In still other embodiments, the invention provides nucleic acid molecules that are substantially identical (e.g., naturally occurring allelic variants) to the nucleotide sequence shown in SEQ ID NO:10 or SEQ ID NO:12. In other embodiments, the invention provides a nucleic acid molecule which hybridizes under stringent hybridization conditions to a nucleic acid molecule comprising the nucleotide sequence of SEQ ID NO:10 or SEQ ID NO:12, wherein the nucleic acid encodes a full length 7716 protein or an active fragment thereof.

In a related aspect, the invention further provides nucleic acid constructs which include a 7716 nucleic acid molecule described herein. In certain embodiments, the nucleic acid molecules of the invention are operatively linked to native or heterologous regulatory sequences. Also included, are vectors and host cells containing the 7716 nucleic acid molecules of the invention e.g., vectors and host cells suitable for producing 7716 nucleic acid molecules and polypeptides.

In another related aspect, the invention provides nucleic acid fragments suitable as primers or hybridization probes for the detection of 7716-encoding nucleic acids.

In still another related aspect, isolated nucleic acid molecules that are antisense to a 7716 encoding nucleic acid molecule are provided.

In another aspect, the invention features 7716 polypeptides, and biologically active or antigenic fragments thereof that are useful, e.g., as reagents or targets in assays applicable to treatment and diagnosis of 7716-mediated or -related disorders. In another embodiment, the invention provides 7716 polypeptides having a 7716 activity. Preferred polypeptides are 7716 proteins including at least one ATPase domain, and, preferably, having a 7716 activity, e.g., a 7716 activity as described herein.

In other embodiments, the invention provides 7716 polypeptides, e.g., a 7716 polypeptide having the amino acid sequence shown in SEQ ID NO:11; an amino acid sequence that is substantially identical to the amino acid sequence shown in SEQ ID NO:11; or an amino acid sequence encoded by a nucleic acid molecule having a nucleotide sequence which hybridizes under stringent hybridization conditions to a nucleic acid molecule comprising the nucleotide sequence of SEQ ID NO:10 or SEQ ID NO:12, wherein the nucleic acid encodes a full length 7716 protein or an active fragment thereof.

In a related aspect, the invention further provides nucleic acid constructs which include a 7716 nucleic acid molecule described herein.

In a related aspect, the invention provides 7716 polypeptides or fragments operatively linked to non-7716 polypeptides to form fusion proteins.

In another aspect, the invention features antibodies and antigen-binding fragments thereof, that react with, or more preferably specifically bind 7716 polypeptides.

In another aspect, the invention provides methods of screening for compounds that modulate the expression or activity of the 7716 polypeptides or nucleic acids.

In still another aspect, the invention provides a process for modulating 7716 polypeptide or nucleic acid expression or activity, e.g. using the screened compounds. In certain embodiments, the methods involve treatment of conditions related to aberrant activity or expression of the 7716 polypeptides or nucleic acids, such as conditions involving aberrant or deficient cellular proliferation or differentiation.

The invention also provides assays for determining the activity of or the presence or absence of 7716 polypeptides or nucleic acid molecules in a biological sample, including for disease diagnosis.

In further aspect the invention provides assays for determining the presence or absence of a genetic alteration in a 7716 polypeptide or nucleic acid molecule, including for disease diagnosis.

Other features and advantages of the invention will be apparent from the following detailed description, Chapter 7, Examples and claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Human 7716

The human 7716 sequence (SEQ ID NO:10), which is approximately 2547 nucleotides long including untranslated regions, contains a predicted methionine-initiated coding sequence of about 2259 nucleotides (nucleotides 63–2324 of SEQ ID NO:10; SEQ ID NO:12). The coding sequence encodes a 753 amino acid protein (SEQ ID NO:11).

Human 7716 contains the following regions or other structural features: a predicted AAA ATPase domain (PFAM Accession PF00004) located at about amino acid residues 236 to 421 of SEQ ID NO:11, a second AAA ATPase domain located at about amino acid residues 500 to 705 of SEQ ID NO:11; and two predicted transmembrane domains, the first which extends from about amino acid residues 144 to 166 of SEQ ID NO:11, and the second which extends from about amino acid residues 225 to 246 of SEQ ID NO:11.

The 7716 protein also includes the following domains: two Prosite AAA-protein family signatures (amino acids 338–356 and 622–640; Prosite Accession No. PS00674), an ATP-binding protease/ATP-dependent cell division protein domain (amino acids 236–705), a cell division protein domain derived from SwissProt Accession No. O83350 (amino acids 233–713), a putative ATP/GTP binding protein domain derived from SwissProt Accession No. O86711, and a PEX6-like domain. For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

The 7716 protein contains a significant number of structural characteristics in common with members of the ATPase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "ATPase" refers to a protein or polypeptide which is capable of catalyzing an ATP hydrolysis reaction. As referred to herein, ATPases preferably include a catalytic domain of about 220–250 amino acid residues in length. An AAA ATPase domain typically includes at least three blocks of amino acid sequence similarity commonly found in members of the AAA-ATPase family: a Walker A domain (found at about amino acids 241–248 and 506–513 of SEQ ID NO:11); a Walker B domain (found at about amino acids 300–307 and 560–568 of SEQ ID NO:11); and an SRH domain, a highly conserved domain among AAA ATPases which is believed to be involved in ATP hydrolysis (found at about amino acids 338–366 and 622–650 of SEQ ID NO:11). Based on these sequence similarities, the 7716 molecules of the present invention are predicted to have similar biological activities as AAA ATPase family members.

Typically, AAA ATPases play a role in diverse cellular processes. For example, AAA ATPases are required for organelle biogenesis, and thus for cell division. Mutations in the genes encoding the peroxisome biogenesis AAA ATPases PEX 1 and PEX 2 are responsible for the majority of neurodegenerative diseases broadly classified as Zellwegger syndrome. AAA ATPases are also involved in other membrane fusion events, including secretion and synaptic transmission. AAA ATPases also play a role in the regulation of proteolysis by the 26S proteasome, and in the regulated degradation of membrane proteins. Thus, the molecules of the present invention may be involved in one or more of: 1) catalyzing the hydrolysis of ATP; 2) the modulation of organelle biogenesis; 3) the regulation of cell division; 4) the regulation of membrane fusion; 5) the modulation of synaptic transmission; 6) the modulation of secretion; 7) the regulation of proteolysis by the 26S proteasome; or 8) the degradation of membrane proteins.

A 7716 polypeptide can include an "ATPase domain" or regions homologous with an "ATPase domain." As used herein, the term "ATPase domain" includes an amino acid sequence of about 80–250 amino acid residues in length and having a bit score for the alignment of the sequence to the ATPase domain (HMM) of at least 8. Preferably, an ATPase domain includes at least about 140–250 amino acids, more preferably about 160–220 amino acid residues, or about 180–210 amino acids and has a bit score for the alignment of the sequence to the ATPase domain (HMM) of at least 16 or greater. The AAA ATPase domain (HMM) has been assigned the PFAM Accession PF00004 (see the Pfam website, wustl.edu/Pfam). An alignment of the AAA ATPase domain 1 (amino acids 236 to 421 of SEQ ID NO:11) and domain 2 (amino acids 500 to 705 of SEQ ID NO:11) of human 7716 with a consensus amino acid sequence derived from a hidden Markov model is depicted in FIG. 12.

In one embodiment, 7716 polypeptide or protein has a "ATPase domain" or a region which includes at least about 140–250 more preferably about 160–220 or 180–210 amino acid residues and has at least about 60%, 70%, 80%, 90%, 95%, 99%, or 100% homology with an "ATPase domain," e.g., the ATPase domains of human 7716 (e.g., amino acid residues 236–421 or 500–705 of SEQ ID NO:11).

To identify the presence of an "ATPase" domain in a 7716 protein sequence, and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, a 7716 protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In a preferred embodiment, a 7716 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 7716 (e.g., amino acid residues 144–166 or 225–246 of SEQ ID NO:11).

In another embodiment, a 7716 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 7716, or 7716-like protein.

In a preferred embodiment, a 7716 polypeptide or protein has a "non-transmembrane domain" or a region which includes at least about 1–350, preferably about 200–320, more preferably about 230–300, and even more preferably about 240–280 amino acid residues, and has at least about 60%, 70% 80% 90% 95%, 99% or 100% homology with a "non-transmembrane domain", e.g., a non-transmembrane domain of human 7716 (e.g., residues 1–143, 167–224, and 247–753 of SEQ ID NO:11). Preferably, a non-transmembrane domain is capable of catalytic activity (e.g., catalyzing an ATP hydrolysis reaction).

A non-transmembrane domain located at the N-terminus of a 7716 protein or polypeptide is referred to herein as an "N-terminal non-transmembrane domain." As used herein, an "N-terminal non-transmembrane domain" includes an amino acid sequence having about 1–350, preferably about 30–325, more preferably about 50–320, or even more preferably about 80–310 amino acid residues in length and is located outside the boundaries of a membrane. For example, an N-terminal non-transmembrane domain is located at about amino acid residues 1–143 of SEQ ID NO:11.

Similarly, a non-transmembrane domain located at the C-terminus of a 7716 protein or polypeptide is referred to herein as a "C-terminal non-transmembrane domain." As used herein, an "C-terminal non-transmembrane domain" includes an amino acid sequence having about 1–300, preferably about 15–290, preferably about 20–270, more preferably about 25–255 amino acid residues in length and is located outside the boundaries of a membrane. For example, an C-terminal non-transmembrane domain is located at about amino acid residues 247–753 of SEQ ID NO:11.

7716 expression in human normal breast and breast tumor tissue, human normal ovary and ovary tumor tissue, human normal lung and lung tumor tissue, human normal colon, colon tumor, colon cancer liver metastases, and normal liver tissue, and human angiogenic tissue is shown in FIGS. 13, 14, 15, 16, and 17, respectively. The methods of the invention are particularly relevant to the tissues and disorders in which 7716 is expressed.

As the 7716 polypeptides of the invention may modulate 7716-mediated activities, they may be useful as of for developing novel diagnostic and therapeutic agents for 7716-mediated or related disorders, as described below.

As used herein, a "7716 activity", "biological activity of 7716" or "functional activity of 7716", refers to an activity exerted by a 7716 protein, polypeptide or nucleic acid molecule on e.g., a 7716-responsive cell or on a 7716 substrate, e.g., a lipid or protein substrate, as determined in vivo or in vitro. In one embodiment, a 7716 activity is a direct activity, such as an association with a 7716 target molecule. A "target molecule" or "binding partner" is a molecule with which a 7716 protein binds or interacts in nature, e.g., an ATP molecule which the 7716 protein hydrolyzes. A 7716 activity can also be an indirect activity, e.g., a cellular signaling activity mediated by interaction of the 7716 protein with a 7716 ligand. For example, the 7716 proteins of the present invention can have one or more of the following activities: 1) catalyzing the hydrolysis of ATP; 2) the modulation of organelle biogenesis; 3) the regulation of cell division; 4) the regulation of membrane fusion; 5) the modulation of synaptic transmission; 6) the modulation of secretion; 7) the regulation of proteolysis by the 26S proteasome; 8) the degradation of membrane proteins or 9) the ability to antagonize or inhibit, competitively or non-competitively, any of 1–8.

Accordingly, 7716 protein may mediate various disorders, including cellular proliferative and/or differentiative disorders, brain disorders, lung disorders, colon disorders, breast disorders, ovary disorders, and liver disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 7716 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders involving the ovary include, for example, polycystic ovarian disease, Stein-leventhal syndrome, Pseudomyxoma peritonei and stromal hyperthecosis; ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

CHAPTER 4

25233, A NOVEL HUMAN AMINOTRANSFERASE AND USES THEREFOR

BACKGROUND OF THE INVENTION

Vitamin $B_6$, in the form of its biologically active phosphorylated derivatives pyridoxal-5'-phosphate (PLP) and pyridoxamine-5'-phosphate, represents one of nature's most versatile cofactors (Schneider et al. 2000, *Structure* 8:R1–R6). Vitamin $B_6$ dependent enzymes have a major role in the metabolism of amino acids, and are found in various pathways ranging from the interconversion of alpha-amino acids to the biosynthesis of antibiotic compounds. In the resting enzyme, the aldehyde group of PLP is covalently linked to a lysine residue at the active site of the enzyme. Upon binding of the amino acid substrate, the lysine residue is exchanged for the amino group of the substrate forming a Schiff-base complex with PLP. In the next step of the reaction, one of the bonds to the C alpha atom of the aldimine is broken forming an enzyme-linked intermediate. This process is facilitated by the electrophilic properties of the cofactor. The multitude of reactions catalyzed by PLP-dependent enzymes thus have several steps in common and variations arise from enzymatic control of the different routes to the central intermediate.

Grishin et al. (1995) *Protein Sci.* 4:1291–1304 have classified the PLP-dependent enzymes into five different fold types on the basis of amino acid sequence comparisons, predicted secondary structure elements and available three-dimensional structural information. These five structural classes are the aspartate aminotransferase family (class-I), the tryptophan synthase beta family (class-II), the alanine racemase family (class-III), the D-amino acid family (class-IV), and the glycogen phosphorylase family (class-V). See Schneider et al. (2000) *Structure* 8:R1–R6.

The alpha-amino groups of the 20 L-amino acids commonly found in proteins are removed during the oxidative degradation of the amino acids (U.S. Pat. No. 6,013,509, herein incorporated by reference). The removal of the alpha-amino groups, the first step in the catabolism of most of the L-amino acids, is promoted by aminotransferases (or transaminases). Cells contain several different aminotransferases.

The measurement of alanine aminotransferase and aspartate aminotransferase levels in blood serum is an important diagnostic procedure in medicine. For instance, these enzymes are used as indicators of heart damage and to monitor tissue recovery following the damage (See U.S. Pat. No. 6,013,509, above). Increased serum levels of the class-I aminotransferase, aspartate aminotransferase, are indicative of muscle, cardiac, kidney, pancreatic, red blood cell, or hepatic injury (see, for example, U.S. Pat. No. 5,834,226, herein incorporated by reference). Generally speaking, aspartate aminotransferase is elevated in diseases affecting tissues rich in aspartate aminotransferase. See U.S. Pat. No. 5,834,226, above. Examples of such conditions include acute myocardial infarction, pulmonary emulsion, acute pancreatitis, viral and toxic hepatitis, and acute cirrhosis. See U.S. Pat. No. 5,834,226, above. Elevated aspartate aminotransferase levels have also been correlated with various cancers and with active periodontal disease.

Accordingly, it is valuable to the field of pharmaceutical development to identify and characterize previously unknown aminotransferases. The present invention advances the state of the art by providing a previously unidentified human aminotransferase.

SUMMARY OF THE INVENTION

The present invention is based, in part, on the discovery of a novel human aminotransferase, referred to herein as "25233". The nucleotide sequence of a cDNA encoding 25233 is shown as SEQ ID NO:14. The amino acid sequence of a 25233 polypeptide is shown as SEQ ID NO:15. In addition, the nucleotide sequence of the coding region of 25233 (nucleotides 94–1665 of SEQ ID NO:14) is SEQ ID NO:16.

Accordingly, in one aspect the invention features a nucleic acid molecule which encodes a 25233 protein or polypeptide, e.g., a biologically active portion of the 25233 protein. In a preferred embodiment, the isolated nucleic acid molecule encodes a polypeptide having the amino acid sequence of SEQ ID NO:15. In other embodiments, the invention provides an isolated 25233 nucleic acid molecule having the nucleotide sequence shown in SEQ ID NO:14, SEQ ID NO:16. In still other embodiments, the invention provides nucleic acid molecules that are substantially identical (e.g., naturally occurring allelic variants) to the nucleotide sequence shown in SEQ ID NO:14, SEQ ID NO:16. In other embodiments, the invention provides a nucleic acid molecule which hybridizes under stringent hybridization conditions to a nucleic acid molecule comprising the nucleotide sequence of SEQ ID NO:14, SEQ ID NO:16, wherein the nucleic acid encodes a full length 25233 protein or an active fragment thereof.

In a related aspect, the invention further provides nucleic acid constructs which include a 25233 nucleic acid molecule described herein. In certain embodiments, the nucleic acid molecules of the invention are operatively linked to native or heterologous regulatory sequences. Also included, are vectors and host cells containing the 25233 nucleic acid molecules of the invention; e.g., vectors and host cells suitable for producing 25233 nucleic acid molecules and polypeptides.

In another related aspect, the invention provides nucleic acid fragments suitable as primers or hybridization probes for the detection of 25233-encoding nucleic acids.

In still another related aspect, isolated nucleic acid molecules that are antisense to a 25233 encoding nucleic acid molecule are provided.

In another aspect, the invention features 25233 polypeptides, and biologically active or antigenic fragments thereof that are useful; e.g., as reagents or targets in assays applicable to treatment and diagnosis of 25233-mediated or -related disorders. In another embodiment, the invention provides 25233 polypeptides having a 25233 activity. Preferred polypeptides are 25233 proteins including at least one aminotransferase domain, and, preferably, having a 25233 activity; e.g., a 25233 activity as described herein.

In other embodiments, the invention provides 25233 polypeptides, e.g., a 25233 polypeptide having the amino acid sequence shown in SEQ ID NO:15; an amino acid sequence that is substantially identical to the amino acid sequence shown in SEQ ID NO:15; or an amino acid sequence encoded by a nucleic acid molecule having a nucleotide sequence which hybridizes under stringent hybridization conditions to a nucleic acid molecule comprising the nucleotide sequence of SEQ ID NO:14, SEQ ID NO:16, wherein the nucleic acid encodes a full length 25233 protein or an active fragment thereof.

In a related aspect, the invention further provides nucleic acid constructs which include a 25233 nucleic acid molecule described herein.

In a related aspect, the invention provides 25233 polypeptides or fragments operatively linked to non-25233 polypeptides to form fusion proteins.

In another aspect, the invention features antibodies and antigen-binding fragments thereof, that react with, or more preferably specifically bind 25233 polypeptides.

In another aspect, the invention provides methods of screening for compounds that modulate the expression or activity of the 25233 polypeptides or nucleic acids.

In still another aspect, the invention provides a process for modulating 25233 polypeptide or nucleic acid expression or activity, e.g. using the screened compounds. In certain embodiments, the methods involve treatment of conditions related to aberrant activity or expression of the 25233 polypeptides or nucleic acids, such as conditions involving aberrant or deficient cellular proliferation or differentiation.

The invention also provides assays for determining the activity of or the presence or absence of 25233 polypeptides or nucleic acid molecules in a biological sample, including for disease diagnosis.

In further aspect the invention provides assays for determining the presence or absence of a genetic alteration in a 25233 polypeptide or nucleic acid molecule, including for disease diagnosis.

Other features and advantages of the invention will be apparent from the following detailed description, Chapter 7, Examples and the claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The human 25233 sequence (SEQ ID NO:14), which is approximately 2127 nucleotides long including untranslated regions, contains a predicted methionine-initiated coding sequence of about 1569 nucleotides (nucleotides 94–1662 of SEQ ID NO:14; nucleotides 1–1569 of SEQ ID NO:16), not including the terminal codon. The coding sequence encodes a 523 amino acid protein (SEQ ID NO:15).

This mature protein form is approximately 523 amino acid residues in length (from about amino acid 1 to amino acid 523 of SEQ ID NO:15). Human 25233 contains the following regions or other structural features: a predicted aminotransferase domain (PFAM Accession PF00155) located at about amino acid residues 83–517 of SEQ ID NO:15; and a predicted transmembrane domain which extends from about amino acid residue 181–199 of SEQ ID NO:15.

The 25233 protein also includes an ICE-like protease (caspase) p20 domain from about amino acid 138–149 of SEQ ID NO:15.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

The 25233 protein contains a significant number of structural characteristics in common with members of the aminotransferase class-I family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "aminotransferase" refers to a protein or polypeptide that is capable of catalyzing a transamination, decarboxylation, deamination, racemization, or aldol cleavage reaction. Aminotransferases are pyridoxal-5'-phosphate (PLP) dependent enzymes and can have a specificity for various amino acid or related substrates. Typically, aminotransferases have a major role in the metabolism of amino acids, and are found in various pathways ranging from the interconversion of alpha-amino acids to the biosynthesis of antibiotic compounds. These PLP-dependent enzymes have been grouped into five different fold types, designated classes I–V, on the basis of amino acid sequence comparisons, predicted secondary structure elements and available three-dimensional structural information. These five structural classes are the aspartate aminotransferase family (class-I), the tryptophan synthase beta family (class-II), the alanine racemase family (class-III), the D-amino acid family (class-IV), and the glycogen phosphorylase family (class-V). The 25233 protein of the present invention is homologous to the class I aminotransferase family members.

The metabolism of amino acids involves specific reversible transfer of nitrogenous groups catalyzed by aminotransferases. Thus, the molecules of the present invention may be involved in one or more of: 1) the transfer of an amino groups; 2) catalysis of certain amino acids; 3) the modulation of the metabolism of various amino acids; 4) the modulation of tumor cell growth and invasion; 5) cellular homeostasis.

A 25233 polypeptide can include an "aminotransferase domain" or regions homologous with an "aminotransferase domain".

As used herein, the term "aminotransferase domain" includes an amino acid sequence of about 400–450 amino acid residues in length and having a bit score for the alignment of the sequence to the aminotransferase domain (HMM) of at least 8. Preferably, an aminotransferase domain includes at least about 410–445 amino acids, more preferably about 420–440 amino acid residues, or about 430–435 amino acids and has a bit score for the alignment of the sequence to the aminotransferase domain (HMM) of at least 10 or greater. The aminotransferase domain (MM) has been assigned the PFAM Accession PF00155 (see the Pfam website, pfam.wustl.edu). An alignment of the aminotransferase domain (amino acids 83–517 of SEQ ID NO:15) of human aminotransferase with a consensus amino acid sequence derived from a hidden Markov model is depicted in FIG. 19.

In a preferred embodiment 25233-like polypeptide or protein has an "aminotransferase domain" or a region which includes at least about 200–450 more preferably about 230–440 or 260–420 amino acid residues and has at least about 60%, 70%, 80%, 90%, 95%, 99%, or 100% sequence identity with an "aminotransferase domain," e.g., the aminotransferase domain of human 25233-like polypeptide (e.g., amino acid residues 83–517 of SEQ ID NO:15).

To identify the presence of an "aminotransferase" domain in a 25233-like protein sequence, and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, an 25233-like protein includes at least one transmembrane domain. As used herein, the term "transmembrane domain" includes an amino acid sequence of about 15 amino acid residues in length that spans a phospholipid membrane. More preferably, a transmembrane domain includes about at least 15, 18, 20, 22, 24, or 25 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In a preferred embodiment, a 25233-like polypeptide or protein has at least one transmembrane domain or a region which includes at least 15, 18, 20, 22, 24, or 25 amino acid residues and has at least about 60%, 70% 80% 90% 95%, 99%, or 100% sequence identity with a "transmembrane domain," e.g., at least one transmembrane domain of human 25233-like polypeptide (e.g., amino acid residues 181–199 of SEQ ID NO:15).

In another embodiment, an 25233-like protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally occurring 25233-like protein.

In a preferred embodiment, an 25233-like polypeptide or protein has a "non-transmembrane domain" or a region which includes at least about 1–320, preferably about 200–310, more preferably about 230–300, and even more preferably about 240–280 amino acid residues, and has at least about 60%, 70% 80% 90% 95%, 99% or 100% sequence identity with a "non-transmembrane domain", e.g., a non-transmembrane domain of human 25233-like polypeptide (e.g., residues 200–523 of SEQ ID NO:15). Preferably, a non-transmembrane domain is capable of catalytic activity (e.g., transamination).

A non-transmembrane domain located at the N-terminus of a 25233-like protein or polypeptide is referred to herein as an "N-terminal non-transmembrane domain." As used herein, an "N-terminal non-transmembrane domain" includes an amino acid sequence having about 1–180, preferably about 30–160, more preferably about 50–140, or even more preferably about 80–120 amino acid residues in length and is located outside the boundaries of a membrane. For example, an N-terminal non-transmembrane domain is located at about amino acid residues 1–180 of SEQ ID NO:15.

Similarly, a non-transmembrane domain located at the C-terminus of a 25233-like protein or polypeptide is referred to herein as a "C-terminal non-transmembrane domain." As used herein, an "C-terminal non-transmembrane domain" includes an amino acid sequence having about 1–323, preferably about 200–310, more preferably about 230–300, and even more preferably about 240–280 amino acid residues in length and is located outside the boundaries of a membrane. For example, an C-terminal non-transmembrane domain is located at about amino acid residues 200–523 of SEQ ID NO:15.

As the 25233 polypeptides of the invention may modulate 25233-mediated activities, they may be useful for developing novel diagnostic and therapeutic agents for 25233-mediated or related disorders, as described below.

As used herein, a "25233 activity", "biological activity of 25233" or "functional activity of 25233", refers to an activity exerted by a 25233 protein, polypeptide or nucleic acid molecule on e.g., a 25233-responsive cell or on a 25233 substrate, e.g., an amino acid or related substrate, as determined in vivo or in vitro. In one embodiment, a 25233 activity is a direct activity, such as an association with a 25233 binding partner. A "binding partner" is a molecule with which a 25233 protein binds or interacts in nature, e.g., an amino acid that the 25233 protein transaminates. A 25233 activity can also be an indirect activity, e.g., a cellular signaling activity mediated by interaction of the 25233 protein with a 25233 binding partner. For example, the molecules of the present invention may be involved in one or more of: 1) the transfer of an amino groups; 2) catalysis of certain amino acids; 3) the modulation of the metabolism of various amino acids; 4) the modulation of tumor cell growth and invasion; 5) cellular homeostasis.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Human 25233 showed elevated levels of expression in tissues and cells including, but not limited to, pancreas, immune cells, brain cortex, glial cells, liver, epithelial cells, breast tumor, lung tumor, and colon tumor. See FIGS. 21 and 22A–D. Thus, the 25233 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjögren syndrome, systemic sclerosis, inflammatory myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Sézary syndrome, and Hodgkin disease.

Diseases of the skin, include but are not limited to, disorders of pigmentation and melanocytes, including but not limited to, vitiligo, freckle, melasma, lentigo, nevocellular nevus, dysplastic nevi, and malignant melanoma; benign epithelial tumors, including but not limited to, seborrheic keratoses, acanthosis nigricans, fibroepithelial polyp, epithelial cyst, keratoacanthoma, and adnexal (appendage) tumors; premalignant and malignant epidermal tumors, including but not limited to, actinic keratosis, squamous cell carcinoma, basal cell carcinoma, and merkel cell carcinoma; tumors of the dermis, including but not limited to, benign fibrous histiocytoma, dermatofibrosarcoma protuberans, xanthomas, and dermal vascular tumors; tumors of cellular immigrants to the skin, including but not limited to, histiocytosis X, mycosis fungoides (cutaneous T-cell lymphoma), and mastocytosis; disorders of epidermal maturation, including but not limited to, ichthyosis; acute inflammatory dermatoses, including but not limited to, urticaria, acute eczematous dermatitis, and erythema multiforme; chronic inflammatory dermatoses, including but not limited to, psoriasis, lichen planus, and lupus erythematosus; blistering (bullous) diseases, including but not limited to, pemphigus, bullous pemphigoid, dermatitis herpetiformis, and noninflammatory blistering diseases: epidermolysis bullosa and porphyria; disorders of epidermal appendages, including but not limited to, acne vulgaris; panniculitis, including but not limited to, erythema nodosum and erythema induratum; and infection and infestation, such as verrucae, molluscum contagiosum, impetigo, superficial fungal infections, and arthropod bites, stings, and infestations.

Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms.

Disorders in the male breast include, but are not limited to, gynecomastia and carcinoma.

Disorders involving the prostate include, but are not limited to, inflammations, benign enlargement, for example, nodular hyperplasia (benign prostatic hypertrophy or hyperplasia), and tumors such as carcinoma.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders involving the pancreas include those of the exocrine pancreas such as congenital anomalies, including but not limited to, ectopic pancreas; pancreatitis, including but not limited to, acute pancreatitis; cysts, including but not limited to, pseudocysts; tumors, including but not limited to, cystic tumors and carcinoma of the pancreas; and disorders of the endocrine pancreas such as, diabetes mellitus; islet cell tumors, including but not limited to, insulinomas, gastrinomas, and other rare islet cell tumors.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

CHAPTER 5

8035, 84242, 55304, 52999, AND 21999, NOVEL HUMAN PROTEINS AND METHODS OF USE THEREOF

BACKGROUND OF THE INVENTION

RING Finger Proteins. Targeted protein proteolysis is increasingly understood to be an important general mechanism by which cells regulate protein levels and, consequently, their functions at specific times. In eukaryotic cells, the main mechanism for such control involves the specific covalent modification by polyubiquitin, which labels target proteins for proteolysis and subsequent degradation. There are many known examples of such events, and ubiquitination is now recognized as a major mechanism for cellular regulation (for review see: Freemont, P. S. (2000) *Current Biology* 10:R84–R87; Joazeiro and Weissman (2000) *Cell* 102:549–552; Jackson et al. (2000) *Trends in Cell Biology* 10:429–439).

Protein ubiquitination begins with the formation of a thiol-ester linkage between ubiquitin and the ubiquitin activating enzyme (E1). Ubiquitin is then transferred to a ubiquitin conjugating enzyme (E2), again through a thiol-ester linkage. The ubiquitin ligases (E3's), which are primarily responsible for providing specificity to the ubiquitin conjugation, interact with both E2 and substrate to promote ubiquitination. The E3 enzymes are thought to be the least conserved component of the ubiquitination pathway.

Recent studies indicate that E3's can be divided into two distinct protein classes; those containing a HECT domain and those containing a RING finger domain. The RING finger class of E3 ubiquitin ligases can be further grouped into the SCF, VBC and anaphase-promoting complexes, and single-polypeptide RING finger E3 enzymes. The RING finger motif and its variants have been found in more than 200 eukaryotic proteins, but interestingly not in any prokaryotic protein. Perhaps the most famous RING finger protein is BRCA1, the product of a breast cancer-associated gene. Point mutations within the RING finger domain of BRCA1 predispose females having the mutations to breast cancer. Other well-known family members include the protooncogene products Cbl, BMI-1, and PML; the immunoglobulin gene recombination enzyme RAG 1; the Rbx1 component of the von Hippel Lindau (VHL) tumor suppressor complex; and the p53 regulator MDM2, to name but a few.

RING finger proteins play pivotal roles in diverse cellular processes and are implicated in contributing to disease. The biological roles of RING finger proteins include regulation of cellular proliferation, apoptosis, the cell cycle, cellular signaling, transcription, DNA repair, degradation from the endoplasmic reticulum (ER), and photomorphogenesis. In addition, RING mutations in the RING finger protein, Parkin, are associated with autosomal juvenile parkinsonism.

The tumor suppressor BRCA1 provides an example where loss of RING finger function is associated with dysregulated growth and malignancy, in the form of familial breast and ovarian cancer. Another example where loss of RING finger function is associated with malignancy is in the case of VHL disease. The RING finger protein Rbx1 is a component of the E3 complex that includes the VHL tumor suppressor protein, and VHL mutations that prevent assembly of this E3 are associated with the malignancies of VHL disease, perhaps due to the stabilization of proteins such as hypoxia inducing factor 1 alpha.

The influence of RING finger E3 ubiquitin ligases on the balance between cellular proliferation and apoptosis is demonstrated by the following examples. First, Mdm2 is a RING finger E3 ubiquitin ligase that functions as a regulator of the tumor suppressor, p53. The regulation of p53 by Mdm2 has been demonstrated to depend on the RING finger domain of Mdm2, thus, implicating this RING finger E3 ubiquitin ligase as a critical regulator of cellular proliferation. Second, the E3 ubiquitin ligase activity of a group of RING finger containing proteins known as Inhibitors of Apoptosis (IAP's) has been demonstrated to be the activity responsible for IAP auto-ubiquitination, degradation, and progression toward cell death in response to apoptotic stimuli (Yang et al. (2000) *Science* 288:874–877). Thus, these E3 ubiquitin ligases play a crucial role in the regulation of apoptosis.

One example of the clearly established role of RING finger proteins in the regulation of the cell cycle is that mitotic cyclins are targeted for degradation by ubiquitination mediated by the APC (or cyclosome) that includes the small RING finger protein, Apc11p.

The RING finger E3 ubiquitin ligases' role in the secretory pathway is through regulation of the disposal of membrane proteins from the endoplasmic reticulum (ER). One example of the impact of this key role in the secretory pathway is the RING finger E3 facilitation of disposal of a membrane protein from the ER contributing to the pathogenesis of AIDS. Beta TrCP, a RING finger protein that targets beta-catenin and $I_{kappa}B_{alpha}$ for ubiquitination, also targets Vpu-bound CD4 for degradation, resulting in an increase in the amount of HIV Env protein available for virus production.

Accordingly, RING finger proteins are a major target for drug action and development. Therefore, it is valuable to the field of pharmaceutical development to identify and characterize previously unknown RING finger proteins. The present invention advances the state of the art by providing two previously unidentified human RING finger proteins.

Aminopeptidases. Aminopeptidases are a group of widely-distributed exopeptidases that catalyze the hydrolysis of amino acid residues from the amino-terminus of peptide substrates. Members of this enzyme family are found throughout the animal and plant kingdoms, and are found subcellularly in organelles, in the cytoplasm, and as membrane components. Aminopeptidases function in many cellular processes, including protein maturation, the regulation of hormone levels (including vasopressin and noradrenaline levels), the regulation of the renin-angiotensin system, and in cell-cycle control (including B cell precursor cell cycle control).

In eukaryotes, aminopeptidases are associated with removal of the initiator methionine. This enzyme family is also involved in the metabolism of secreted regulatory molecules, such as hormones and neurotransmitters, and modulation of cell-cell interactions. In mammalian cells and tissues, these enzymes play a role in the terminal stages of protein degradation, and in cell-cycle control. Aminopeptidase also have a role in protein turnover and selective elimination of obsolete or defective proteins.

Industrial uses of this enzyme family include modification of amino termini in recombinantly expressed proteins. See A. Taylor (1993) *TIBS* 18: 1993:167–172.

Many aminopeptidases are metalloenzymes, requiring divalent cations for proteolytic activity. Most aminopeptidase metal binding sites coordinate $Zn^{2+}$ or $Co^{2+}$. However, the metal binding sites of certain aminopeptidases can readily bind $Mn^{2+}$ and $Mg^{2+}$. Sites involved in $Zn^{2+}$ coordination include the "His His Glu" and "Asp Glu Lys" motifs.

Several aminopeptidase inhibitors have been identified. These inhibitors include bestatin (which has been shown to bind to the aminopeptidase active site), boronic and phosphonic acids, α-methylleucine and isoamylthioamide. See A. Taylor (1993) TIBS 18: 1993:167–172; Burley et al. (1992) J. Mol. Biol. 224:113–140; Taylor et al. (1993) *Biochemistry* 32:784–790.

Aminopeptidases play a role in the pathogenesis of a number of disorders including hypertension, cancer, cataracts, and leukemia, and inhibitors of these enzymes are currently being evaluated as potential therapeutics for many of these disorders. Aminopeptidase activity is also believed to contribute to the aging process. Accordingly, aminopeptidases are a major target for drug action and development. Therefore, it is valuable to the field of pharmaceutical development to identify and characterize previously unknown aminopeptidases.

Metallopeptidases. Proteases function in carcinogenesis by inactivating or activating regulators of the cell cycle, differentiation, programmed cell death, or other processes affecting cancer development and/or progression. Consistent with the model involving protease activity and tumor progression, certain protease inhibitors have been shown to be effective inhibitors of carcinogenesis both in vitro and in vivo.

Metallopeptidases are a group of widely distributed proteases that depend on bound $Ca^{2+}$ or $Zn^{2+}$ for activity; however, certain metallopeptidases can readily utilize $Mn^{2+}$ and $Mg^{2+}$. The biological functions of metallopeptidases include protein maturation and protein degradation, such as the degradation of extracellular matrix proteins. As such, metallopeptidases have been shown to have a role in tumor growth, metastasis, and angiogenesis.

Accordingly, metallopeptidases are a major target for drug action and development. Therefore, it is valuable to the field of pharmaceutical development to identify and characterize previously unknown metallopeptidases. The present invention advances the state of the art by providing a previously unidentified human metallopeptidase.

ADP-ribosyltransferases. Mono (ADP-ribosyl) transferase (EC 2.4.2.31) catalyzes the transfer of the ADP-ribose moiety of nicotinamide adenine dinucleotide (NAD) to an acceptor amino acid in proteins. In vertebrates, there is a family of such enzymes that transfer an NAD group to arginine. At least five distinct forms of this enzyme have been identified so far. Some of the forms are attached to the membrane by a GPI anchor while others seem to be secreted. These proteins are typically about 250 to 300 amino acid residues.

Mono-ADP ribosylation is a post-translational modification of proteins in which the ADP-ribose moiety of NAD is transferred to an acceptor protein and is responsible for the toxicity of some bacterial toxins, e.g., cholera toxin and pertussis toxin. ADP-ribosyltransferase activity has been detected in viruses, bacteria, and eukaryotic cells. For example, cholera toxin ADP-ribosylates an arginine in the α-subunit of the stimulatory heterotrimeric guanine nucleotide-binding (G) protein, resulting in the activation of adenylyl cyclase and an increase in intracellular cyclic AMP. Eukaryotic ADP-ribosyltransferase activity has been detected in several tissues, and cDNAs have been cloned from rabbit, human skeletal muscle, chicken polymorphonuclear granulocytes, and nucleoblasts, and mouse lymphoma cells. Studies have shown that when the transferase cDNAs are transfected into mammalian cells, the skeletal muscle and mouse lymphocyte enzymes are extracellular glycosylphosphatidylinositol (GPI)-anchored proteins. Consistent with its extracellular location, the GPI-linked muscle transferase ADP-ribosylates integrin α-7 on cultured myotubes (Zolkiewska et al. (1993) *J. Biol. Chem.* 268:25273–25276). Also, inhibitor studies suggest that the muscle transferase may participate in the regulation of myogenesis (Kharadia, S. V. et al. (1992) *Exp. Cell Res.* 201:33–42). The muscle and lymphocyte ADP-ribosyltransferases catalyze the ADP-ribosylation of arginine, agmatine, and other simple guanidino compounds (Zolkiewska, A. et al. (1992) *Proc. Natl. Acad. Sci. U.S.A.* 89:11352–11356).

SUMMARY OF THE INVENTION

The present invention is based, in part, on the discovery of novel human RING finger proteins, referred to herein as "8035 and 84242". The nucleotide sequences of the cDNA's encoding 8035 and 84242 are shown in SEQ ID NO:18 and SEQ ID NO:22, respectively, and the amino acid sequences of the 8035 and 84242 polypeptides are shown in SEQ ID NO:19 and SEQ ID NO:23, respectively. In addition, the nucleotide sequences of the coding regions of these cDNA's are depicted in SEQ ID NO:20 and SEQ ID NO:24, respectively.

Accordingly, in one aspect the invention features nucleic acid molecules that encode the 8035 and 84242 proteins or polypeptides, e.g., biologically active portions of the 8035 and 84242 proteins. In a preferred embodiment, the isolated nucleic acid molecules encode polypeptides having the amino acid sequence of SEQ ID NO:19 or SEQ ID NO:23. In other embodiments, the invention provides isolated 8035 and 84242 nucleic acid molecules having the nucleotide sequences shown in SEQ ID NO:18, SEQ ID NO:20, SEQ ID NO:22 or SEQ ID NO:24. In still other embodiments, the invention provides nucleic acid molecules that are substantially identical (e.g., naturally occurring allelic variants) to the nucleotide sequences shown in SEQ ID NO:18, SEQ ID NO:20, SEQ ID NO:22 or SEQ ID NO:24. In other embodiments, the invention provides nucleic acid molecules that hybridize under stringent hybridization conditions to a nucleic acid molecule comprising the nucleotide sequence of SEQ ID NO:18, SEQ ID NO:20, SEQ ID NO:22 or SEQ ID NO:24, wherein the nucleic acid encodes a full length 8035 or 84242 protein or an active fragment thereof.

In a related aspect, the invention further provides nucleic acid constructs that include a 8035 or 84242 nucleic acid molecule described herein. In certain embodiments, the nucleic acid molecules of the invention are operatively linked to native or heterologous regulatory sequences. Also included, are vectors and host cells containing the 8035 and 84242 nucleic acid molecules of the invention e.g., vectors and host cells suitable for producing 8035 and 84242 nucleic acid molecules and polypeptides.

In another related aspect, the invention provides nucleic acid fragments suitable as primers or hybridization probes for the detection of 8035 and 84242-encoding nucleic acids.

In still another related aspect, isolated nucleic acid molecules that are antisense to an 8035 or an 84242 encoding nucleic acid molecule are provided.

In another aspect, the invention features 8035 and 84242 polypeptides, and biologically active or antigenic fragments thereof that are useful, e.g., as reagents or targets in assays applicable to treatment and diagnosis of 8035 and 84242-mediated or -related disorders. In another embodiment, the invention provides 8035 and 84242 polypeptides having 8035 or 84242 activity, respectively. Preferred polypeptides are 8035 proteins including at least one RING finger protein domain (C3HC4 type) and, preferably, having an 8035 activity, e.g., an 8035 activity as described herein; and 84242 proteins including at least one IBR (In Between RING Finger) domain and, preferably, having an 84242 activity, e.g., an 84242 activity as described herein.

In other embodiments, the invention provides 8035 and 84242 polypeptides, e.g., an 8035 or 84242 polypeptide having the amino acid sequence shown in SEQ ID NO:19 or SEQ ID NO:23, respectively; an amino acid sequence that is substantially identical to the amino acid sequence shown in SEQ ID NO:19 or SEQ ID NO:23; or an amino acid sequence encoded by a nucleic acid molecule having a nucleotide sequence that hybridizes under stringent hybridization conditions to a nucleic acid molecule comprising the nucleotide sequence of SEQ ID NO:18, SEQ ID NO:20, SEQ ID NO:22 or SEQ ID NO:24, wherein the nucleic acids encode a full length 8035 or 84242 protein or an active fragment thereof.

In a related aspect, the invention further provides nucleic acid constructs that include an 8035 or 84242 nucleic acid molecule described herein.

In a related aspect, the invention provides 8035 and 84242 polypeptides or fragments operatively linked to non-8035 and non-84242 polypeptides to form fusion proteins.

In another aspect, the invention features antibodies and antigen-binding fragments thereof, that react with, or more preferably specifically bind 8035 or 84242 polypeptides.

In another aspect, the invention provides methods of screening for compounds that modulate the expression or activity of the 8035 and 84242 polypeptides or nucleic acids.

In still another aspect, the invention provides a process for modulating 8035 and 84242 polypeptide or nucleic acid expression or activity, e.g., using the screened compounds. In certain embodiments, the methods involve treatment of conditions related to aberrant activity or expression of the 8035 and 84242 polypeptides or nucleic acids, such as conditions involving aberrant regulation of cellular proliferation and/or differentiation.

The invention also provides assays for determining the activity of or the presence or absence of 8035 and 84242 polypeptides or nucleic acid molecules in a biological sample, including for disease diagnosis.

In further aspect the invention provides assays for determining the presence or absence of a genetic alteration in a 8035 or 84242 polypeptide or nucleic acid molecule, including for disease diagnosis.

The present invention is also based, in part, on the discovery of a novel human aminopeptidase, referred to herein as "55304". The nucleotide sequence of a cDNA encoding 55304 is shown in SEQ ID NO:26, and the amino acid sequence of a 55304 polypeptide is shown in SEQ ID NO:27. In addition, the nucleotide sequence of the coding region is depicted in SEQ ID NO:28.

Accordingly, in one aspect the invention features a nucleic acid molecule which encodes a 55304 protein or polypeptide, e.g., a biologically active portion of the 55304 protein. In a preferred embodiment, the isolated nucleic acid molecule encodes a polypeptide having the amino acid sequence of SEQ ID NO:27. In other embodiments, the invention provides an isolated 55304 nucleic acid molecule having the nucleotide sequence shown in SEQ ID NO:26 or SEQ ID NO:28. In still other embodiments, the invention provides nucleic acid molecules that are substantially identical (e.g., naturally occurring allelic variants) to the nucleotide sequence shown in SEQ ID NO:26 or SEQ ID NO:28. In other embodiments, the invention provides a nucleic acid molecule which hybridizes under stringent hybridization conditions to a nucleic acid molecule comprising the nucleotide sequence of SEQ ID NO:26 or SEQ ID NO:28, wherein the nucleic acid encodes a full length 55304 protein or an active fragment thereof.

In a related aspect, the invention further provides nucleic acid constructs which include a 55304 nucleic acid molecule described herein. In certain embodiments, the nucleic acid molecules of the invention are operatively linked to native or heterologous regulatory sequences. Also included, are vectors and host cells containing the 55304 nucleic acid molecules of the invention e.g., vectors and host cells suitable for producing 55304 nucleic acid molecules and polypeptides.

In another related aspect, the invention provides nucleic acid fragments suitable as primers or hybridization probes for the detection of 55304-encoding nucleic acids.

In still another related aspect, isolated nucleic acid molecules that are antisense to a 55304 encoding nucleic acid molecule are provided.

In another aspect, the invention features 55304 polypeptides, and biologically active or antigenic fragments thereof that are useful, e.g., as reagents or targets in assays applicable to treatment and diagnosis of 55304-mediated or -related disorders. In another embodiment, the invention provides 55304 polypeptides having a 55304 activity. Preferred polypeptides are 55304 proteins including at least one aminopeptidase domain, and, preferably, having a 55304 activity, e.g., a 55304 activity as described herein.

In other embodiments, the invention provides 55304 polypeptides, e.g., a 55304 polypeptide having the amino acid sequence shown in SEQ ID NO:27; an amino acid sequence that is substantially identical to the amino acid sequence shown in SEQ ID NO:27; or an amino acid sequence encoded by a nucleic acid molecule having a nucleotide sequence which hybridizes under stringent hybridization conditions to a nucleic acid molecule comprising the nucleotide sequence of SEQ ID NO:26 or SEQ ID NO:28, wherein the nucleic acid encodes a full length 55304 protein or an active fragment thereof.

In a related aspect, the invention further provides nucleic acid constructs which include a 55304 nucleic acid molecule described herein.

In a related aspect, the invention provides 55304 polypeptides or fragments operatively linked to non-55304 polypeptides to form fusion proteins.

In another aspect, the invention features antibodies and antigen-binding fragments thereof, that react with, or more preferably specifically bind 55304 polypeptides.

In another aspect, the invention provides methods of screening for compounds that modulate the expression or activity of the 55304 polypeptides or nucleic acids.

In still another aspect, the invention provides a process for modulating 55304 polypeptide or nucleic acid expression or activity, e.g. using the screened compounds. In certain embodiments, the methods involve treatment of conditions related to aberrant activity or expression of the 55304 polypeptides or nucleic acids, such as conditions involving aberrant or deficient cellular proliferation or differentiation.

The invention also provides assays for determining the activity of or the presence or absence of 55304 polypeptides or nucleic acid molecules in a biological sample, including for disease diagnosis.

In further aspect the invention provides assays for determining the presence or absence of a genetic alteration in a 55304 polypeptide or nucleic acid molecule, including for disease diagnosis.

The present invention is based, in part, on the discovery of a novel human metallopeptidase, referred to herein as "52999". The nucleotide sequence of a cDNA encoding 52999 is shown in SEQ ID NO:29, and the amino acid sequence of a 52999 polypeptide is shown in SEQ ID NO:30. In addition, the nucleotide sequence of the coding region is depicted in SEQ ID NO:31.

Accordingly, in one aspect the invention features a nucleic acid molecule which encodes a 52999 protein or polypeptide, e.g., a biologically active portion of the 52999 protein. In a preferred embodiment, the isolated nucleic acid molecule encodes a polypeptide having the amino acid sequence of SEQ ID NO:30. In other embodiments, the invention provides an isolated 52999 nucleic acid molecule having the nucleotide sequence shown in SEQ ID NO:29 SEQ ID NO:31. In still other embodiments, the invention provides nucleic acid molecules that are substantially identical (e.g., naturally occurring allelic variants) to the nucleotide sequence shown in SEQ ID NO:29 or SEQ ID NO:31. In other embodiments, the invention provides a nucleic acid molecule which hybridizes under stringent hybridization conditions to a nucleic acid molecule comprising the nucleotide sequence of SEQ ID NO:29 or SEQ ID NO:31, wherein the nucleic acid encodes a full length 52999 protein or an active fragment thereof.

In a related aspect, the invention further provides nucleic acid constructs which include a 52999 nucleic acid molecule described herein. In certain embodiments, the nucleic acid molecules of the invention are operatively linked to native or heterologous regulatory sequences. Also included, are vectors and host cells containing the 52999 nucleic acid molecules of the invention e.g., vectors and host cells suitable for producing 52999 nucleic acid molecules and polypeptides.

In another related aspect, the invention provides nucleic acid fragments suitable as primers or hybridization probes for the detection of 52999-encoding nucleic acids.

In still another related aspect, isolated nucleic acid molecules that are antisense to a 52999 encoding nucleic acid molecule are provided.

In another aspect, the invention features 52999 polypeptides, and biologically active or antigenic fragments thereof that are useful, e.g., as reagents or targets in assays applicable to treatment and diagnosis of 52999-mediated or -related disorders. In another embodiment, the invention provides 52999 polypeptides having a 52999 activity. Preferred polypeptides are 52999 proteins including at least one metallopeptidase domain, and, preferably, having a 52999 activity, e.g., a 52999 activity as described herein.

In other embodiments, the invention provides 52999 polypeptides, e.g., a 52999 polypeptide having the amino acid sequence shown in SEQ ID NO:30; an amino acid sequence that is substantially identical to the amino acid sequence shown in SEQ ID NO:30; or an amino acid sequence encoded by a nucleic acid molecule having a nucleotide sequence which hybridizes under stringent hybridization conditions to a nucleic acid molecule comprising the nucleotide sequence of SEQ ID NO:29 or SEQ ID NO:31, wherein the nucleic acid encodes a full length 52999 protein or an active fragment thereof.

In a related aspect, the invention further provides nucleic acid constructs which include a 52999 nucleic acid molecule described herein.

In a related aspect, the invention provides 52999 polypeptides or fragments operatively linked to non-52999 polypeptides to form fusion proteins.

In another aspect, the invention features antibodies and antigen-binding fragments thereof, that react with, or more preferably specifically bind 52999 polypeptides.

In another aspect, the invention provides methods of screening for compounds that modulate the expression or activity of the 52999 polypeptides or nucleic acids.

In still another aspect, the invention provides a process for modulating 52999 polypeptide or nucleic acid expression or activity, e.g. using the screened compounds. In certain embodiments, the methods involve treatment of conditions related to aberrant activity or expression of the 52999 polypeptides or nucleic acids, such as inflammatory conditions and conditions involving aberrant or deficient cellular proliferation or differentiation.

The invention also provides assays for determining the activity of or the presence or absence of 52999 polypeptides or nucleic acid molecules in a biological sample, including for disease diagnosis.

In further aspect the invention provides assays for determining the presence or absence of a genetic alteration in a 52999 polypeptide or nucleic acid molecule, including for disease diagnosis.

The present invention is based, in part, on the discovery of a novel human ribosyltransferase referred to herein as mono-ADP ribosyltransferase. The nucleotide sequence of a cDNA encoding ADP-ribosyltransferase is shown in SEQ ID NO:36, and the amino acid sequence of a ADP-ribosyltransferase polypeptide is shown in SEQ ID NO:37.

Accordingly, in one aspect the invention features a nucleic acid molecule which encodes a ADP-ribosyltransferase protein or polypeptide, e.g., a biologically active portion of the ADP-ribosyltransferase protein. In a preferred embodiment, the isolated nucleic acid molecule encodes a polypeptide having the amino acid sequence of SEQ ID NO:37. In other embodiments, the invention provides an isolated ADP-ribosyltransferase nucleic acid molecule having the nucleotide sequence shown in SEQ ID NO:36. In still other embodiments, the invention provides nucleic acid molecules that are substantially identical (e.g., naturally occurring allelic variants) to the nucleotide sequence shown in SEQ ID NO:36. In other embodiments, the invention provides a nucleic acid molecule which hybridizes under stringent hybridization conditions to a nucleic acid molecule comprising the nucleotide sequence of SEQ ID NO:36, wherein the nucleic acid encodes a full length ADP-ribosyltransferase protein or an active fragment thereof.

In a related aspect, the invention further provides nucleic acid constructs which include a ADP-ribosyltransferase nucleic acid molecule described herein. In certain embodiments, the nucleic acid molecules of the invention are operatively linked to native or heterologous regulatory sequences. Also included, are vectors and host cells containing the ADP-ribosyltransferase nucleic acid molecules of the invention e.g., vectors and host cells suitable for producing ADP-ribosyltransferase nucleic acid molecules and polypeptides.

In another related aspect, the invention provides nucleic acid fragments suitable as primers or hybridization probes for the detection of ADP-ribosyltransferase-encoding nucleic acids.

In still another related aspect, isolated nucleic acid molecules that are antisense to a ADP-ribosyltransferase encoding nucleic acid molecule are provided.

In another aspect, the invention features ADP-ribosyltransferase polypeptides, and biologically active or antigenic fragments thereof that are useful, e.g., as reagents or targets in assays applicable to treatment and diagnosis of ADP-ribosyltransferase-mediated or -related disorders. Treatment is defined as the application or administration of a therapeutic agent to a patient, or application or administration of a therapeutic agent to an isolated tissue or cell line from a patient, who has a disease, symptom of disease or a predispoisition toward a disease, with the purpose to cure, heal, alleviate, relieve, alter, remedy, ameliorate, improve or affect the disease, the symptoms of disease or the predisposition toward a disease. A therapeutic agent includes, but is not limited to, small molecules, peptides, antibodies, ribozymes and antisense oligonucleotides.

In another embodiment, the invention provides ADP-ribosyltransferase polypeptides having a ADP-ribosyltransferase activity. Preferred polypeptides are ADP-ribosyltransferase proteins including at least one transferase domain, and, preferably, having a ADP-ribosyltransferase activity, e.g., a ADP-ribosyltransferase activity described herein.

In other embodiments, the invention provides ADP-ribosyltransferase polypeptides, e.g., a ADP-ribosyltransferase polypeptide having the amino acid sequence shown in SEQ ID NO:37; an amino acid sequence that is substantially identical to the amino acid sequence shown in SEQ ID NO:37; or an amino acid sequence encoded by a nucleic acid molecule having a nucleotide sequence which hybridizes under stringent hybridization conditions to a nucleic acid molecule comprising the nucleotide sequence of SEQ ID NO:36, wherein the nucleic acid encodes a full length ADP-ribosyltransferase protein or an active fragment thereof.

In a related aspect, the invention further provides nucleic acid constructs which include a ADP-ribosyltransferase nucleic acid molecule described herein.

In a related aspect, the invention provides ADP-ribosyltransferase polypeptides or fragments operatively linked to non-ADP-ribosyltransferase polypeptides to form fusion proteins.

In another aspect, the invention features antibodies and antigen-binding fragments thereof, that react with, or more preferably specifically bind ADP-ribosyltransferase polypeptides.

In another aspect, the invention provides methods of screening for compounds that modulate the expression or activity of the ADP-ribosyltransferase polypeptides or nucleic acids.

In still another aspect, the invention provides a process for modulating ADP-ribosyltransferase polypeptide or nucleic acid expression or activity, e.g. using the screened compounds. In certain embodiments, the methods involve treatment of conditions related to aberrant activity or expression of the ADP-ribosyltransferase polypeptides or nucleic acids, such as conditions involving aberrant or deficient cellular proliferation/differentiation or aberrant metabolic function.

The invention also provides assays for determining the activity of or the presence or absence of ADP-ribosyltransferase polypeptides or nucleic acid molecules in a biological sample, including for disease diagnosis.

In further aspect the invention provides assays for determining the presence or absence of a genetic alteration in a ADP-ribosyltransferase polypeptide or nucleic acid molecule, including for disease diagnosis.

Other features and advantages of the invention will be apparent from the following detailed description, Chapter 7, Examples and the claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Human 8035 and 84242

The human 8035 and 84242 sequences (SEQ ID NO:18 and SEQ ID NO:22, respectively), that are approximately 2876 and 2810 nucleotides long including untranslated regions, respectively, contain predicted methionine-initiated coding sequences of about 1302 and 1212 nucleotides (nucleotides 613–1914 of SEQ ID NO:18; SEQ ID NO:20, and nucleotides 744–1955 of SEQ ID NO:22; SEQ ID NO:24, respectively). The coding sequences encode a 433 and 403 amino acid protein (SEQ ID NO:19 and SEQ ID NO:23, respectively).

Human 8035 contains a predicted RING finger protein domain (C3HC4 type) (PFAM Accession PF00097) located at about amino acid residues 380–421 of SEQ ID NO:19; and potential transmembrane domains are recognized from about amino acid residue 26–43, 50–69, 78–94, 136–152, 162–178, 185–203, and 221–245 of SEQ ID NO:19.

Human 84242 contains a predicted IBR (In Between RING Fingers) domain (PFAM Accession PF01485) located at about amino acid residues 2–67 of SEQ ID NO:23; and potential transmembrane domains are recognized from about amino acid residue 174–195, 221–245, and 329–345 of SEQ ID NO:23.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

As stated above the 8035 proteins share significant structural characteristics with members of the C3HCH type RING finger protein family and the 84242 protein contains another cysteine-rich domain termed, IBR (In Between RING Fingers). The IBR domain has a C6HC consensus pattern that defines this structure as the forth family member of the zinc-binding RING, LIM, and LAP/PHD fingers (van der Reijden et al. (1999) *Protein Sci.* 8:1557–1561). The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

A number of eukaryotic and viral proteins contain a C3HCH type RING finger domain. This conserved cysteine-rich RING domain binds two atoms of zinc, and is likely involved in mediating protein-protein interactions. The 3 dimensional structure of the zinc ligation system is unique to the RING domain and is referred to as the "cross-brace" motif.

As such, the 84242 polypeptides of the present invention can be expected to possess similar biological activities as the 8035 polypeptides of the invention and other RING finger protein family members.

Typically, RING finger family proteins play a role in diverse cellular processes. For example, proteins currently known to include the C3HC4 domain have a role in the mediation of such functions as recombination, particularly the rearrangement of immunoglobulin and T-cell receptor genes; the regulation of gene expression, particularly in various tumor cells, and as a trans-activator and/or -repressor of the expression of many viral and cellular promoters including the interleukin-2 receptor alpha chain; the maintenance of the segment-specific repression of homeotic selector genes and as a DNA-binding protein involved in X chromosome dosage compensation; developmental regulation, particularly male germ cell development and the regulation of photomorphogenesis; cellular differentiation, particularly differentiation of acute leukemia cells; the stabilization of protein-protein interactions, particularly the stabilization of the complex between the CDK7 kinase and cyclin H; peroxisome biogenesis, particularly in Zellweger syndrome, an autosomal recessive disorder associated with peroxisomal deficiencies; the postranscriptional regulation of genes, particularly in VSG expression sites; the regulation of adenylate cyclase activity; and the regulation of DNA repair.

Genetic mutations, recombinations and chromosomal translocations in RING finger protein family members have been implicated in diseases such as cancer, particularly mammalian breast and ovarian cancer, systemic lupus erythematosus, acute promyelocytic leukemia (APL), VHL disease, primary Sjogren's syndrome, Zellweger syndrome, and autosomal juvenile parkinsonism. In addition, RING finger protein family members have been shown to contribute to the pathogenesis of certain viral diseases including those caused by HSV and HIV.

Thus, the molecules of the present invention may be involved in one or more of: 1) regulation of recombination; 2) regulation of gene expression; 3) developmental regulation; 4) regulation of cellular proliferation and differentiation; 5) regulation of tumor cell growth; 6) stabilization of protein-protein interactions; 7) postranscriptional regulation of genes; 8) regulation of adenylate cyclase activity; 9) regulation of the cell cycle; 10) regulation of X chromosome dosage compensation; 11) regulation of DNA repair; 12) regulation of viral pathogenesis; 13) regulation of protein degradation from the ER; and 14) regulation of apoptosis.

As used herein, the term "RING finger protein domain" includes an amino acid sequence of about 30–60 amino acid residues in length and having a bit score for the alignment of the sequence to the RING finger protein domain (HMM) of at least 8. Preferably, a RING finger protein domain has a bit score for the alignment of the sequence to the RING finger protein domain (HMM) of at least 16 or greater. The RING finger protein domain (mm) has been assigned the PFAM Accession PF00097 (pfam.wustl.edu/). An alignment of the RING finger protein domain (amino acids 380–421 of SEQ ID NO:19) of human 8035 with a consensus amino acid sequence derived from a hidden Markov model is depicted in FIG. 27.

Herein, the term "RING finger protein family member" may also include a polypeptide that possess an IBR domain as described above. An IBR domain includes an amino acid sequence of about 45–70 amino acid residues in length and having a bit score for the alignment of the sequence to the IBR protein domain (HMM) of at least 8. Preferably, an IBR protein domain has a bit score for the alignment of the sequence to the IBR domain (HMM) of at least 16 or greater. The IBR domain (HMM) has been assigned the PFAM Accession PF01485 (pfam.wustl.edu/). An alignment of the IBR protein domain (amino acids 2–67 of SEQ ID NO:23) of human 84242 with a consensus amino acid sequence derived from a hidden Markov model is depicted in FIG. 28.

In a preferred embodiment an 8035 polypeptide or protein has at least one RING finger domain or region that includes at least about 30–60 amino acid residues with at least about 60%, 70%, 80%, 90%, 95%, 99%, or 100% homology with a RING finger domain, e.g., the RING finger protein domains of human 8035 (e.g., amino acid residues 380–421 of SEQ ID NO:19).

In another preferred embodiment an 84242 polypeptide or protein has at least one RING finger domain as described above as well as an IBR domain or region that includes at least about 45–70 amino acid residues with at least about 60%, 70%, 80%, 90%, 95%, 99%, or 100% homology with an IBR domain, e.g., the IBR protein domain of human 84242 (e.g., amino acid residues 2–67 of SEQ ID NO:23).

To identify the presence of a RING finger domain and/or an IBR domain in a 8035 or 84242 protein sequence, and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the R package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

As the 8035 and 84242 polypeptides of the invention may modulate 8035 and 84242-mediated activities, they may be useful for developing novel diagnostic and therapeutic agents for 8035 and 84242-mediated or related disorders, as described below.

As used herein, an "8035 or 84242 activity", "biological activity of 8035 or 84242" or "functional activity of 8035 or 84242", refers to an activity exerted by an 8035 or 84242 protein, polypeptide or nucleic acid molecule on e.g., an 8035 or 84242-responsive cell or on an 8035 or 84242 substrate, e.g., a protein substrate, as determined in vivo or in vitro. In one embodiment, an 8035 or 84242 activity is a direct activity, such as an association with an 8035 or 84242 target molecule. A 8035 or 84242 "target molecule" or "binding partner" or "ligand" or "substrate" is a molecule with which an 8035 or 84242 protein binds or interacts in nature, e.g., an E2 polypeptide or other protein substrate that an 8035 or 84242 protein binds to facilitate protein ubiquitination and protein degradation.

An 8035 or 84242 activity can also be an indirect activity, e.g., a cellular signaling activity mediated by interaction of the 8035 or 84242 protein with an 8035 or 84242 ligand. For example, the 8035 and 84242 proteins of the present invention can have one or more of the following activities: 1) regulation of recombination, including the rearrangement of immunoglobulin and T-cell receptor genes; 2) regulation of gene expression such as by the transactivation and/or repression of the expression of various promoters; 3) developmental regulation including regulation of male germ cell development, and maintenance of the segment-specific repression of homeotic selector genes; 4) regulation of cellular proliferation and differentiation; 5) regulation of tumor cell growth; 6) stabilization of protein-protein interactions such as stabilization of the complex between certain cyclin regulated kinases; 7) postranscriptional regulation of genes including VSG genes; 8) regulation of adenylate cyclase activity; 9) regulation of the cell cycle such as regulation of mitosis; 10) regulation of X chromosome dosage compensation; 11) regulation of DNA repair; 12) regulation of viral pathogenesis; 13) regulation of protein degradation from the ER; 14) regulation of photomorphogenesis; 15) regulation of peroxisome biogenesis; and 16) regulation of apoptosis.

Accordingly, 8035 and 84242 protein may be mediate various disorders, particularly cellular proliferative and/or differentiative disorders. Indeed, genetic mutations, recombinations and chromosomal translocations in RING finger protein family members have been implicated in diseases such as cancer, particularly mammalian breast and ovarian cancer; systemic lupus erythematosus; acute promyelocytic leukemia (APL); VHL disease; primary Sjogren's syndrome; Zellweger syndrome; and autosomal juvenile parkinsonism. In addition, RING finger protein family members have been shown to contribute to the pathogenesis of certain viral diseases including those caused by HSV and HIV.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 8035 and 84242 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Human 55304

The human 55304 sequence (SEQ ID NO:26), which is approximately 5502 nucleotides long including untranslated regions, contains a predicted methionine-initiated coding sequence of about 2043 nucleotides (nucleotides 803–2845 of SEQ ID NO:26; SEQ ID NO:28). The coding sequence encodes a 680 amino acid protein (SEQ ID NO:27).

Human 55304 shows a high degree of sequence conservation with known aminopeptidases at 16 key residues (amino acid numbers 318, 336, 344, 346, 363, 374, 397, 399, 410, 411, 412, 425, 448, 450, 489, 508 of SEQ ID NO:27). These amino acids are conserved between the 55340 polypeptide and the corresponding residues from a leucyl aminopeptidase from *Vibrio proteolyticus* (SwissProt Accession No. Q01693), an aminopeptidase from *Streptomyces griseus* (SwissProt Accession No. P80561), and aminopeptidase Y from *Saccharomyces cerevisiae* (SwissProt Accession No. P37302).

The 55304 polypeptide contains 8 putative transmembrane domains. These domains are located at amino acids 192–208, 227–251, 264–286, 302–318, 326–343, 356–379, 397–421, and 428–448 of the 55304 amino acid sequences shown in SEQ ID NO:27.

The 55304 protein also contains the following ProDom domain matches: protein aminopeptidase/T1F15.12/HSP26-TIF32 hydrolase (amino acids 1–69 of SEQ ID NO:27) and YBS_4/HSP26-TIF32 hydrolase/aminopeptidase zinc metalloprotease (amino acids 83–206 of SEQ ID NO:27).

The 55304 protein contains structural characteristics in common with members of the aminopeptidase family.

As used herein, the term "aminopeptidase" refers to a protein or polypeptide which is capable of catalyzing the removal of an amino acid from the amino terminus of a peptide substrate. Aminopeptidases can have a specificity for specific amino acids. For example, the removal of the amino-terminal methionine from proteins and peptides is catalyzed by the methionine aminopeptidase class of aminopeptidases.

As referred to herein, aminopeptidases preferably include a catalytic domain of about 100–250 amino acid residues in length, preferably about 130–210 amino acid residues in length, or more preferably about 180–200 amino acid residues in length. An aminopeptidase domain typically includes conserved residues (i.e. identical residues or conservatively substituted residues as defined elsewhere herein) in at least 8, at least 9, at least 10, at least 11, at least 12, at least 13, at least 14, at least 15, or at 16 sites in the amino acid sequence of the protein. These sites are located at amino acids 318, 336, 344, 346, 363, 374, 397, 399, 410, 411, 412, 425, 448, 450, 489, 508 of SEQ ID NO:27.

Typically, aminopeptidases play a role in diverse cellular processes. For example, aminopeptidases function in protein maturation, in the terminal degradation of polypeptides, in hormone level regulation, in the regulation of the renin-angiotensin system, and in cell cycle control.

Thus, the molecules of the present invention may be involved in one or more of: 1) the removal of an amino acid from the amino terminus of a peptide substrate; 2) protein maturation; 3) the terminal degradation of proteins; 4) the modulation of hormone levels; 5) the regulation of the cell cycle; or 6) the regulation of the renin-angiotensin system.

In a preferred embodiment 55304 polypeptide or protein has an "aminopeptidase domain" or a region which includes at least about 100–250 more preferably about 130–200 or 160–200 amino acid residues and has at least about 60%, 70%, 80%, 90%, 95%, 99%, or 100% homology with an "aminopeptidase domain," e.g., the aminopeptidase domain of human 55304 (e.g., amino acid residues 318–508, particularly amino acid residues 318, 336, 344, 346, 363, 374, 397, 399, 410, 411, 412, 425, 448, 450, 489, and 508 of SEQ ID NO:27).

In one embodiment, a 55304 protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In a preferred embodiment, a 55304 polypeptide or protein has at least one transmembrane domain or a region which includes at least 18, 20, 22, 24, 25, 30, 35 or 40 amino acid residues and has at least about 60%, 70% 80% 90% 95%, 99%, or 100% sequence identity with a "transmembrane domain," e.g., at least one transmembrane domain of human 55304 (e.g., amino acid residues 192–208, 227–251, 264–286, 302–318, 326–343, 356–379, 397–421, or 428–448 of SEQ ID NO:27).

In another embodiment, a 55304 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 55304, or 55304-like protein.

In a preferred embodiment, a 55304 polypeptide or protein has a "non-transmembrane domain" or a region which includes at least about 1–250, preferably about 1–2311, more preferably about 5–231 amino acid residues, and has at least about 60%, 70% 80% 90% 95%, 99% or 100% sequence identity with a "non-transmembrane domain", e.g., a non-transmembrane domain of human 55304 (e.g., residues 1–191, 209–226, 252–263, 287–301, 319–325, 344–355, 380–396, 422–427, or 449–680 of SEQ ID NO:27). Preferably, a non-transmembrane domain is capable of catalytic activity (e.g., catalyzing the removal of an amino terminal amino acid from a peptide substrate).

A non-transmembrane domain located at the N-terminus of a 55304 protein or polypeptide is referred to herein as an "N-terminal non-transmembrane domain." As used herein, an "N-terminal non-transmembrane domain" includes an amino acid sequence having about 1–350, preferably about 50–325, more preferably about 80–320, or even more preferably about 120–191 amino acid residues in length and is located outside the boundaries of a membrane. For example, an N-terminal non-transmembrane domain is located at about amino acid residues 1–191 of SEQ ID NO:27.

Similarly, a non-transmembrane domain located at the C-terminus of a 55304 protein or polypeptide is referred to herein as a "C-terminal non-transmembrane domain." As used herein, an "C-terminal non-transmembrane domain" includes an amino acid sequence having about 1–300, preferably about 15–290, preferably about 20–270, more preferably about 25–231 amino acid residues in length and is located outside the boundaries of a membrane. For example, a C-terminal non-transmembrane domain is located at about amino acid residues 680–449 of SEQ ID NO:27.

As the 55304 polypeptides of the invention may modulate 55304-mediated activities, they may be useful as of for developing novel diagnostic and therapeutic agents for 55304-mediated or related disorders, as described below.

As used herein, a "55304 activity", "biological activity of 55304" or "functional activity of 55304", refers to an activity exerted by a 55304 protein, polypeptide or nucleic acid molecule on e.g., a 55304-responsive cell or on a 55304 substrate, e.g., a protein substrate, as determined in vivo or in vitro. In one embodiment, a 55304 activity is a direct activity, such as an association with a 55304 target molecule. A "target molecule" or is a molecule with which a 55304 protein binds or interacts in nature, e.g., a peptide substrate from which 55304 removes an amino acid. A 55304 activity can also be an indirect activity, e.g., a cellular signaling activity mediated by the product of 55304 proteolysis. For example, the 55304 proteins of the present invention can have one or more of the following activities: 1) the removal of an amino acid from the amino terminus of a peptide substrate 2) protein maturation 3) the terminal degradation of proteins; 4) the modulation of hormone levels; 5) the regulation of the cell cycle; or 6) the regulation of the renin-angiotensin system.

Accordingly, 55304 protein may be mediate various disorders, including cellular proliferative and/or differentiative-disorders, hypertensive disorders, hormonal disorders, and disorders related to protein maturation and degradation.

The 55304 nucleic acid and protein of the invention can be used to treat and/or diagnose a variety of proliferative disorders (see above for examples of such disorders).

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Human 52999

The present invention provides the human 52999 sequence (SEQ ID NO:29), which is approximately 2566 nucleotides long including untranslated regions, contains a predicted methionine-initiated coding sequence of about 2277 nucleotides (nucleotides 194 to 2470 of SEQ ID NO:29; SEQ ID NO:31). The coding sequence encodes a 758 amino acid protein (SEQ ID NO:30).

The protein form of 52999 after cleavage of the predicted signal sequence is approximately 739 amino acid residues in length (from about amino acid 20 to amino acid 758 of SEQ ID NO:30). Human 52999 (SEQ ID NO:30) contains regions of high homology located at about amino acid residues 180 to 192, 230 to 290, 354 to 409, and 520 to 554 of SEQ ID NO:30 that are consistent with 52999 belonging to the Peptidase_M8 family of zinc metallopeptidases (PFAM Accession PF01457; FIG. 31).

The majority of zinc-dependent metallopeptidases (with the notable exception of the carboxypeptidases) such as the Peptidase_M8 family share a common pattern of primary structure in the part of their sequence involved in the binding of zinc, and can be grouped together as a superfamily, known as the metzincins, on the basis of this sequence similarity. From the tertiary structure of thermolysin, the position of the residues acting as zinc ligands and those involved in the catalytic activity are known. Two of the zinc ligands are histidines which are very close together in the sequence; C-terminal to the first histidine is a glutamic acid residue which acts as a nucleophile and promotes the attack of a water molecule on the carbonyl carbon of the substrate. A signature pattern which includes the two histidine and the glutamic acid residues is sufficient to detect this superfamily of proteins (Rawlings and Barrett (1995) *Methods Enzymol.* 248:183–228).

The 52999 protein includes such a zinc metallopeptidase zinc-binding signature sequence (ATLHELLHAL) from amino acids 272–281 of SEQ ID NO:30 (ProSite PS0014/PDOC00129), consistent with the catalytic HEXXH zinc-binding motif of the zinc metallopeptidases.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

The 52999 protein also contains predicted transmembrane domains that extend from about amino acid 632–649 and 706–722 of SEQ ID NO:30.

As used herein, the term "metallopeptidase" refers to a protein or polypeptide that is capable of catalyzing the cleavage of a polypeptide bond through hydrolysis (i.e., possessing polypeptide hydrolytic activity) and contains at least one co-factor selected from the group consisting of $Zn^{2+}$, $Mn^{2+}$, $Mg^{2+}$, and $Ca^{2+}$. Metallopeptidases can have a specificity for various polypeptide substrates including a preference for hydrophobic residues at P1 and P1' and basic residues at P2 and P3'. Based on the sequence similarities described above, the 52999 molecules of the present invention are predicted to have similar biological activities as metallopeptidase family members.

The 52999 protein contains a significant number of structural characteristics in common with members of the metallopeptidase family as described above.

As the biological functions of metallopeptidases include protein maturation and protein degradation, they typically play a role in diverse cellular processes. In particular, metallopeptidases have been shown to have a role in tumor growth, metastasis, and angiogenesis; in inflammatory disorders including, but not limited to osteoarthritis and rheumatoid arthritis, multiple sclerosis, Crohn disease, psoriasis, periodontal disease, and asthma; in macular degeneration; in restenosis; and in Alzheimer's disease.

A 52999 polypeptide can include a "metallopeptidase zinc-binding motif" or regions homologous with the "Peptidase_M8 family of metallopeptidases".

As used herein, the term "Peptidase_M8 family of metallopeptidases" includes an amino acid sequence having a bit score for the alignment of the sequence to the Peptidase_M8 family domain (HMM) of at least 8. Preferably, a Peptidase_M8 family domain has a bit score for the alignment of the sequence to the metallopeptidase domain (HMM) of at least 16 or greater. The Peptidase_M8 family (HMM) has been assigned the PFAM Accession PF01457 (pfam.wustl.edu/). An alignment of the Peptidase_M8 family domain of human 52999 (amino acids 180 to 192, 230 to 290, 354 to 409, and 520 to 554 of SEQ ID NO:30) with the consensus amino acid sequences derived from a hidden Markov model is depicted in FIG. 31.

In a preferred embodiment 52999 polypeptide or protein has regions with at least about 60%, 70%, 80%, 90%, 95%, 99%, or 100% homology with the Peptidase_M8 family of metallopeptidases (e.g., amino acid residues 180 to 192, 230 to 290, 354 to 409, and 520 to 554 of SEQ ID NO:30).

To identify the presence of a Peptidase_M8 metallopeptidase region of homology in a 52999 protein sequence, and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, a 52999 protein includes at least one transmembrane domain. As used herein, the term "transmembrane domain" includes an amino acid sequence of at least about 15 amino acid residues in length that spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In a preferred embodiment, a 52999 polypeptide or protein has at least one transmembrane domain or a region which includes at least 15, 16, 17, 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 52999 (e.g., amino acid residues 632–649 and 706–722 of SEQ ID NO:30).

In another embodiment, a 52999 protein includes at least one non-transmembrane domain. As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 52999, or 52999-like protein.

In a preferred embodiment, a 52999 polypeptide or protein has two non-transmembrane domains wherein the larger of the non-transmembrane domains includes an amino acid sequence having at least about 100–300, 300–500, or 500–600 or more amino acid residues in length, and has at least about 60%, 70% 80% 90% 95%, 99% or 100% homology with the larger of the two non-transmembrane domains of human 52999 (e.g., residues 21–612 of SEQ ID NO:30). Preferably, the non-transmembrane domain is capable of polypeptide hydrolytic activity.

A non-transmembrane domain located at the N-terminus of a 52999 protein or polypeptide is referred to herein as an "N-terminal non-transmembrane domain." As used herein, an "N-terminal non-transmembrane domain" includes an amino acid sequence having at least about 1–300, 300–500, or 500–600 or more amino acid residues in length, and is located outside the boundaries of a membrane. For example, an N-terminal non-transmembrane domain is located at about amino acid residues 21–612 of SEQ ID NO:30.

Similarly, a non-transmembrane domain located at the C-terminus of a 52999 protein or polypeptide is referred to herein as a "C-terminal non-transmembrane domain." As used herein, an "C-terminal non-transmembrane domain" includes an amino acid sequence having at least about 1–15, 15–25, or 25–36 or more amino acid residues in length and is located outside the boundaries of a membrane. For example, a C-terminal non-transmembrane domain is located at about amino acid residues 723–758 of SEQ ID NO:30.

A 52999 molecule can further include a signal sequence. As used herein, a "signal sequence" refers to a peptide of about 20–80 amino acid residues in length which occurs at the N-terminus of secretory and integral membrane proteins and which contains a majority of hydrophobic amino acid residues. For example, a signal sequence contains at least about 20–25, 25–50, or 50–80 amino acid residues and has at least about 40–90%, hydrophobic amino acid residues (e.g., alanine, valine, leucine, isoleucine, phenylalanine, tyrosine, tryptophan, or proline). Such a signal sequence, also referred to in the art as a "signal peptide", serves to direct a protein containing such a sequence to a lipid bilayer. For example, in one embodiment, a 52999 protein contains a signal sequence of about amino acids 1–20 of SEQ ID NO:30. The signal sequence is cleaved during processing of the metallopeptidase. The processed 52999 protein corresponds to amino acids 21 to 758 of SEQ ID NO:30.

As the 52999 polypeptides of the invention may modulate 52999-mediated activities, they may be useful for developing novel diagnostic and therapeutic agents for 52999-mediated or related disorders, as described below.

As used herein, a "52999 activity", "biological activity of 52999" or "functional activity of 52999", refers to an activity exerted by a 52999 protein, polypeptide or nucleic acid molecule on e.g., a 52999-responsive cell or on a 52999 polypeptide substrate, as determined in vivo or in vitro. In one embodiment, a 52999 activity is a direct activity, such as an association with a 52999 target molecule. A "target molecule" or "binding partner" or "ligand" or "substrate" is a molecule with which a 52999 protein binds or interacts in nature, e.g., a polypeptide that a 52999 protein cleaves. A 52999 activity can also be an indirect activity, e.g., a cellular signaling activity mediated by interaction of the 52999 protein with a 52999 ligand. For example, the 52999 proteins of the present invention can have one or more of the following activities: 1) cleavage of a protein precursor to maturation; 2) cleavage of a proenzyme to its active state; 3) catalysis of protein degradation; 4) catalysis of the degradation of extracellular matrix proteins; 5) modulation of tumor cell growth and invasion; and 6) modulation of angiogenesis.

Accordingly, 52999 protein may be mediate various disorders, including cellular proliferative and/or differentiative disorders; inflammatory disorders including, but not limited to osteoarthritis and rheumatoid arthritis, multiple sclerosis, Crohn disease, psoriasis, periodontal disease, and asthma; macular degeneration; restenosis; and Alzheimer's disease (see above for examples of such disorders).

Human 21999

The human ADP-ribosyltransferase sequence (SEQ ID NO:36), which is approximately 1485 nucleotides long including untranslated regions, contains a predicted methionine-initiated coding sequence of about 879 nucleotides. The coding sequence encodes a 292 amino acid protein (SEQ ID NO:37).

As the ADP-ribosyltransferase polypeptides of the invention may modulate ADP-ribosyltransferase-mediated activities, they may be useful as of for developing novel diagnostic and therapeutic agents for ADP-ribosyltransferase-mediated or related disorders, as described below.

As used herein, a "ADP-ribosyltransferase activity", "biological activity of ADP-ribosyltransferase" or "functional activity of ADP-ribosyltransferase", refers to an activity exerted by a ADP-ribosyltransferase protein, polypeptide or nucleic acid molecule on e.g., a ADP-ribosyltransferase-responsive cell or on a ADP-ribosyltransferase substrate, e.g., an ADP-ribose moiety substrate, as determined in vivo or in vitro. In one embodiment, a ADP-ribosyltransferase activity is a direct activity, such as an association with a ADP-ribosyltransferase target molecule. A "target molecule" or "binding partner" is a molecule with which a ADP-ribosyltransferase protein binds or interacts in nature, e.g., an ADP-ribose moiety of NAD.

ADP-ribosyltransferase protein can be detected in a variety of cell types, including viruses, bacteria and eukaryotic cells. ADP-ribosylation of target proteins by bacterial toxin transferases such as cholera, diptheria and pertussis toxins alters critical pathways. For example, cholera toxin ADP-ribosylates an arginine in the ∀-subunit of the stimulatory heterotrimeric guanine nucleotide-binding (G) protein, resulting in the activation of adenylyl cyclase and in increase in intracellular cAMP. Eukaryotic ADP-ribosyltransferase activity has been detected in several tissues including human skeletal muscle. In fact, inhibitor studies suggest that the muscle transferase may participate in the regulation of myogenesis (Kharadia, S. V. et al. (1992) *Exp. Cell. Res.* 201: 33–42).

Accordingly, the ADP-ribosyltransferase may be involved in various cellular metabolic and proliferative/differentiative disorders. Examples of cellular proliferative and/or differentiative disorders include cancer, e.g., carcinoma, sarcoma, metastatic disorders or hematopoietic neoplastic disorder.

The ADP-ribosyltransferase nucleic acid and protein of the invention can be used to treat and/or diagnose a variety of proliferative disorders (see above, for examples).

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyangiitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

CHAPTER 6

52020, A NOVEL HUMAN MELANOMA ASSOCIATED ANTIGEN AND USES THEREFOR

BACKGROUND OF THE INVENTION

The immune system has the ability to mount responses that can destroy tumor cells. Among the various elements of the immune system, cytotoxic T lymphocytes (CTL) are highly effective in mediating the rejection of established tumors. CTL's recognize antigenic determinants produced from any protein synthesized within the cell, while antibodies recognize and bind only integral cell surface molecules.

The anti-tumor activity of tumor-specific CTL is the result of a series of complex molecular events. After cellular processing of proteins in the cytoplasm of the tumor cells, small peptides are transported to the endoplasmic reticulum, where they bind to newly synthesized major histocompatibility gene complex (MHC) class I molecules or HLA's. HLA/peptide complexes are then exported to the surface of the tumor cell where they are recognized by antigen-specific Class I-restricted CTL's. In addition to lysing the tumor cell, the CTL's may also secrete lymphokines such as tumor necrosis factor (TNF), and gamma-interferon ($\gamma$-IFN), which also contribute to the overall anti-tumor effect.

A family of genes referred to as the "MAGE" family after the melanoma associated antigen encoding gene, MAGE-1, has been discovered which are processed into peptides and expressed on tumor cell surfaces as HLA/peptide complexes. The MAGE peptides are recognized by specific CTL's leading to lysis of the tumor cells from which they are expressed. The genes code for "tumor rejection antigen precursors" and the peptides derived therefrom are referred to as "tumor rejection antigens" (see Traversari et al. (1992) *Immunogenetics* 35:145; van der Bruggen et al (1991), *Science* 254:1643; and U.S. Pat. No. 5,342,774; all of which are herein incorporated by reference).

In fact, the MAGE-1 encoded human melanoma specific antigen, MZ2-E, is recognized by CTL's derived from a cancer patient (Van der Bruggen et al. (1991) *Science* 254:1643–1647). The MAGE-1 gene is expressed by various melanoma cell lines as well as several other types of tumor cells, but is not expressed in a panel of normal tissues. Eleven additional members of the MAGE family, map to the q28 region of chromosome X and have between 64% and 85% identity in amino acid sequence to MAGE-1 (Chen et al. (1994) *Proc. Natl. Acad. Sci.* 91:1004–1008); De Plaen et al. (1994) *Immunogenetics* 40:360–369; Wang et al. (1994) *Cytogenet. Cell Genet.* 67:116–119). These genes on the q28 region of chromosome X are referred to as the MAGE-A family genes (MAGE-A1 to A12) (Duffour et al. (1999) *Eur. J. Immunol.* 29:3329–3337).

The MAGE-A family of genes have been found to be expressed at a high level in a number of tumors of various histologic types including those from colorectal, lung, ovarian, breast, colon, lung, liver, thyroid, and skin cancers (Mori et al. (1996) *Ann. Surg.* 183–188; Sakata M. (1996) *Kurume Med. J.* 43:55–61; Yamada et al. (1995) *Int. J. Cancer* 64:388–393; Zukut R. et al. (1993) *Cancer Res.* 53:5–8; Zakut R. et al. (1990) *Cancer Res.* 53:5–8). In addition, significantly increased levels of MAGE-A4 have been detected in the sera of patients with hepatitis C virus (HCV)-associated cancer and HCV-associated liver cirrhosis indicating (Tsuzurahara et al. (1997) *Jpn. J. Cancer Res.* 88:915–918.) Examination of a large panel of healthy tissues revealed expression of MAGE genes only in testis and placenta (De Plaen et al., supra).

For example, the MAGE-A1 gene is expressed in approximately 40% of melanomas and in some other tumors and the MAGE-A2 and MAGE-A3 genes are expressed in approximately 80–90% of the melanoma lines that have been examined. Activation of MAGE-A1 in cancer cells may be due to demethylation of the promoter sequence. Treatment with the demethylating agent 5-aza-2'-deoxycytidine activated MAGE-A1 expression not only in tumor cell lines, but also in primary fibroblasts (De Smet C. et al. (1996) *Proc. Natl. Acad. Sci.* 93:7149–7153).

Another family of tumor rejection antigen precursor genes has been identified on the Xp arm of the X chromosome. These genes are referred to as the MAGE-B family of genes (MAGE-B 1 to B4). The MAGE-B 1 and MAGE-B2 genes are similarly expressed in tumors of various histological origins, silent in normal tissues with the exception of testis, and activated by a demethylation process (Lurquin et al. (1997) *Genomics* 46:397–408). In addition, studies by McCurdy et al. indicate that MAGE Xp-2 (MAGE-B2) is the target of autoantibodies in systemic Lupus Erythematosus (SLE), suggesting that this protein may also have a role in autoimmune and inflammatory disorders (McCurdy et al. (1998) *Molec. Genet. Metab.* 63:3–13). A gene designated MAGE-C1 has also been identified.

The identification of tumor specific antigens, such as those encoded by MAGE genes, and the corresponding T cell epitopes have provided novel peptide-based vaccines useful in treating cancer patients. For example, a nonapeptide fragment of MAGE-A1 stimulates CTL's that respond to antigen MZ2-E (Traversari et al. (1992) *J. Exp. Med.* 176:1453–1457). Cells that present the nonapeptide, EADPT-GHSY, were used to immunize MAGE-A positive melanoma patients (Hu et al. (1996) *Cancer Res.* 56:2479–2483). The immunization increased the frequency of autologous melanoma-reactive CTL precursors in the circulation. In combination with interleukin-2 the MAGE-A1 nonapeptide immunization led to a significant expansion of the peptide-specific and autologous melanoma-reactive CTL response (Hu et al., supra). In addition, a tumor rejection antigen derived from MAGE-A3 tumor rejection antigen precursors is presented by HLA-A1 molecules, and tumor rejection antigens derived from MAGE-A2 complex with MHC class I molecule HLA-A2.

More recently it has been demonstrated that an anti-MAGE-A4 tumor rejection antigen CTL clone can lyse HLA-A2 tumor cells expressing MAGE-A4 tumor rejection antigen precursors (Duffour et al., supra). These data are especially important as MAGE-A4 is expressed in 51% of lung carcinomas and 63% of esophageal carcinomas, whereas about 50% of Caucasians and Asians express HLA-A2. These results indicate that MAGE proteins other than MAGE-A1 are likely to be valuable for cancer immunotherapy.

In addition to their value as anticancer agents, there is evidence that MAGE proteins may also have use in the treatment of neurodegenerative conditions. For example, MAGE genes are related to the necdin gene, and the small potential transmembrane domain of the MAGE proteins shows a particularly high degree of conservation with the transmembrane domain of the necdin protein. It has been postulated that this region associates with the transmembrane domain of another protein (De Plaen et al, supra).

Necdin is a nuclear protein, first identified in neuronally differentiated embryonal carcinoma cells and in the brain of adult mice (Maruyama et al. (1991) Biochem. Biophys. Res. Commun. 178:291–296). Necdin is expressed in virtually all postmitotic neurons in the central nervous system at all stages of development (Uetsuki et al. (1996), J. Biol. Chem. 271:918–924). However, necdin is not expressed in proliferative neuron-like cells originating from tumors, and ectopic expression of necdin in NIH3T3 cells suppresses cell growth without affecting cell viability (Aizawa et al., (1992) Dev. Brain Res. 63:265–274); Hayashi et al., (1995) Biochem. Biophys. Res. Commun. 213:317–324). Therefore, necdin is likely to affect the transition in developing neurons from proliferative to non-proliferative states (Uetsuki et al., supra). Furthermore, necdin has been shown to interact with viral transforming proteins such as SV40 large T antigen and adenovirus E1A, and with the transcription factor E2F1. Necdin can also functionally replace the Rb as a growth suppressor in Rb deficient osteosarcoma cells, suggesting that necdin is a neuron-specific growth suppressor with a function similar to that of Rb (Taniura et al. (1998) J. Biol. Chem. 273:720–728). Therefore, MAGE proteins may also function to suppress growth in neuronal cells and, thus, be involved in the pathophysiology of neurodegenerative conditions.

It is well established that members of the MAGE protein family play critical roles in a variety of important cellular processes including the regulation of cellular growth and differentiation; T-cell activation; CTL effector cell function; and elicitation of auto-antibodies. As a result of these roles, the MAGE proteins are involved in such important diseases and disorders as cancers, tissue repair, neurodegenerative disorders, autoimmune disorders, and inflammatory disorders.

Accordingly, the discovery of polynucleotides encoding MAGE-like proteins, and the proteins themselves, provides a means to investigate MAGE-mediated disorders, and provides new compositions useful in the diagnosis and/or treatment of cancers, neurodegenerative disorders, autoimmune disorders such as SLE, and inflammatory disorders.

BRIEF SUMMARY OF THE INVENTION

The present invention is based, in part, on the discovery of a novel human MAGE-like polypeptide, referred to herein as "52020". The nucleotide sequence of a cDNA encoding 52020 is shown in SEQ ID NO:40, and the amino acid sequence of a 52020 polypeptide is shown in SEQ ID NO:41. In addition, the nucleotide sequence of the coding region is depicted in SEQ ID NO:42.

Accordingly, in one aspect the invention features a nucleic acid molecule which encodes a 52020 protein or polypeptide, e.g., a biologically active portion of the 52020 protein. In a preferred embodiment, the isolated nucleic acid molecule encodes a polypeptide having the amino acid sequence of SEQ ID NO:41. In other embodiments, the invention provides an isolated 52020 nucleic acid molecule having the nucleotide sequence shown in SEQ ID NO:40 or SEQ ID NO:42. In still other embodiments, the invention provides nucleic acid molecules that are substantially identical (e.g., naturally occurring allelic variants) to the nucleotide sequence shown in SEQ ID NO:40 or SEQ ID NO:42. In other embodiments, the invention provides a nucleic acid molecule which hybridizes under stringent hybridization conditions to a nucleic acid molecule comprising the nucleotide sequence of SEQ ID NO:40 or SEQ ID NO:42, wherein the nucleic acid encodes a full length 52020 protein or an active fragment thereof.

In a related aspect, the invention further provides nucleic acid constructs which include a 52020 nucleic acid molecule described herein. In certain embodiments, the nucleic acid molecules of the invention are operatively linked to native or heterologous regulatory sequences. Also included, are vectors and host cells containing the 52020 nucleic acid molecules of the invention e.g., vectors and host cells suitable for producing 52020 nucleic acid molecules and polypeptides.

In another related aspect, the invention provides nucleic acid fragments suitable as primers or hybridization probes for the detection of 52020-encoding nucleic acids.

In still another related aspect, isolated nucleic acid molecules that are antisense to a 52020 encoding nucleic acid molecule are provided.

In another aspect, the invention features 52020 polypeptides, and biologically active or antigenic fragments thereof that are useful, e.g., as reagents or targets in assays applicable to treatment and diagnosis of 52020-mediated or -related disorders. In another embodiment, the invention provides 52020 polypeptides having a 52020 activity. Preferred polypeptides are 52020 proteins including at least one MAGE domain, and, preferably, having a 52020 activity, e.g., a 52020 activity as described herein.

In other embodiments, the invention provides 52020 polypeptides, e.g., a 52020 polypeptide having the amino acid sequence shown in SEQ ID NO:41; an amino acid sequence that is substantially identical to the amino acid sequence shown in SEQ ID NO:41; or an amino acid sequence encoded by a nucleic acid molecule having a nucleotide sequence which hybridizes under stringent hybridization conditions to a nucleic acid molecule comprising the nucleotide sequence of SEQ ID NO:40 or SEQ ID NO:42, wherein the nucleic acid encodes a full length 52020 protein or an active fragment thereof.

In a related aspect, the invention further provides nucleic acid constructs which include a 52020 nucleic acid molecule described herein.

In a related aspect, the invention provides 52020 polypeptides or fragments operatively linked to non-52020 polypeptides to form fusion proteins.

In another aspect, the invention features antibodies and antigen-binding fragments thereof, that react with, or more preferably specifically bind 52020 polypeptides.

In another aspect, the invention provides methods of screening for compounds that modulate the expression or activity of the 52020 polypeptides or nucleic acids.

In still another aspect, the invention provides a process for modulating 52020 polypeptide or nucleic acid expression or activity, e.g. using the screened compounds. In certain embodiments, the methods involve treatment of conditions related to aberrant activity or expression of the 52020 polypeptides or nucleic acids, such as conditions involving aberrant: cellular proliferation or differentiation, T-cell activation, CTL effector function, or elicitation of autoantibodies.

The invention also provides assays for determining the activity of or the presence or absence of 52020 polypeptides or nucleic acid molecules in a biological sample, including for disease diagnosis.

In further aspect the invention provides assays for determining the presence or absence of a genetic alteration in a 52020 polypeptide or nucleic acid molecule, including for disease diagnosis.

Other features and advantages of the invention will be apparent from the following detailed description, Chapter 7, Examples and the claims.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Human 52020

The human 52020 sequence (SEQ ID NO:40), which is approximately 2183 nucleotides long including untranslated regions, contains a predicted methionine-initiated coding sequence of about 912 nucleotides (nucleotides 782 to 1693 of SEQ ID NO:40; SEQ ID NO:42), not including the terminal codon. The coding sequence encodes a 304 amino acid protein (SEQ ID NO:41).

Human 52020 contains the following regions or other structural features: a predicted MAGE domain (PFAM Accession PF01454) located at about amino acid residues 1–208 of SEQ ID NO:41; and a predicted transmembrane domain which extends from about amino acid residue 172–188 of SEQ ID NO:41.

For general information regarding PFAM identifiers, PS prefix and PF prefix domain identification numbers, refer to Sonnhammer et al. (1997) *Protein* 28:405–420 and the Pfam website maintained in several locations, e.g. by the Sanger Institute (sanger.ac.uk/Software/Pfam).

The 52020 protein contains a significant number of structural characteristics in common with members of the MAGE family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "MAGE" refers to a protein or polypeptide that is capable of regulating cellular growth and differentiation; activating T-cells; effecting CTL cell function; and/or eliciting auto-antibodies. MAGE-like proteins can be divided into several subfamilies based upon their homology to a MAGE family consensus sequence that is depicted in FIG. 35. These classes consist of the MAGE-A proteins (MAGE-A1 through -A-12), MAGE-B proteins (MAGE-B1 through -B4), and the MAGE-C1 protein. The 52020 MAGE-like protein of the invention shows the most homology to the MAGE-A4 and MAGE-B 1 proteins.

Prodom analysis indicated amino acids from about 101 to about 206 of SEQ ID NO:41 have about 45% sequence identity to the consensus sequence of Prodom class PD003141. Polypeptides belong to this Prodom classification include, for example, Melanoma-associated Antigen B2 (MAGE-B2 Antigen) from *Homo sapiens*; MAGE-B1 from *Homo sapiens*; MAGE-B4 antigen from *Homo sapiens*; MAGE-B3 antigen from *Homo sapiens*; Melanoma-associated antigen MAGE-like protein from *Homo sapiens*. See, for example, Lurquin et al. (1997) *Genomics* 46:397–408; and Muscatelli et al. (1995) *Proc. Natl. Acad. Sci. U.S.A.* 92:4987–4991.

Prodom analysis further indicated amino acids from about 207–275 of SEQ ID NO:41 have about 59% sequence identity to the consensus sequence of Prodom class PD003293. Polypeptides belonging to this Prodom classification include, for example, MAGE-12, MAGE-1, MAGE-11, MAGE-10 antigen from *Homo sapiens*; Melanoma Antigen Related Sequence 2 (SMAGE-2) from *Mus musculus*; and Necdin from *Mus musculus*. The MAGE antigens from human belonging to this Prodom class have been implicated in tumor transformation or various aspects of tumor regression. See, for example, de Smet et al. (1994) *Immunogenetics* 39:121–129; Ding et al. (1994) *Biochem. Biophys. Res. Commun.* 202:549–555; and Gaugler et al. (1994) *J. Exp. Med.* 179:921–930; and Schultz-Thater et al. (1994) *Int. J. Cancer* 59:435–439. Based on these sequence similarities, the 52020 molecules of the present invention are predicted to have similar biological activities as MAGE family members.

MAGE proteins play a role in diverse cellular processes. For example, MAGE proteins are processed into peptides and expressed on tumor cell surfaces as HLA/peptide complexes. The MAGE peptides are recognized by specific CTL's leading to lysis of the tumor cells from which they are expressed. In addition, to their role as tumor specific antigens, MAGE proteins may also function as cell growth suppressors. MAGE proteins may also function to suppress growth in neuronal cells and, thus, be involved in the pathophysiology of neurodegenerative conditions. Furthermore, MAGE-B2 is the target of autoantibodies in SLE, suggesting that MAGE proteins function to elicit autoantibodies and, thus, have a role in autoimmune and inflammatory disorders.

Thus, the molecules of the present invention may be involved in one or more of: 1) the regulation of cellular growth and differentiation; 2) tissue repair; 3) T-cell activation; 4) CTL effector cell function; and 5) elicitation of autoantibodies.

In one embodiment of the invention the 52020 MAGE-like protein, or fragments thereof, are used as vaccines for treating various cancerous conditions. There is ample evidence that points to the presentation of MAGE tumor rejection antigens on tumor cells, followed by the development of an immune response and deletion of the tumor cells expressing the tumor rejection antigens (see U.S. Pat. Nos. 5,342,774; 6,063,900; 6,034,214; and 6,019,987 all of which are herein incorporated in their entirety by reference). The evidence in the art shows that when various MAGE tumor rejection antigens are administered to cells, a CTL response is mounted and presenting cells are lysed. This is behavior characteristic of vaccines, and hence MAGE tumor rejection antigen precursors's, or the resulting tumor rejection antigens may be used, either alone or in pharmaceutically appropriate compositions, as vaccines.

In another embodiment of the invention, specific anti-52020 CTL clones, or antibodies to a 52020 tumor rejection antigen are used to diagnose or monitor cancerous conditions as is described in more detail infra (see U.S. Pat. Nos. 5,908,778 and 5,763,165 herein incorporated by reference), by monitoring the CTL's in a sample from a subject, binding of antibodies to tumor rejection antigens, or the activity of anti-tumor rejection antigen CTL's in connection with subject samples. Similarly, the expression of nucleic acid molecules encoding tumor rejection antigen precursors's can be monitored via amplification (e.g., polymerase chain reaction (PCR)), anti-sense hybridization, probe technologies, and so forth and described in more detail infra. Various subject samples, including body fluids (e.g., blood, serum, and other exudates), tissues and tumors may be so assayed.

Expression of the 52020 MAGE-like proteins of the invention may distinguish cells of particular tumors from normal cells.

In another embodiment, antagonists or inhibitors of 52020 MAGE-like protein may be administered to a subject to treat or prevent neurodegenerative conditions. Such conditions include, but are not limited to, those brought on by ischemia, epilepsy, convulsions, AIDS-related dementia, Alzheimer's disease, schizophrenia, Alzheimer's and Parkinson's disease, amyotrophic lateral sclerosis, and lathyrism.

In another embodiment, antibodies which specifically bind 52020 MAGE-like protein may be used for the diagnosis of conditions or diseases characterized by expression of 52020 MAGE-like protein, or in assays to monitor patients being treated with 52020 MAGE-like protein agonists, antagonists or inhibitors. The antibodies useful for diagnostic purposes may be prepared in the same manner as those described above for therapeutics and in more detail infra. Diagnostic assays for 52020 MAGE-like protein include methods which utilize the antibody and a label to detect 52020 MAGE-like protein in human body fluids or extracts of cells or tissues. The antibodies may be used with or without modification, and may be labeled by joining them, either covalently or non-covalently, with a reporter molecule. A wide variety of reporter molecules which are known in the art may be used (described in more detail infra).

In another embodiment of the invention, the polynucleotides encoding 52020 MAGE-like protein may be used for diagnostic purposes. The polynucleotides which may be used include oligonucleotide sequences, antisense RNA and DNA molecules, and PNA's. The polynucleotides may be used to detect and quantify gene expression in biopsied tissues in which expression of 52020 MAGE-like may be correlated with disease (see U.S. Pat. No. 6,140,050 herein incorporated by reference). The diagnostic assay may be used to distinguish between absence, presence, and excess expression of 52020 MAGE-like, and to monitor regulation of 52020 MAGE-like levels.

A 52020 polypeptide can include a "MAGE domain" or regions homologous with an "MAGE domain".

As used herein, the term "MAGE domain" includes an amino acid sequence of about 80–208 amino acid residues in length and having a bit score for the alignment of the sequence to the MAGE domain (HMM) of at least 8. Preferably, a MAGE domain includes at least about 208 amino acids and has a bit score for the alignment of the sequence to the MAGE domain (HMM) of at least 16 or greater. The MAGE domain (HMM) has been assigned the PFAM Accession PF01454 (pfam.wustl.edu/). An alignment of the MAGE domain (amino acids 1 to 208 of SEQ ID NO:41) of human 52020 with a consensus amino acid sequence derived from a hidden Markov model is depicted in FIG. 35 and results in a bit score of 127.

In a preferred embodiment 52020 polypeptide or protein has a "MAGE domain" or a region which includes at least about 80–208 more preferably about 208 amino acid residues and has at least about 60%, 70%, 80%, 90%, 95%, 99%, or 100% homology with a "MAGE domain," e.g., the MAGE domain of human 52020 (e.g., amino acid residues 1–208 of SEQ ID NO:41).

To identify the presence of an "MAGE" domain in a 52020 protein sequence, and make the determination that a polypeptide or protein of interest has a particular profile, the amino acid sequence of the protein can be searched against a database of HMMs (e.g., the Pfam database, release 2.1) using the default parameters (sanger.ac.uk/Software/Pfam). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3): 405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, a 52020 protein includes at least one transmembrane domain. As used herein, the term "transmembrane domain" includes an amino acid sequence of about 15 amino acid residues in length that spans a phospholipid membrane. More preferably, a transmembrane domain includes about at least 17, 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, the Pfam website at 7tm_1 (pfam.wustl.edu) and Zagotta W. N. et al. (1996) *Annual Rev. Neuronsci.* 19:235–63, the contents of which are incorporated herein by reference.

In a preferred embodiment, a 52020 polypeptide or protein has at least one transmembrane domain or a region which includes at least 17, 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 52020 (e.g., amino acid residues 172–188 of SEQ ID NO:41).

In another embodiment, a 52020 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 52020, or 52020-like protein.

In a preferred embodiment, a 52020 polypeptide or protein has a "non-transmembrane domain" or a region which includes at least about 1–200, preferably about 100–180, more preferably about 125–175, and even more preferably about 140–171 amino acid residues, and has at least about 60%, 70% 80% 90% 95%, 99% or 100% homology with a "non-transmembrane domain", e.g., a non-transmembrane domain of human 52020 (e.g., residues 1–171 and 188–304 of SEQ ID NO:41). Preferably, a non-transmembrane domain is capable of catalytic activity (e.g., catalyzing an acylation reaction).

A non-transmembrane domain located at the N-terminus of a 52020 protein or polypeptide is referred to herein as an "N-terminal non-transmembrane domain." As used herein, an "N-terminal non-transmembrane domain" includes an amino acid sequence having about 1–200 and preferably about 30–200 amino acid residues and is located outside the boundaries of a membrane. For example, an N-terminal non-transmembrane domain is located at about amino acid residues 1–171 of SEQ ID NO:41.

Similarly, a non-transmembrane domain located at the C-terminus of a 52020 protein or polypeptide is referred to herein as a "C-terminal non-transmembrane domain." As used herein, an "C-terminal non-transmembrane domain" includes an amino acid sequence having about 1–150, preferably about 15–150, preferably about 20–150, more preferably about 30–150 amino acid residues in length and is located outside the boundaries of a membrane. For example, a C-terminal non-transmembrane domain is located at about amino acid residues 189–304 of SEQ ID NO:41.

As the 52020 polypeptides of the invention may modulate 52020-mediated activities, they may be useful as of for developing novel diagnostic and therapeutic agents for 52020-mediated or related disorders, as described below.

As used herein, a "52020 activity", "biological activity of 52020" or "functional activity of 52020", refers to an activity exerted by a 52020 protein, polypeptide or nucleic acid molecule on e.g., a 52020-responsive cell or on a 52020 substrate, e.g., a CTL or protein substrate, as determined in vivo or in vitro. In one embodiment, a 52020 activity is a direct activity, such as an association with a 52020 target molecule. A "target molecule" or "binding partner" is a molecule or cell with which a 52020 protein binds or interacts in nature. A 52020 activity can also be an indirect activity, e.g., a cellular signaling activity mediated by interaction of the 52020 protein with a 52020 ligand. For example, the 52020 proteins of the present invention can have one or more of the following activities: 1) regulation of cellular growth and differentiation; 2) tissue repair; 3) T-cell activation; 4) CTL effector cell function; and 5) elicitation of autoantibodies.

Accordingly, 52020 protein may mediate various disorders, including cancers, tissue repair, neurodegenerative disorders, autoimmune disorders, and inflammatory disorders.

Examples of cellular proliferative and/or differentiative disorders include cancer, e.g., carcinoma, sarcoma, and metastatic disorders. A metastatic tumor can arise from a multitude of primary tumor types, including but not limited to those of colon, lung, breast, ovary, epithelium, and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the lung, breast, head and neck, esophagus, epithelium (especially melanoma), colon, and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

The 52020 molecules can be used to treat and/or diagnose neurodegenerative disorders such as, but not limited to, those brought on by ischemia, epilepsy, convulsions, AIDS-related dementia, Alzheimer's disease, schizophrenia, Alzheimer's and Parkinson's disease, amyotrophic lateral sclerosis, and lathyrism.

The 52020 molecules be used to treat and/or diagnose inflammatory disorders including, but not limited to osteoarthritis and rheumatoid arthritis, multiple sclerosis, Crohn disease, psoriasis, periodontal disease, and asthma; macular degeneration; restenosis; and Alzheimer's disease.

Similarly, aberrant expression and/or activity of 52020 molecules may mediate autoimmune diseases including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

CHAPTER 7

22406, ACYLTRANSFERASE (32447), 7716, 25233, 8035, 84242, 55304, 52999, 21999, AND 52020 COMBINED SPECIFICATION

The 22406, acyltransferase, 7716, 25233, 8035, 84242, 55304, 52999, 21999, and 52020 protein, fragments thereof, and derivatives and other variants of the sequence in SEQ ID NO:2, SEQ ID NO:7, SEQ ID NO:11, SEQ ID NO:15, SEQ ID NO:19, SEQ ID NO:23, SEQ ID NO:27, SEQ ID NO:30, SEQ ID NO:37 and SEQ ID NO:41, respectively, are collectively referred to as "polypeptides or proteins of the invention" or "22406, acyltransferase, 7716, 25233, 8035, 84242, 55304, 52999, and 21999, 52020 polypeptides or proteins". Nucleic acid molecules encoding such polypeptides or proteins are collectively referred to as "nucleic acids of the invention" or "22406, acyltransferase, 7716, 25233, 8035, 84242, 55304, 52999, 21999 and 52020 nucleic acids." 22406, acyltransferase, 7716, 25233, 8035, 84242, 55304, 52999, 21999 and 52020 molecules refer to 22406, acyltransferase, 7716, 25233, 8035, 84242, 55304, 52999, 21999 and 52020 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in Current Protocols in Molecular Biology John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2×SSC, 0.1% SDS at 55° C. A further example of stringent hybridization conditions are hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule that hybridizes under stringent conditions to an acyltransferase-like sequence of the invention corresponds to a naturally-occurring nucleic acid molecule.

Preferably, an isolated nucleic acid molecule of the invention that hybridizes under stringent conditions to the sequence of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:38, SEQ ID NO:40, or SEQ ID NO:42 corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules that include an open reading frame encoding a 22406, acyltransferase, 7716, 25233, 8035, 84242, 55304, 52999, 21999, or 52020 protein, preferably a mammalian 22406, acyltransferase, 7716, 25233, 8035, 84242, 55304, 52999, 21999, or 52020 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means a preparation of 22406, acyltransferase, 7716, 25233, 8035, 84242, 55304, 52999, 21999, or 52020 protein having less than about 30%, 20%, 10% and more preferably 5% (by dry weight), of non-22406, acyltransferase, 7716, 25233, 8035, 84242, 55304, 52999, 21999, or 52020 protein, respectively, (also referred to herein as a "contaminating protein"), or of chemical precursors or non-22406, acyltransferase, 7716, 25233, 8035, 84242, 55304, 52999, 21999, or 52020 chemicals, respectively. When the 22406, acyltransferase, 7716, 25233, 8035, 84242, 55304, 52999, 21999, or 52020 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 22406, acyltransferase, 7716, 25233, or 52020 or of 8035, 84242, 55304, 52999, or 21999 (e.g., the sequence of SEQ ID NO:19, SEQ ID NO:23, SEQ ID NO:27, SEQ ID NO:30, or SEQ ID NO:37) without abolishing or more preferably, without substantially altering a biological activity, whereas an "essential" amino acid residue results in such a change. For example, amino acid residues that are conserved among the 22406 polypeptides of the present invention, e.g., those present in the pyridoxal-phosphate attachment site, are predicted to be particularly unamenable to alteration. Amino acid residues that are conserved among the acyltransferase polypeptides of the present invention, e.g., those present in the fatty acid synthase domain, are predicted to be particularly unamenable to alteration. Amino acid residues that are conserved among the 7716 polypeptides of the present invention, e.g., those present in the ATPase domain, are predicted to be particularly unamenable to alteration. Amino acid residues that are conserved among the 25233 polypeptides of the present invention, e.g., those present in the aminotransferase domain, are predicted to be particularly unamenable to alteration. Amino acid residues that are conserved among the 84242 or 8035 polypeptides of the present invention, e.g., those present in the RING or IBR protein domains, are predicted to be particularly unamenable to alteration. Similarly, amino acid residues that are conserved among the 55304 polypeptides of the present invention, e.g., those present in the aminopeptidase domain, are predicted to be particularly unamenable to alteration. Amino acid residues that are conserved among the 52999 polypeptides of the present invention, in particular those present in the metal-binding active site domain, are also not predicted to be amenable to alteration. Amino acid residues that are conserved among the 21999 polypeptides of the present invention, e.g., those present in the transferase domain, are predicted to be particularly unamenable to alteration, as well. Amino acid residues that are conserved among the 52020 polypeptides of the present invention, e.g., those present in the MAGE domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a 22406, acyltransferase, 7716, 25233, 8035, 84242, 55304, 52999, 21999, or 52020 protein is preferably replaced with another amino acid residue from the same side chain family. Alternatively, in another embodiment, mutations can be introduced randomly along all or part of a 22406, acyltransferase, 7716, 25233, 8035, 84242, 55304, 52999, 21999, or 52020 coding sequence, such as by saturation mutagenesis, and the resultant mutants can be screened for 22406, acyltransferase, 7716, 25233, 8035, 84242, 55304, 52999, 21999, or 52020 biological activity to identify mutants that retain activity. Following mutagenesis of the sequence of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:38, SEQ ID NO:40, or SEQ ID NO:42, the encoded protein can be expressed recombinantly and the activity of the protein can be determined.

As used herein, a "biologically active portion" of a 22406 protein includes a fragment of a 22406 protein which participates in an interaction between a 22406 molecule and a non-22406 molecule. Biologically active portions of a 22406 protein include peptides comprising amino acid sequences sufficiently homologous to or derived from the amino acid sequence of the 22406 protein, e.g., the amino acid sequence shown in SEQ ID NO:2, which include less amino acids than the full length 22406 proteins, and exhibit at least one activity of a 22406 protein. Typically, biologically active portions comprise a domain or motif with at least one activity of the 22406 protein, e.g., pyridoxal-phosphate dependent enzyme family member activity. A biologically active portion of a 22406 protein can be a polypeptide which is, for example, 10, 25, 50, 100, 200 or more amino acids in length. Biologically active portions of a 22406 protein can be used as targets for developing agents which modulate a 22406 mediated activity, e.g., pyridoxal-phosphate dependent enzyme family member activity.

As used herein, a "biologically active portion" of an acyltransferase protein includes a fragment of an acyltransferase protein which participates in an interaction between an acyltransferase molecule and a non-acyltransferase molecule. Biologically active portions of an acyltransferase protein include peptides comprising amino acid sequences sufficiently homologous to or derived from the amino acid sequence of the acyltransferase protein, e.g., the amino acid sequence shown in SEQ ID NO:7, which include less amino acids than the full length acyltransferase proteins, and exhibit at least one activity of an acyltransferase protein. Typically, biologically active portions comprise a domain or motif with at least one activity of the acyltransferase protein, e.g., transfer of an acyl group. A biologically active portion of an acyltransferase protein can be a polypeptide which is, for example, 10, 25, 50, 100, 200 or more amino acids in length. Alternatively, a fragment of a polypeptide of the present invention comprises an amino acid sequence consisting of amino acid residues 1–20, 20–40, 40–60, 60–80, 80–100, 100–120, 120–140, 140–160, 160–180, 180–200, 200–220, 220–240, 240–260, 260–280, 280–300, 300–320, 320–340, 340–360, 360–380, 380–400, 400–420, 420–440, 440–460, 460–480, 480–500, 500–520, 520–540 of SEQ ID NO:7. Biologically active portions of an acyltransferase protein can be used as targets for developing agents which modulate an acyltransferase mediated activity, e.g., fatty acid synthase activity.

As used herein, a "biologically active portion" of a 7716 protein includes a fragment of a 7716 protein which participates in an interaction between a 7716 molecule and a non-7716 molecule. Biologically active portions of a 7716 protein include peptides comprising amino acid sequences sufficiently homologous to or derived from the amino acid sequence of the 7716 protein, e.g., the amino acid sequence shown in SEQ ID NO:11, which include less amino acids than the full length 7716 proteins, and exhibit at least one activity of a 7716 protein. Typically, biologically active portions comprise a domain or motif with at least one activity of the 7716 protein, e.g., ATPase activity. A biologically active portion of a 7716 protein can be a polypeptide which is, for example, 10, 25, 50, 100, 200 or more amino acids in length. Biologically active portions of a 7716 protein can be used as targets for developing agents which modulate a 7716 mediated activity, e.g., ATPase activity.

As used herein, a "biologically active portion" of a 25233 protein includes a fragment of a 25233 protein which participates in an interaction between a 25233 molecule and a non-25233 molecule. Biologically active portions of a 25233 protein include peptides comprising amino acid sequences sufficiently homologous to or derived from the amino acid sequence of the 25233 protein, e.g., the amino acid sequence shown in SEQ ID NO:15, which include less amino acids than the full length 25233 proteins, and exhibit at least one activity of a 25233 protein. Typically, biologically active portions comprise a domain or motif with at least one activity of the 25233 protein, e.g., aminotransferase activity. A biologically active portion of a 25233 protein can be a polypeptide which is, for example, 10, 25, 50, 100, 200 or more amino acids in length. Alternatively, a fragment of a polypeptide of the present invention comprises an amino acid sequence consisting of amino acid residues 1–20, 20–40, 40–60, 60–80, 80–100, 100–120, 120–140, 140–160, 160–180, 180–200, 200–220, 220–240, 240–260, 260–280, 280–300, 300–320, 320–340, 340–360, 360–380, 380–400, 400–420, 420–440, 440–460, 460–480, 480–500, 500–520, or 520–523 of SEQ ID NO:15. Biologically active portions of a 25233 protein can be used as targets for developing agents which modulate a 25233 mediated activity, e.g., aminotransferase activity.

As used herein, a "biologically active portion" of an 8035, 84242, 55304, 52999, or 21999 protein includes a fragment of an 8035, 84242, 55304, 52999, or 21999 protein that participates in an interaction between an 8035, 84242, 55304, 52999, or 21999 molecule and a non-8035, non-84242, non-55304, non-52999, or non-21999 molecule. Biologically active portions of 8035, 84242, 55304, 52999, or 21999 proteins include peptides comprising amino acid sequences sufficiently homologous to or derived from the amino acid sequence of the 8035, 84242, 55304, 52999, or 21999 protein, e.g., the amino acid sequence shown in SEQ ID NO:19, SEQ ID NO:23, SEQ ID NO:27, SEQ ID NO:30, and SEQ ID NO:37, respectively, that include less amino acids than the full length 8035, 84242, 55304, 52999, or 21999 protein, and exhibit at least one activity of an 8035, 84242, 55304, 52999, or 21999 protein. Typically, biologically active portions comprise a domain or motif with at least one activity of the 8035, 84242, 55304, 52999, or 21999 protein, e.g., in the case of 8035, or 84242, RING finger protein activity; in the case of 55304, aminopeptidase protein activity; in the case of 52999, metallopeptidase protein activity; and in the case of 21999, ribosyltransferase activity. A biologically active portion of an 8035, 84242, 55304, 52999, or 21999 protein can be a polypeptide that is, for example, 10, 25, 50, 100, 200 or more amino acids in length. Biologically active portions of an 8035, 84242, 55304, 52999, or 21999 protein can be used as targets for developing agents that modulate an 8035, 84242, 55304, 52999, or 21999 mediated activity, e.g., in the case of 8035 or 84242, RING finger protein activity; in the case of 55304, aminopeptidase protein activity; in the case of 52999, metallopeptidase protein activity; and in the case of 21999, ribosyltransferase activity.

As used herein, a "biologically active portion" of a 52020 protein includes a fragment of a 52020 protein which participates in an interaction between a 52020 molecule and a non-52020 molecule. Biologically active portions of a 52020 protein include peptides comprising amino acid sequences sufficiently homologous to or derived from the amino acid sequence of the 52020 protein, e.g., the amino acid sequence shown in SEQ ID NO:41, which include less amino acids than the full length 52020 proteins, and exhibit at least one activity of a 52020 protein. Typically, biologically active portions comprise a domain or motif with at least one activity of the 52020 protein, e.g., MAGE activity as described herein. A biologically active portion of a 52020 protein can be a polypeptide which is, for example, 5, 6, 7, 8, 9, 10, 11, 12, 13, 14, 15, 25, 50, 100, 200 or more amino acids in length. Biologically active portions of a 52020 protein can be used as targets for developing agents which modulate a 52020 mediated activity, e.g., MAGE activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 22406 amino acid sequence of SEQ ID NO:2 having 340 amino acid residues, at least 102, preferably at least 136, more preferably at least 170, even more preferably at least 204, and even more preferably at least 238, 272, 306 or 340 amino acid residues are aligned; e.g., when aligning a second sequence to the 7716 amino acid sequence of SEQ ID NO:11 having 226 amino acid residues, at least 302, preferably at least 377, more preferably at least 452, even more preferably at least 528, and even more preferably at least 603, 679 or 753 amino acid residues are aligned; e.g., when aligning a second sequence to the 8035 amino acid sequence of SEQ ID NO:19 having 130 amino acid residues, at least 173, preferably at least 217, more preferably at least 260, even more preferably at least 303, and even more preferably at least 346, 390 or 433 amino acid residues are aligned; when aligning a second sequence to the 84242 amino acid sequence of SEQ ID NO:23 having 121 amino acid residues, at least 161, preferably at least 202, more preferably at least 242, even more preferably at least 282, and even more preferably at least 322, 363 or 403 amino acid residues are aligned; when aligning a second sequence to the 55304 amino acid sequence of SEQ ID NO:27 having 204 amino acid residues, at least 272, preferably at least, more preferably at least 340, even more preferably at least 408, and even more preferably at least 544, 612 or 680 amino acid residues are aligned; when aligning a second sequence to the 52999 amino acid sequence of SEQ ID NO:30 having 227 amino acid residues, at least 303, preferably at least 379, more preferably at least 455, even more preferably at least 530, and even more preferably at least 606, 682 or 758 amino acid residues are aligned; and, when aligning a second sequence to the ADP-ribosyltransferase amino acid sequence of SEQ ID NO:37 having 88 amino acid residues, at least 117, preferably at least 146, more preferably at least 177, even more preferably at least 204, and even more preferably at least 234, 263 or 292 amino acid residues are aligned; e.g., when aligning a second sequence to the 52020 amino acid sequence of SEQ ID NO:41 having 91 amino acid residues, at least 122, preferably at least 152, more preferably at least 182, even more preferably at least 213, and even more preferably at least 243, 24 or 304 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at the bioinformatics page of the website maintained by Accelrys, Inc., San Diego, Calif., USA), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403–10. BLAST nucleotide searches can be performed with the NBLAST program, score=100, wordlength=12 to obtain nucleotide sequences homologous to 22406, acyltransferase, 7716, 25233, 8035, 84242, 55304, 52999, 21999, or 52020 nucleic acid molecules of the invention. BLAST protein searches can be performed with the XBLAST program, score=50, wordlength=3 to obtain amino acid sequences homologous to 22406, acyltransferase, 7716, 25233, 8035, 84242, 55304, 52999, 21999, or 52020 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA).

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, isolated or purified, nucleic acid molecules that encode a 22406, acyltransferase, 7716, 25233, 8035, 84242, 55304, 52999, 21999, or 52020 polypeptide described herein, e.g., a full length 22406, acyltransferase, 7716, 25233, 8035, 84242, 55304, 52999, 21999, or 52020 protein or a fragment thereof, e.g., a biologically active portion of 22406, acyltransferase, 7716, 25233, 8035, 84242, 55304, 52999, 21999, or 52020 protein. Also included are nucleic acid fragments suitable for use as a hybridization probes, that can be used, e.g., to identify a nucleic acid molecule encoding a polypeptide of the invention, 22406, acyltransferase, 7716, 25233, 8035, 84242, 55304, 52999, 21999, or 52020 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of these nucleotide sequences. In one embodiment, the nucleic acid molecule includes sequences encoding the human 22406 protein (i.e., "the coding region", from nucleotides 69–1088 of SEQ ID NO:1, not including the terminal codon), as well as 5' untranslated sequences (nucleotides 1–68 of SEQ ID NO:1).

Alternatively, the nucleic acid molecule can include only the coding region of SEQ ID NO:1 (e.g., nucleotides 69–1088 of SEQ ID NO:1, corresponding to SEQ ID NO:3) and, e.g., no flanking sequences which normally accompany the subject sequence. In another embodiment, the nucleic acid molecule encodes a sequence corresponding to the mature protein of SEQ ID NO:2.

In one embodiment, an isolated nucleic acid molecule of the invention includes the nucleotide sequence shown in SEQ ID NO:6, or a portion of any of these nucleotide sequences. In one embodiment, the nucleic acid molecule includes sequences encoding the human acyltransferase protein (i.e., "the coding region", from nucleotides of SEQ ID NO:6, not including the terminal codon), as well as 5' untranslated sequences (nucleotides of SEQ ID NO:6). Alternatively, the nucleic acid molecule can include only the coding region of SEQ ID NO:6 (e.g., nucleotides of SEQ ID NO:6). and e.g., no flanking sequences which normally accompany the subject sequence. In another embodiment, the nucleic acid molecule encodes a sequence corresponding to the mature protein of SEQ ID NO:7.

In one embodiment, an isolated nucleic acid molecule of the invention includes the nucleotide sequence shown in SEQ ID NO:10, SEQ ID NO:12, or a portion of any of these nucleotide sequences. In one embodiment, the nucleic acid molecule includes sequences encoding the human 7716 protein (i.e., "the coding region", from nucleotides 63–2321 of SEQ ID NO:10, not including the terminal codon), as well as 5' untranslated sequences (nucleotides 1–62 of SEQ ID NO:10). Alternatively, the nucleic acid molecule can include only the coding region of SEQ ID NO: 10 (e.g., nucleotides 63–2321 of SEQ ID NO:10, corresponding to SEQ ID NO:12) and, e.g., no flanking sequences which normally accompany the subject sequence. In another embodiment, the nucleic acid molecule encodes a sequence corresponding to the mature protein of SEQ ID NO:11.

In one embodiment, an isolated nucleic acid molecule of the invention includes the nucleotide sequence shown in SEQ ID NO:14, or a portion of any of these nucleotide sequences. In one embodiment, the nucleic acid molecule includes sequences encoding the human 25233 protein (i.e., "the coding region", from nucleotides 94 to 1662 of SEQ ID NO:14, not including the terminal codon), as well as 5' untranslated sequences (nucleotides 1–93 of SEQ ID NO:14). Alternatively, the nucleic acid molecule can include only the coding region of SEQ ID NO:14 (e.g., nucleotides 94 to 1662 of SEQ ID NO:14, corresponding to SEQ ID NO:16) and, e.g., no flanking sequences which normally accompany the subject sequence. In another embodiment, the nucleic acid molecule encodes a sequence corresponding to the mature protein of SEQ ID NO: 15.

In one embodiment, an isolated nucleic acid molecule of the invention includes the nucleotide sequence shown in SEQ ID NO:18, or a portion of any of these nucleotide sequences. In one embodiment, an isolated nucleic acid molecule of the invention includes the nucleotide sequence shown in SEQ ID NO:22, or a portion of any of these nucleotide sequences. In one embodiment, the nucleic acid molecule includes sequences encoding the human 8035 protein (i.e., "the coding region", from nucleotides 613–1914 of SEQ ID NO:18), as well as 5' untranslated sequences (nucleotides 1–612 of SEQ ID NO: 18). In one embodiment, the nucleic acid molecule includes sequences encoding the human 84242 protein (i.e., "the coding region", from nucleotides 744–1038 of SEQ ID NO:22), as well as 5' untranslated sequences (nucleotides 1–743 of SEQ ID NO:22). Alternatively, the nucleic acid molecule can include only the coding region of SEQ ID NO:18 or SEQ ID NO:22 (e.g., nucleotides 613–1914 of SEQ ID NO:18, corresponding to SEQ ID NO:20, and nucleotides 744–1955 of SEQ ID NO:22, corresponding to SEQ ID NO:24, respectively) and, e.g., no flanking sequences which normally accompany the subject sequence. In another embodiment, the nucleic acid molecule encodes a sequence corresponding to the mature protein of SEQ ID NO:19 or SEQ ID NO:23.

In one embodiment, an isolated nucleic acid molecule of the invention includes the nucleotide sequence shown in SEQ ID NO:26, or a portion of any of these nucleotide sequences. In one embodiment, the nucleic acid molecule includes sequences encoding the human 55304 protein (i.e., "the coding region", from nucleotides 803–2845 of SEQ ID NO:26), as well as 5' untranslated sequences (nucleotides 1–802 of SEQ ID NO:26). Alternatively, the nucleic acid molecule can include only the coding region of SEQ ID NO:26 (e.g., nucleotides 803–2845 of SEQ ID NO:26, corresponding to SEQ ID NO:28) and, e.g., no flanking sequences which normally accompany the subject sequence. In another embodiment, the nucleic acid molecule encodes a sequence corresponding to the mature protein of SEQ ID NO:27.

In one embodiment, an isolated nucleic acid molecule of the invention includes the nucleotide sequence shown in SEQ ID NO:29, or a portion of any of these nucleotide sequences. In one embodiment, the nucleic acid molecule includes sequences encoding the human 52999 protein (i.e., "the coding region", from nucleotides 194–2470 of SEQ ID NO:29), as well as 5' untranslated sequences (nucleotides 1–193 of SEQ ID NO:29). Alternatively, the nucleic acid molecule can include only the coding region of SEQ ID NO:29 (e.g., nucleotides 194–2470 of SEQ ID NO:29, corresponding to SEQ ID NO:31) and, e.g., no flanking sequences which normally accompany the subject sequence. In another embodiment, the nucleic acid molecule encodes a sequence corresponding to the mature protein of SEQ ID NO:30.

In one embodiment, an isolated nucleic acid molecule of the invention includes the nucleotide sequence shown in SEQ ID NO:36, or a portion of any of these nucleotide sequences. In one embodiment, the nucleic acid molecule includes sequences encoding the human ADP-ribosyltransferase protein (i.e., "the coding region", from nucleotides 255 to 1133 of SEQ ID NO:36), as well as 5' untranslated sequences of SEQ ID NO:36. Alternatively, the nucleic acid molecule can include only the coding region of SEQ ID NO:36 and, e.g., no flanking sequences which normally accompany the subject sequence. In another embodiment, the nucleic acid molecule encodes a sequence corresponding to the mature protein of SEQ ID NO:37.

In one embodiment, an isolated nucleic acid molecule of the invention includes the nucleotide sequence shown in SEQ ID NO:40, or a portion of any of these nucleotide sequences. In one embodiment, the nucleic acid molecule includes sequences encoding the human 52020 protein (i.e., "the coding region", from nucleotides 782–1693 of SEQ ID NO:40, not including the terminal codon), as well as 5' untranslated sequences (nucleotides 1–781 of SEQ ID NO:40). Alternatively, the nucleic acid molecule can include only the coding region of SEQ ID NO:40 (e.g., nucleotides 782–1693 of SEQ ID NO:40, corresponding to SEQ ID NO:42) and, e.g., no flanking sequences which normally accompany the subject sequence. In another embodiment, the nucleic acid molecule encodes a sequence corresponding to the mature protein of SEQ ID NO:41.

In another embodiment, an isolated nucleic acid molecule of the invention includes a nucleic acid molecule which is a complement of the nucleotide sequence shown in SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:38, SEQ ID NO:40, or SEQ ID NO:42, or a portion of any of these nucleotide sequences. In other embodiments, the nucleic acid molecule of the invention is sufficiently complementary to the nucleotide sequence shown in SEQ ID NO:1, SEQ ID NO:3, SEQ ID NO:6, SEQ ID NO:8, SEQ ID NO:10, SEQ ID NO:12, SEQ ID NO:14, SEQ BD NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:38, SEQ ID NO:40, or SEQ ID NO:42, such that it can hybridize to the nucleotide sequences shown in SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ BD NO:28, SEQ ID NO:29, SEQ ID NO:31, SEQ ID NO:36, SEQ ID NO:38, SEQ ID NO:40, or SEQ ID NO:42, thereby forming a stable duplex.

In one embodiment, an isolated nucleic acid molecule of the present invention includes a nucleotide sequence which is at least about 95%, 96%, 97%, 98%, 99%, or more homologous to the nucleotide sequence shown in SEQ ID NO:1 or SEQ ID NO:3. In the case of an isolated nucleic acid molecule which is longer than or equivalent in length to the reference sequence, e.g., SEQ ID NO:1, or SEQ ID NO:3, the comparison is made with the full length of the reference sequence. Where the isolated nucleic acid molecule is shorter than the reference sequence, e.g., shorter than SEQ ID NO:1, or SEQ ID NO:3, the comparison is made to a segment of the reference sequence of the same length (excluding any loop required by the homology calculation).

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:29, or SEQ ID NO:31, SEQ ID NO:36, SEQ ID NO:40 or SEQ ID NO:42. In the case of an isolated nucleic acid molecule which is longer than or equivalent in length to the reference sequence, e.g., SEQ ID NO:6, SEQ ID NO:10, or SEQ ID NO:12, SEQ ID NO:14 or SEQ ID NO:16, SEQ ID NO:18 or SEQ ID NO:20, and SEQ ID NO:22 or SEQ ID NO:24, SEQ ID NO:29, or SEQ ID NO:31, SEQ ID NO:36, SEQ ID NO:40, SEQ ID NO:42, the comparison is made with the full length of the reference sequence. Where the isolated nucleic acid molecule is shorter than the reference sequence, e.g., shorter than SEQ ID NO:6, SEQ ID NO:10, or SEQ ID NO:12, SEQ ID NO:14 or SEQ ID NO:16, SEQ ID NO:18 or SEQ ID NO:20, and SEQ ID NO:22 or SEQ ID NO:24, SEQ ID NO:29, or SEQ ID NO:31, SEQ ID NO:36, SEQ ID NO:40, SEQ ID NO:42, the comparison is made to a segment of the reference sequence of the same length (excluding any loop required by the homology calculation).

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:26 or SEQ ID NO:28. In the case of an isolated nucleic acid molecule which is longer than or equivalent in length to the reference sequence, e.g., SEQ ID NO:26, or SEQ ID NO:28, the comparison is made with the full length of the reference sequence. Where the isolated nucleic acid molecule is shorter than the reference sequence, e.g., shorter than SEQ ID NO:26, or SEQ ID NO:28, the comparison is made to a segment of the reference sequence of the same length (excluding any gap required by the alignment calculation).

22406 Nucleic Acid Fragments

A nucleic acid molecule of the invention can include only a portion of the nucleic acid sequence of SEQ ID NO:1 or SEQ ID NO:3. For example, such a nucleic acid molecule can include a fragment which can be used as a probe or primer or a fragment encoding a portion of a 22406 protein, e.g., an immunogenic or biologically active portion of a 22406 protein. A fragment can comprise: nucleotides 19–315 of SEQ ID NO:1, which encodes an pyridoxal-phosphate dependent enzyme family member domain of human 22406. Alternatively, a fragment can comprise: nucleotides 47–60 of SEQ ID NO:1, which encodes an pyridoxal-phosphate attachment site of human 22406. The nucleotide sequence determined from the cloning of the 22406 gene allows for the generation of probes and primers designed for use in identifying and/or cloning other 22406 family members, or fragments thereof, as well as 22406 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an pyridoxal-phosphate dependent enzyme family member domain. In a preferred embodiment the fragment is at least, 50, 100, 200, 300, 400, 500, 600, 700, or 885 base pairs in length.

22406 probes and primers are provided. Typically a probe/primer is an isolated or purified oligonucleotide. The oligonucleotide typically includes a region of nucleotide sequence that hybridizes under stringent conditions to at least about 15, 20, 25, 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In one embodiment the nucleic acid is a probe which is at least 5, 10, 20 or 30, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a 22406 pyridoxal-phosphate dependent enzyme family member domain (e.g., about amino acid residues 19–315 of SEQ ID NO:2).

In another embodiment a set of primers is provided, e.g., primers suitable for use in a PCR, which can be used to amplify a selected region of a 22406 sequence, e.g., a region described herein. The primers should be at least 5, 10, 20, 30, or 50 base pairs in length and less than 100, or less than 200, base pairs in length. The primers should be identical, or differs by one base from a sequence disclosed herein or from a naturally occurring variant; e.g., primers suitable for amplifying all or a portion of any of the following regions are provided: a 22406 pyridoxal-phosphate dependent enzyme family member domain (e.g., about amino acid residues 19–315 of SEQ ID NO:2).

A nucleic acid fragment can encode an epitope bearing region of a polypeptide described herein.

A nucleic acid fragment encoding a "biologically active portion of a 22406 polypeptide" can be prepared by isolating a portion of the nucleotide sequence of SEQ ID NO:1 or SEQ ID NO:3, which encodes a polypeptide having a 22406 biological activity (e.g., the biological activities of the 22406 proteins as described herein), expressing the encoded portion of the 22406 protein (e.g., by recombinant expression in vitro) and assessing the activity of the encoded portion of the 22406 protein. For example, a nucleic acid fragment encoding a biologically active portion of 22406 includes a pyridoxal-phosphate dependent enzyme family member domain (e.g., about amino acid residues 19–315 of SEQ ID NO:2). A nucleic acid fragment encoding a biologically active portion of a 22406 polypeptide, may comprise a nucleotide sequence which is greater than 300–885 or more nucleotides in length.

In preferred embodiments, nucleic acids include a nucleotide sequence which is about 100, 200, 300, 400, 500, 600, 700, 800, 900, 1000, 1100, 1200, 1300, 1400, 1500, 1600, 1700 nucleotides in length and hybridizes under stringent hybridization conditions to a nucleic acid molecule of SEQ ID NO:1 or SEQ ID NO:3. A fragment of a nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1770 of SEQ ID NO:1.

Acyltransferase Nucleic Acid Fragments

A nucleic acid molecule of the invention can include only a portion of the nucleic acid sequence of SEQ ID NO:6. For example, such a nucleic acid molecule can include a fragment which can be used as a probe or primer or a fragment encoding a portion of an acyltransferase protein, e.g., an immunogenic or biologically active portion of an acyltransferase protein. A fragment can comprise nucleotides of SEQ ID NO:6, which encode a domain or active site of the native human acyltransferase. The nucleotide sequence determined from the cloning of the acyltransferase gene allows for the generation of probes and primers designed for use in identifying and/or cloning other acyltransferase family members, or fragments thereof, as well as acyltransferase homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an acyltransferase. In a preferred embodiment the fragment is at least, 50, 100, 200, 300, 400, 500, 600, 700, 900, 1000, 1100, 1200, 1300, 1400, 1500, or 1600 base pairs in length.

Acyltransferase probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:6 or SEQ ID NO:8, or of a naturally occurring allelic variant or mutant of SEQ ID NO:6 or SEQ ID NO:8.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an acyltransferase domain.

In another embodiment a set of primers is provided, e.g., primers suitable for use in a PCR, which can be used to amplify a selected region of an acyltransferase sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: an acyltransferase domain (e.g., about amino acid residues of SEQ ID NO:7).

A nucleic acid fragment can encode an epitope bearing region of a polypeptide described herein.

A nucleic acid fragment encoding a "biologically active portion of an acyltransferase polypeptide" can be prepared by isolating a portion of the nucleotide sequence of SEQ ID NO:6, which encodes a polypeptide having an acyltransferase biological activity (e.g., the biological activities of the acyltransferase proteins as described herein), expressing the encoded portion of the acyltransferase protein (e.g., by recombinant expression in vitro) and assessing the activity of the encoded portion of the acyltransferase protein. For example, a nucleic acid fragment encoding a biologically active portion of acyltransferase includes an fatty acid synthase domain (e.g., about amino acid residues of SEQ ID NO:7). A nucleic acid fragment encoding a biologically active portion of an acyltransferase polypeptide, may comprise a nucleotide sequence which is greater than 300–1400 or more nucleotides in length.

In preferred embodiments, nucleic acids include a nucleotide sequence which is about 300, 400, 500, 600, 700, 800, 900, 1000, 1100, 1200, 1300, 1400, 1500, 1600, 1700, 1800, or 1900 nucleotides in length and hybridizes under stringent hybridization conditions to a nucleic acid molecule of SEQ ID NO:6.

7716 Nucleic Acid Fragments

A nucleic acid molecule of the invention can include only a portion of the nucleic acid sequence of SEQ ID NO:10 or SEQ ID NO:12. For example, such a nucleic acid molecule can include a fragment which can be used as a probe or primer or a fragment encoding a portion of a 7716 protein, e.g., an immunogenic or biologically active portion of a 7716 protein. A fragment can comprise: nucleotides 706–1263 or 1498–2115 of SEQ ID NO:10, each of which encodes an ATPase domain of human 7716. The nucleotide sequence determined from the cloning of the 7716 gene allows for the generation of probes and primers designed for use in identifying and/or cloning other 7716 family members, or fragments thereof, as well as 7716 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an ATPase domain. In a preferred embodiment the fragment is at least, 50, 100, 200, 300, 400, 500, 600, 700, or 900 base pairs in length.

7716 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:10 or SEQ ID NO: 12, or of a naturally occurring allelic variant or mutant of SEQ ID NO:10 or SEQ ID NO:12.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an ATPase domain (e.g., about amino acid residues 236–421 or 500–705 of SEQ ID NO:11).

In another embodiment a set of primers is provided, e.g., primers suitable for use in a PCR, which can be used to amplify a selected region of a 7716 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: an ATPase domain (e.g., about amino acid residues 236–421 or 500–705 of SEQ ID NO:11).

A nucleic acid fragment can encode an epitope bearing region of a polypeptide described herein.

A nucleic acid fragment encoding a "biologically active portion of a 7716 polypeptide" can be prepared by isolating a portion of the nucleotide sequence of SEQ ID NO:10 or SEQ ID NO:12, which encodes a polypeptide having a 7716 biological activity (e.g., the biological activities of the 7716 proteins as described herein), expressing the encoded portion of the 7716 protein (e.g., by recombinant expression in vitro) and assessing the activity of the encoded portion of the 7716 protein. For example, a nucleic acid fragment encoding a biologically active portion of 7716 includes an ATPase domain (e.g., about amino acid residues 236–421 or 500–705 of SEQ ID NO:11). A nucleic acid fragment encoding a biologically active portion of a 7716 polypeptide, may comprise a nucleotide sequence which is greater than 300–1200 or more nucleotides in length.

In preferred embodiments, nucleic acids include a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, or 2600 nucleotides in length and hybridizes under stringent hybridization conditions to a nucleic acid molecule of SEQ ID NO:10 or SEQ ID NO:12.

25233 Nucleic Acid Fragments

A nucleic acid molecule of the invention can include only a portion of the nucleic acid sequence of SEQ ID NO:14 or SEQ ID NO:16. For example, such a nucleic acid molecule can include a fragment which can be used as a probe or primer or a fragment encoding a portion of a 25233 protein, e.g., an immunogenic or biologically active portion of a 25233 protein. A fragment can comprise: nucleotides 339–1644 of SEQ ID NO:14, which encodes an aminotransferase domain of human 25233. The nucleotide sequence determined from the cloning of the 25233 gene allows for the generation of probes and primers designed for use in identifying and/or cloning other 25233 family members, or fragments thereof, as well as 25233 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an aminotransferase domain. In a preferred embodiment the fragment is at least 15, 20, 50, 100, 200, 300, 400, 500, 600, 700, or 900 base pairs in length. Alternatively, a nucleic acid molecules that is a fragment of a 25233-like nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1800, 1800–1900, 1900–2000, 2000–2100, or 2100–2127 of SEQ ID NO:14 or nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, or 1500–1572 of SEQ ID NO:16.

25233 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:14 or SEQ ID NO:16, or of a naturally occurring allelic variant or mutant of SEQ ID NO:14 or SEQ ID NO:16.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an aminotransferase domain (e.g., about nucleotides 339–1644 of SEQ ID NO:14 or nucleotides 247–1551 of SEQ ID NO:16).

In another embodiment a set of primers is provided, e.g., primers suitable for use in a PCR, which can be used to amplify a selected region of a 25233 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: a nucleic acid encoding an aminotransferase domain (e.g., about nucleic acid residues 339–1644 of SEQ ID NO:14 or 247–1551 of SEQ ID NO:16).

A nucleic acid fragment can encode an epitope bearing region of a polypeptide described herein.

A nucleic acid fragment encoding a "biologically active portion of a 25233 polypeptide" can be prepared by isolating a portion of the nucleotide sequence of SEQ ID NO:14 or SEQ ID NO:16, which encodes a polypeptide having a 25233 biological activity (e.g., the biological activities of the 25233 proteins as described herein), expressing the encoded portion of the 25233 protein (e.g., by recombinant expression in vitro) and assessing the activity of the encoded portion of the 25233 protein. For example, a nucleic acid fragment encoding a biologically active portion of 25233 includes an aminotransferase domain (e.g., about nucleic acid residues 339–1644 of SEQ ID NO:14 or 247–1551 of SEQ ID NO:16). A nucleic acid fragment encoding a biologically active portion of a 25233 polypeptide, may comprise a nucleotide sequence which is greater than 300–1200 or more nucleotides in length.

In preferred embodiments, nucleic acids include a nucleotide sequence which is about 400, 600, 800, 1000, 1200, 1400, 1600, 1700, 1800, 1900, 2000, 2100, or 2127 nucleotides in length and hybridizes under stringent hybridization conditions to a nucleic acid molecule of SEQ ID NO:14, or SEQ ID NO:16.

8035 and 84242 Nucleic Acid Fragments

A nucleic acid molecule of the invention can include only a portion of the nucleic acid sequence of SEQ ID NO:18, SEQ ID NO:20, SEQ ID NO:22 or SEQ ID NO:24. For example, such a nucleic acid molecule can include a fragment which can be used as a probe or primer or a fragment encoding a portion of an 8035 or 84242 protein, e.g., an immunogenic or biologically active portion of an 8035 or 84242 protein. A fragment can comprise nucleotides 1750–1875 of SEQ ID NO:18, that encodes a RING finger protein domain of human 8035. A fragment can comprise nucleotides 837–1038 of SEQ ID NO:22, that encodes an IBR protein domain of human 84242. The nucleotide sequences determined from the cloning of the 8035 and 84242 genes allow for the generation of probes and primers designed for use in identifying and/or cloning other 8035 and 84242 family members, or fragments thereof, as well as 8035 and 84242 homologues, or fragments thereof, from other species.

In another embodiment, a nucleic acid includes a nucleotide sequence that includes part, or all, of the coding regions and extends into either (or both) the 5' or 3' non-coding regions. Other embodiments include a fragment that includes a nucleotide sequence encoding an amino acid fragment described herein. Nucleic acid fragments can encode a specific domain or site described herein or fragments thereof, or fragments comprising a specific domain or site described herein that are at least 150 amino acids in length. Fragments also include nucleic acid sequences corresponding to specific amino acid sequences described above or fragments thereof. Nucleic acid fragments should not be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include a RING finger protein domain and/or an IBR protein domain. In a preferred embodiment the fragment is at least, 50, 75, 100, 125, 150, 200, 250, 300, 400, 500, 600, 700, 900, 1100, 1200 or 1300 base pairs in length.

8035 and 84242 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:18, SEQ ID NO:20, of SEQ ID NO:22 or SEQ ID NO:24, or of a naturally occurring allelic variant or mutant of SEQ ID NO:18, SEQ ID NO:20, of SEQ ID NO:22 or SEQ ID NO:24.

In a preferred embodiment the nucleic acid is a probe that is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid that encodes a RING finger protein domain and/or an IBR protein domain (e.g., about amino acid residues 380–421 of SEQ ID NO:19 and about amino acid residues 2–67 or 102–133 of SEQ ID NO:23).

In another embodiment a set of primers is provided, e.g., primers suitable for use in a PCR, which can be used to amplify a selected region of an 8035 or 84242 sequence, e.g., a region described herein. The primers should be at least 5, 10, or 50 base pairs in length and less than 100, or less than 200, base pairs in length. The primers should be identical, or differ by one base from a sequence disclosed herein or from a naturally occurring variant. E.g., primers suitable for amplifying all or a portion of any of the following regions are provided: a RING finger protein domain (e.g., about amino acid residues 380–421 of SEQ ID NO:19; an IBR protein domain (e.g., about amino acid residues 2–67 of SEQ ID NO:23).

A nucleic acid fragment can encode an epitope bearing region of a polypeptide described herein.

A nucleic acid fragment encoding a "biologically active portion of an 8035 or 84242 polypeptide" can be prepared by isolating a portion of the nucleotide sequence of SEQ ID NO:18, SEQ ID NO:20, SEQ ID NO:22 or SEQ ID NO:24, that encodes a polypeptide having an 8035 or 84242 biological activity (e.g., the biological activities of the 8035 and 84242 proteins as described herein), expressing the encoded portion of the 8035 or 84242 protein (e.g., by recombinant expression in vitro) and assessing the activity of the encoded portion of the 8035 or 84242 protein. For example, a nucleic acid fragment encoding a biologically active portion of 8035 includes an RING finger protein domain (e.g., about amino acid residues 380–421 of SEQ ID NO:19). A nucleic acid fragment encoding a biologically active portion of an 8035 polypeptide, may comprise a nucleotide sequence which is greater than 125–1200 or more nucleotides in length. For example, a nucleic acid fragment encoding a biologically active portion of 84242 includes an IBR domain and/or a RING finger protein domain (e.g., about amino acid residues 2–67 and 102–133 of SEQ ID NO:23, respectively). A nucleic acid fragment encoding a biologically active portion of an 84242 polypeptide, may comprise a nucleotide sequence which is greater than 125–1200 or more nucleotides in length.

In preferred embodiments, nucleic acids include a nucleotide sequence which is about 125, 150, 200, 300, 500, 600, 700, 800, 900, 1000, 1100, 1200, 1300, or 1302 nucleotides in length in the case of 8035 and which is about 125, 150, 200, 300, 500, 600, 700, 800, 900, 1000, 1100, 1200, or 1212 nucleotides in length in the case of 84242 and hybridizes under stringent hybridization conditions to a nucleic acid molecule of SEQ ID NO:18, SEQ ID NO:20, SEQ ID NO:22 or SEQ ID NO:24.

55304 Nucleic Acid Fragments

A nucleic acid molecule of the invention can include only a portion of the nucleic acid sequence of SEQ ID NO:26 or SEQ ID NO:28. For example, such a nucleic acid molecule can include a fragment which can be used as a probe or primer or a fragment encoding a portion of a 55304 protein, e.g., an immunogenic or biologically active portion of a 55304 protein. A fragment can comprise: nucleotides 803–2845 of SEQ ID NO:26, which encodes an aminopeptidase domain of human 55304. The nucleotide sequence determined from the cloning of the 55304 gene allows for the generation of probes and primers designed for use in identifying and/or cloning other 55304 family members, or fragments thereof, as well as 55304 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an Aminopeptidase domain. In a preferred embodiment the fragment is at least, 50, 100, 200, 300, 400, 500, 600, 700, 800, 900, 1000, or 1500 base pairs in length.

55304 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:26 or SEQ ID NO:28, or of a naturally occurring allelic variant or mutant of SEQ ID NO:26 or SEQ ID NO:28.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an Aminopeptidase domain (e.g., about amino acid residues 318–508 of SEQ ID NO:27).

In another embodiment a set of primers is provided, e.g., primers suitable for use in a PCR, which can be used to amplify a selected region of a 55304 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: an Aminopeptidase domain (e.g., about amino acid residues 318–508 of SEQ ID NO:27).

A nucleic acid fragment can encode an epitope bearing region of a polypeptide described herein.

A nucleic acid fragment encoding a "biologically active portion of a 55304 polypeptide" can be prepared by isolating a portion of the nucleotide sequence of SEQ ID NO:26 or SEQ ID NO:28, which encodes a polypeptide having a 55304 biological activity (e.g., the biological activities of the 55304 proteins as described herein), expressing the encoded portion of the 55304 protein (e.g., by recombinant expression in vitro) and assessing the activity of the encoded portion of the 55304 protein. For example, a nucleic acid fragment encoding a biologically active portion of 55304 includes an aminopeptidase domain (e.g., about amino acid residues 318–508 of SEQ ID NO:27). A nucleic acid fragment encoding a biologically active portion of a 55304 polypeptide, may comprise a nucleotide sequence which is greater than 300–1200 or more nucleotides in length.

In preferred embodiments, nucleic acids include a nucleotide sequence which is about 300, 400, 500, 600, 700, 800, 900, 1000, 1100, 1200, 1300, 1400, 1500, 1600, 1700, 1800, 1900, 2000, or 2043 nucleotides in length and hybridizes under stringent hybridization conditions to a nucleic acid molecule of SEQ ID NO:26 or SEQ ID NO:28.

52999 Nucleic Acid Fragments

A nucleic acid molecule of the invention can include only a portion of the nucleic acid sequence of SEQ ID NO:29 or SEQ ID NO:31. For example, such a nucleic acid molecule can include a fragment which can be used as a probe or primer or a fragment encoding a portion of a 52999 protein, e.g., an immunogenic or biologically active portion of a 52999 protein. A fragment can comprise all or a portion of the nucleotides from about nucleotide 253–2086 of SEQ ID NO:29, that encode a polypeptide hydrolytic domain of human 52999. The nucleotide sequence determined from the cloning of the 52999 gene allows for the generation of probes and primers designed for use in identifying and/or cloning other 52999 family members, or fragments thereof, as well as 52999 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a region or functional site described herein. A nucleic acid fragment can also include one or more regions or functional sites described herein. Thus, for example, a nucleic acid fragment can include a polypeptide hydrolytic domain or a conserved region or motif. In a preferred embodiment the fragment is at least 50, 100, 200, 400, 600, 800, 1000, 1200, 1400, 1600, 1800 or more base pairs in length.

52999 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:29 or SEQ ID NO:31, or of a naturally occurring allelic variant or mutant of SEQ ID NO:29 or SEQ ID NO:31.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a portion of an endopepdidase domain (e.g., about amino acid residues 21–631 of SEQ ID NO:30).

In another embodiment a set of primers is provided, e.g., primers suitable for use in a PCR, which can be used to amplify a selected region of a 52999 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of a polypeptide hydrolytic domain (e.g., about amino acid residues 21–631 of SEQ ID NO:30).

A nucleic acid fragment can encode an epitope bearing region of a polypeptide described herein.

A nucleic acid fragment encoding a "biologically active portion of a 52999 polypeptide" can be prepared by isolating a portion of the nucleotide sequence of SEQ ID NO:29 or SEQ ID NO:31, which encodes a polypeptide having a 52999 biological activity (e.g., the biological activities of the 52999 proteins as described herein), expressing the encoded portion of the 52999 protein (e.g., by recombinant expression in vitro) and assessing the activity of the encoded portion of the 52999 protein. For example, a nucleic acid fragment encoding a biologically active portion of 52999 may include a polypeptide hydrolytic domain (e.g., about amino acid residues 21–631 of SEQ ID NO:30). A nucleic acid fragment encoding a biologically active portion of a 52999 polypeptide, may comprise a nucleotide sequence that is 300–1800 or more nucleotides in length.

In preferred embodiments, nucleic acids include a nucleotide sequence that is about 300, 400, 500, 600, 700, 800, 900, 1000, 1100, 1200, 1300, 1400, 1600, 1800, 2000, 2200 or 2277 nucleotides in length and hybridizes under stringent hybridization conditions to a nucleic acid molecule of SEQ ID NO:29 or SEQ ID NO:31.

21999 Nucleic Acid Fragments

A nucleic acid molecule of the invention can include only a portion of the nucleic acid sequence of SEQ ID NO:36. For example, such a nucleic acid molecule can include a fragment which can be used as a probe or primer or a fragment encoding a portion of a ADP-ribosyltransferase protein, e.g., an immunogenic or biologically active portion of a ADP-ribosyltransferase protein. A fragment can comprise nucleotide sequences which code for a portion of the ADP-ribosyltransferase protein of SEQ ID NO:37 and retains biological activity. The nucleotide sequence determined from the cloning of the ADP-ribosyltransferase gene allows for the generation of probes and primers designed for use in identifying and/or cloning other ADP-ribosyltransferase family members, or fragments thereof, as well as ADP-ribosyltransferase homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. In a preferred embodiment the fragment is at least, 50, 100, 200, 300, 400, 500, 600, 700, or 900 base pairs in length.

ADP-ribosyltransferase probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:36, or of a naturally occurring allelic variant or mutant of SEQ ID NO:36.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a fragment of SEQ ID NO:37.

In another embodiment a set of primers is provided, e.g., primers suitable for use in a PCR, which can be used to amplify a selected region of a ADP-ribosyltransferase sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the region of SEQ ID NO:37 are provided.

A nucleic acid fragment can encode an epitope bearing region of a polypeptide described herein.

A nucleic acid fragment encoding a "biologically active portion of a ADP-ribosyltransferase polypeptide" can be prepared by isolating a portion of the nucleotide sequence of SEQ ID NO:36, which encodes a polypeptide having a ADP-ribosyltransferase biological activity (e.g., the biological activities of the ADP-ribosyltransferase proteins as described herein), expressing the encoded portion of the ADP-ribosyltransferase protein (e.g., by recombinant expression in vitro) and assessing the activity of the encoded portion of the ADP-ribosyltransferase protein.

In preferred embodiments, nucleic acids include a nucleotide sequence which is about 300, 400, 500, 600, 700, 800, or 879 nucleotides in length and hybridizes under stringent hybridization conditions to a nucleic acid molecule of SEQ ID NO:36.

52020 Nucleic Acid Fragments

A nucleic acid molecule of the invention can include only a portion of the nucleic acid sequence of SEQ ID NO:40 or SEQ ID NO:42. For example, such a nucleic acid molecule can include a fragment which can be used as a probe or primer or a fragment encoding a portion of a 52020 protein, e.g., an immunogenic or biologically active portion of a 52020 protein, e.g., such as tumor rejection antigen. A fragment can comprise: nucleotides 1–208 of SEQ ID NO:40, which encodes an MAGE domain of human 52020. The nucleotide sequence determined from the cloning of the 52020 gene allows for the generation of probes and primers designed for use in identifying and/or cloning other 52020 family members, or fragments thereof, as well as 52020 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an MAGE domain. In a preferred embodiment the fragment is at least, 50, 100, 200, 300, 400, 500, 600, 700, or 900 base pairs in length.

52020 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:40 or SEQ ID NO:42, or of a naturally occurring allelic variant or mutant of SEQ ID NO:40 or SEQ ID NO:42.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a MAGE domain (e.g., about amino acid residues 1–208 of SEQ ID NO:41).

In another embodiment a set of primers is provided, e.g., primers suitable for use in a PCR, which can be used to amplify a selected region of a 52020 sequence, e.g., a region described herein. The primers should be at least 5, 10, or 50 base pairs in length and less than 100, or less than 200, base pairs in length. The primers should be identical, or differs by one base from a sequence disclosed herein or from a naturally occurring variant. E.g., primers suitable for amplifying all or a portion of any of the following regions are provided: a MAGE domain (e.g., about amino acid residues 1–208 of SEQ ID NO:41).

A nucleic acid fragment can encode an epitope bearing region of a polypeptide described herein.

A nucleic acid fragment encoding a "biologically active portion of a 52020 polypeptide" can be prepared by isolating a portion of the nucleotide sequence of SEQ ID NO:40 or SEQ ID NO:42, which encodes a polypeptide having a 52020 biological activity (e.g., the biological activities of the 52020 proteins as described herein), expressing the encoded portion of the 52020 protein (e.g., by recombinant expression in vitro) and assessing the activity of the encoded portion of the 52020 protein. For example, a nucleic acid fragment encoding a biologically active portion of 52020 includes a MAGE domain (e.g., about amino acid residues 1–208 of SEQ ID NO:41). A nucleic acid fragment encoding a biologically active portion of a 52020 polypeptide, may comprise a nucleotide sequence which is about 300–900 or more nucleotides in length. In another embodiment a nucleic acid fragment of a 52020 polynucleotide may encode a biologically active polypeptide that functions as a tumor rejection antigen. This nucleic acid fragment may comprise a nucleotide sequence of SEQ ID NO:42 consisting of 5, 6, 7, 8, 9, 10, 11, 12, 13, 14, 15, 16, 17, 18, 19, 20, 25 or more nucleic acid residues.

In other embodiments, the nucleic acid fragments may include nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1800, 1800–1900, 1900–2000, 200–2100, or 2100–2183 of SEQ ID NO:40. In other embodiments, nucleic acids include a nucleotide sequence that is about 300, 400, 500, 600, 700, 800, 900, 1000, 1100, 1200, 1300, 1400, 1500, 1600, 1700, 1800, 1900, 2000, 2100, or 2183 nucleotides in length and hybridizes under stringent hybridization conditions to a nucleic acid molecule of SEQ ID NO:40 or SEQ ID NO:42.

Nucleic Acid Variants

The invention further encompasses nucleic acid molecules that differ from the nucleotide sequence shown in SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:40, or SEQ ID NO:42. Such differences can be due to degeneracy of the genetic code (and result in a nucleic acid which encodes the same 22406, acyltransferase, 7716, 25233, 8035, 84242, 55304, 52999, ADP-ribosyltransferase, or 52020 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues than that that is shown in SEQ ID NO:2, SEQ ID NO:7, SEQ ID NO:11, SEQ ID NO:15, SEQ ID NO:19, SEQ ID NO:23, SEQ ID NO:27, SEQ ID NO:30, SEQ ID NO:37 or SEQ ID NO:41. If alignment is needed for this comparison the sequences should be aligned for maximum homology. "Looped" out sequences from deletions or insertions, or mismatches, are considered differences.

Nucleic acids of the invention can be chosen for having codons, which are preferred, or non preferred, for a particular expression system. E.g., the nucleic acid can be one in which at least one codon, preferably at least 10%, or 20% of the codons have been altered such that the sequence is optimized for expression in E. coli, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:40, or SEQ ID NO:42, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is at least about 95%, 96%, 97%, 98%, 99% or more identical to the amino acid sequence shown in SEQ ID NO:2 or a fragment of this sequence. Such nucleic acid molecules can readily be obtained as being able to hybridize under stringent conditions, to the nucleotide sequence shown in SEQ ID NO:3 or a fragment of this sequence. Nucleic acid molecules corresponding to orthologs, homologs, and allelic variants of the 22406 cDNAs of the invention can further be isolated by mapping to the same chromosome or locus as the 22406 gene. Preferred variants include those that are correlated with pyridoxal-phosphate dependent racemase activity.

Allelic variants of 22406, e.g., human 22406, include both functional and non-functional proteins. Functional allelic variants are naturally occurring amino acid sequence variants of the 22406 protein within a population that maintain the ability to form D-serine from L-serine. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 22406, e.g., human 22406, protein within a population that do not have the ability to form D-serine from L-serine. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:7 or a fragment of this sequence. Nucleic acid molecules corresponding to orthologs, homologs, and allelic variants of the acyltransferase cDNAs of the invention can further be isolated by mapping to the same chromosome or locus as the acyltransferase gene. Preferred variants include those that are correlated with fatty acid synthase activity.

Allelic variants of acyltransferase, e.g., human acyltransferase, include both functional and non-functional proteins. Functional allelic variants are naturally occurring amino acid sequence variants of the acyltransferase protein within a population that maintain the ability to modulate the phosphorylation state of itself or another protein or polypeptide. Functional allelic variants will typically contain only conservative substitution of one or more amino acids of SEQ ID NO:7, or substitution, deletion or insertion of non-critical residues in non-critical regions of the protein. Non-functional allelic variants are naturally-occurring amino acid sequence variants of the acyltransferase, e.g., human acyltransferase, protein within a population that do not have the ability to attach an acyl chain to a lipid precursor. Non-functional allelic variants will typically contain a non-conservative substitution, a deletion, or insertion, or premature truncation of the amino acid sequence of SEQ ID NO:7, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:11 or a fragment of this sequence. Such nucleic acid molecules can readily be obtained as being able to hybridize under stringent conditions, to the nucleotide sequence shown in SEQ ID NO:12 or a fragment of this sequence. Nucleic acid molecules corresponding to orthologs, homologs, and allelic variants of the 7716 cDNAs of the invention can further be isolated by mapping to the same chromosome or locus as the 7716 gene. Preferred variants include those that are correlated with ATPase activity.

Allelic variants of 7716, e.g., human 7716, include both functional and non-functional proteins. Functional allelic variants are naturally occurring amino acid sequence variants of the 7716 protein within a population that maintain the ability to hydrolyze ATP. Functional allelic variants will typically contain only conservative substitution of one or more amino acids of SEQ ID NO:11, or substitution, deletion or insertion of non-critical residues in non-critical regions of the protein. Non-functional allelic variants are naturally-occurring amino acid sequence variants of the 7716, e.g., human 7716, protein within a population that do not have the ability to hydrolyze ATP. Non-functional allelic variants will typically contain a non-conservative substitution, a deletion, or insertion, or premature truncation of the amino acid sequence of SEQ ID NO:11, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, 65%, preferably about 75%, 85%, 95%, or 98% identical to SEQ ID NO:15 or a fragment of this sequence. Such nucleic acid molecules can readily be obtained as being able to hybridize under stringent conditions, to the nucleotide sequence shown in SEQ ID NO:16 or a fragment of this sequence. Nucleic acid molecules corresponding to orthologs, homologs, and allelic variants of the 25233 cDNAs of the invention can further be isolated by mapping to the same chromosome or locus as the 25233 gene. Preferred variants include those that are correlated with aminotransferase activity.

Allelic variants of 25233, e.g., human 25233, include both functional and non-functional proteins. Functional allelic variants are naturally occurring amino acid sequence variants of the 25233 protein within a population that maintain the ability to catalyze transamination, decarboxylation, deamination, racemization, or aldol cleavage reactions. Functional allelic variants will typically contain only conservative substitution of one or more amino acids of SEQ ID NO:15, or substitution, deletion or insertion of non-critical residues in non-critical regions of the protein. Non-functional allelic variants are naturally-occurring amino acid sequence variants of the 25233, e.g., human 25233, protein within a population that do not have the ability to catalyze transamination, decarboxylation, deamination, racemization, or aldol cleavage reactions. Non-functional allelic variants will typically contain a non-conservative substitution, a deletion, or insertion, or premature truncation of the amino acid sequence of SEQ ID NO:15, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:19 or SEQ ID NO:23, or fragments of these sequences. Such nucleic acid molecules can readily be obtained as being able to hybridize under stringent conditions, to the nucleotide sequence shown in SEQ ID NO:20 or SEQ ID NO:24, or fragments of these sequences. Nucleic acid molecules corresponding to orthologs, homologs, and allelic variants of the 8035 and 84242 cDNAs of the invention can further be isolated by mapping to the same chromosome or locus as the 8035 or 84242 gene. Preferred variants include those that are correlated with RING finger protein activity (E3 ubiquitin ligase activity), e.g. variants that comprise nucleotide sequences encoding polypeptides that share identity to the amino acid sequence shown in SEQ ID NO:19 or SEQ ID NO:23 or a fragment of these sequences retain RING finger protein activity (E3 ubiquitin ligase activity).

Allelic variants of 8035 and 84242, e.g., human 8035 and 84242, include both functional and non-functional proteins. Functional allelic variants are naturally occurring amino acid sequence variants of the 8035 and 84242 proteins within a population that maintain the ability to function as E3 ubiquitin ligases. Functional allelic variants will typically contain only conservative substitution of one or more amino acids of SEQ ID NO:19 or SEQ ID NO:23 or substitution, deletion, or insertion of non-critical residues in non-critical regions of these proteins. Non-functional allelic variants are naturally-occurring amino acid sequence variants of 8035 and 84242, e.g., human 8035 and 84242, proteins within a population that do not have the ability function as E3 ubiquitin ligases. Non-functional allelic variants will typically contain a non-conservative substitution, a deletion, or insertion, or premature truncation of the amino acid sequence of SEQ ID NO:19 or SEQ ID NO:23, or a substitution, insertion, or deletion in critical residues or critical regions of these proteins.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:27 or a fragment of this sequence. Such nucleic acid molecules can readily be obtained as being able to hybridize under stringent conditions, to the nucleotide sequence shown in SEQ ID NO:28 or a fragment of this sequence. Nucleic acid molecules corresponding to orthologs, homologs, and allelic variants of the 55304 cDNAs of the invention can further be isolated by mapping to the same chromosome or locus as the 55304 gene. Preferred variants include those that are correlated with aminopeptidase activity.

Allelic variants of 55304, e.g., human 55304, include both functional and non-functional proteins. Functional allelic variants are naturally occurring amino acid sequence variants of the 55304 protein within a population that maintain the ability to hydrolyse the amino terminal amino acid from a peptide substrate. Functional allelic variants will typically contain only conservative substitution of one or more amino acids of SEQ ID NO:27, or substitution, deletion or insertion of non-critical residues in non-critical regions of the protein. Non-functional allelic variants are naturally-occurring amino acid sequence variants of the 55304, e.g., human 55304, protein within a population that do not have the ability to remove the amino terminal amino acid from a peptide substrate. Non-functional allelic variants will typically contain a non-conservative substitution, a deletion, or insertion, or premature truncation of the amino acid sequence of SEQ ID NO:27, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:30 or a fragment of this sequence. Such nucleic acid molecules can readily be obtained as being able to hybridize under stringent conditions, to the nucleotide sequence shown in SEQ ID NO:31 or a fragment of this sequence. Nucleic acid molecules corresponding to orthologs, homologs, and allelic variants of the 52999 cDNAs of the invention can further be isolated by mapping to the same chromosome or locus as the 52999 gene. Preferred variants include those that are correlated with metallopeptidase activity, e.g. variants that comprise nucleotide sequences encoding polypeptides that share identity to the amino acid sequence shown in SEQ ID NO: 30 or a fragment of this sequence retain metallopeptidase activity.

Allelic variants of 52999, e.g., human 52999, include both functional and non-functional proteins. Functional allelic variants are naturally occurring amino acid sequence variants of the 52999 protein within a population that maintain polypeptide hydrolytic activity. Functional allelic variants will typically contain only conservative substitution of one or more amino acids of SEQ ID NO:30, or substitution, deletion or insertion of non-critical residues in non-critical regions of the protein. Non-functional allelic variants are naturally-occurring amino acid sequence variants of the 52999, e.g., human 52999, protein within a population that do not have the ability to catalyze the cleavage of polypeptide bonds. Non-functional allelic variants will typically contain a non-conservative substitution, a deletion, or insertion, or premature truncation of the amino acid sequence of SEQ ID NO:30, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:37 or a fragment of this sequence. Such nucleic acid molecules can readily be obtained as being able to hybridize under stringent conditions, to the nucleotide sequence shown in SEQ ID NO:36 or a fragment of this sequence. Nucleic acid molecules corresponding to orthologs, homologs, and allelic variants of the ADP-ribosyltransferase cDNAs of the invention can further be isolated by mapping to the same chromosome or locus as the ADP-ribosyltransferase gene.

Allelic variants of ADP-ribosyltransferase, e.g., human ADP-ribosyltransferase, include both functional and non-functional proteins. Functional allelic variants are naturally occurring amino acid sequence variants of the ADP-ribosyltransferase protein within a population that maintain the ability to transfer an ADP-ribose moiety to an acceptor protein. Functional allelic variants will typically contain only conservative substitution of one or more amino acids of SEQ ID NO:37, or substitution, deletion or insertion of non-critical residues in non-critical regions of the protein. Non-functional allelic variants are naturally-occurring amino acid sequence variants of the ADP-ribosyltransferase, e.g., human ADP-ribosyltransferase, protein within a population that do not have the ability to transfer an ADP-ribose moiety to an acceptor protein. Non-functional allelic variants will typically contain a non-conservative substitution, a deletion, or insertion, or premature truncation of the amino acid sequence of SEQ ID NO:37, or a substitution, insertion, or deletion in critical residues or critical regions of the protein.

Orthologs, homologs, and allelic variants can be identified using methods known in the art. These variants comprise a nucleotide sequence encoding a polypeptide that is 50%, at least about 55%, typically at least about 70% or 75%, more typically at least about 80% or 85%, and most typically at least about 90%, 95%, 96%, 97%, 98% or 94% or more identical to the amino acid sequence shown in SEQ ID NO:41 or a fragment of this sequence. Such nucleic acid molecules can readily be obtained as being able to hybridize under stringent conditions, to the nucleotide sequence shown in SEQ ID NO:42 or a fragment of this sequence. Nucleic acid molecules corresponding to orthologs, homologs, and allelic variants of the 52020 cDNAs of the invention can further be isolated by mapping to the same chromosome or locus as the 52020 gene. Preferred variants include those that are correlated with MAGE activity.

Allelic variants of 52020, e.g., human 52020, include both functional and non-functional proteins. Functional allelic variants are naturally occurring amino acid sequence variants of the 52020 protein within a population that maintain the activity of 52020 MAGE-like protein as described herein and possess the amino acid sequence conservation with SEQ ID NO:41 as described in the previous paragraph. Functional allelic variants will typically contain only conservative substitution of one or more amino acids of SEQ ID NO:41, or substitution, deletion or insertion of non-critical residues in non-critical regions of the protein. Non-functional allelic variants are naturally-occurring amino acid sequence variants of the 52020, e.g., human 52020, protein within a population that do not retain 52020 MAGE-like protein activity. Non-functional allelic variants will typically contain a non-conservative substitution, a deletion, or insertion, or premature truncation of the amino acid sequence of SEQ ID NO:41, or a substitution, insertion, or deletion in critical residues or critical regions of the protein.

Moreover, nucleic acid molecules encoding other 22406, acyltransferase, 7716, 25233, 8035, 84242, 55304, 52999, ADP-ribosyltransferase, or 52020 family members and, thus, which have a nucleotide sequence which differs from the 22406, acyltransferase, 7716, 25233, 8035, 84242, 55304, 52999, ADP-ribosyltransferase, or 52020 sequences of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:40, SEQ ID NO:42, are intended to be within the scope of the invention.

Antisense Nucleic Acid Molecules, Ribozymes and Modified 22406, Acyltransferase, 7716, 25233, 8035, 84242, 55304, 52999, 21999, or 52020 Nucleic Acid Molecules In another aspect, the invention features, an isolated nucleic acid molecule which is antisense to 22406, acyltransferase, 7716, 25233, 8035, 84242, 55304, 52999, 21999, or 52020. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 22406, acyltransferase, 7716, 25233, 8035, 84242, 55304, 52999, 21999, or 52020 coding strand, or to only a portion thereof (e.g., the coding region of human 22406, acyltransferase, 7716, 25233, 8035, 84242, 55304, 52999, 21999, or 52020 corresponding to SEQ ID NO:3, SEQ ID NO:8, SEQ ID NO:12, SEQ ID NO:16, SEQ ID NO:20, SEQ ID NO:24, SEQ ID NO:28, SEQ ID NO:31, SEQ ID NO:38, SEQ ID NO:42, respectively). In another embodiment, the antisense nucleic acid molecule is antisense to a "noncoding region" of the coding strand of a nucleotide sequence encoding 22406, acyltransferase, 7716, 25233, 8035, 84242, 55304, 52999, 21999, or 52020 (e.g., the 5' and 3' untranslated regions).

An antisense nucleic acid can be designed such that it is complementary to the entire coding region of 22406, acyltransferase, 7716, 25233, 8035, 84242, 55304, 52999, 21999, or 52020 mRNA, but more preferably is an oligonucleotide which is antisense to only a portion of the coding or noncoding region of 22406, acyltransferase, 7716, 25233, 8035, 84242, 55304, 52999, 21999, or 52020 mRNA. For example, the antisense oligonucleotide can be complementary to the region surrounding the translation start site of 22406, acyltransferase, 7716, 25233, 8035, 84242, 55304, 52999, 21999, or 52020 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 22406, acyltransferase, 7716, 25233, 8035, 84242, 55304, 52999, 21999, or 52020 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215: 327–330).

In still another embodiment, an antisense nucleic acid of the invention is a ribozyme. A ribozyme having specificity for a 22406, acyltransferase, 7716, 25233, 8035, 84242, 55304, 52999, 21999, or 52020-encoding nucleic acid can include one or more sequences complementary to the nucleotide sequence of a 22406, acyltransferase, 7716, 25233, 8035, 84242, 55304, 52999, 21999, or 52020 cDNA disclosed herein (i.e., the sequence of SEQ ID NO:1, SEQ ID NO:3, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:36, SEQ ID NO:38, SEQ ID NO:40, or SEQ ID NO:42), and a sequence having known catalytic sequence responsible for mRNA cleavage (see U.S. Pat. No. 5,093, 246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 22406, acyltransferase, 7716, 25233, 8035, 84242, 55304, 52999, 21999, or 52020-encoding mRNA. See, e.g., Cech et al. U.S. Pat. No. 4,987,071; and Cech et al. U.S. Pat. No. 5,116,742. Alternatively, 22406, acyltransferase, 7716, 25233, 8035, 84242, 55304, 52999, 21999, or 52020 mRNA can be used to select a catalytic RNA having a specific ribonuclease activity from a pool of RNA molecules. See, e.g., Bartel, D. and Szostak, J. W. (1993) *Science* 261:1411–1418.

22406, acyltransferase, 7716, 25233, 8035, 84242, 55304, 52999, 21999, or 52020 gene expression can be inhibited by targeting nucleotide sequences complementary to the regulatory region of the 22406, acyltransferase, 7716, 25233, 8035, 84242, 55304, 52999, 21999, or 52020 (e.g., the 22406, acyltransferase, 7716, 25233, 8035, 84242, 55304, 52999, 21999, or 52020 promoter and/or enhancers) to form triple helical structures that prevent transcription of the 22406, acyltransferase, 7716, 25233, 8035, 84242, 55304, 52999, 21999, or 52020 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992 *Bioassays* 14(12):807–15. The potential sequences that can be targeted for triple helix formation can be increased by creating a so-called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 22406, acyltransferase, 7716, 25233, 8035, 84242, 55304, 52999, 21999, or 52020 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93:14670–675.

PNAs of 22406, acyltransferase, 7716, 25233, 8035, 84242, 55304, 52999, 21999, or 52020 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 22406, acyltransferase, 7716, 25233, 8035, 84242, 55304, 52999, 21999, or 52020 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 22406, acyltransferase, 7716, 25233, 8035, 84242, 55304, 52999, 21999, or 52020 nucleic acid of the invention, two complementary regions one having a fluorophore and one a quencher such that the molecular beacon is useful for quantitating the presence of the 22406, acyltransferase, 7716, 25233, 8035, 84242, 55304, 52999, 21999, or 52020 nucleic acid of the invention in a sample. Molecular beacon nucleic acids are described, for example, in Lizardi et al. U.S. Pat. No. 5,854,033; Nazarenko et al. U.S. Pat. No. 5,866,336, and Livak et al. U.S. Pat. No. 5,876,930.

Isolated 22406 Polypeptides

In another aspect, the invention features, an isolated 22406 protein, or fragment, e.g., a biologically active portion, for use as immunogens or antigens to raise or test (or more generally to bind) anti-22406 antibodies. 22406 protein can be isolated from cells or tissue sources using standard protein purification techniques. 22406 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 22406 polypeptide has one or more of the following characteristics:

(i) it has the ability to form D-serine from L-serine;

(ii) it has a molecular weight, e.g., a deduced molecular weight, amino acid composition or other physical characteristic of the polypeptide of SEQ ID NO:2;

(iii) it has an overall sequence identity of at least 95%, 96%, 97%, 98%, or 99%, with a polypeptide of SEQ ID NO:2;

(iv) it has an pyridoxal-phosphate dependent enzyme family member domain which preferably has an overall sequence identity of about 70%, 80%, 90% or 95% with amino acid residues 19–315 of SEQ ID NO:2;

(v) it has a pyridoxal-phosphate attachment site conserved sequence as described herein; and (vi) it has at least 70%, preferably 80%, and most preferably 95% of the cysteines found amino acid sequence of the native protein.

In a preferred embodiment the 22406 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the pyridoxal-phosphate dependent enzyme family member domain. In another preferred embodiment one or more differences are in non-active site residues, e.g. outside of the pyridoxal-phosphate dependent enzyme family member domain.

Other embodiments include a protein that contain one or more changes in amino acid sequence, e.g., a change in an amino acid residue which is not essential for activity. Such 22406 proteins differ in amino acid sequence from SEQ ID NO:2, yet retain biological activity.

In one embodiment, a biologically active portion of a 22406 protein includes an pyridoxal-phosphate dependent enzyme family member domain. In another embodiment, a biologically active portion of a 22406 protein includes a pyridoxal-phosphate attachment site domain. Moreover, other biologically active portions, in which other regions of the protein are deleted, can be prepared by recombinant techniques and evaluated for one or more of the functional activities of a native 22406 protein.

In a preferred embodiment, the 22406 protein has an amino acid sequence shown in SEQ ID NO:2. In other embodiments, the 22406 protein is substantially identical to SEQ ID NO:2. In yet another embodiment, the 22406 protein is substantially identical to SEQ ID NO:2 and retains the functional activity of the protein of SEQ ID NO:2, as described in detail above. Accordingly, in another embodiment, the 22406 protein is a protein which includes an amino acid sequence at least about 95%, 96%, 97%, 98%, 99%, or more identical to SEQ ID NO:2.

Isolated Acyltransferase Polypeptides

In another aspect, the invention features, an isolated acyltransferase protein, or fragment, e.g., a biologically active portion, for use as immunogens or antigens to raise or test (or more generally to bind) anti-acyltransferase antibodies. Acyltransferase protein can be isolated from cells or tissue sources using standard protein purification techniques. Acyltransferase protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, an acyltransferase polypeptide has one or more of the following characteristics:

(i) it is involved in transfer of an acyl group from Acyl-Co onto a substrate;

(ii) it has a molecular weight, e.g., a deduced molecular weight, amino acid composition or other physical characteristic of the polypeptide of SEQ ID NO:7;

(iii) it has an overall sequence similarity of at least 50%, preferably at least 60%, more preferably at least 70, 80, 90, or 95%, with a polypeptide of SEQ ID NO:7;

(iv) it has an acyltransferase active site which preferably has an overall sequence similarity of about 70%, 80%, 90% or 95% with amino acid residues 200–216 of SEQ ID NO:7;

In a preferred embodiment the acyltransferase protein, or fragment thereof, differs from the corresponding sequence in SEQ ID NO:7. In one embodiment it differs by at least one but by less than 15, 10 or 5 amino acid residues. In another it differs from the corresponding sequence in SEQ ID NO:7 by at least one residue but less than 20%, 15%, 10% or 5% of the residues in it differ from the corresponding sequence in SEQ ID NO:7. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the fatty acid synthase domain. In another preferred embodiment one or more differences are in non-active site residues, e.g. outside of the fatty acid synthase domain.

Other embodiments include a protein that contain one or more changes in amino acid sequence, e.g., a change in an amino acid residue which is not essential for activity. Such acyltransferase proteins differ in amino acid sequence from SEQ ID NO:7, yet retain biological activity.

In one embodiment, a biologically active portion of an acyltransferase protein includes an fatty acid synthase domain. In another embodiment, a biologically active portion of an acyltransferase protein includes a domain. Moreover, other biologically active portions, in which other regions of the protein are deleted, can be prepared by recombinant techniques and evaluated for one or more of the functional activities of a native acyltransferase protein.

In a preferred embodiment, the acyltransferase protein has an amino acid sequence shown in SEQ ID NO:7. In other embodiments, the acyltransferase protein is substantially identical to SEQ ID NO:7. In yet another embodiment, the acyltransferase protein is substantially identical to SEQ ID NO:7 and retains the functional activity of the protein of SEQ ID NO:7, as described in detail above. Accordingly, in another embodiment, the acyltransferase protein is a protein which includes an amino acid sequence at least about 60%, 65%, 70%, 75%, 80%, 85%, 90%, 95%, 98% or more identical to SEQ ID NO:7.

Isolated 7716 Polypeptides

In another aspect, the invention features, an isolated 7716 protein, or fragment, e.g., a biologically active portion, for use as immunogens or antigens to raise or test (or more generally to bind) anti-7716 antibodies. 7716 protein can be isolated from cells or tissue sources using standard protein purification techniques. 7716 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 7716 polypeptide has one or more of the following characteristics:

(i) it hydrolyzes ATP;

(ii) it has a molecular weight, e.g., a deduced molecular weight, amino acid composition or other physical characteristic of the polypeptide of SEQ ID NO:11;

(iii) it has an overall sequence identity of at least 50%, preferably at least 60%, more preferably at least 70, 80, 90, or 95%, with a polypeptide of SEQ ID NO:11;

(iv) it has an ATPase domain which preferably has an overall sequence identity of about 70%, 80%, 90%, 91%, 92%, 93%, 94%, 95%, 96%, 97%, 98% or 99% with amino acid residues 236–421 or 500–705 of SEQ ID NO:11;

(v) it has at least 70%, preferably 80%, and most preferably 95% of the cysteines found amino acid sequence of the native protein.

In a preferred embodiment the 7716 protein, or fragment thereof, differs from the corresponding sequence in SEQ ID NO:11. In one embodiment it differs by at least one but by less than 15, 10 or 5 amino acid residues. In another it differs from the corresponding sequence in SEQ ID NO:11 by at least one residue but less than 20%, 15%, 10% or 5% of the residues in it differ from the corresponding sequence in SEQ ID NO:11. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the ATPase domain. In another preferred embodiment one or more differences are in non-active site residues, e.g. outside of the ATPase domain.

Other embodiments include a protein that contain one or more changes in amino acid sequence, e.g., a change in an amino acid residue which is not essential for activity. Such 7716 proteins differ in amino acid sequence from SEQ ID NO:11, yet retain biological activity.

In one embodiment, a biologically active portion of a 7716 protein includes an ATPase domain. In another embodiment, a biologically active portion of a 7716 protein includes a ATP Binding Protease/ATP-dependent cell division protein domain. Moreover, other biologically active portions, in which other regions of the protein are deleted, can be prepared by recombinant techniques and evaluated for one or more of the functional activities of a native 7716 protein.

In a preferred embodiment, the 7716 protein has an amino acid sequence shown in SEQ ID NO:11. In other embodiments, the 7716 protein is substantially identical to SEQ ID NO:11. In yet another embodiment, the 7716 protein is substantially identical to SEQ ID NO:11 and retains the functional activity of the protein of SEQ ID NO:11, as described in detail above. Accordingly, in another embodiment, the 7716 protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:11.

Isolated 25233 Polypeptides

In another aspect, the invention features, an isolated 25233 protein, or fragment, e.g., a biologically active portion, for use as immunogens or antigens to raise or test (or more generally to bind) anti-25233 antibodies. 25233 protein can be isolated from cells or tissue sources using standard protein purification techniques. 25233 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 25233 polypeptide has one or more of the following characteristics:

(i) it is capable of catalyzing a transamination, decarboxylation, deamination, racemization, or aldol cleavage reaction;

(ii) it has a molecular weight, e.g., a deduced molecular weight, amino acid composition or other physical characteristic of the polypeptide of SEQ ID NO:15;

(iii) it has an overall sequence identity of at least 50%, preferably at least 60%, more preferably at least 70, 80, 90, 91, 92, 93, 94, 95, 96, 97, 98, or 99%, with a polypeptide of SEQ ID NO:15;

(iv) it has an aminotransferase domain which preferably has an overall sequence identity of about 70%, 80%, 90% or 95% with amino acid residues 83–517 of SEQ ID NO:15;

(v) it has at least 70%, preferably 80%, and most preferably 95% of the cysteines found in the amino acid sequence of the native protein.

In a preferred embodiment the 25233 protein, or fragment thereof, differs from the corresponding sequence in SEQ ID NO:15. In one embodiment it differs by at least one but by less than 15, 10 or 5 amino acid residues. In another it differs from the corresponding sequence in SEQ ID NO:15 by at least one residue but less than 20%, 15%, 10% or 5% of the residues in it differ from the corresponding sequence in SEQ ID NO:15. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the aminotransferase domain. In another preferred embodiment one or more differences are in non-active site residues, e.g. outside of the aminotransferase domain.

Other embodiments include a protein that contain one or more changes in amino acid sequence, e.g., a change in an amino acid residue which is not essential for activity. Such 25233 proteins differ in amino acid sequence from SEQ ID NO:15, yet retain biological activity.

In one embodiment, a biologically active portion of a 25233 protein includes an aminotransferase domain. Moreover, other biologically active portions, in which other regions of the protein are deleted, can be prepared by recombinant techniques and evaluated for one or more of the functional activities of a native 25233 protein.

In a preferred embodiment, the 25233 protein has an amino acid sequence shown in SEQ ID NO:15. In other embodiments, the 25233 protein is substantially identical to SEQ ID NO:15. In yet another embodiment, the 25233 protein is substantially identical to SEQ ID NO:15 and retains the functional activity of the protein of SEQ ID NO:15, as described in detail above. Accordingly, in another embodiment, the 25233 protein is a protein which includes an amino acid sequence at least about 60%, 65%, 70%, 75%, 80%, 85%, 90%, 91%, 92%, 93%, 94%, 95%, 96%, 97%, 98%, or 99% or more identical to SEQ ID NO:15.

Isolated 8035 and 84242 Polypeptides

In another aspect, the invention features, an isolated 8035 or 84242 protein, or fragment, e.g., a biologically active portion, for use as immunogens or antigens to raise or test (or more generally to bind) anti-8035 or anti-84242 antibodies. 8035 and 84242 protein can be isolated from cells or tissue sources using standard protein purification techniques. 8035 and 84242 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, an 8035 or 84242 polypeptide has one or more of the following characteristics:

(i) it functions as an E3 ubiquitin ligase;

(ii) it has a molecular weight, e.g., a deduced molecular weight, amino acid composition or other physical characteristic of the polypeptide of SEQ ID NO:19 or SEQ ID NO:23;

(iii) it has an overall sequence identity of at least 50%, preferably at least 60%, more preferably at least 70, 80, 90, 91%, 92%, 93%, 94%, 95%, 96%, 97%, 98%, or 99%, with a polypeptide of SEQ ID NO:19 or SEQ ID NO:23;

(iv) it has at least one RING finger protein domain and/or an IBR protein domain which preferably have an overall sequence identity of about 70%, 80%, 90% or 95% with amino acid residues 380–421 of SEQ ID NO:19 (RING), amino acid residues 2–67 of SEQ ID NO:23 (IBR), or amino acid residues 102–133 of SEQ ID NO:23 (RING);

(v) it has at least 70%, preferably 80%, and most preferably 95% of the cysteines found in the amino acid sequence of the native proteins.

In a preferred embodiment the 8035 or 84242 protein, or fragments thereof, differs from the corresponding sequence in SEQ ID NO:19 or SEQ ID NO:23, respectively. In one embodiment it differs by at least 1 but by less than 15, 10 or 5 amino acid residues. In another it differs from the corresponding sequence in SEQ ID NO:19 or SEQ ID NO:23 by at least 1 residue but less than 20%, 15%, 10% or 5% of the residues in it differ from the corresponding sequence in SEQ ID NO:19 or SEQ ID NO:23. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the RING finger protein domain. In another preferred embodiment one or more differences are in non-active site residues, e.g. outside of the RING finger protein domain.

Other embodiments include proteins that contain one or more changes in amino acid sequence, e.g., a change in an amino acid residue which is not essential for activity. Such 8035 and 84242 proteins differ in amino acid sequence from SEQ ID NO:19 and SEQ ID NO:23, yet retain biological activity.

In one embodiment, a biologically active portion of an 8035 or 84242 protein includes a RING finger protein domain. In another embodiment, a biologically active portion of an 8035 or 84242 protein includes an IBR protein domain and a RING finger protein domain. Moreover, other biologically active portions, in which other regions of the proteins are deleted, can be prepared by recombinant techniques and evaluated for one or more of the functional activities of a native 8035 or 84242 protein.

In a preferred embodiment, the 8035 or 84242 protein has an amino acid sequence shown in SEQ ID NO:19 or SEQ ID NO:23, respectively. In other embodiments, the 8035 or 84242 protein is substantially identical to SEQ ID NO:19 or SEQ ID NO:23, respectively. In yet another embodiment, the 8035 or 84242 protein is substantially identical to SEQ ID NO:19 or SEQ ID NO:23 and retains the functional activity of the protein of SEQ ID NO:19 or SEQ ID NO:23, respectively, as described in detail above. Accordingly, in another embodiment, the 8035 or 84242 protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:19 or SEQ ID NO:23, respectively.

Isolated 55304 Polypeptides

In another aspect, the invention features, an isolated 55304 protein, or fragment, e.g., a biologically active portion, for use as immunogens or antigens to raise or test (or more generally to bind) anti-55304 antibodies. 55304 protein can be isolated from cells or tissue sources using standard protein purification techniques. 55304 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 55304 polypeptide has one or more of the following characteristics:

(i) it catalyzes the removal of an amino terminal amino acid from a peptide substrate;

(ii) it has a molecular weight, e.g., a deduced molecular weight, amino acid composition or other physical characteristic of the polypeptide of SEQ ID NO:27;

(iii) it has an overall sequence identity of at least 50%, preferably at least 60%, more preferably at least 70, 80, 90, 91%, 92%, 93%, 94%, 95%, 96%, 97%, 98%, or 99%, with a polypeptide of SEQ ID NO:27 as determined using the preferred algorithm described elsewhere herein;

(iv) it has an aminopeptidase domain which preferably has an overall sequence identity of about 68%, 75%, 81%, 87.5% or 93% with amino acid residues 318, 336, 344, 346, 363, 374, 397, 399, 410, 411, 412, 425, 448, 450, 489, and 508 of SEQ ID NO:27, i.e. 11, 12, 13, 14, or 15 of these amino acids are conserved between the 5304 protein and the corresponding residues of the amino acid sequence set forth in SEQ ID NO:27;

(v) it has at least 70%, preferably 80%, and most preferably 95% of the cysteines found amino acid sequence of the native protein.

In a preferred embodiment the 55304 protein, or fragment thereof, differs from the corresponding sequence in SEQ ID NO:27. In one embodiment it differs by at least one but by less than 15, 10 or 5 amino acid residues. In another it differs from the corresponding sequence in SEQ ID NO:27 by at least one residue but less than 20%, 15%, 10% or 5% of the residues in it differ from the corresponding sequence in SEQ ID NO:27. (If this comparison requires alignment the sequences should be aligned for maximum homology, e.g. by the GAP algorithm described elsewhere herein. Gapped sequences from deletions or insertions, or mismatches, are considered differences.) The differences are, preferably, differences or changes at a non-essential residue or a conservative substitution. In a preferred embodiment the differences are not in the aminopeptidase domain. In another preferred embodiment one or more differences are in non-active site residues, e.g. outside of the aminopeptidase domain.

Other embodiments include a protein that contain one or more changes in amino acid sequence, e.g., a change in an amino acid residue which is not essential for activity. Such 55304 proteins differ in amino acid sequence from SEQ ID NO:27, yet retain biological activity.

In one embodiment, a biologically active portion of a 55304 protein includes an Aminopeptidase domain. Moreover, other biologically active portions, in which other regions of the protein are deleted, can be prepared by recombinant techniques and evaluated for one or more of the functional activities of a native 55304 protein.

In a preferred embodiment, the 55304 protein has an amino acid sequence shown in SEQ ID NO:27. In other embodiments, the 55304 protein is substantially identical to SEQ ID NO:27. In yet another embodiment, the 55304 protein is substantially identical to SEQ ID NO:27 and retains the functional activity of the protein of SEQ ID NO:27, as described in detail above. Accordingly, in another embodiment, the 55304 protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:27.

Isolated 52999 Polypeptides

In another aspect, the invention features, an isolated 52999 protein, or fragment, e.g., a biologically active portion, for use as immunogens or antigens to raise or test (or more generally to bind) anti-52999 antibodies. 52999 protein can be isolated from cells or tissue sources using standard protein purification techniques. 52999 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 52999 polypeptide has one or more of the following characteristics:

(i) it is capable of catalyzing the cleavage of a polypeptide through hydrolysis;

(ii) it has a molecular weight, e.g., a deduced molecular weight, amino acid composition or other physical characteristic of the polypeptide of SEQ ID NO:30;

(iii) it has an overall sequence identity of at least 50%, preferably at least 60%, more preferably at least 70, 80, 90, 91%, 92%, 93%, 94%, 95%, 96%, 97%, 98%, or 99%, with a polypeptide of SEQ ID NO:30;

(iv) it has a zinc-binding signature sequence that preferably has an overall sequence identity of about 70%, 80%, 90%, or 95% or more with amino acid residues 272–281 of SEQ ID NO:30;

(v) it has at least 70%, preferably 80%, and most preferably 95% of the cysteines found amino acid sequence of the native protein.

In a preferred embodiment the 52999 protein, or fragment thereof, differs from the corresponding sequence in SEQ ID NO:30. In one embodiment it differs by at least one but by less than 15, 10 or 5 amino acid residues. In another it differs from the corresponding sequence in SEQ ID NO:30 by at least one residue but less than 20%, 15%, 10% or 5% of the residues in it differ from the corresponding sequence in SEQ ID NO:30. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the metallopeptidase domain. In another preferred embodiment one or more differences are in non-active site residues, e.g. outside of the metallopeptidase domain.

Other embodiments include a protein that contain one or more changes in amino acid sequence, e.g., a change in an amino acid residue which is not essential for activity. Such 52999 proteins differ in amino acid sequence from SEQ ID NO:30, yet retain biological activity.

In one embodiment, a biologically active portion of a 52999 protein includes a polypeptide hydrolytic domain. In another embodiment, a biologically active portion of a 52999 protein includes a portion of the polypeptide hydrolytic domain that includes the zinc-binding signature sequence. Moreover, other biologically active portions, in which other regions of the protein are deleted, can be prepared by recombinant techniques and evaluated for the functional activities of a native 52999 protein.

In a preferred embodiment, the 52999 protein has an amino acid sequence shown in SEQ ID NO:30. In other embodiments, the 52999 protein is substantially identical to SEQ ID NO:30. In yet another embodiment, the 52999 protein is substantially identical to SEQ ID NO:30 and retains the functional activity of the protein of SEQ ID NO:30, as described in detail above. Accordingly, in another embodiment, the 52999 protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:30.

Isolated 21999 Polypeptides

In another aspect, the invention features, an isolated ADP-ribosyltransferase protein, or fragment, e.g., a biologically active portion, for use as immunogens or antigens to raise or test (or more generally to bind) anti-ADP-ribosyltransferase antibodies. ADP-ribosyltransferase protein can be isolated from cells or tissue sources using standard protein purification techniques. ADP-ribosyltransferase protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a ADP-ribosyltransferase polypeptide has one or more of the following characteristics:

(i) can act to transfer an ADP-ribose moiety of NAD to an acceptor protein;

(ii) it has a molecular weight, e.g., a deduced molecular weight, amino acid composition or other physical characteristic of the polypeptide of SEQ ID NO:37;

(iii) it has an overall sequence identity of at least 50%, preferably at least 60%, more preferably at least 70, 80, 90, 91%, 92%, 93%, 94%, 95%, 96%, 97%, 98%, or 99%, with a polypeptide of SEQ ID NO:37.

In a preferred embodiment the ADP-ribosyltransferase protein, or fragment thereof, differs from the corresponding sequence in SEQ ID NO:37. In one embodiment it differs by at least one but by less than 15, 10 or 5 amino acid residues. In another it differs from the corresponding sequence in SEQ ID NO:37 by at least one residue but less than 20%, 15%, 10% or 5% of the residues in it differ from the corresponding sequence in SEQ ID NO:37. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the transferase domain. In another preferred embodiment one or more differences are in non-active site residues, e.g. outside of the transferase domain.

Other embodiments include a protein that contain one or more changes in amino acid sequence, e.g., a change in an amino acid residue which is not essential for activity. Such ADP-ribosyltransferase proteins differ in amino acid sequence from SEQ ID NO:37, yet retain biological activity.

In one embodiment, a biologically active portion of a ADP-ribosyltransferase protein includes a transferase domain. Moreover, other biologically active portions, in which other regions of the protein are deleted, can be prepared by recombinant techniques and evaluated for one or more of the functional activities of a native ADP-ribosyltransferase protein.

In a preferred embodiment, the ADP-ribosyltransferase protein has an amino acid sequence shown in SEQ ID NO:37. In other embodiments, the ADP-ribosyltransferase protein is substantially identical to SEQ ID NO:37. In yet another embodiment, the ADP-ribosyltransferase protein is substantially identical to SEQ ID NO:37 and retains the functional activity of the protein of SEQ ID NO:37, as described in detail above. Accordingly, in another embodiment, the ADP-ribosyltransferase protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:37.

Isolated 52020 Polypeptides

In another aspect, the invention features, an isolated 52020 protein, or fragment, e.g., a biologically active portion, for use as immunogens or antigens to raise or test (or more generally to bind) anti-52020 antibodies. 52020 protein can be isolated from cells or tissue sources using standard protein purification techniques. 52020 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 52020 polypeptide has one or more of the following characteristics:

(i) it is capable of regulating cellular and differentiation, tissue repair, activating T-cells, effective CTL cell function, and eliciting auto-antibodies (ii) it has a molecular weight, e.g., a deduced molecular weight, amino acid composition or other physical characteristic of the polypeptide of SEQ ID NO:41;

(iii) it has an overall sequence identity of at least 50%, preferably at least 60%, more preferably at least 70%, 80%, 90%, 91%, 92%, 93%, 94%, 95%, 96%, 97%, 98%, or 99%, with a polypeptide of SEQ ID NO:41;

(iv) it has a MAGE domain as defined by the consensus amino acid sequence shown in FIG. 35 which preferably has an overall sequence identity of about 60%, 70%, 80%, 90% or 95% with amino acid residues 1–208 of SEQ ID NO:41;

(v) it has at least 70%, preferably 80%, and most preferably 95% of the cysteines found amino acid sequence of the native protein.

In a preferred embodiment the 52020 protein, or fragment thereof, differs from the corresponding sequence in SEQ ID NO:41. In one embodiment it differs by at least one but by less than 15, 10 or 5 amino acid residues. In another it differs from the corresponding sequence in SEQ ID NO:41 by at least one residue but less than 20%, 15%, 10% or 5% of the residues in it differ from the corresponding sequence in SEQ ID NO:41. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the MAGE domain. In another preferred embodiment one or more differences are in residues without activity.

Other embodiments include a protein that contain one or more changes in amino acid sequence, e.g., a change in an amino acid residue which is not essential for activity. Such 52020 proteins differ in amino acid sequence from SEQ ID NO:41, yet retain biological activity.

In one embodiment, a biologically active portion of a 52020 protein includes an MAGE domain. In another embodiment, a biologically active portion of a 52020 protein includes amino acid residues capable of being processed to function as tumor rejection antigens. Moreover, other biologically active portions, in which other regions of the protein are deleted, can be prepared by recombinant techniques and evaluated for one or more of the functional activities of a native 52020 protein.

In a preferred embodiment, the 52020 protein has an amino acid sequence shown in SEQ ID NO:41. In other embodiments, the 52020 protein is substantially identical to SEQ ID NO:41. In yet another embodiment, the 52020 protein is substantially identical to SEQ ID NO:41 and retains the functional activity of the protein of SEQ ID NO:41, as described in detail herein supra. Accordingly, in another embodiment, the 52020 protein is a protein which includes an amino acid sequence at least about 60%, 65%, 70%, 75%, 80%, 85%, 90%, 91%, 92%, 93%, 94%, 95%, 96%, 97%, 98%, 99%, or more identical to SEQ ID NO:41.

22406, Acyltransferase, 7716, 25233, 8035, 84242, 55304, 52999, 21999, or 52020 Chimeric or Fusion Proteins In another aspect, the invention provides 22406, acyltransferase, 7716, 25233, 8035, 84242, 55304, 52999, 21999, or 52020 chimeric or fusion proteins. As used herein, a 22406, acyltransferase, 7716, 25233, 8035, 84242, 55304, 52999, 21999, or 52020 "chimeric protein" or "fusion protein" includes a 22406, acyltransferase, 7716, 25233, 8035, 84242, 55304, 52999, 21999, or 52020 polypeptide linked to a non-22406, non-acyltransferase, non-7716, non-25233, non-8035, non-84242, non-55304, non-52999, non-21999 or non-52020 polypeptide. A "non-22406, non-acyltransferase, non-7716, non-25233, non-8035, non-84242, non-55304, non-52999, non-21999 or non-52020 polypeptide" refers to a polypeptide having an amino acid sequence corresponding to a protein which is not substantially homologous to the 22406, acyltransferase, 7716, 25233, 8035, 84242, 55304, 52999, 21999, or 52020 protein, respectively, e.g., a protein which is different from the 22406, acyltransferase, 7716, 25233, 8035, 84242, 55304, 52999, 21999, or 52020 protein and which is derived from the same or a different organism. The 22406, acyltransferase, 7716, 25233, 8035, 84242, 55304, 52999, 21999, or 52020 polypeptides of the fusion proteins can correspond to all or a portion e.g., a fragment described herein of a 22406, acyltransferase, 7716, 25233, 8035, 84242, 55304, 52999, 21999, or 52020 amino acid sequence. In a preferred embodiment, a 22406, acyltransferase, 7716, 25233, 8035, 84242, 55304, 52999, 21999, or 52020 fusion protein includes at least one biologically active portion of a 22406, acyltransferase, 7716, 25233, 8035, 84242, 55304, 52999, 21999, or 52020 protein or at least one (or two) biologically active portion of a 22406, acyltransferase, 7716, 25233, 8035, 84242, 55304, 52999, 21999, or 52020 protein. The non-22406, non-acyltransferase, non-7716, non-25233, non-8035, non-84242, non-55304, non-52999, non-21999 or non-52020 polypeptide can be fused to the N-terminus or C-terminus of the 22406, acyltransferase, 7716, 25233, 8035, 84242, 55304, 52999, 21999, or 52020 polypeptide.

The fusion protein can include a moiety which has a high affinity for a ligand. For example, the fusion protein can be a GST-22406, GST-acyltransferase, GST-7716, GST-25233, GST-8035, GST-84242, GST-55304, GST-52999, GST-21999 or GST-52020 fusion protein in which the 22406, acyltransferase, 7716, 25233, 8035, 84242, 55304, 52999, 21999, or 52020 sequences are fused to the C-terminus of the GST sequences. Such fusion proteins can facilitate the purification of recombinant 22406, acyltransferase, 7716, 25233, 8035, 84242, 55304, 52999, 21999, or 52020. Alternatively, the fusion protein can be a 22406, acyltransferase, 7716, 25233, 8035, 84242, 55304, 52999, 21999, or 52020 protein containing a heterologous signal sequence at its N-terminus. In certain host cells (e.g., mammalian host cells), expression and/or secretion of 22406, acyltransferase, 7716, 25233, 8035, 84242, 55304, 52999, 21999, or 52020 can be increased through use of a heterologous signal sequence.

Fusion proteins can include all or a part of a serum protein, e.g., an IgG constant region, or human serum albumin.

The 22406, acyltransferase, 7716, 25233, 8035, 84242, 55304, 52999, 21999, or 52020 fusion proteins of the invention can be incorporated into pharmaceutical compositions and administered to a subject in vivo. The 22406, acyltransferase, 7716, 25233, 8035, 84242, 55304, 52999, 21999, or 52020 fusion proteins can be used to affect the bioavailability of a 22406, acyltransferase, 7716, 25233, 8035, 84242, 55304, 52999, 21999, or 52020 substrate. 22406, acyltransferase, 7716, 25233, 8035, 84242, 55304, 52999, 21999, or 52020 fusion proteins may be useful therapeutically for the treatment of disorders caused by, for example, (i) aberrant modification or mutation of a gene encoding a 22406, acyltransferase, 7716, 25233, 8035, 84242, 55304, 52999, 21999, or 52020 protein; (ii) misregulation of the 22406, acyltransferase, 7716, 25233, 8035, 84242, 55304, 52999, 21999, or 52020 gene; and (iii) aberrant post-translational modification of a 22406, acyltransferase, 7716, 25233, 8035, 84242, 55304, 52999, 21999, or 52020 protein. "Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" as defined herein, includes, but is not limited to, small molecules, peptides, antibodies, ribozymes and antisense oligonucleotides.

Moreover, the 22406, acyltransferase, 7716, 25233, 8035, 84242, 55304, 52999, 21999, or 52020-fusion proteins of the invention can be used as immunogens to produce anti-22406, anti-acyltransferase, anti-7716, anti-25233, anti-8035, anti-84242, anti-55304, anti-52999, anti-21999 or anti-52020 antibodies, respectively, in a subject, to purify 22406, acyltransferase, 7716, 25233, 8035, 84242, 55304, 52999, 21999, or 52020 ligands and in screening assays to identify molecules which inhibit the interaction of 22406, acyltransferase, 7716, 25233, 8035, 84242, 55304, 52999, 21999, or 52020 with a 22406, acyltransferase, 7716, 25233, 8035, 84242, 55304, 52999, 21999, or 52020 substrate.

Expression vectors are commercially available that already encode a fusion moiety (e.g., a GST polypeptide). A 22406, acyltransferase, 7716, 25233, 8035, 84242, 55304, 52999, 21999, or 52020-encoding nucleic acid can be cloned into such an expression vector such that the fusion moiety is linked in-frame to the 22406, acyltransferase, 7716, 25233, 8035, 84242, 55304, 52999, 21999, or 52020 protein.

Variants of 22406, Acyltransferase, 7716, 25233, 8035, 84242, 55304, 52999, 21999, or 52020 Proteins In another aspect, the invention also features a variant of a 22406, acyltransferase, 7716, 25233, 8035, 84242, 55304, 52999, 21999, or 52020 polypeptide, e.g., which functions as an agonist (mimetics) or as an antagonist. Variants of the 22406, acyltransferase, 7716, 25233, 8035, 84242, 55304, 52999, 21999, or 52020 proteins can be generated by mutagenesis, e.g., discrete point mutation, the insertion or deletion of sequences or the truncation of a 22406, acyltransferase, 7716, 25233, 8035, 84242, 55304, 52999, 21999, or 52020 protein. An agonist of the 22406, acyltransferase, 7716, 25233, 8035, 84242, 55304, 52999, 21999, or 52020 proteins can retain substantially the same, or a subset, of the biological activities of the naturally occurring form of a 22406, acyltransferase, 7716, 25233, 8035, 84242, 55304, 52999, 21999, or 52020 protein. An antagonist of a 22406, acyltransferase, 7716, 25233, 8035, 84242, 55304, 52999, 21999, or 52020 protein can inhibit one or more of the activities of the naturally occurring form of the 22406, acyltransferase, 7716, 25233, 8035, 84242, 55304, 52999, 21999, or 52020 protein by, for example, competitively modulating a 22406, acyltransferase, 7716, 25233, 8035, 84242, 55304, 52999, 21999, or 52020-mediated activity of a 22406, acyltransferase, 7716, 25233, 8035, 84242, 55304, 52999, 21999, or 52020 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 22406, acyltransferase, 7716, 25233, 8035, 84242, 55304, 52999, 21999, or 52020 protein.

Variants of a 22406, acyltransferase, 7716, 25233, 8035, 84242, 55304, 52999, 21999, or 52020 protein can be identified by screening combinatorial libraries of mutants, e.g., truncation mutants, of a 22406, acyltransferase, 7716, 25233, 8035, 84242, 55304, 52999, 21999, or 52020 protein for agonist or antagonist activity.

Libraries of fragments e.g., N terminal, C terminal, or internal fragments, of a 22406, acyltransferase, 7716, 25233, 8035, 84242, 55304, 52999, 21999, or 52020 protein coding sequence can be used to generate a variegated population of fragments for screening and subsequent selection of variants of a 22406, acyltransferase, 7716, 25233, 8035, 84242, 55304, 52999, 21999, or 52020 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 22406, acyltransferase, 7716, 25233, 8035, 84242, 55304, 52999, 21999, or 52020 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 22406, acyltransferase, 7716, 25233, 8035, 84242, 55304, 52999, 21999, or 52020 library. For example, a library of expression vectors can be transfected into a cell line, e.g., a cell line, which ordinarily responds to 22406, acyltransferase, 7716, 25233, 8035, 84242, 55304, 52999, 21999, or 52020 in a substrate-dependent manner. The transfected cells are then contacted with 22406, acyltransferase, 7716, 25233, 8035, 84242, 55304, 52999, 21999, or 52020 and the effect of the expression of the mutant on signaling by the 22406, acyltransferase, 7716, 25233, 8035, 84242, 55304, 52999, 21999, or 52020 substrate can be detected. For example, 22406-transfected cells are then contacted with D-serine and the effect of the expression of the mutant on signaling by the D-serine 22406 substrate can be detected, e.g., by measuring serine racemase activity; the effect of the expression of the mutant on signaling by the acyltransferase substrate can be detected, e.g., by measuring fatty acid synthase activity; effect of the expression of the mutant on signaling by the 7716 substrate can be detected, e.g., by measuring ATPase activity; the effect of the expression of the mutant on signaling by the 25233 substrate can be detected, e.g., by measuring aminotransferase activity; where 8035 or 84242 is tested, detection can be accomplished by measuring RING finger protein-mediated activity; where 55304 is tested, detection can be accomplished by measuring aminopeptidase activity; where 52999 is tested, detection can be accomplished by measuring polypeptide hydrolytic activity; where 21999 is tested, detection can be accomplished by measuring transferase activity in the reaction wherein NAD(+) and L-arginine are converted by the ADP-ribosyltransferase enzyme to form the end-products nicotinamide and N2-(ADP-D-ribosyl)-L-arginine; and the effect of the expression of the mutant on signaling by the 52020 substrate can be detected, e.g., by measuring MAGE activity. Plasmid DNA can then be recovered from the cells which score for inhibition, or alternatively, potentiation of signaling by the 22406, acyltransferase, 7716, 25233, 8035, 84242, 55304, 52999, 21999, or 52020 substrate, and the individual clones further characterized.

In another aspect, the invention features a method of making a 22406, acyltransferase, 7716, 25233, 8035, 84242, 55304, 52999, 21999, or 52020 polypeptide, e.g., a peptide having a non-wild type activity, e.g., an antagonist, agonist, or super agonist of a naturally occurring 22406, acyltransferase, 7716, 25233, 8035, 84242, 55304, 52999, 21999, or 52020 polypeptide, e.g., a naturally occurring 22406, acyltransferase, 7716, 25233, 8035, 84242, 55304, 52999, 21999, or 52020 polypeptide. The method includes: altering the sequence of a 22406, acyltransferase, 7716, 25233, 8035, 84242, 55304, 52999, 21999, or 52020 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 22406, acyltransferase, 7716, 25233, 8035, 84242, 55304, 52999, 21999, or 52020 polypeptide having a biological activity of a naturally occurring 22406, acyltransferase, 7716, 25233, 8035, 84242, 55304, 52999, 21999, or 52020 polypeptide. The method includes: altering the sequence, e.g., by substitution or deletion of one or more residues, of a 22406, acyltransferase, 7716, 25233, 8035, 84242, 55304, 52999, 21999, or 52020 polypeptide, e.g., altering the sequence of a non-conserved region, or a domain or residue described herein, and testing the altered polypeptide for the desired activity.

Anti-22406, Anti-Acyltransferase, Anti-7716, Anti-25233, Anti-8035, Anti-84242, Anti-55304, Anti-52999, Anti-21999, and Anti-52020 Antibodies In another aspect, the invention provides an anti-22406, anti-acyltransferase, anti-7716, anti-25233, anti-8035, anti-84242, anti-55304, anti-52999, anti-21999, and anti-52020 antibody. The term "antibody" as used herein refers to an immunoglobulin molecule or immunologically active portion thereof, i.e., an antigen-binding portion. Examples of immunologically active portions of immunoglobulin molecules include F(ab) and F(ab)$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 22406, acyltransferase, 7716, 25233, 8035, 84242, 55304, 52999, 21999, or 52020 protein or, antigenic peptide fragment of 22406, acyltransferase, 7716, 25233, 8035, 84242, 55304, 52999, 21999, or 52020 can be used as an immunogen or can be used to identify anti-22406, anti-acyltransferase, anti-7716, anti-25233, anti-8035, anti-84242, anti-55304, anti-52999, anti-21999 or anti-52020 antibodies made with other immunogens, e.g., cells, membrane preparations, and the like. The antigenic peptide of 22406, acyltransferase, 7716, 25233, 8035, 84242, 55304, 52999, 21999, or 52020 should include at least 8 amino acid residues of the amino acid sequence shown in SEQ ID NO:2, SEQ ID NO:7, SEQ ID NO:11, SEQ ID NO:15, SEQ ID NO: 19, SEQ ID NO:23, SEQ ID NO:27, SEQ ID NO:30, SEQ ID NO:37 or SEQ ID NO:41 respectively, and encompasses an epitope of 22406, acyltransferase, 7716, 25233, 8035, 84242, 55304, 52999, 21999, or 52020. Preferably, the antigenic peptide includes at least 10 amino acid residues, more preferably at least 15 amino acid residues, even more preferably at least 20 amino acid residues, and most preferably at least 30 amino acid residues.

Fragments of 22406 which include, e.g., residues 130–150 of SEQ ID NO:2 of SEQ ID NO:5 can be used to make, e.g., used as immunogens, or used to characterize the specificity of an antibody or antibodies against what are believed to be hydrophilic regions of the 22406 protein. Similarly, a fragment of 22406 which includes, e.g., residues 175–200 of SEQ ID NO:2 can be used to make an antibody against what is believed to be a hydrophobic region of the 22406 protein; a fragment of 22406 which includes residues 45–62 of SEQ ID NO:2 can be used to make an antibody against the pyridoxal-phosphate dependent enzyme family member region of the 22406 protein. Antibodies reactive with, or specific for, any of these regions, or other regions or domains described herein are provided.

Fragments of 7716 which include, e.g., residues 255–290 of SEQ ID NO:11 can be used to make, e.g., used as immunogens, or used to characterize the specificity of an antibody or antibodies against what are believed to be hydrophilic regions of the 7716 protein. Similarly, a fragment of 7716 which includes, e.g., residues 385–410 of SEQ ID NO:11 can be used to make an antibody against what is believed to be a hydrophobic region of the 7716 protein; a fragment of 7716 which includes residues 236–421 or 500–705 of SEQ ID NO:11 can be used to make an antibody against an ATPase region of the 7716 protein. Antibodies reactive with, or specific for, any of these regions, or other regions or domains described herein are provided.

Fragments of 25233 which include, e.g., residues 122–137 or residues 243–256 of SEQ ID NO:15 can be used to make, e.g., used as immunogens, or used to characterize the specificity of an antibody or antibodies against what are believed to be hydrophilic regions of the 25233 protein. Similarly, a fragment of 25233 which includes, e.g., residues 363–393 of SEQ ID NO:15 can be used to make an antibody against what is believed to be a hydrophobic region of the 25233 protein; a fragment of 25233 which includes residues 83–517 of SEQ ID NO:15 can be used to make an antibody against the aminotransferase region of the 25233 protein. Antibodies reactive with, or specific for, any of these regions, or other regions or domains described herein are provided.

Fragments of 8035 which include, e.g., residues 350–390 of SEQ ID NO:19 can be used to make, e.g., used as immunogens, or used to characterize the specificity of an antibody or antibodies against what are believed to be hydrophilic regions of the 8035 protein. Similarly, a fragment of 8035 which includes, e.g., residues 200–230 of SEQ ID NO:19 can be used to make an antibody against what is believed to be a hydrophobic region of the 8035 protein; a fragment of 8035 which includes residues 380–421 of SEQ ID NO:19 can be used to make an antibody against the RING finger protein region of the 8035 protein. Antibodies reactive with, or specific for, any of these regions, or other regions or domains described herein are provided.

Fragments of 84242 which include, e.g., residues 190–220 of SEQ ID NO:23 can be used to make, e.g., used as immunogens, or used to characterize the specificity of an antibody or antibodies against what are believed to be hydrophilic regions of the 84242 protein. Similarly, a fragment of 84242 which includes, e.g., residues 115–150 of SEQ ID NO:23 can be used to make an antibody against what is believed to be a hydrophobic region of the 84242 protein; a fragment of 84242 which includes residues 2–67 of SEQ ID NO:23 can be used to make an antibody against the IBR protein region of the 84242 protein. Antibodies reactive with, or specific for, any of these regions, or other regions or domains described herein are provided.

Fragments of 55304 which include, e.g., residues 650–670 of SEQ ID NO:27 of SEQ ID NO:22 can be used to make, e.g., used as immunogens, or used to characterize the specificity of an antibody or antibodies against what are believed to be hydrophilic regions of the 55304 protein. Similarly, a fragment of 55304 which includes, e.g., residues 240–260 of SEQ ID NO:27 can be used to make an antibody against what is believed to be a hydrophobic region of the 55304 protein; a fragment of 55304 which includes residues 318–508 of SEQ ID NO:27 can be used to make an antibody against the aminopeptidase region of the 55304 protein.

Fragments of 52999 that include residues from about amino acid 291–320 of SEQ ID NO:30 can be used to make, e.g., used as immunogens, or characterize the specificity of an antibody or antibodies against what are believed to be hydrophilic regions of the 52999 protein. Similarly, a fragment of 52999 that includes residues from about amino acid 321–345 of SEQ ID NO:30 can be used to make an antibody against what is believed to be a hydrophobic region of the 52999 protein; a fragment of 52999 that includes residues from about amino acid 270–290 of SEQ ID NO:30 can be used to make an antibody against the active site region of the 52999 protein.

Fragments of 21999 can be used to make immunogens, or used to characterize the specificity of an antibody or antibodies against what are believed to be hydrophilic regions of the ADP-ribosyltransferase protein.

Fragments of 52020 which include, e.g., residues 1–30 of SEQ ID NO:41 of SEQ ID NO:5 can be used to make, e.g., used as immunogens, or used to characterize the specificity of an antibody or antibodies against what are believed to be hydrophilic regions of the 52020 protein. Similarly, a fragment of 52020 which includes, e.g., residues 170–190 of SEQ ID NO:41 can be used to make an antibody against what is believed to be a hydrophobic region of the 52020 protein; a fragment of 52020 which includes residues 1–208 of SEQ ID NO:41 can be used to make an antibody against the MAGE consensus region of the 52020 protein. Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of 22406, acyltransferase, 7716, 25233, 8035, 84242, 55304, 52999, 21999, or 52020 that are located on the surface of the proteins, e.g., hydrophilic regions, as well as regions with high antigenicity. For example, an Emini surface probability analysis of the human 22406, acyltransferase, 7716, 25233, 8035, 84242, 55304, 52999, 21999, or 52020 protein sequence can be used to indicate the regions that have a particularly high probability of being localized to the surface of the 22406, acyltransferase, 7716, 25233, 8035, 84242, 55304, 52999, 21999, or 52020 protein, respectively, and are thus likely to constitute surface residues useful for targeting antibody production.

In a preferred embodiment the antibody binds an epitope on any domain or region on 22406, acyltransferase, 7716, 25233, 8035, 84242, 55304, 52999, 21999, or 52020 proteins described herein.

Chimeric, humanized, but most preferably, completely human antibodies are desirable for applications which include repeated administration, e.g., therapeutic treatment (and some diagnostic applications) of human patients.

The anti-22406, anti-acyltransferase, anti-7716, anti-25233, anti-8035, anti-84242, anti-55304, anti-52999, anti-21999 or anti-52020 antibody can be a single chain antibody. A single-chain antibody (scFV) may be engineered (see, for example, Colcher, D. et al. (1999, Jun. 30) *Ann. NY Acad. Sci.* 880:263–80; and Reiter, Y. (1996 February) *Clin. Cancer Res.* 2(2):245–52). The single chain antibody can be dimerized or multimerized to generate multivalent antibodies having specificities for different epitopes of the same target 22406, acyltransferase, 7716, 25233, 8035, 84242, 55304, 52999, 21999, or 52020 protein.

An anti-22406, anti-acyltransferase, anti-7716, anti-25233, anti-8035, anti-84242, anti-55304, anti-52999, anti-21999 or anti-52020 antibody (e.g., monoclonal antibody) can be used to isolate 22406, acyltransferase, 7716, 25233, 8035, 84242, 55304, 52999, 21999, or 52020 by standard techniques, such as affinity chromatography or immunoprecipitation. Moreover, an anti-22406, anti-acyltransferase, anti-7716, anti-25233, anti-8035, anti-84242, anti-55304, anti-52999, anti-21999 or anti-52020 antibody can be used to detect 22406, acyltransferase, 7716, 25233, 8035, 84242, 55304, 52999, 21999, or 52020 protein (e.g., in a cellular lysate or cell supernatant) in order to evaluate the abundance and pattern of expression of the protein. Anti-22406, anti-acyltransferase, anti-7716, anti-25233, anti-8035, anti-84242, anti-55304, anti-52999, anti-21999 or anti-52020 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 22406, acyltransferase, 7716, 25233, 8035, 84242, 55304, 52999, 21999, or 52020 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 22406, acyltransferase, 7716, 25233, 8035, 84242, 55304, 52999, 21999, or 52020 proteins, mutant forms of 22406, acyltransferase, 7716, 25233, 8035, 84242, 55304, 52999, 21999, or 52020 proteins, fusion proteins, and the like).

The recombinant expression vectors of the invention can be designed for expression of 22406, acyltransferase, 7716, 25233, 8035, 84242, 55304, 52999, 21999, or 52020 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 22406, acyltransferase, 7716, 25233, 8035, 84242, 55304, 52999, 21999, or 52020 activity assays, (e.g., direct assays or competitive assays described in detail below), or to generate antibodies specific for 22406, acyltransferase, 7716, 25233, 8035, 84242, 55304, 52999, 21999, or 52020 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

The 22406, acyltransferase, 7716, 25233, 8035, 84242, 55304, 52999, 21999, or 52020 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264, 166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al. (1986) Antisense RNA as a molecular tool for genetic analysis, *Reviews—Trends in Genetics*, Vol. 1(1).

Another aspect the invention provides a host cell which includes a nucleic acid molecule described herein, e.g., a 22406, acyltransferase, 7716, 25233, 8035, 84242, 55304, 52999, 21999, or 52020 nucleic acid molecule within a recombinant expression vector or a 22406, acyltransferase, 7716, 25233, 8035, 84242, 55304, 52999, 21999, or 52020 nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 22406, acyltransferase, 7716, 25233, 8035, 84242, 55304, 52999, 21999, or 52020 protein can be expressed in bacterial cells such as *E. coli*, insect cells, yeast or mammalian cells (such as Chinese hamster ovary cells (CHO) or COS cells). Other suitable host-cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 22406, acyltransferase, 7716, 25233, 8035, 84242, 55304, 52999, 21999, or 52020 protein. Accordingly, the invention further provides methods for producing a 22406, acyltransferase, 7716, 25233, 8035, 84242, 55304, 52999, 21999, or 52020 protein using the host cells of the invention. In one embodiment, the method includes culturing the host cell of the invention (into which a recombinant expression vector encoding a 22406, acyltransferase, 7716, 25233, 8035, 84242, 55304, 52999, 21999, or 52020 protein has been introduced) in a suitable medium such that a 22406, acyltransferase, 7716, 25233, 8035, 84242, 55304, 52999, 21999, or 52020 protein is produced. In another embodiment, the method further includes isolating a 22406, acyltransferase, 7716, 25233, 8035, 84242, 55304, 52999, 21999, or 52020 protein from the medium or the host cell.

In another aspect, the invention features, a cell or purified preparation of cells which include a 22406, acyltransferase, 7716, 25233, 8035, 84242, 55304, 52999, 21999, or 52020 transgene, or which otherwise misexpress 22406, acyltransferase, 7716, 25233, 8035, 84242, 55304, 52999, 21999, or 52020. The cell preparation can consist of human or non-human cells, e.g., rodent cells, e.g., mouse or rat cells, rabbit cells, or pig cells. In preferred embodiments, the cell or cells include a 22406, acyltransferase, 7716, 25233, 8035, 84242, 55304, 52999, 21999, or 52020 transgene, e.g., a heterologous form of a 22406, acyltransferase, 7716, 25233, 8035, 84242, 55304, 52999, 21999, or 52020, e.g., a gene derived from humans (in the case of a non-human cell). The 22406, acyltransferase, 7716, 25233, 8035, 84242, 55304, 52999, 21999, or 52020 transgene can be misexpressed, e.g., overexpressed or underexpressed. In other preferred embodiments, the cell or cells include a gene which misexpress an endogenous 22406, acyltransferase, 7716, 25233, 8035, 84242, 55304, 52999, 21999, or 52020, e.g., a gene the expression of which is disrupted, e.g., a knockout. Such cells can serve as a model for studying disorders which are related to mutated or misexpressed 22406, acyltransferase, 7716, 25233, 8035, 84242, 55304, 52999, 21999, or 52020 alleles or for use in drug screening.

In another aspect, the invention features, a human cell, e.g., a brain cell, transformed with nucleic acid which encodes a subject 22406 polypeptide.

In another aspect, the invention features, a human cell, e.g., a hematopoietic stem cell, transformed with nucleic acid which encodes a subject acyltransferase, 7716, 25233, 8035, 84242, 55304, 52999, 21999 or 52020 polypeptide.

Also provided are cells or a purified preparation thereof, e.g., human cells, in which an endogenous 22406, acyltransferase, 7716, 25233, 8035, 84242, 55304, 52999, 21999, or 52020 is under the control of a regulatory sequence that does not normally control the expression of the endogenous 22406, acyltransferase, 7716, 25233, 8035, 84242, 55304, 52999, 21999, or 52020 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 22406, acyltransferase, 7716, 25233, 8035, 84242, 55304, 52999, 21999, or 52020 gene. For example, an endogenous 22406, acyltransferase, 7716, 25233, 8035, 84242, 55304, 52999, 21999, or 52020 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published on May 16, 1991.

Transgenic Animals

The invention provides non-human transgenic animals. Such animals are useful for studying the function and/or activity of a 22406, acyltransferase, 7716, 25233, 8035, 84242, 55304, 52999, 21999, or 52020 protein and for identifying and/or evaluating modulators of 22406, acyltransferase, 7716, 25233, 8035, 84242, 55304, 52999, 21999, or 52020 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 22406, acyltransferase, 7716, 25233, 8035, 84242, 55304, 52999, 21999, or 52020 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 22406, acyltransferase, 7716, 25233, 8035, 84242, 55304, 52999, 21999, or 52020 protein to particular cells. A transgenic founder animal can be identified based upon the presence of a 22406, acyltransferase, 7716, 25233, 8035, 84242, 55304, 52999, 21999, or 52020 transgene in its genome and/or expression of 22406, acyltransferase, 7716, 25233, 8035, 84242, 55304, 52999, 21999, or 52020 mRNA in tissues or cells of the animals. A transgenic founder animal can then be used to breed additional animals carrying the transgene. Moreover, transgenic animals carrying a transgene encoding a 22406, acyltransferase, 7716, 25233, 8035, 84242, 55304, 52999, 21999, or 52020 protein can further be bred to other transgenic animals carrying other transgenes.

22406, acyltransferase, 7716, 25233, 8035, 84242, 55304, 52999, 21999, or 52020 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 22406, acyltransferase, 7716, 25233, 8035, 84242, 55304, 52999, 21999, or 52020 protein (e.g., via a recombinant expression vector in a host cell in gene therapy applications), to detect a 22406, acyltransferase, 7716, 25233, 8035, 84242, 55304, 52999, 21999, or 52020 mRNA (e.g., in a biological sample) or a genetic alteration in a 22406, acyltransferase, 7716, 25233, 8035, 84242, 55304, 52999, 21999, or 52020 gene, and to modulate 22406, acyltransferase, 7716, 25233, 8035, 84242, 55304, 52999, 21999, or 52020 activity, as described further below. The 22406, acyltransferase, 7716, 25233, 8035, 84242, 55304, 52999, 21999, or 52020 proteins can be used to treat disorders characterized by insufficient or excessive production of a 22406, acyltransferase, 7716, 25233, 8035, 84242, 55304, 52999, 21999, or 52020 substrate or production of 22406, acyltransferase, 7716, 25233, 8035, 84242, 55304, 52999, 21999, or 52020 inhibitors.

In addition, the 22406 proteins can be used to screen for naturally occurring 22406 substrates, to screen for drugs or compounds which modulate 22406 activity, as well as to treat disorders characterized by insufficient or excessive production of 22406 protein or production of 22406 protein forms which have decreased, aberrant or unwanted activity compared to 22406 wild-type protein. Such disorders include those of the brain, particularly those disorders associated with convulsion, anxiety, and neurodengeneration.

In addition, the acyltransferase proteins can be used to screen for naturally occurring acyltransferase substrates, to screen for drugs or compounds which modulate acyltransferase activity, as well as to treat disorders characterized by insufficient or excessive production of acyltransferase protein or production of acyltransferase protein forms which have decreased, aberrant or unwanted activity compared to acyltransferase wild-type protein. Such disorders include those characterized by aberrant signaling or aberrant, e.g., hyperproliferative, cell growth.

In addition, the 7716 proteins can be used to screen for naturally occurring 7716 substrates, to screen for drugs or compounds which modulate 7716 activity, as well as to treat disorders characterized by insufficient or excessive production of 7716 protein or production of 7716 protein forms which have decreased, aberrant or unwanted activity compared to 7716 wild-type protein. Such disorders include those characterized by aberrance in organelle biogenesis, cell proliferation, membrane fusion, degradation of membrane proteins, or degradation of ubiquitin pathway target proteins.

In addition, the 25233 proteins can be used to screen for naturally occurring 25233 substrates, to screen for drugs or compounds which modulate 25233 activity, as well as to treat disorders characterized by insufficient or excessive production of 25233 protein or production of 25233 protein forms which have decreased, aberrant or unwanted activity compared to 25233 wild-type protein. Such disorders include those characterized by increased serum levels of aminotransferase.

In addition, the 8035, 84242, 55304, 52999, or 21999 proteins can be used to screen for naturally occurring 8035, 84242, 55304, 52999, or 21999 substrates, to screen for drugs or compounds which modulate 8035, 84242, 55304, 52999, or 21999 activity, as well as to treat disorders characterized by insufficient or excessive production of 8035, 84242, 55304, 52999, or 21999 protein or production of 8035, 84242, 55304, 52999, or 21999 protein forms which have decreased, aberrant or unwanted activity compared to 8035, 84242, 55304, 52999, or 21999 wild-type protein. In the case of 8035 and 84242, such disorders include those characterized by aberrant cellular proliferative and/or differentiative disorders. In the case of 55304, such disorders include those characterized by aberrant protein proteolysis or maturation or aberrant, e.g. hyperproliferative, cell growth. In the case of 52999, such disorders include those characterized by aberrant protein processing or protein degradation. In the case of 21999, such disorders include those characterized by aberrant cellular metabolism or aberrant growth, e.g., hyperproliferative, cell growth.

In addition, the 52020 proteins can be used to screen for naturally occurring 52020 binding partners, to screen for drugs or compounds which modulate 52020 activity, as well as to treat disorders characterized by insufficient or excessive production of 52020 protein or production of 52020 protein forms which have decreased, aberrant or unwanted activity compared to 52020 wild-type protein. Such disorders include those characterized by aberrant cell growth.

Moreover, the anti-22406, anti-acyltransferase, anti-7716, anti-25233, anti-8035, anti-84242, anti-55304, anti-52999, anti-21999 or anti-52020 antibodies of the invention can be used to detect and isolate 22406, acyltransferase, 7716, 25233, 8035, 84242, 55304, 52999, 21999 or 52020 proteins, regulate the bioavailability of 22406, acyltransferase, 7716, 25233, 8035, 84242, 55304, 52999, 21999 or 52020 proteins, and modulate 22406, acyltransferase, 7716, 25233, 8035, 84242, 55304, 52999, 21999 or 52020 activity, respectively.

A method of evaluating a compound for the ability to interact with, e.g., bind, a subject 22406, acyltransferase, 7716, 25233, 8035, 84242, 55304, 52999, 21999, or 52020 polypeptide is provided. The method includes: contacting the compound with the subject 22406, acyltransferase, 7716, 25233, 8035, 84242, 55304, 52999, 21999, or 52020 polypeptide; and evaluating ability of the compound to interact with, e.g., to bind or form a complex with the subject 22406, acyltransferase, 7716, 25233, 8035, 84242, 55304, 52999, 21999, or 52020 polypeptide. This method can be performed in vitro, e.g., in a cell free system, or in vivo, e.g., in a two-hybrid interaction trap assay. This method can be used to identify naturally occurring molecules which interact with subject 22406, acyltransferase, 7716, 25233, 8035, 84242, 55304, 52999, 21999, or 52020 polypeptide. It can also be used to find natural or synthetic inhibitors of subject 22406, acyltransferase, 7716, 25233, 8035, 84242, 55304, 52999, 21999, or 52020 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 22406, acyltransferase, 7716, 25233, 8035, 84242, 55304, 52999, 21999, or 52020 proteins, have a stimulatory or inhibitory effect on, for example, 22406, acyltransferase, 7716, 25233, 8035, 84242, 55304, 52999, 21999, or 52020 expression or 22406, acyltransferase, 7716, 25233, 8035, 84242, 55304, 52999, 21999, or 52020 activity, or have a stimulatory or inhibitory effect on, for example, the expression or activity of a 22406, acyltransferase, 7716, 25233, 8035, 84242, 55304, 52999, 21999, or 52020 substrate. Compounds thus identified can be used to modulate the activity of target gene products (e.g., 22406, acyltransferase, 7716, 25233, 8035, 84242, 55304, 52999, 21999, or 52020 genes) in a therapeutic protocol, to elaborate the biological function of the target gene product, or to identify compounds that disrupt normal target gene interactions.

In one embodiment, the invention provides assays for screening candidate or test compounds which are substrates of a 22406, acyltransferase, 7716, 25233, 8035, 84242, 55304, 52999, 21999, or 52020 protein or polypeptide or a biologically active portion thereof. In another embodiment, the invention provides assays for screening candidate or test compounds which bind to or modulate the activity of a 22406, acyltransferase, 7716, 25233, 8035, 84242, 55304, 52999, 21999, or 52020 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria or spores (Ladner, U.S. Pat. No. 5,223,409), plasmids (Cull et al. (1992) *Proc. Natl. Acad. Sci. USA* 89:1865–1869) or on phage (Scott and Smith (1990) *Science* 249:386–390); (Devlin (1990) *Science* 249: 404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a 22406, acyltransferase, 7716, 25233, 8035, 84242, 55304, 52999, 21999, or 52020 protein or biologically active portion thereof is contacted with a test compound, and the ability of the test compound to modulate 22406, acyltransferase, 7716, 25233, 8035, 84242, 55304, 52999, 21999, or 52020 activity is determined. Determining the ability of the test compound to modulate 22406 activity can be accomplished by monitoring, for example, serine racemase activity. Determining the ability of the test compound to modulate acyltransferase activity can be accomplished by monitoring, for example, fatty acid synthase activity. Determining the ability of the test compound to modulate 7716 activity can be accomplished by monitoring, for example, ATPase activity. Determining the ability of the test compound to modulate 25233 activity can be accomplished by monitoring, for example, aminotransferase activity. Determining the ability of the test compound to modulate 8035 or 84242 activity can be accomplished by monitoring, for example, RING finger E3 ubiquitin ligase protein activity. Determining the ability of the test compound to modulate 55304 activity can be accomplished by monitoring, for example, aminopeptidase activity. Determining the ability of the test compound to modulate 52999 activity can be accomplished by monitoring, for example, polypeptide hydrolytic activity. Determining the ability of the test compound to modulate 21999 activity can be accomplished by monitoring, for example, ADP-moiety transferase activity. Determining the ability of the test compound to modulate 52020 activity can be accomplished by monitoring, for example, MAGE activity. The cell, for example, can be of mammalian origin, e.g., human. Cell homogenates, or fractions, preferably membrane containing fractions, can also be tested.

The ability of the test compound to modulate 22406, acyltransferase, 7716, 25233, 8035, 84242, 55304, 52999, 21999, or 52020 binding to a compound, e.g., a 22406, acyltransferase, 7716, 25233, 8035, 84242, 55304, 52999, 21999, or 52020 substrate, or to bind to 22406, acyltransferase, 7716, 25233, 8035, 84242, 55304, 52999, 21999, or 52020 can also be evaluated. This can be accomplished, for example, by coupling the compound, e.g., the substrate, with a radioisotope or enzymatic label such that binding of the compound, e.g., the substrate, to 22406, acyltransferase, 7716, 25233, 8035, 84242, 55304, 52999, 21999, or 52020 can be determined by detecting the labeled compound, e.g., substrate, in a complex. Alternatively, 22406, acyltransferase, 7716, 25233, 8035, 84242, 55304, 52999, 21999, or 52020 could be coupled with a radioisotope or enzymatic label to monitor the ability of a test compound to modulate 22406, acyltransferase, 7716, 25233, 8035, 84242, 55304, 52999, 21999, or 52020 binding to a 22406, acyltransferase, 7716, 25233, 8035, 84242, 55304, 52999, 21999, or 52020 substrate in a complex. For example, compounds (e.g., 22406, acyltransferase, 7716, 25233, 8035, 84242, 55304, 52999, 21999, or 52020 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 22406, acyltransferase, 7716, 25233, 8035, 84242, 55304, 52999, 21999, or 52020 substrate) to interact with 22406, acyltransferase, 7716, 25233, 8035, 84242, 55304, 52999, 21999, or 52020 with or without the labeling of any of the interactants can be evaluated. For example, a microphysiometer can be used to detect the interaction of a compound with 22406, acyltransferase, 7716, 25233, 8035, 84242, 55304, 52999, 21999, or 52020 without the labeling of either the compound or the 22406, acyltransferase, 7716, 25233, 8035, 84242, 55304, 52999, 21999, or 52020. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 22406, acyltransferase, 7716, 25233, 8035, 84242, 55304, 52999, 21999, or 52020.

In yet another embodiment, a cell-free assay is provided in which a 22406, acyltransferase, 7716, 25233, 8035, 84242, 55304, 52999, 21999, or 52020 protein or biologically active portion thereof is contacted with a test compound and the ability of the test compound to bind to the 22406, acyltransferase, 7716, 25233, 8035, 84242, 55304, 52999, 21999, or 52020 protein or biologically active portion thereof is evaluated. Preferred biologically active portions of the 22406, acyltransferase, 7716, 25233, 8035, 84242, 55304, 52999, 21999, or 52020 proteins to be used in assays of the present invention include fragments which participate in interactions with non-22406, acyltransferase, 7716, 25233, 8035, 84242, 55304, 52999, 21999, or 52020 molecules, e.g., fragments with high surface probability scores.

Soluble and/or membrane-bound forms of isolated proteins (e.g., 22406, acyltransferase, 7716, 25233, 8035, 84242, 55304, 52999, 21999, or 52020 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block pyridoxal-phosphate dependent serine racemase activity within a cell is evaluated.

In one embodiment, assays are performed where the ability of an agent to block fatty acid synthase activity within a cell is evaluated.

In one embodiment, assays are performed where the ability of an agent to block ATPase activity within a cell is evaluated.

In one embodiment, assays are performed where the ability of an agent to block aminotransferase activity within a cell is evaluated.

In one embodiment related to 8035 and 84242, assays are performed where the ability of an agent to block RING finger protein E3 ubiquitin ligase activity within a cell is evaluated. In another embodiment involving 55304, assays are performed where the ability of an agent to block aminopeptidase activity within a cell is evaluated. In yet another embodiment related to 52999, assays are performed where the ability of an agent to block metallopeptidase activity within a cell is evaluated. In another embodiment related to 21999, an assay is a cell-based assay in which a cell which expresses a ADP-ribosyltransferase protein or biologically active portion thereof is contacted with a test compound, and the ability of the test compound to modulate ADP-ribosyltransferase activity is determined. Determining the ability of the test compound to modulate ADP-ribosyltransferase activity can be accomplished by monitoring, for example, ADP-moiety transferase activity. The cell, for example, can be of mammalian origin, e.g., human. Cell homogenates, or fractions, preferably membrane containing fractions, can also be tested.

In one embodiment, assays are performed where the ability of an agent to block MAGE activity within a cell is evaluated.

The interaction between two molecules can also be detected, e.g., using fluorescence energy transfer (FET) (see, for example, Lakowicz et al. U.S. Pat. No. 5,631,169; Stavrianopoulos, et al. U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 22406, acyltransferase, 7716, 25233, 8035, 84242, 55304, 52999, 21999, or 52020 protein to bind to a target molecule can be accomplished using real-time Biomolecular Interaction Analysis (BIA) (see, e.g., Sjolander, S. and Urbaniczky, C. (1991) Anal. Chem. 63:2338–2345 and Szabo et al. (1995) Curr. Opin. Struct. Biol. 5:699–705). "Surface plasmon resonance" or "BIA" detects biospecific interactions in real time, without labeling any of the interactants (e.g., BIACORE™). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 22406, acyltransferase, 7716, 25233, 8035, 84242, 55304, 52999, 21999, or 52020, an anti-22406, anti-acyltransferase, anti-7716, anti-25233, anti-8035, anti-84242, anti-55304, anti-52999, anti-21999 or anti-52020 antibody, or its target molecule, respectively, to facilitate separation of complexed from uncomplexed forms of one or both of the proteins, as well as to accommodate automation of the assay. Binding of a test compound to a 22406, acyltransferase, 7716, 25233, 8035, 84242, 55304, 52999, 21999, or 52020 protein, or interaction of a 22406, acyltransferase, 7716, 25233, 8035, 84242, 55304, 52999, 21999, or 52020 protein with a target molecule, respectively, in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/22406, glutathione-S-transferase/acyltransferase, glutathione-S-transferase/7716, glutathione-S-transferase/25233, glutathione-S-transferase/8035, glutathione-S-transferase/84242, glutathione-S-transferase/55304, glutathione-S-transferase/52999, glutathione-S-transferase/21999 or glutathione-S-transferase/52020 fusion proteins or glutathione-S-transferase/target fusion proteins can be adsorbed onto glutathione SEPHAROSE™ beads (Sigma Chemical, St. Louis, Mo.) or glutathione derivatized microtiter plates, which are then combined with the test compound or the test compound and either the non-adsorbed target protein or 22406, acyltransferase, 7716, 25233, 8035, 84242, 55304, 52999, 21999, or 52020 protein, respectively, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 22406, acyltransferase, 7716, 25233, 8035, 84242, 55304, 52999, 21999, or 52020 binding or activity determined using standard techniques.

Other techniques for immobilizing either a 22406, acyltransferase, 7716, 25233, 8035, 84242, 55304, 52999, 21999, or 52020 protein or a target molecule on matrices include using conjugation of biotin and streptavidin. Biotinylated 22406, acyltransferase, 7716, 25233, 8035, 84242, 55304, 52999, 21999, or 52020 protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 22406, acyltransferase, 7716, 25233, 8035, 84242, 55304, 52999, 21999, or 52020 protein or target molecules but which do not interfere with binding of the 22406, acyltransferase, 7716, 25233, 8035, 84242, 55304, 52999, 21999, or 52020 protein, respectively, to its target molecule. Such antibodies can be derivatized to the wells of the plate, and unbound target or 22406, acyltransferase, 7716, 25233, 8035, 84242, 55304, 52999, 21999, or 52020 protein trapped in the wells by antibody conjugation. Methods for detecting such complexes, in addition to those described above for the GST-immobilized complexes, include immunodetection of complexes using antibodies reactive with the 22406, acyltransferase, 7716, 25233, 8035, 84242, 55304, 52999, 21999, or 52020 protein or target molecule, as well as enzyme-linked assays which rely on detecting an enzymatic activity associated with the 22406, acyltransferase, 7716, 25233, 8035, 84242, 55304, 52999, 21999, or 52020 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P. (1993 August) *Trends Biochem Sci* 18(8):284–7); chromatography (gel filtration chromatography, ion-exchange chromatography); electrophoresis (see, e.g., Ausubel, F. et al. eds. *Current Protocols in Molecular Biology* 1999, J. Wiley: New York.); and immunoprecipitation (see, for example, Ausubel, F. et al. eds. *Current Protocols in Molecular Biology* 1999, J. Wiley: New York). Such resins and chromatographic techniques are known to one skilled in the art (see, e.g., Heegaard, N. H. (1998 Winter) *J. Mol. Recognit.* 11(1–6):141–8; Hage, D. S., and Tweed, S. A. (1997, Oct. 10) *J. Chromatogr. B Biomed. Sci. Appl.* 699(1–2):499–525). Further, fluorescence energy transfer may also be conveniently utilized, as described herein, to detect binding without further purification of the complex from solution.

In a preferred embodiment, the assay includes contacting the 22406, acyltransferase, 7716, 25233, 8035, 84242, 55304, 52999, 21999, or 52020 protein or biologically active portion thereof with a known compound which binds 22406, acyltransferase, 7716, 25233, 8035, 84242, 55304, 52999, 21999, or 52020, respectively, to form an assay mixture, contacting the assay mixture with a test compound, and determining the ability of the test compound to interact with a 22406, acyltransferase, 7716, 25233, 8035, 84242, 55304, 52999, 21999, or 52020 protein, wherein determining the ability of the test compound to interact with a 22406, acyltransferase, 7716, 25233, 8035, 84242, 55304, 52999, 21999, or 52020 protein includes determining the ability of the test compound to preferentially bind to 22406, acyltransferase, 7716, 25233, 8035, 84242, 55304, 52999, 21999, or 52020 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 22406, acyltransferase, 7716, 25233, 8035, 84242, 55304, 52999, 21999, or 52020 genes herein identified. In an alternative embodiment, the invention provides methods for determining the ability of the test compound to modulate the activity of a 22406, acyltransferase, 7716, 25233, 8035, 84242, 55304, 52999, 21999, or 52020 protein through modulation of the activity of a downstream effector of a 22406, acyltransferase, 7716, 25233, 8035, 84242, 55304, 52999, 21999, or 52020 target molecule, respectively. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 22406, acyltransferase, 7716, 25233, 8035, 84242, 55304, 52999, 21999, or 52020 proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with 22406, acyltransferase, 7716, 25233, 8035, 84242, 55304, 52999, 21999, or 52020 ("22406, acyltransferase, 7716, 25233, 8035, 84242, 55304, 52999, 21999, or 52020-binding proteins" or "22406, acyltransferase, 7716, 25233, 8035, 84242, 55304, 52999, 21999, or 52020-bp") and are involved in 22406, acyltransferase, 7716, 25233, 8035, 84242, 55304, 52999, 21999, or 52020 activity, respectively. Such 22406, acyltransferase, 7716, 25233, 8035, 84242, 55304, 52999, 21999, or 52020-bps can be activators or inhibitors of signals by the 22406, acyltransferase, 7716, 25233, 8035, 84242, 55304, 52999, 21999, or 52020 proteins or 22406, acyltransferase, 7716, 25233, 8035, 84242, 55304, 52999, 21999, or 52020 targets, respectively, as, for example, downstream elements of a 22406, acyltransferase, 7716, 25233, 8035, 84242, 55304, 52999, 21999, or 52020-mediated signaling pathway.

The two-hybrid system is based on the modular nature of most transcription factors, which consist of separable DNA-binding and activation domains. Briefly, the assay utilizes two different DNA constructs. In one construct, the gene that codes for a 22406, acyltransferase, 7716, 25233, 8035, 84242, 55304, 52999, 21999, or 52020 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 22406, acyltransferase, 7716, 25233, 8035, 84242, 55304, 52999, 21999, or 52020 protein can be fused to the activator domain.) If the "bait" and the "prey" proteins are able to interact, in vivo, forming a 22406, acyltransferase, 7716, 25233, 8035, 84242, 55304, 52999, 21999, or 52020-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 22406, acyltransferase, 7716, 25233, 8035, 84242, 55304, 52999, 21999, or 52020 protein.

In another embodiment, modulators of 22406, acyltransferase, 7716, 25233, 8035, 84242, 55304, 52999, 21999, or 52020 expression are identified. For example, a cell or cell free mixture is contacted with a candidate compound and the expression of 22406, acyltransferase, 7716, 25233, 8035, 84242, 55304, 52999, 21999, or 52020 mRNA or protein evaluated relative to the level of expression of 22406, acyltransferase, 7716, 25233, 8035, 84242, 55304, 52999, 21999, or 52020 mRNA or protein in the absence of the candidate compound. When expression of 22406, acyltransferase, 7716, 25233, 8035, 84242, 55304, 52999, 21999, or 52020 mRNA or protein is greater in the presence of the candidate compound than in its absence, the candidate compound is identified as a stimulator of 22406, acyltransferase, 7716, 25233, 8035, 84242, 55304, 52999, 21999, or 52020 mRNA or protein expression, respectively. Alternatively, when expression of 22406, acyltransferase, 7716, 25233, 8035, 84242, 55304, 52999, 21999, or 52020 mRNA or protein is less (statistically significantly less) in the presence of the candidate compound than in its absence, the candidate compound is identified as an inhibitor of 22406, acyltransferase, 7716, 25233, 8035, 84242, 55304, 52999, 21999, or 52020 mRNA or protein expression, respectively.

The level of 22406, acyltransferase, 7716, 25233, 8035, 84242, 55304, 52999, 21999, or 52020 mRNA or protein expression can be determined by methods described herein for detecting 22406, acyltransferase, 7716, 25233, 8035, 84242, 55304, 52999, 21999, or 52020 mRNA or protein, respectively.

In another aspect, the invention pertains to a combination of two or more of the assays described herein. For example, a modulating agent can be identified using a cell-based or a cell free assay, and the ability of the agent to modulate the activity of a 22406, acyltransferase, 7716, 25233, 8035, 84242, 55304, 52999, 21999, or 52020 protein can be confirmed in vivo, e.g., in an animal.

This invention further pertains to novel agents identified by the above-described screening assays. Accordingly, it is within the scope of this invention to further use an agent identified as described herein (e.g., a 22406, acyltransferase, 7716, 25233, 8035, 84242, 55304, 52999, 21999, or 52020 modulating agent, an antisense 22406, acyltransferase, 7716, 25233, 8035, 84242, 55304, 52999, 21999, or 52020 nucleic acid molecule, a 22406, acyltransferase, 7716, 25233, 8035, 84242, 55304, 52999, 21999, or 52020-specific antibody, or a 22406, acyltransferase, 7716, 25233, 8035, 84242, 55304, 52999, 21999, or 52020-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 22406, acyltransferase, 7716, 25233, 8035, 84242, 55304, 52999, 21999, or 52020 with a disease; (ii) identify an individual from a minute biological sample (tissue typing); and (iii) aid in forensic identification of a biological sample. These applications are described in the subsections below.

Chromosome Mapping

The 22406, acyltransferase, 7716, 25233, 8035, 84242, 55304, 52999, 21999, or 52020 nucleotide sequences or portions thereof can be used to map the location of the 22406, acyltransferase, 7716, 25233, 8035, 84242, 55304, 52999, 21999, or 52020 genes, respectively, on a chromosome. This process is called chromosome mapping. Chromosome mapping is useful in correlating the 22406, acyltransferase, 7716, 25233, 8035, 84242, 55304, 52999, 21999, or 52020 sequences with genes associated with disease.

Briefly, 22406, acyltransferase, 7716, 25233, 8035, 84242, 55304, 52999, 21999, or 52020 genes can be mapped to chromosomes by preparing PCR primers (preferably 15–25 bp in length) from the 22406, acyltransferase, 7716, 25233, 8035, 84242, 55304, 52999, 21999, or 52020 nucleotide sequences. These primers can then be used for PCR screening of somatic cell hybrids containing individual human chromosomes. Only those hybrids containing the human gene corresponding to the 22406, acyltransferase, 7716, 25233, 8035, 84242, 55304, 52999, 21999, or 52020 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al. (1983) Science 220:919–924).

Other mapping strategies e.g., in situ hybridization (described in Fan, Y. et al. (1990) Proc. Natl. Acad. Sci. USA 87:6223–27), pre-screening with labeled flow-sorted chromosomes, and pre-selection by hybridization to chromosome specific cDNA libraries can be used to map 22406, acyltransferase, 7716, 25233, 8035, 84242, 55304, 52999, 21999, or 52020 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature 325:783–787.

Moreover, differences in the DNA sequences between individuals affected and unaffected with a disease associated with the 22406, acyltransferase, 7716, 25233, 8035, 84242, 55304, 52999, 21999, or 52020 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 22406, acyltransferase, 7716, 25233, 8035, 84242, 55304, 52999, 21999, or 52020 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 22406, acyltransferase, 7716, 25233, 8035, 84242, 55304, 52999, 21999, or 52020 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1, SEQ ID NO:6, SEQ ID NO:10, SEQ ID NO:14, SEQ ID NO:18, SEQ ID NO:22, SEQ ID NO:26, SEQ ID NO:29, SEQ ID NO:36 and SEQ ID NO:40 can provide positive individual identification with a panel of perhaps 10 to 1,000 primers which each yield a noncoding amplified sequence of 100 bases. If predicted coding sequences, such as those in SEQ ID NO:3, SEQ ID NO:8, SEQ ID NO:12, SEQ ID NO:16, SEQ ID NO:20, SEQ ID NO:24, SEQ ID NO:28, SEQ ID NO:31, SEQ ID NO:38 or SEQ ID NO:42 are used, a more appropriate number of primers for positive individual identification would be 500–2,000.

If a panel of reagents from 22406, acyltransferase, 7716, 25233, 8035, 84242, 55304, 52999, 21999, or 52020 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 22406, Acyltransferase, 7716, 25233, 8035, 84242, 55304, 52999, 21999 or 52020 Sequences in Forensic Biology DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1, SEQ ID NO:6, SEQ ID NO:10, SEQ ID NO:14, SEQ ID NO:18, SEQ ID NO:22, SEQ ID NO:26, SEQ ID NO:29, SEQ ID NO:36 or SEQ ID NO:40 (e.g., fragments derived from the noncoding regions of SEQ ID NO:1, SEQ ID NO:6, SEQ ID NO:10, SEQ ID NO:14, SEQ ID NO:18, SEQ ID NO:22, SEQ ID NO:26, SEQ ID NO:29, SEQ ID NO:36 or SEQ ID NO:40 having a length of at least 20 bases, preferably at least 30 bases) are particularly appropriate for this use.

The 22406 nucleotide sequences described herein can further be used to provide polynucleotide reagents, e.g., labeled or labelable probes which can be used in, for example, an in situ hybridization technique, to identify a specific tissue, e.g., a tissue containing pyridoxal-phosphate dependent serine racemase activity. The acyltransferase nucleotide sequences described herein can further be used to provide polynucleotide reagents, e.g., labeled or labelable probes which can be used in, for example, an in situ hybridization technique, to identify a specific tissue, e.g., a tissue containing fatty acid synthase activity. The 7716 nucleotide sequences described herein can further be used to provide polynucleotide reagents, e.g., labeled or labelable probes which can be used in, for example, an in situ hybridization technique, to identify a specific tissue, e.g., a tissue containing ATPase activity. The 25233 nucleotide sequences described herein can further be used to provide polynucleotide reagents, e.g., labeled or labelable probes which can be used in, for example, an in situ hybridization technique, to identify a specific tissue, e.g., a tissue containing aminotransferase activity. The 8035, 84242, 55304, 52999, or 21999 nucleotide sequences described herein can further be used to provide polynucleotide reagents, e.g., labeled or labelable probes which can be used in, for example, an in situ hybridization technique, to identify a specific tissue, e.g., a tissue containing RING finger E3 ubiquitin ligase protein activity (8035 and 84242), aminopeptidase activity (55304), metallopreptidase activity (52999), and ADP-ribosyltransferase activity (21999). The 52020 nucleotide sequences described herein can further be used to provide polynucleotide reagents, e.g., labeled or labelable probes which can be used in, for example, an in situ hybridization technique, to identify a specific tissue, e.g., a tissue containing MAGE activity. This can be very useful in cases where a forensic pathologist is presented with a tissue of unknown origin. Panels of such 22406, acyltransferase, 7716, 25233, 8035, 84242, 55304, 52999, 21999, or 52020 probes can be used to identify tissue by species and/or by organ type.

In a similar fashion, these reagents, e.g., 22406, acyltransferase, 7716, 25233, 8035, 84242, 55304, 52999, 21999, or 52020 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 22406, acyltransferase, 7716, 25233, 8035, 84242, 55304, 52999, 21999, or 52020.

Such disorders include, e.g., a disorder associated with the misexpression of 22406, or a neurological disorder.

Such disorders include, e.g., a disorder associated with the misexpression of acyltransferase, or fatty acid biosynthesis or lipid metabolism related disorder.

Such disorders include, e.g., a disorder associated with the misexpression of 7716, or lipid metabolism related disorder.

Such disorders include, e.g., a disorder associated with the misexpression of 25233, or lipid metabolism related disorder.

Such disorders include, e.g., a disorder associated with the misexpression of 8035 or 84242, those disorders resulting from aberrant cellular proliferation and/or differentiation including diseases such as cancer, acute promyelocytic leukemia (APL), VHL disease, and systemic lupus erythematosus. In addition, RING finger protein family members have been shown to contribute to the pathogenesis of certain viral diseases including those caused by HSV and HIV. Other such disorders include, e.g., a disorder associated with the misexpression of 55304, 52999, 21999, or lipid metabolism related disorder.

Such disorders include, e.g., 52020-mediated aberrant cell growth.

The method includes one or more of the following:

detecting, in a tissue of the subject, the presence or absence of a mutation which affects the expression of the 22406, acyltransferase, 7716, 25233, 8035, 84242, 55304, 52999, 21999, or 52020 gene, or detecting the presence or absence of a mutation in a region which controls the expression of the gene, e.g., a mutation in the 5' control region;

detecting, in a tissue of the subject, the presence or absence of a mutation which alters the structure of the 22406, acyltransferase, 7716, 25233, 8035, 84242, 55304, 52999, 21999, or 52020 gene;

detecting, in a tissue of the subject, the misexpression of the 22406, acyltransferase, 7716, 25233, 8035, 84242, 55304, 52999, 21999, or 52020 gene, at the mRNA level, e.g., detecting a non-wild type level of an mRNA;

detecting, in a tissue of the subject, the misexpression of the gene, at the protein level, e.g., detecting a non-wild type level of a 22406, acyltransferase, 7716, 25233, 8035, 84242, 55304, 52999, 21999, or 52020 polypeptide.

In preferred embodiments the method includes: ascertaining the existence of at least one of: a deletion of one or more nucleotides from the 22406, acyltransferase, 7716, 25233, 8035, 84242, 55304, 52999, 21999, or 52020 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, SEQ ID NO:6, SEQ ID NO:10, SEQ ID NO:14, SEQ ID NO:18, SEQ ID NO:22, SEQ ID NO:26, SEQ ID NO:29, SEQ ID NO:36, SEQ ID NO:40, naturally occurring mutants thereof or 5' or 3' flanking sequences naturally associated with the 22406, acyltransferase, 7716, 25233, 8035, 84242, 55304, 52999, 21999, or 52020 gene, respectively; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 22406, acyltransferase, 7716, 25233, 8035, 84242, 55304, 52999, 21999, or 52020 gene; the presence of a non-wild type splicing pattern of a messenger RNA transcript of the gene; or a non-wild type level of 22406, acyltransferase, 7716, 25233, 8035, 84242, 55304, 52999, 21999, or 52020.

Methods of the invention can be used prenatally or to determine if a subject's offspring will be at risk for a disorder.

In preferred embodiments the method includes determining the structure of a 22406, acyltransferase, 7716, 25233, 8035, 84242, 55304, 52999, 21999, or 52020 gene, an abnormal structure being indicative of risk for the disorder.

In preferred embodiments the method includes contacting a sample form the subject with an antibody to the 22406, acyltransferase, 7716, 25233, 8035, 84242, 55304, 52999, 21999, or 52020 protein or a nucleic acid, which hybridizes specifically with the gene. These and other embodiments are discussed below.

Diagnostic and Prognostic Assays

The presence, level, or absence of 22406, acyltransferase, 7716, 25233, 8035, 84242, 55304, 52999, 21999, or 52020 protein or nucleic acid in a biological sample can be evaluated by obtaining a biological sample from a test subject and contacting the biological sample with a compound or an agent capable of detecting 22406, acyltransferase, 7716, 25233, 8035, 84242, 55304, 52999, 21999, or 52020 protein or nucleic acid (e.g., mRNA, genomic DNA) that encodes 22406, acyltransferase, 7716, 25233, 8035, 84242, 55304, 52999, 21999, or 52020 protein such that the presence of 22406, acyltransferase, 7716, 25233, 8035, 84242, 55304, 52999, 21999, or 52020 protein or nucleic acid is detected in the biological sample. The term "biological sample" includes tissues, cells and biological fluids isolated from a subject, as well as tissues, cells and fluids present within a subject. The level of expression of the 22406, acyltransferase, 7716, 25233, 8035, 84242, 55304, 52999, 21999, or 52020 gene can be measured in a number of ways, including, but not limited to: measuring the mRNA encoded by the 22406, acyltransferase, 7716, 25233, 8035, 84242, 55304, 52999, 21999, or 52020 genes; measuring the amount of protein encoded by the 22406, acyltransferase, 7716, 25233, 8035, 84242, 55304, 52999, 21999, or 52020 genes; or measuring the activity of the protein encoded by the 22406, acyltransferase, 7716, 25233, 8035, 84242, 55304, 52999, 21999, or 52020 genes.

The level of mRNA corresponding to the 22406, acyltransferase, 7716, 25233, 8035, 84242, 55304, 52999, 21999, or 52020 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 22406, acyltransferase, 7716, 25233, 8035, 84242, 55304, 52999, 21999, or 52020 nucleic acid, such as the nucleic acid of SEQ ID NO:1, SEQ ID NO:6, SEQ ID NO:10, SEQ ID NO:14, SEQ ID NO:18, SEQ ID NO:22, SEQ ID NO:26, SEQ ID NO:29, SEQ ID NO:36 or SEQ ID NO:40, or a portion thereof, such as an oligonucleotide of at least 7, 15, 30, 50, 100, 250 or 500 nucleotides in length and sufficient to specifically hybridize under stringent conditions to 22406, acyltransferase, 7716, 25233, 8035, 84242, 55304, 52999, 21999, or 52020 mRNA or genomic DNA, respectively. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 22406, acyltransferase, 7716, 25233, 8035, 84242, 55304, 52999, 21999, or 52020 genes.

The level of mRNA in a sample that is encoded by one of 22406, acyltransferase, 7716, 25233, 8035, 84242, 55304, 52999, 21999, or 52020 can be evaluated with nucleic acid amplification, e.g., by rtPCR (Mullis, 1987, U.S. Pat. No. 4,683,202), ligase chain reaction (Barany (1991) *Proc. Natl. Acad. Sci. USA* 88:189–193), self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), rolling circle replication (Lizardi et al. U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 22406, acyltransferase, 7716, 25233, 8035, 84242, 55304, 52999, 21999, or 52020 gene being analyzed.

In another embodiment, the methods further contacting a control sample with a compound or agent capable of detecting 22406, acyltransferase, 7716, 25233, 8035, 84242, 55304, 52999, 21999, or 52020 mRNA, or genomic DNA, and comparing the presence of 22406, acyltransferase, 7716, 25233, 8035, 84242, 55304, 52999, 21999, or 52020 mRNA or genomic DNA in the control sample with the presence of 22406, acyltransferase, 7716, 25233, 8035, 84242, 55304, 52999, 21999, or 52020 mRNA or genomic DNA, respectively, in the test sample.

A variety of methods can be used to determine the level of protein encoded by 22406, acyltransferase, 7716, 25233, 8035, 84242, 55304, 52999, 21999, or 52020. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab)$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 22406, acyltransferase, 7716, 25233, 8035, 84242, 55304, 52999, 21999, or 52020 protein in a biological sample in vitro as well as in vivo. In vitro techniques for detection of 22406, acyltransferase, 7716, 25233, 8035, 84242, 55304, 52999, 21999, or 52020 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 22406, acyltransferase, 7716, 25233, 8035, 84242, 55304, 52999, 21999, or 52020 protein include introducing into a subject a labeled anti-22406, anti-acyltransferase, anti-7716, anti-25233, anti-8035, anti-84242, anti-55304, anti-52999, anti-21999, or anti-52020 antibody. For example, the antibody can be labeled with a radioactive marker whose presence and location in a subject can be detected by standard imaging techniques.

In another embodiment, the methods further include contacting the control sample with a compound or agent capable of detecting 22406, acyltransferase, 7716, 25233, 8035, 84242, 55304, 52999, 21999, or 52020 protein, and comparing the presence of 22406, acyltransferase, 7716, 25233, 8035, 84242, 55304, 52999, 21999, or 52020 protein in the control sample with the presence of 22406, acyltransferase, 7716, 25233, 8035, 84242, 55304, 52999, 21999, or 52020 protein, respectively, in the test sample.

The invention also includes kits for detecting the presence of 22406, acyltransferase, 7716, 25233, 8035, 84242, 55304, 52999, 21999, or 52020 in a biological sample. For example, the kit can include a compound or agent capable of detecting 22406, acyltransferase, 7716, 25233, 8035, 84242, 55304, 52999, 21999, or 52020 protein or mRNA in a biological sample; and a standard. The compound or agent can be packaged in a suitable container. The kit can further comprise instructions for using the kit to detect 22406, acyltransferase, 7716, 25233, 8035, 84242, 55304, 52999, 21999, or 52020 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 22406, acyltransferase, 7716, 25233, 8035, 84242, 55304, 52999, 21999, or 52020 expression or activity. As used herein, the term "unwanted" includes an unwanted phenomenon involved in a biological response such as, for example, in the case of 22406, neurodegeneration, in the case of acyltranferase, pain or deregulated cell proliferation, in the case of 7716, neurodegeneration or deregulated cell proliferation, in the case of 25233, muscle, cardiac, kidney, pancreatic, red blood cell, or hepatic injury, or cancer, or active periodontal disease, in the case of 8035 and 84242, deregulated cell proliferation and/or differentiation, in the case of 55304 deregulated cell proliferation or hypertension, in the case of 52999, inflammation or deregulated cell proliferation, in the case of 21999, deregulated cell proliferation or depressed cellular metabolism, or in the case of 52020, deregulated cell growth.

In one embodiment, a disease or disorder associated with aberrant or unwanted 22406, acyltransferase, 7716, 25233, 8035, 84242, 55304, 52999, 21999, or 52020 expression or activity is identified. A test sample is obtained from a subject and 22406, acyltransferase, 7716, 25233, 8035, 84242, 55304, 52999, 21999, or 52020 protein or nucleic acid (e.g., mRNA or genomic DNA) is evaluated, wherein the level, e.g., the presence or absence, of 22406, acyltransferase, 7716, 25233, 8035, 84242, 55304, 52999, 21999, or 52020 protein or nucleic acid is diagnostic for a subject having or at risk of developing a disease or disorder associated with aberrant or unwanted 22406, acyltransferase, 7716, 25233, 8035, 84242, 55304, 52999, 21999, or 52020 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 22406 expression or activity. For example, such methods can be used to determine whether a subject can be effectively treated with an agent for a neurodegenerative disorder.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 7716 expression or activity. For example, such methods can be used to determine whether a subject can be effectively treated with an agent for neurodegeneration or a cellular growth related disorder.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 25233 expression or activity. For example, such methods can be used to determine whether a subject can be effectively treated with an agent for muscle, cardiac, kidney, pancreatic, red blood cell, or hepatic injury, or cancer, or active periodontal disease.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted acyltransferase, 8035, 84242, 55304, 52999, 21999, or 52020 expression or activity. For example, such methods can be used to determine whether a subject can be effectively treated with an agent for a cellular growth related disorder.

The methods of the invention can also be used to detect genetic alterations in a 22406 gene, thereby determining if a subject with the altered gene is at risk for a disorder characterized by misregulation in 22406 protein activity or nucleic acid expression, such as a neurodegenerative disorder. The methods of the invention can also be used to detect genetic alterations in a 7716 gene, thereby determining if a subject with the altered gene is at risk for a disorder characterized by misregulation in 7716 protein activity or nucleic acid expression, such as neurodegeneration or a cellular growth related disorder. The methods of the invention can also be used to detect genetic alterations in a 25233 gene, thereby determining if a subject with the altered gene is at risk for a disorder characterized by misregulation in 25233 protein activity or nucleic acid expression, such as those arising as a result of a metabolic defect. The methods of the invention can also be used to detect genetic alterations in a acyltransferase, 8035, 84242, 55304, 52999, 21999 or 52020 gene, thereby determining if a subject with the altered gene is at risk for a disorder characterized by misregulation in 8035, 84242, 55304, 52999, 21999 or 52020 protein activity or nucleic acid expression, such as a cellular growth related disorder. In preferred embodiments, the methods include detecting, in a sample from the subject, the presence or absence of a genetic alteration characterized by at least one of an alteration affecting the integrity of a gene encoding a 22406, acyltransferase, 7716, 25233, 8035, 84242, 55304, 52999, 21999, or 52020-protein, or the misexpression of the 22406, acyltransferase, 7716, 25233, 8035, 84242, 55304, 52999, 21999, or 52020 gene. For example, such genetic alterations can be detected by ascertaining the existence of at least one of 1) a deletion of one or more nucleotides from a 22406, acyltransferase, 7716, 25233, 8035, 84242, 55304, 52999, 21999, or 52020 gene; 2) an addition of one or more nucleotides to a 22406, acyltransferase, 7716, 25233, 8035, 84242, 55304, 52999, 21999, or 52020 gene; 3) a substitution of one or more nucleotides of a 22406, acyltransferase, 7716, 25233, 8035, 84242, 55304, 52999, 21999, or 52020 gene, 4) a chromosomal rearrangement of a 22406, acyltransferase, 7716, 25233, 8035, 84242, 55304, 52999, 21999, or 52020 gene; 5) an alteration in the level of a messenger RNA transcript of a 22406, acyltransferase, 7716, 25233, 8035, 84242, 55304, 52999, 21999, or 52020 gene, 6) aberrant modification of a 22406, acyltransferase, 7716, 25233, 8035, 84242, 55304, 52999, 21999, or 52020 gene, such as of the methylation pattern of the genomic DNA, 7) the presence of a non-wild type splicing pattern of a messenger RNA transcript of a 22406, acyltransferase, 7716, 25233, 8035, 84242, 55304, 52999, 21999, or 52020 gene, 8) a non-wild type level of a 22406, acyltransferase, 7716, 25233, 8035, 84242, 55304, 52999, 21999, or 52020-protein, 9) allelic loss of a 22406, acyltransferase, 7716, 25233, 8035, 84242, 55304, 52999, 21999, or 52020 gene, and 10) inappropriate post-translational modification of a 22406, acyltransferase, 7716, 25233, 8035, 84242, 55304, 52999, 21999, or 52020-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 22406, acyltransferase, 7716, 25233, 8035, 84242, 55304, 52999, 21999, or 52020-gene. This method can include the steps of collecting a sample of cells from a subject, isolating nucleic acid (e.g., genomic, mRNA or both) from the sample, contacting the nucleic acid sample with one or more primers which specifically hybridize to a 22406, acyltransferase, 7716, 25233, 8035, 84242, 55304, 52999, 21999, or 52020 gene under conditions such that hybridization and amplification of the 22406, acyltransferase, 7716, 25233, 8035, 84242, 55304, 52999, 21999, or 52020-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) *Proc. Natl. Acad. Sci. USA* 87:1874–1878), transcriptional amplification system (Kwoh, D. Y. et al. (1989) *Proc. Natl. Acad. Sci. USA* 86:1173–1177), Q-Beta Replicase (Lizardi, P. M. et al. (1988) *Bio-Technology* 6:1197), or other nucleic acid amplification methods, followed by the detection of the amplified molecules using techniques known to those of skill in the art.

In another embodiment, mutations in a 22406, acyltransferase, 7716, 25233, 8035, 84242, 55304, 52999, 21999, or 52020 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 22406, acyltransferase, 7716, 25233, 8035, 84242, 55304, 52999, 21999, or 52020 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al. (1996) *Human Mutation* 7: 244–255; Kozal, M. J. et al. (1996) *Nature Medicine* 2:753–759). For example, genetic mutations in 22406, acyltransferase, 7716, 25233, 8035, 84242, 55304, 52999, 21999, or 52020 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 22406, acyltransferase, 7716, 25233, 8035, 84242, 55304, 52999, 21999, or 52020 gene and detect mutations by comparing the sequence of the sample 22406, acyltransferase, 7716, 25233, 8035, 84242, 55304, 52999, 21999, or 52020 with the corresponding wild-type (control) sequence. Automated sequencing procedures can be utilized when performing the diagnostic assays (Naeve et al. (1995) *Biotechniques* 19:448–453), including sequencing by mass spectrometry.

Other methods for detecting mutations in the 22406, acyltransferase, 7716, 25233, 8035, 84242, 55304, 52999, 21999, or 52020 gene include methods in which protection from cleavage agents is used to detect mismatched bases in RNA/RNA or RNA/DNA heteroduplexes (Myers et al. (1985) *Science* 230:1242–1246; Cotton et al. (1988) *Proc. Natl. Acad. Sci. USA* 85:4397–4401; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 22406, acyltransferase, 7716, 25233, 8035, 84242, 55304, 52999, 21999, or 52020 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 22406, acyltransferase, 7716, 25233, 8035, 84242, 55304, 52999, 21999, or 52020 genes. For example, single strand conformation polymorphism (SSCP) may be used to detect differences in electrophoretic mobility between mutant and wild type nucleic acids (Orita et al. (1989) *Proc. Natl. Acad. Sci. USA:* 86:2766–2770, see also Cotton (1993) *Mutat. Res.* 285:125–144; and Hayashi (1992) *Genet. Anal. Tech. Appl.* 9:73–79). Single-stranded DNA fragments of sample and control 22406, acyltransferase, 7716, 25233, 8035, 84242, 55304, 52999, 21999, or 52020 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495–498). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci. USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1–7). It is anticipated that in certain embodiments amplification may also be performed using Taq ligase for amplification (Barany (1991) *Proc. Natl. Acad. Sci USA* 88:189–193). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 22406, acyltransferase, 7716, 25233, 8035, 84242, 55304, 52999, 21999, or 52020 gene.

Use of 22406, Acyltransferase, 7716, 25233, 8035, 84242, 55304, 52999, 21999 or 52020 Molecules as Surrogate Markers The 22406, acyltransferase, 7716, 25233, 8035, 84242, 55304, 52999, 21999, or 52020 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 22406, acyltransferase, 7716, 25233, 8035, 84242, 55304, 52999, 21999, or 52020 molecules of the invention may be detected, and may be correlated with one or more biological states in vivo. For example, the 22406, acyltransferase, 7716, 25233, 8035, 84242, 55304, 52999, 21999, or 52020 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 22406, acyltransferase, 7716, 25233, 8035, 84242, 55304, 52999, 21999, or 52020 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 22406, acyltransferase, 7716, 25233, 8035, 84242, 55304, 52999, 21999, or 52020 marker) transcription or expression, the amplified marker may be in a quantity which is more readily detectable than the drug itself. Also, the marker may be more easily detected due to the nature of the marker itself; for example, using the methods described herein, anti-22406, anti-acyltransferase, anti-7716, anti-25233, anti-8035, anti-84242, anti-55304, anti-52999, anti-21999 or anti-52020 antibodies may be employed in an immune-based detection system for a 22406, acyltransferase, 7716, 25233, 8035, 84242, 55304, 52999, 21999, or 52020 protein marker, respectively, or 22406, acyltransferase, 7716, 25233, 8035, 84242, 55304, 52999, 21999, or 52020-specific radiolabeled probes may be used to detect a 22406, acyltransferase, 7716, 25233, 8035, 84242, 55304, 52999, 21999, or 52020 mRNA marker, respectively. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229–238; Schentag (1999) *Am. J. Health-Syst. Pharm.* 56 Suppl. 3:S21–S24; and Nicolau (1999) *Am, J. Health-Syst. Pharm.* 56 Suppl. 3:S16–S20.

The 22406, acyltransferase, 7716, 25233, 8035, 84242, 55304, 52999, 21999, or 52020 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 22406, acyltransferase, 7716, 25233, 8035, 84242, 55304, 52999, 21999, or 52020 protein or RNA) for specific tumor markers in a subject, a drug or course of treatment may be selected that is optimized for the treatment of the specific tumor likely to be present in the subject. Similarly, the presence or absence of a specific sequence mutation in 22406, acyltransferase, 7716, 25233, 8035, 84242, 55304, 52999, 21999, or 52020 DNA may correlate 22406, acyltransferase, 7716, 25233, 8035, 84242, 55304, 52999, 21999, or 52020 drug response, respectively. The use of pharmacogenomic markers therefore permits the application of the most appropriate treatment for each subject without having to administer the therapy.

Pharmaceutical Compositions

The nucleic acid and polypeptides, fragments thereof, as well as anti-22406, anti-acyltransferase, anti-7716, anti-25233, anti-8035, anti-84242, anti-55304, anti-52999, anti-21999, or anti-52020 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL solubilizer (BASF; Florham Park, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e, including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 22406, acyltransferase, 7716, 25233, 8035, 84242, 55304, 52999, 21999, or 52020 expression or activity.

The present invention provides for both prophylactic and therapeutic methods of treating a subject at risk of (or susceptible to) a disorder or having a disorder associated with aberrant or unwanted acyltransferase expression or activity. "Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" includes, but is not limited to, small molecules, peptides, antibodies, ribozymes and antisense oligonucleotides. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 22406, acyltransferase, 7716, 25233, 8035, 84242, 55304, 52999, 21999, or 52020 molecules of the present invention or 22406, acyltransferase, 7716, 25233, 8035, 84242, 55304, 52999, 21999, or 52020 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 22406, acyltransferase, 7716, 25233, 8035, 84242, 55304, 52999, 21999, or 52020 expression or activity, by administering to the subject a 22406, acyltransferase, 7716, 25233, 8035, 84242, 55304, 52999, 21999, or 52020 agent which modulates 22406, acyltransferase, 7716, 25233, 8035, 84242, 55304, 52999, 21999, or 52020 expression or at least one 22406, acyltransferase, 7716, 25233, 8035, 84242, 55304, 52999, 21999, or 52020 activity, respectively. Subjects at risk for a disease which is caused or contributed to by aberrant or unwanted 22406, acyltransferase, 7716, 25233, 8035, 84242, 55304, 52999, 21999, or 52020 expression or activity can be identified by, for example, any or a combination of diagnostic or prognostic assays as described herein. Administration of a prophylactic agent can occur prior to the manifestation of symptoms characteristic of the 22406, acyltransferase, 7716, 25233, 8035, 84242, 55304, 52999, 21999, or 52020 aberrance, such that a disease or disorder is prevented or, alternatively, delayed in its progression. Depending on the type of 22406, acyltransferase, 7716, 25233, 8035, 84242, 55304, 52999, 21999, or 52020 aberrance, for example, a 22406, acyltransferase, 7716, 25233, 8035, 84242, 55304, 52999, 21999, or 52020 agonist, or a 22406, acyltransferase, 7716, 25233, 8035, 84242, 55304, 52999, 21999, or 52020 antagonist agent can be used for treating the subject. The appropriate agent can be determined based on screening assays described herein.

It is possible that some 22406, acyltransferase, 7716, 25233, 8035, 84242, 55304, 52999, 21999, or 52020 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 22406, acyltransferase, 7716, 25233, 8035, 84242, 55304, 52999, 21999, or 52020 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 22406, acyltransferase, 7716, 25233, 8035, 84242, 55304, 52999, 21999, or 52020 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 22406, acyltransferase, 7716, 25233, 8035, 84242, 55304, 52999, 21999, or 52020 expression is through the use of aptamer molecules specific for 22406, acyltransferase, 7716, 25233, 8035, 84242, 55304, 52999, 21999, or 52020 protein, respectively. Aptamers are nucleic acid molecules having a tertiary structure which permits them to specifically bind to protein ligands (see, e.g., Osborne, et al. (1997) *Curr. Opin. Chem. Biol.* 1(1):5–9; and Patel, D. J. (1997 June) *Curr. Opin. Chem. Biol.* 1(1):32–46). Since nucleic acid molecules may in many cases be more conveniently introduced into target cells than therapeutic protein molecules may be, aptamers offer a method by which 22406, acyltransferase, 7716, 25233, 8035, 84242, 55304, 52999, 21999, or 52020 protein activity may be specifically decreased without the introduction of drugs or other molecules which may have pluripotent effects.

Antibodies can be generated that are both specific for target gene product and that reduce target gene product activity. Such antibodies may, therefore, be administered in instances whereby negative modulatory techniques are appropriate for the treatment of 22406, acyltransferase, 7716, 25233, 8035, 84242, 55304, 52999, 21999, or 52020 disorders. For a description of antibodies, see the Antibody section above.

In circumstances wherein injection of an animal or a human subject with a 22406, acyltransferase, 7716, 25233, 8035, 84242, 55304, 52999, 21999, or 52020 protein or epitope for stimulating antibody production is harmful to the subject, it is possible to generate an immune response against 22406, acyltransferase, 7716, 25233, 8035, 84242, 55304, 52999, 21999, or 52020 through the use of anti-idiotypic antibodies (see, for example, Herlyn, D. (1999) *Ann. Med.* 31(1):66–78; and Bhattacharya-Chatterjee, M., and Foon, K. A. (1998) *Cancer Treat. Res.* 94:51–68). If an anti-idiotypic antibody is introduced into a mammal or human subject, it should stimulate the production of anti-anti-idiotypic antibodies, which should be specific to the 22406, acyltransferase, 7716, 25233, 8035, 84242, 55304, 52999, 21999, or 52020 protein. Vaccines directed to a disease characterized by 22406, acyltransferase, 7716, 25233, 8035, 84242, 55304, 52999, 21999, or 52020 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 22406, acyltransferase, 7716, 25233, 8035, 84242, 55304, 52999, 21999, or 52020 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 22406, acyltransferase, 7716, 25233, 8035, 84242, 55304, 52999, 21999, or 52020 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al. (1996) *Current Opinion in Biotechnology* 7:89–94 and in Shea, K. J. (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al. (1993) *Nature* 361:645–647. Through the use of isotope-labeling, the "free" concentration of compound which modulates the expression or activity of 22406, acyltransferase, 7716, 25233, 8035, 84242, 55304, 52999, 21999, or 52020 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al. (1995) *Analytical Chemistry* 67:2142–2144.

Another aspect of the invention pertains to methods of modulating 22406, acyltransferase, 7716, 25233, 8035, 84242, 55304, 52999, 21999, or 52020 expression or activity for therapeutic purposes. Accordingly, in an exemplary embodiment, the modulatory method of the invention involves contacting a cell with a 22406, acyltransferase, 7716, 25233, 8035, 84242, 55304, 52999, 21999, or 52020 agent that modulates one or more of the activities of 22406, acyltransferase, 7716, 25233, 8035, 84242, 55304, 52999, 21999, or 52020 protein activity, respectively, associated with the cell. An agent that modulates 22406, acyltransferase, 7716, 25233, 8035, 84242, 55304, 52999, 21999, or 52020 protein activity can be an agent as described herein, such as a nucleic acid or a protein, a naturally-occurring target molecule of a 22406, acyltransferase, 7716, 25233, 8035, 84242, 55304, 52999, 21999, or 52020 protein (e.g., a 22406, acyltransferase, 7716, 25233, 8035, 84242, 55304, 52999, 21999, or 52020 substrate or binding partner), a 22406, acyltransferase, 7716, 25233, 8035, 84242, 55304, 52999, 21999, or 52020 antibody, a 22406, acyltransferase, 7716, 25233, 8035, 84242, 55304, 52999, 21999, or 52020 agonist or antagonist, a peptidomimetic of a 22406, acyltransferase, 7716, 25233, 8035, 84242, 55304, 52999, 21999, or 52020 agonist or antagonist, or other small molecule.

In one embodiment, the agent stimulates one or more 22406, acyltransferase, 7716, 25233, 8035, 84242, 55304, 52999, 21999, or 52020 activities. Examples of such stimulatory agents include active 22406, acyltransferase, 7716, 25233, 8035, 84242, 55304, 52999, 21999, or 52020 protein and a nucleic acid molecule encoding 22406, acyltransferase, 7716, 25233, 8035, 84242, 55304, 52999, 21999, or 52020, respectively. In another embodiment, the agent inhibits one or more 22406, acyltransferase, 7716, 25233, 8035, 84242, 55304, 52999, 21999, or 52020 activities. Examples of such inhibitory agents include antisense 22406, acyltransferase, 7716, 25233, 8035, 84242, 55304, 52999, 21999, or 52020 nucleic acid molecules, anti-22406, anti-acyltransferase, anti-7716, anti-25233, anti-8035, anti-84242, anti-55304, anti-52999, anti-21999, or anti-52020 antibodies, and 22406, acyltransferase, 7716, 25233, 8035, 84242, 55304, 52999, 21999, or 52020 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 22406, acyltransferase, 7716, 25233, 8035, 84242, 55304, 52999, 21999, or 52020 protein or nucleic acid molecule. In one embodiment, the method involves administering an agent (e.g., an agent identified by a screening assay described herein), or combination of agents that modulates (e.g., upregulates or downregulates) 22406, acyltransferase, 7716, 25233, 8035, 84242, 55304, 52999, 21999, or 52020 expression or activity. In another embodiment, the method involves administering a 22406, acyltransferase, 7716, 25233, 8035, 84242, 55304, 52999, 21999, or 52020 protein or nucleic acid molecule as therapy to compensate for reduced, aberrant, or unwanted 22406, acyltransferase, 7716, 25233, 8035, 84242, 55304, 52999, 21999, or 52020 expression or activity, respectively.

Stimulation of 22406, acyltransferase, 7716, 25233, 8035, 84242, 55304, 52999, 21999, or 52020 activity is desirable in situations in which 22406, acyltransferase, 7716, 25233, 8035, 84242, 55304, 52999, 21999, or 52020 is abnormally downregulated and/or in which increased 22406, acyltransferase, 7716, 25233, 8035, 84242, 55304, 52999, 21999, or 52020 activity is likely to have a beneficial effect. For example, stimulation of 22406, acyltransferase, 7716, 25233, 8035, 84242, 55304, 52999, 21999, or 52020 activity is desirable in situations in which 22406, acyltransferase, 7716, 25233, 8035, 84242, 55304, 52999, 21999, or 52020 is downregulated and/or in which increased 22406, acyltransferase, 7716, 25233, 8035, 84242, 55304, 52999, 21999, or 52020 activity is likely to have a beneficial effect. Likewise, inhibition of 22406, acyltransferase, 7716, 25233, 8035, 84242, 55304, 52999, 21999, or 52020 activity is desirable in situations in which 22406, acyltransferase, 7716, 25233, 8035, 84242, 55304, 52999, 21999, or 52020 is abnormally upregulated and/or in which decreased 22406, acyltransferase, 7716, 25233, 8035, 84242, 55304, 52999, 21999, or 52020 activity is likely to have a beneficial effect.

The 22406 molecules can act as novel diagnostic targets and therapeutic agents for controlling one or more of brain disorders, including but not limited to, behavioral changes associated with learning, memory, convulsion, anxiety, psychotomimetic induced abnormal behavior, cerebellar ataxia, and neurodengeneration. Inhibitors of 22406 protein can be expected to quell anxiety and epilepsy and to prevent damage from stroke and certain neurodegenerative conditions including Alzheimer's disease. On the other hand, stimulating 22406 protein might improve schizophrenia symptoms, which are partly caused by depressed NMDA receptor function. In addition, 22406 protein can be expected to be involved in various disorders of the tissues in which it is expressed, including heart disorders, liver disorders, prostrate disorders, skeletal muscle disorders, dermal fibroblast disorders, and blood vessel disorders. All of the disorders described supra are disorders that may be treated or diagnosed by methods described herein.

The acyltransferase molecules can act as novel diagnostic targets and therapeutic agents for controlling one or more of cellular proliferative and/or differentiative disorders, cardiovascular disorders, as described above, as well as disorders associated with lipid metabolism, hematopoietic disorders, liver disorders, viral diseases, pain or metabolic disorders.

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, acyltransferase molecules may play an important role in the etiology of certain viral diseases, including but not limited to, Hepatitis B, Hepatitis C and Herpes Simplex Virus (HSV). Modulators of acyltransferase activity could be used to control viral diseases. The modulators can be used in the treatment and/or diagnosis of viral infected tissue or virus-associated tissue fibrosis, especially liver and liver fibrosis. Also, acyltransferase modulators can be used in the treatment and/or diagnosis of virus-associated carcinoma, especially hepatocellular cancer.

Additionally, acyltransferase may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain*, New York:McGraw-Hill); pain associated with muscoloskeletal disorders, e.g., joint pain; tooth pain; headaches; pain associated with surgery.

The 7716 molecules can act as novel diagnostic targets and therapeutic agents for controlling one or more of cellular proliferative and/or differentiative disorders, organelle biogenesis disorders (including those resulting in neurodegeneration, membrane fusion disorders (including disorders relating to secretion or synaptic transmission) as well as disorders associated with aberrant regulation of proteolysis of targets of the 26S proteasome, and aberrant degradation of membrane proteins.

Aberrant expression and/or activity of 7716 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 7716 molecules effects in bone cells, e.g. osteoclasts and osteoblasts, that may in turn result in bone formation and degeneration. For example, 7716 molecules may support different activities of bone resorbing osteoclasts such as the stimulation of differentiation of monocytes and mononuclear phagocytes into osteoclasts. Accordingly, 7716 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anticonvulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 7716 molecules may play an important role in the etiology of certain viral diseases, including but not limited to, Hepatitis B, Hepatitis C and Herpes Simplex Virus (HSV). Modulators of 7716 activity could be used to control viral diseases. The modulators can be used in the treatment and/or diagnosis of viral infected tissue or virus-associated tissue fibrosis, especially liver and liver fibrosis. Also, 7716 modulators can be used in the treatment and/or diagnosis of virus-associated carcinoma, especially hepatocellular cancer.

Additionally, 7716 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with muscoloskeletal disorders, e.g., joint pain; tooth pain; headaches; pain associated with surgery; pain related to irritable bowel syndrome; or chest pain.

The 25233 molecules can act as novel diagnostic targets and therapeutic agents for controlling one or more of muscle, cardiac, kidney, pancreatic, red blood cell, or hepatic disorders, cancer, or active periodontal disease. Examples of disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

The 8035, 84242, 55304, 52999, or 21999 molecules can act as novel diagnostic targets and therapeutic agents for controlling one or more of cellular proliferative and/or differentiative disorders, viral diseases, or metabolic disorders.

Aberrant expression and/or activity of 8035 and 84242 molecules may lead to disorders resulting from aberrant cellular proliferation and/or differentiation including diseases such as cancer, acute promyelocytic leukemia (APL), VHL disease, and systemic lupus erythematosus. In addition, RING finger protein family members such as 8035 and 84242 have been shown to contribute to the pathogenesis of certain viral diseases including those caused by HSV and HIV.

The 55304 molecules can act as novel diagnostic targets and therapeutic agents for controlling one or more of cellular proliferative and/or differentiative disorders, hypertensive disorders, hormone disorders, and disorders associated with protein maturation as described above, as well as disorders associated with bone metabolism, hematopoietic disorders, liver disorders, viral diseases, pain or metabolic disorders.

Aberrant expression and/or activity of 55304 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 55304 molecules effects in bone cells, e.g. osteoclasts and osteoblasts, that may in turn result in bone formation and degeneration. For example, 55304 molecules may support different activities of bone resorbing osteoclasts such as the stimulation of differentiation of monocytes and mononuclear phagocytes into osteoclasts. Accordingly, 55304 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isoniazid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 55304 molecules may play an important role in the etiology of certain viral diseases, including but not limited to, Hepatitis B, Hepatitis C and Herpes Simplex Virus (HSV). Modulators of 55304 activity could be used to control viral diseases. The modulators can be used in the treatment and/or diagnosis of viral infected tissue or virus-associated tissue fibrosis, especially liver and liver fibrosis. Also, 55304 modulators can be used in the treatment and/or diagnosis of virus-associated carcinoma, especially hepatocellular cancer.

Additionally, 55304 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L. (1987) *Pain*, New York:McGraw-Hill); pain associated with musculoskeletal disorders, e.g., joint pain; tooth pain; headaches; pain associated with surgery; pain related to irritable bowel syndrome; or chest pain.

The 52999 molecules can act as novel diagnostic targets and therapeutic agents for controlling one or more of cellular proliferative and/or differentiative disorders; inflammatory disorders including, but not limited to osteoarthritis and rheumatoid arthritis, multiple sclerosis, Crohn disease, psoriasis, periodontal disease, and asthma; macular degeneration; restenosis; and Alzheimer's disease.

Similarly, aberrant expression and/or activity of 52999 molecules may mediate disorders associated with, for example, hematopoietic disorders including, but not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 21999 molecules can act as novel diagnostic targets and therapeutic agents for controlling one or more of cellular proliferative and/or differentiative disorders, cardiovascular disorders, as described above, as well as disorders associated with hematopoietic disorders, liver disorders, viral diseases, or metabolic disorders. Examples of these disorders may be found above.

The 52020 molecules can act as novel diagnostic targets and therapeutic agents for controlling one or more of cancers, tissue repair, neurodegenerative disorders, autoimmune disorders, and inflammatory disorders as described herein supra.

Pharmacogenomics

The 22406, acyltransferase, 7716, 25233, 8035, 84242, 55304, 52999, 21999, or 52020 molecules of the present invention, as well as agents, or modulators which have a stimulatory or inhibitory effect on 22406, acyltransferase, 7716, 25233, 8035, 84242, 55304, 52999, 21999, or 52020 activity (e.g., 22406, acyltransferase, 7716, 25233, 8035, 84242, 55304, 52999, 21999, or 52020 gene expression) as identified by a screening assay described herein can be administered to individuals to treat (prophylactically or therapeutically) 22406, acyltransferase, 7716, 25233, 8035, 84242, 55304, 52999, 21999, or 52020 associated disorders (e.g., cellular growth related disorders) associated with aberrant or unwanted 22406, acyltransferase, 7716, 25233, 8035, 84242, 55304, 52999, 21999, or 52020 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 22406, acyltransferase, 7716, 25233, 8035, 84242, 55304, 52999, 21999, or 52020 molecule or a 22406, acyltransferase, 7716, 25233, 8035, 84242, 55304, 52999, 21999, or 52020 modulator as well as tailoring the dosage and/or therapeutic regimen of treatment with a 22406, acyltransferase, 7716, 25233, 8035, 84242, 55304, 52999, 21999, or 52020 molecule or 22406, acyltransferase, 7716, 25233, 8035, 84242, 55304, 52999, 21999, or 52020 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11):983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 22406, acyltransferase, 7716, 25233, 8035, 84242, 55304, 52999, 21999, or 52020 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 22406, acyltransferase, 7716, 25233, 8035, 84242, 55304, 52999, 21999, or 52020 molecule or 22406, acyltransferase, 7716, 25233, 8035, 84242, 55304, 52999, 21999, or 52020 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 22406, acyltransferase, 7716, 25233, 8035, 84242, 55304, 52999, 21999, or 52020 molecule or 22406, acyltransferase, 7716, 25233, 8035, 84242, 55304, 52999, 21999, or 52020 modulator, such as a modulator identified by one of the exemplary screening assays described herein.

The present invention further provides methods for identifying new agents, or combinations, that are based on identifying agents that modulate the activity of one or more of the gene products encoded by one or more of the 22406, acyltransferase, 7716, 25233, 8035, 84242, 55304, 52999, 21999, or 52020 genes of the present invention, wherein these products may be associated with resistance of the cells to a therapeutic agent. Specifically, the activity of the proteins encoded by the 22406, acyltransferase, 7716, 25233, 8035, 84242, 55304, 52999, 21999, or 52020 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 22406, acyltransferase, 7716, 25233, 8035, 84242, 55304, 52999, 21999, or 52020 protein can be applied in clinical trials. For example, the effectiveness of an agent determined by a screening assay as described herein to increase 22406, acyltransferase, 7716, 25233, 8035, 84242, 55304, 52999, 21999, or 52020 gene expression, protein levels, or upregulate 22406, acyltransferase, 7716, 25233, 8035, 84242, 55304, 52999, 21999, or 52020 activity, can be monitored in clinical trials of subjects exhibiting decreased 22406, acyltransferase, 7716, 25233, 8035, 84242, 55304, 52999, 21999, or 52020 gene expression, protein levels, or downregulated 22406, acyltransferase, 7716, 25233, 8035, 84242, 55304, 52999, 21999, or 52020 activity, respectively. Alternatively, the effectiveness of an agent determined by a screening assay to decrease 22406, acyltransferase, 7716, 25233, 8035, 84242, 55304, 52999, 21999, or 52020 gene expression, protein levels, or downregulate 22406, acyltransferase, 7716, 25233, 8035, 84242, 55304, 52999, 21999, or 52020 activity, can be monitored in clinical trials of subjects exhibiting increased 22406, acyltransferase, 7716, 25233, 8035, 84242, 55304, 52999, 21999, or 52020 gene expression, protein levels, or upregulated 22406, acyltransferase, 7716, 25233, 8035, 84242, 55304, 52999, 21999, or 52020 activity, respectively.

In such clinical trials, the expression or activity of a 22406, acyltransferase, 7716, 25233, 8035, 84242, 55304, 52999, 21999, or 52020 gene, and preferably, other genes that have been implicated in, for example, a 22406, acyltransferase, 7716, 25233, 8035, 84242, 55304, 52999, 21999, or 52020-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 22406, acyltransferase, 7716, 25233, 8035, 84242, 55304, 52999, 21999, or 52020, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 22406, acyltransferase, 7716, 25233, 8035, 84242, 55304, 52999, 21999, or 52020 nucleic acid, polypeptide, or antibody.

The capture probes can be a set of nucleic acids from a selected sample, e.g., a sample of nucleic acids derived from a control or non-stimulated tissue or cell.

The method can include contacting the 22406, acyltransferase, 7716, 25233, 8035, 84242, 55304, 52999, 21999, or 52020 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 22406, acyltransferase, 7716, 25233, 8035, 84242, 55304, 52999, 21999, or 52020. Such methods can be used to diagnose a subject, e.g., to evaluate risk for a disease or disorder, to evaluate suitability of a selected treatment for a subject, to evaluate whether a subject has a disease or disorder. 22406 is associated with pyridoxal-phosphate dependent serine racemase activity, thus it is useful for disorders associated with the brain. Acyltransferase is associated with fatty acid synthase activity, thus it is useful for disorders associated with abnormal lipid metabolism. 7716 is associated with ATPase activity, thus it is useful for disorders associated with abnormal lipid metabolism. 25233 is associated with aminotransferase activity, thus it is useful for disorders associated with abnormal lipid metabolism. 8035 and 84242 are associated with RING finger protein activity, thus it is useful for disorders associated with abnormal cellular proliferation and/or differentiation. 55304 is associated with aminopeptidase activity, thus it is useful for disorders associated with abnormal lipid metabolism. 52999 is associated with metallopeptidase activity, thus it, too, is useful for disorders associated with abnormal lipid metabolism. 52020 is associated with MAGE activity, thus it is useful for disorders associated with abnormal cell growth.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 22406, acyltransferase, 7716, 25233, 8035, 84242, 55304, 52999, 21999, or 52020 or from a cell or subject in which a 22406, acyltransferase, 7716, 25233, 8035, 84242, 55304, 52999, 21999, or 52020 mediated response has been elicited, e.g., by contact of the cell with 22406, acyltransferase, 7716, 25233, 8035, 84242, 55304, 52999, 21999, or 52020 nucleic acid or protein, or administration to the cell or subject 22406, acyltransferase, 7716, 25233, 8035, 84242, 55304, 52999, 21999, or 52020 nucleic acid or protein; contacting the array with one or more inquiry probe, wherein an inquiry probe can be a nucleic acid, polypeptide, or antibody (which is preferably other than 22406, acyltransferase, 7716, 25233, 8035, 84242, 55304, 52999, 21999, or 52020 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 22406, acyltransferase, 7716, 25233, 8035, 84242, 55304, 52999, 21999, or 52020 (or does not express as highly as in the case of the 22406, acyltransferase, 7716, 25233, 8035, 84242, 55304, 52999, 21999, or 52020 positive plurality of capture probes) or from a cell or subject which in which a 22406, acyltransferase, 7716, 25233, 8035, 84242, 55304, 52999, 21999, or 52020 mediated response has not been elicited (or has been elicited to a lesser extent than in the first sample); contacting the array with one or more inquiry probes (which is preferably other than a 22406, acyltransferase, 7716, 25233, 8035, 84242, 55304, 52999, 21999, or 52020 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 22406, acyltransferase, 7716, 25233, 8035, 84242, 55304, 52999, 21999, or 52020, e.g., analyzing structure, function, or relatedness to other nucleic acid or amino acid sequences. The method includes: providing a 22406, acyltransferase, 7716, 25233, 8035, 84242, 55304, 52999, 21999, or 52020 nucleic acid or amino acid sequence; comparing the 22406, acyltransferase, 7716, 25233, 8035, 84242, 55304, 52999, 21999, or 52020 sequence with one or more preferably a plurality of sequences from a collection of sequences, e.g., a nucleic acid or protein sequence database; to thereby analyze 22406, acyltransferase, 7716, 25233, 8035, 84242, 55304, 52999, 21999, or 52020.

Preferred databases include GenBank™. The method can include evaluating the sequence identity between a 22406, acyltransferase, 7716, 25233, 8035, 84242, 55304, 52999, 21999, or 52020 sequence and a database sequence. The method can be performed by accessing the database at a second site, e.g., over the internet.

In another aspect, the invention features, a set of oligonucleotides, useful, e.g., for identifying SNP's, or identifying specific alleles of 22406, acyltransferase, 7716, 25233, 8035, 84242, 55304, 52999, 21999, or 52020. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1

Identification and Characterization of Human 22406 cDNAs

The human 22406 sequence (SEQ ID NO:1), which is approximately 1770 nucleotides long including untranslated regions, contains a predicted methionine-initiated coding sequence of about 1020 nucleotides (nucleotides 69–1088 of SEQ ID NO:1; SEQ ID NO:3). The coding sequence encodes a 340 amino acid protein (SEQ ID NO:2).

Example 2

Tissue Distribution of 22406 mRNA

Expression levels of 22406 in various tissue and cell types were determined by quantitative RT-PCR (Reverse Transcriptase Polymerase Chain Reaction; Taqman® brand PCR kit, Applied Biosystems) (FIG. 8). The quantitative RT-PCR reactions were performed according to the kit manufacturer's instructions.

Northern blot hybridizations with various RNA samples can be performed under standard conditions and washed under stringent conditions, i.e., 0.2×SSC at 65° C. A DNA probe corresponding to all or a portion of the 22406 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

FIGS. 4 and 8 show expression of the 22406 protein in various human tissues. In FIG. 8 the tissue types are as follows from left to right: Aorta/Normal, Fetal Heart/Normal, Heart/Normal, Heart/CHF, Vein/Normal, SMC/Aortic, Nerve/Normal, Spinal Cord/Normal, Brain Cord/Normal, Brain Cortex/Normal, Brain Hypothalmus/Normal, Glial Cells (Astrocytes), Glioblastoma, Breast/Normal, Breast/Tumor, Ovary/Normal, Ovary/Tumor, Pancreas/Normal, Prostate/Normal, Prostate/Tumor, Colon/Normal, Colon/Tumor, Colon/IBD, Kidney/Normal, Liver/Normal, Liver/Fibrosis, Fetal Liver/Normal, Lung/Normal, Lung/COPD, Spleen/Normal, Tonsil/Normal, Lymph Node/Normal, Thymus/Normal, Epithelial Cells (Prostate), Endothelial Cells (Aortic), Skeletal Muscle/Normal, Fibroblasts (Dermal), Skin/Normal, Adipose/Normal, Osteoblasts (Primary), Osteoblasts (Undiff), Osteoblasts (Diff), Osteoclasts, NTC.

Example 3

Identification and Characterization of Human Acyltransferase cDNAs

The human acyltransferase sequence (SEQ ID NO:6), which is approximately 2465 nucleotides long including untranslated regions, contains a predicted methionine-initiated coding sequence of about 1632 nucleotides (from nucleotide position 495 to position 2126 of SEQ ID NO:6). The coding sequence (SEQ ID NO:8) encodes a 554 amino acid protein (SEQ ID NO:7).

Example 4

Tissue Distribution of Acyltransferase mRNA

Northern blot hybridizations with various RNA samples can be performed under standard conditions and washed under stringent conditions, i.e., 0.2×SSC at 65° C. A DNA probe corresponding to all or a portion of the acyltransferase cDNA (SEQ ID NO:6). The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 5

Identification and Characterization of Human 7716 cDNAs

The human 7716 sequence (SEQ ID NO:10), which is approximately 2547 nucleotides long including untranslated regions, contains a predicted methionine-initiated coding sequence of about 2259 nucleotides (nucleotides 63–2321 of SEQ ID NO:10; SEQ ID NO:12). The coding sequence encodes a 753 amino acid protein (SEQ ID NO:11).

Example 6

Tissue Distribution of 7716 mRNA

Northern blot hybridizations with various RNA samples can be performed under standard conditions and washed under stringent conditions, i.e., 0.2×SSC at 65° C. A DNA probe corresponding to all or a portion of the 7716 cDNA (SEQ ID NO:10) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 7

Identification and Characterization of Human 25233 cDNAs

The human 25233 sequence (SEQ ID NO:14), which is approximately 2127 nucleotides long including untranslated regions, contains a predicted methionine-initiated coding sequence of about 1572 nucleotides (nucleotides 94–1665 of SEQ ID NO:14; nucleotides 1–1572 of SEQ ID NO:16). The coding sequence encodes a 523 amino acid protein (SEQ ID NO:15).

Example 8

Distribution of Human 25233 in Various Cells and Tissues

Figure 23A:
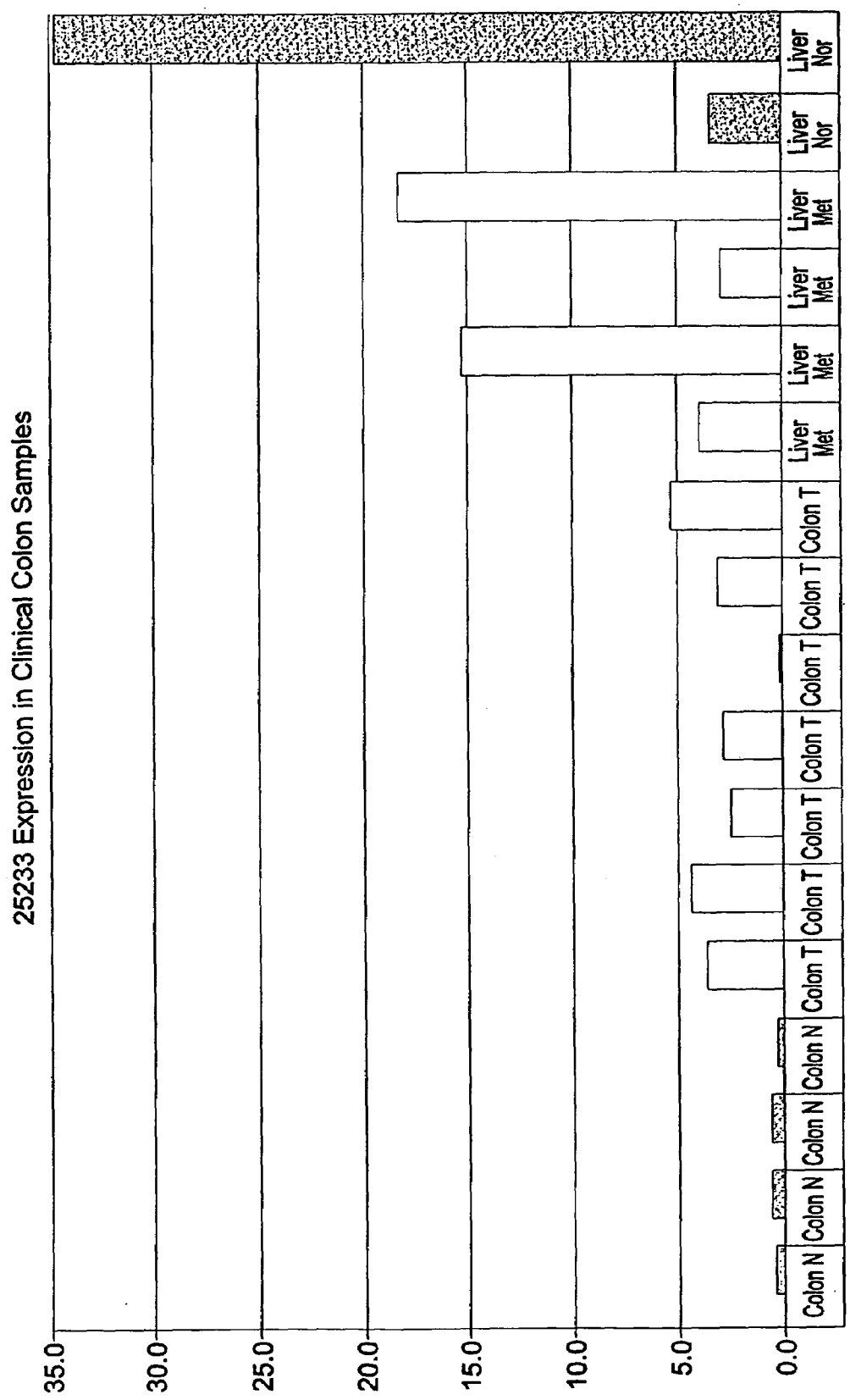
FIGS. 23A–23B show the expression of 25233 in human tissues and cell lines, as follows.
Figure 23B:
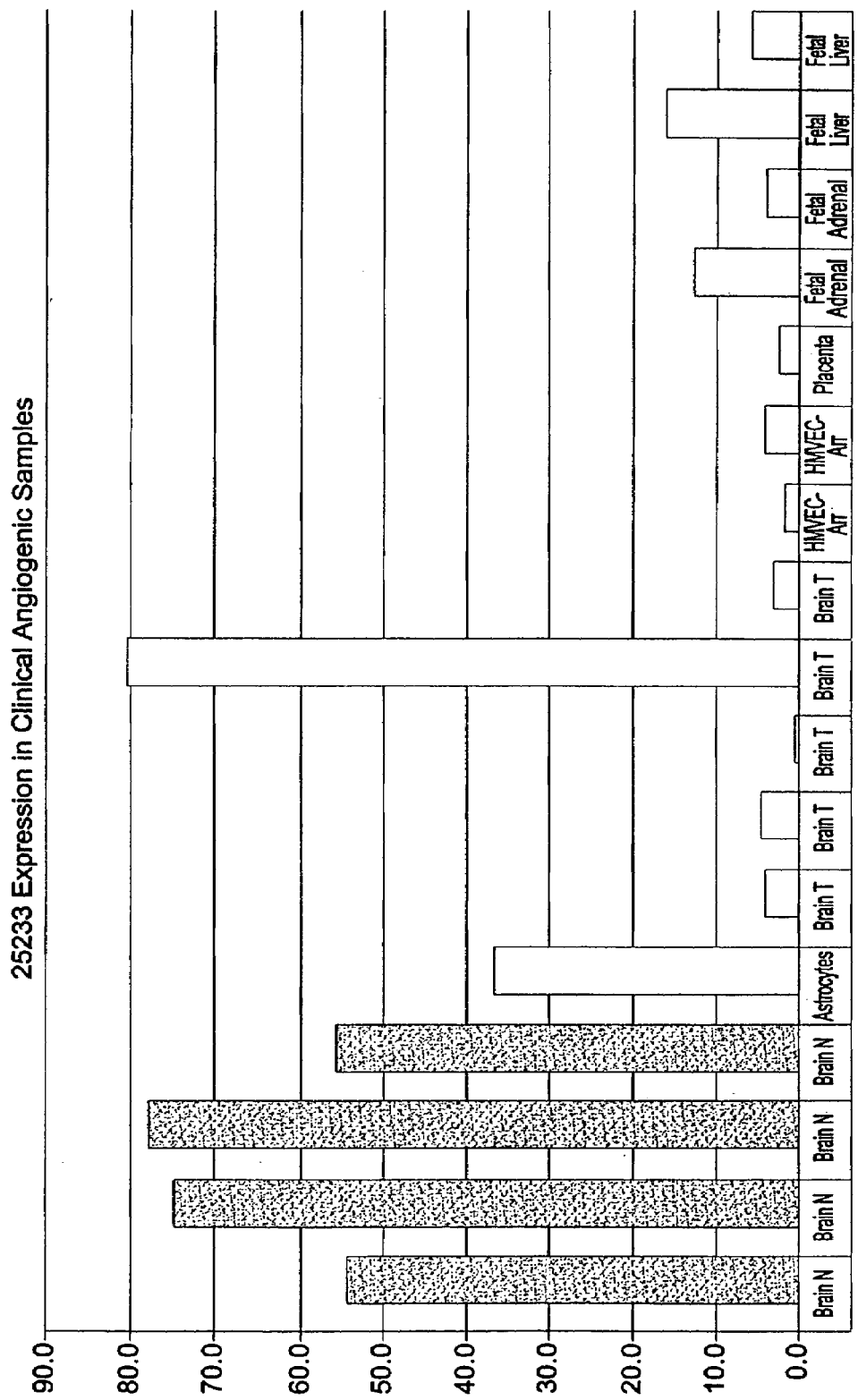
Figure 24:
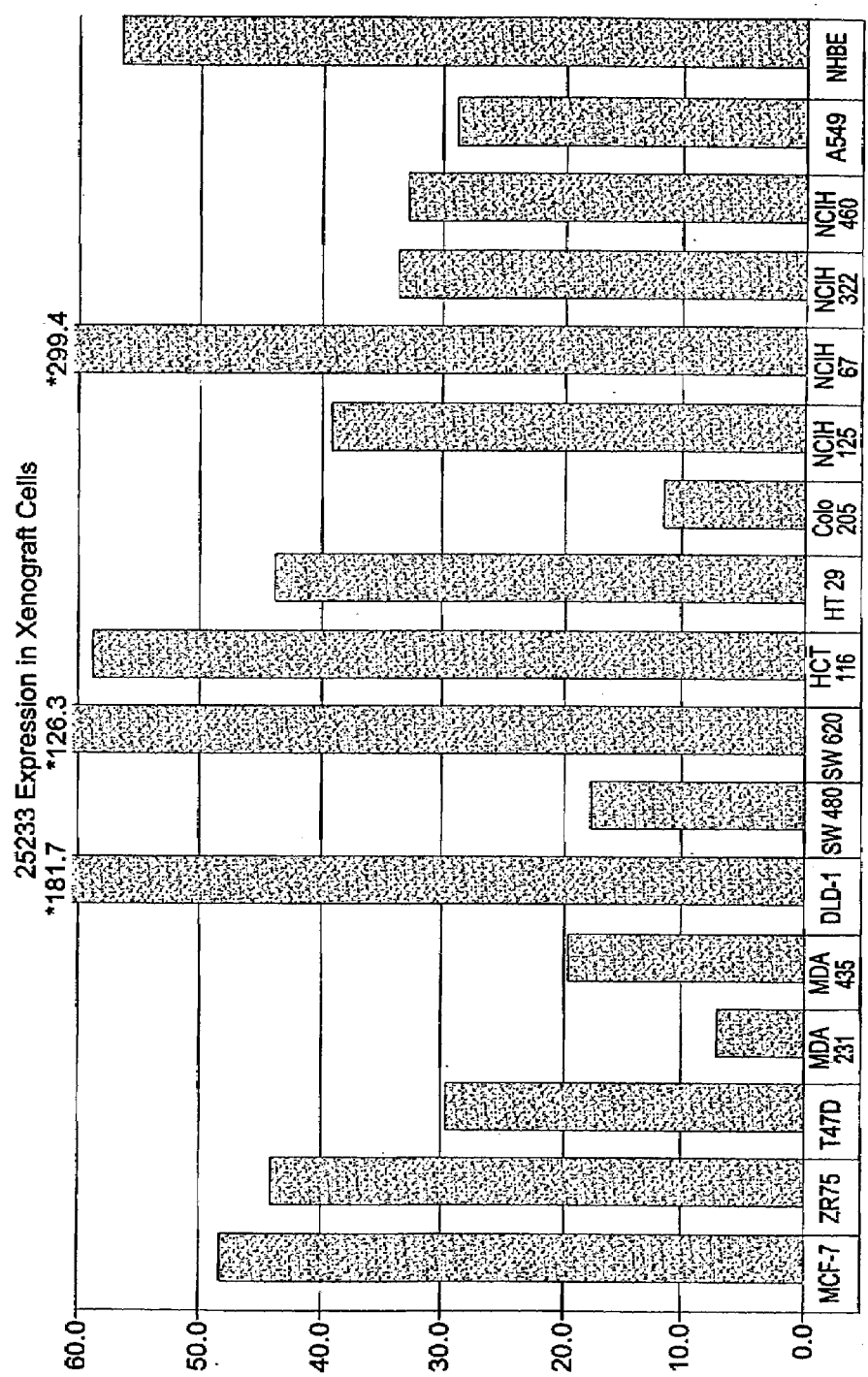
FIG. 24 shows the expression of 25233 in the following cell lines: Breast cancer cell lines MCF-7 (column 1); ZR75 (column 2); T47D (column 3); MDA 231 (column 4); and MDA 435 (column 5). Colon cancer cell lines DLD-1 (column 6); SW 480 (column 7); SW 620 (column 8); HCT 116 (column 9); HT 29 (column 10); and Colo 205 (column 11). Lung cancer cell lines NCIH 125 (column 12); NCIH 67 (column 13); NCIH 322 (column 14); NCIH 460 (column 15); and A549 (column 16). NHBE (Normal human bronchial epithelial cells) (column 17). Expression levels were determined as in FIG. 21.
Figure 29:
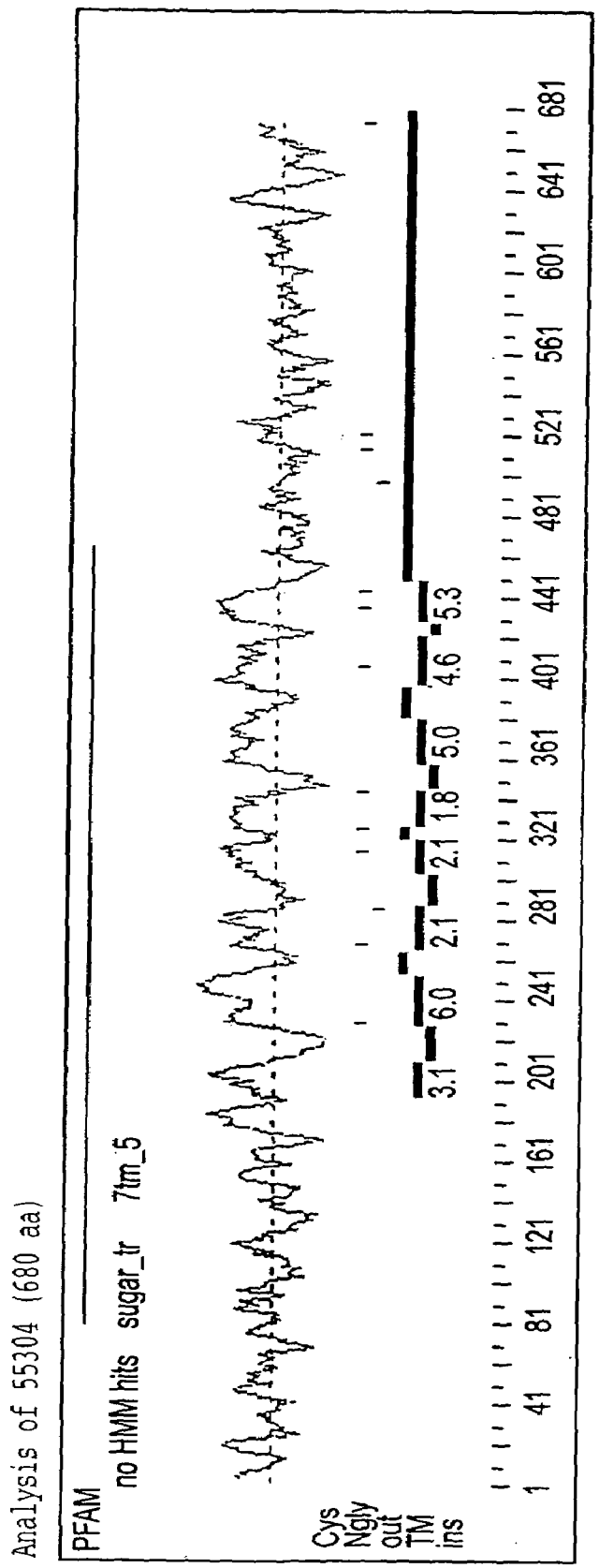
FIG. 29 depicts a hydropathy plot of human 55304. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:27) of human 55304 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.
Figure 30:
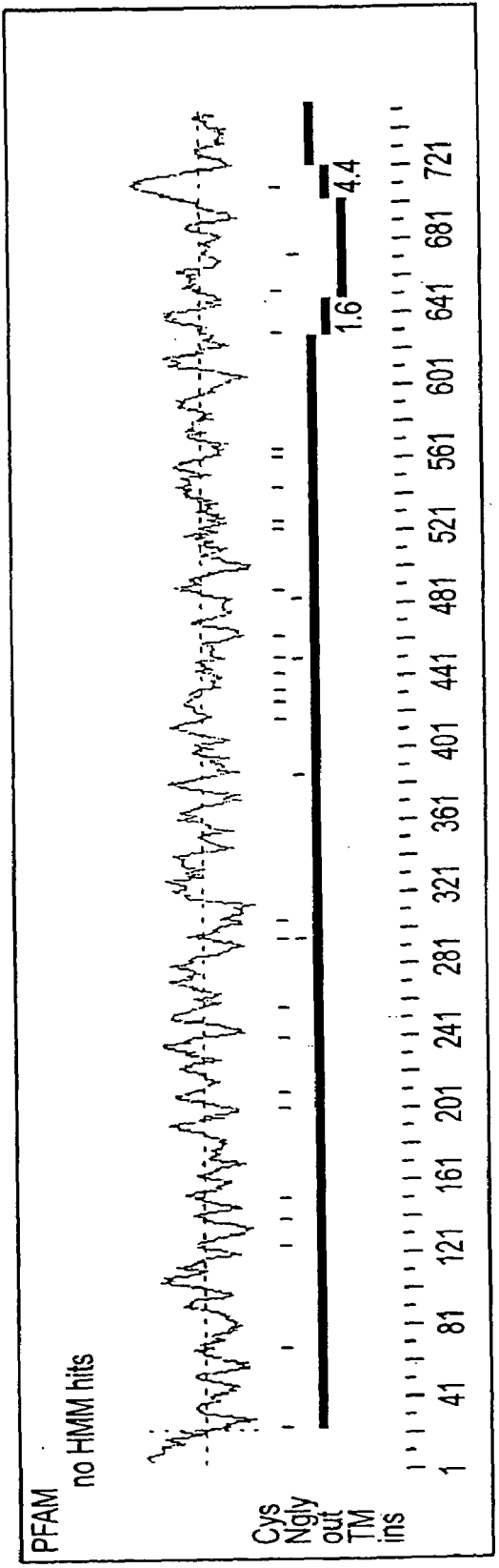
FIG. 30 depicts a hydropathy plot of human 52999. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:30) of human 52999 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site.
Figure 32:
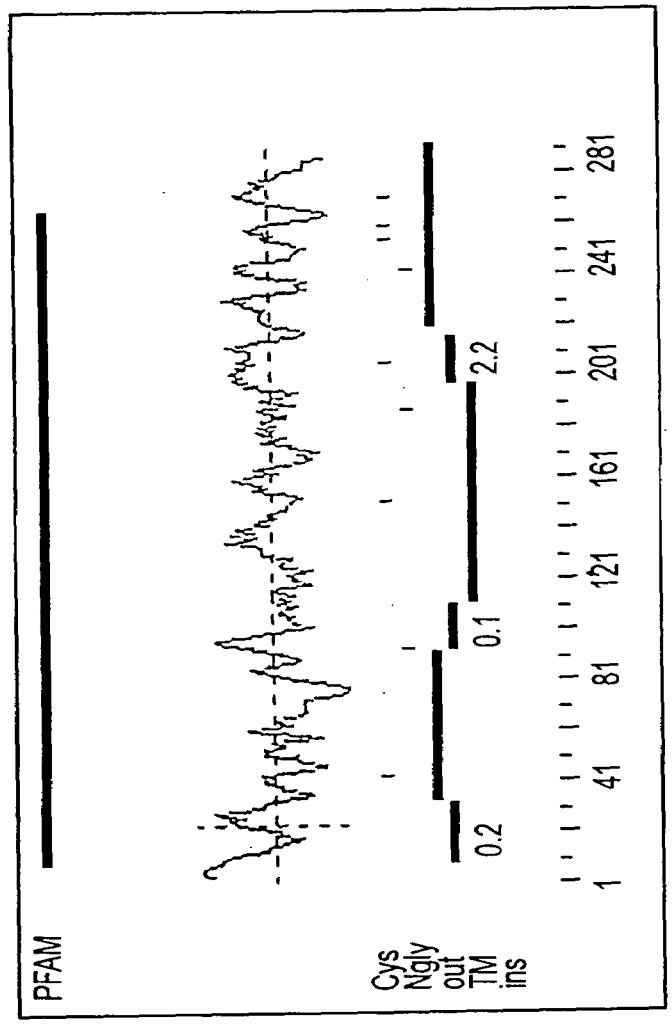
FIG. 32 depicts a hydropathy plot of human ADP-ribosyltransferase. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:37) of human ADP-ribosyltransferase are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.
Figure 34:
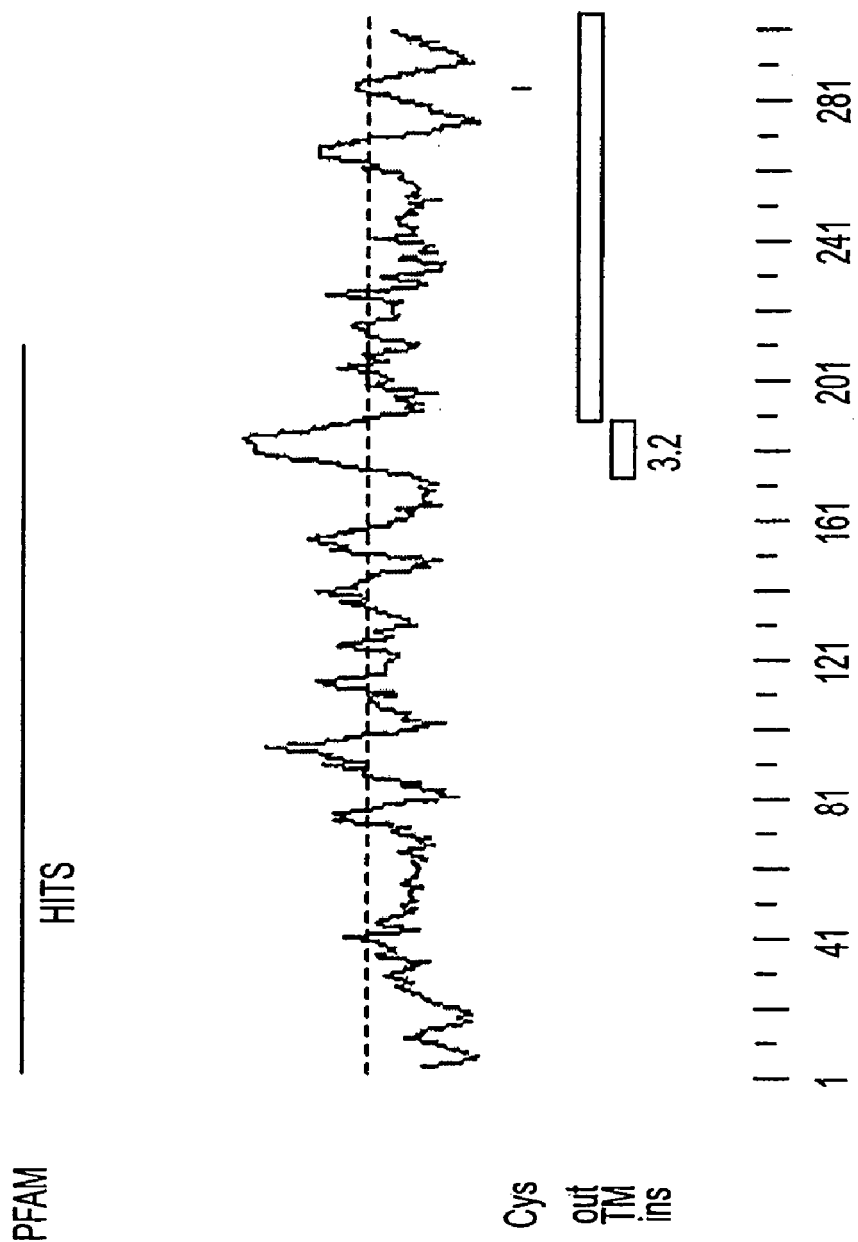
FIG. 34 depicts a hydropathy plot of human 52020. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:41) of human 52020 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

Human 25233 showed elevated levels of expression in pancreas, brain cortex, glial cells, breast tumor, epithelial cells, and liver. See FIG. 21. Expression levels of 25233 were observed to be higher in tumors of the breast, ovary and lung, as compared with 25233 expression levels in normal breast, ovary, and lung tissue. See FIGS. 22A–D. 25233 expression levels were somewhat higher in tumors of the colon, as compared to normal colon tissue. See FIGS. 23A–B. Generally, 25233 expression levels increased over time in the human cancer cell line H460 with and without p16. See FIG. 22D. On the other hand,

TABLE 1

Expression of 25233 in breast cancer cell lines MCF10A and MCF3B at various intervals after exposure to EGF (1–6 and 7–12, respectively). Expression in tumorigenic and non-tumorigenic breast cancer cell lines (13–22) are shown, as well.

|    | Cell Line          | Relative Expression |
|----|--------------------|---------------------|
| 1  | MCF10A EGF 0 hr    | 16.9                |
| 2  | MCF10A EGF 0.5 hr  | 19.0                |
| 3  | MCF10A EGF 1 hr    | 16.5                |
| 4  | MCF10A EGF 2 hr    | 16.2                |
| 5  | MCF10A EGF 4 hr    | 28.6                |
| 6  | MCF10A EGF 8 hr    | 20.1                |
| 7  | MCF3B EGF 0 hr     | 58.1                |
| 8  | MCF3B EGF 0.5 hr   | 49.5                |
| 9  | MCF3B EGF 1 hr     | 43.6                |
| 10 | MCF3B EGF 2 hr     | 57.1                |
| 11 | MCF3B EGF 4 hr     | 58.3                |
| 12 | MCF3B EGF 8 hr     | 52.6                |
| 13 | MCF10A -NT         | 24.4                |
| 14 | MCF10AT.c11 -NT    | 23.9                |
| 15 | MCF10AT.c13 -NT    | 60.2                |
| 16 | MCF10MS -NT        | 19.6                |
| 17 | MCF10CA1a.cl1 -T   | 8.2                 |
| 18 | MCF10AT1 -T        | 62.7                |
| 19 | MCF10AT3B -T       | 15.5                |
| 20 | MCF10AT3B-agar     | 20.5                |
| 21 | MCF10CA1a.cl1-agar | 37.4                |
| 22 | MCF10A-m25-plastic | 58.9                |

25233 expression levels appeared steady over time in breast tissue cell lines treated with EGF, as well. See Table 1. Expression levels were determined by quantitative PCR (Taqman® brand quantitative PCR kit, Applied Biosystems). The quantitative PCR reactions were performed according to the kit manufacturer's instructions.

In situ hybridization analysis was also carried out (data not shown). In lung tumor and colon metastasis tissue, expression of 25233 was observed in immune cells; 25233 expression was not observed in the tumor tissue itself.

Example 9

Identification and Characterization of Human 8035 and 84242 cDNAs

The human 8035 sequence (SEQ ID NO:18), which is approximately 2876 nucleotides long including untranslated regions, contains a predicted methionine-initiated coding sequence of about 1299 nucleotides (nucleotides 613–1914 of SEQ ID NO:18; SEQ ID NO:20). The coding sequence encodes a 433 amino acid protein (SEQ ID NO:19).

The human 84242 sequence (SEQ ID NO:22), which is approximately 2810 nucleotides long including untranslated regions, contains a predicted methionine-initiated coding sequence of about 1209 nucleotides (nucleotides 744–1955 of SEQ ID NO:22; SEQ ID NO:24). The coding sequence encodes a 403 amino acid protein (SEQ ID NO:23).

Example 10

Distribution of Human 84242 in Various Cells and Tissues

Human 84242 showed elevated levels of expression in coronary smooth muscle, human umbilical vein endothelia, heart, kidney, skeletal muscle, brain, dorsal root ganglion, breast, prostate, colon, lung, skin, bone marrow, blood, and erythroid cells and tissues. See Table 2. Expression levels of 84242 were observed to be higher in tumors of the breast, prostate, colon, and lung, relative to normal tissue. See Table 2, rows 22, 26, 29, and 31.

TABLE 2

Expression of 84242 in various cells and tissues.
PHASE 1.5.1 EXPRESSION OF 84242(F1R1)

|    | TISSUE TYPE                                      | RELATIVE EXPRESSION |
|----|--------------------------------------------------|---------------------|
| 1  | Artery normal                                    | 9.2907              |
| 2  | Aorta diseased                                   | 8.2294              |
| 3  | Vein normal                                      | 2.9399              |
| 4  | Coronary SMC (Smooth Muscle Cell)                | 12.4734             |
| 5  | HUVEC (Human Umbilical Vein Endothelial Cells)   | 40.9498             |
| 6  | Hemangioma                                       | 3.5697              |
| 7  | Heart normal                                     | 11.6381             |
| 8  | Heart CHF (Congestive Heart Failure)             | 12.6038             |
| 9  | Kidney                                           | 11.5577             |
| 10 | Skeletal Muscle                                  | 18.6459             |
| 11 | Adipose normal                                   | 2.7717              |
| 12 | Pancreas                                         | 4.8259              |
| 13 | primary osteoblasts                              | 9.1946              |
| 14 | Osteoclasts (Differentiated)                     | 2.9913              |
| 15 | Skin normal                                      | 6.2584              |
| 16 | Spinal cord normal                               | 4.3043              |
| 17 | Brain Cortex normal                              | 50.942              |
| 18 | Brain Hypothalamus, normal                       | 9.9575              |
| 19 | Nerve                                            | 5.8393              |
| 20 | DRG (Dorsal Root Ganglion)                       | 12.8241             |
| 21 | Breast normal                                    | 4.6453              |
| 22 | Breast tumor                                     | 10.1667             |
| 23 | Ovary normal                                     | 8.5789              |
| 24 | Ovary Tumor                                      | 3.0968              |
| 25 | Prostate Normal                                  | 4.5027              |
| 26 | Prostate Tumor                                   | 12.0904             |
| 27 | Salivary glands                                  | 1.816               |
| 28 | Colon normal                                     | 6.9682              |
| 29 | Colon Tumor                                      | 20.0535             |
| 30 | Lung normal                                      | 4.4253              |
| 31 | Lung tumor                                       | 21.7175             |
| 32 | Lung COPD (Chronic Obstructive Pulmonary Disease) | 6.0872              |
| 33 | Colon IBD (Inflammatory Bowel Disease)           | 7.8125              |

TABLE 2-continued

Expression of 84242 in various cells and tissues.
PHASE 1.5.1 EXPRESSION OF 84242(F1R1)

| TISSUE TYPE | RELATIVE EX-PRESSION |
|---|---|
| 34 Liver normal | 2.7241 |
| 35 Liver fibrosis | 4.9102 |
| 36 Spleen normal | 2.5241 |
| 37 Tonsil normal | 8.7591 |
| 38 Lymph node, normal | 4.4253 |
| 39 Small intestine normal | 6.5241 |
| 40 Skin-Decubitus | 12.7355 |
| 41 Synovium | 2.4129 |
| 42 BM-MNC (Bone Marrow-Mononuclear Cell) | 15.0405 |
| 43 Activated PBMC (Peripheral Blood Mononuclear Cell) | 15.2505 |
| 44 Neutrophils | 3.2848 |
| 45 Megakaryocytes | 4.996 |
| 46 Erythroid | 17.337 |

Expression levels were determined by quantitative PCR (Taqman® brand quantitative PCR kit, Applied Biosystems). The quantitative PCR reactions were performed according to the kit manufacturer's instructions.

Example 11

Identification and Characterization of Human 55304 cDNAs

The human 55304 sequence (SEQ ID NO:26), which is approximately 5502 nucleotides long including untranslated regions, contains a predicted methionine-initiated coding sequence of about 2039 nucleotides (nucleotides 803–2845 of SEQ ID NO:26; SEQ ID NO:28). The coding sequence encodes a 680 amino acid protein (SEQ ID NO:27).

Example 12

Distribution of Human 55304 in Various Cells and Tissues

Human 555304 showed elevated levels of expression in brain, kidney, testes, and epithelial cells of the prostate. See Tables 3 and 4.

TABLE 3

Expression of 55304 in various cells and tissues.
55304 HUMAN PANEL PHASE I

| TISSUE | RELATIVE EXPRESSION |
|---|---|
| 1 Adrenal Gland | 0.95 |
| 2 Brain | 2.66 |
| 3 Heart | 0.32 |
| 4 Kidney | 3.66 |
| 5 Liver | 0.12 |
| 6 Lung | 0.15 |
| 7 Mammary Gland | 0.25 |
| 8 Placenta | 1.18 |
| 9 Prostate | 0.68 |
| 10 Salivary Gland | 1.55 |
| 11 Muscle | 0.74 |
| 12 Sm. Intestine | 0.42 |
| 13 Spleen | 0.08 |
| 14 Stomach | 0.68 |
| 15 Testes | 5 |
| 16 Thymus | 0.34 |

TABLE 3-continued

Expression of 55304 in various cells and tissues.
55304 HUMAN PANEL PHASE I

| TISSUE | RELATIVE EXPRESSION |
|---|---|
| 17 Trachea | 0.45 |
| 18 Uterus | 0.16 |
| 19 Spinal Cord | 1.19 |
| 20 Skin | 0.20 |
| 21 DRG (Dorsal Root Ganglion) | 0.45 |

Expression levels of 55304 were observed to be higher in tumors of the colon and lung, relative to normal tissue. See Table 4, rows 31 and 33.

TABLE 4

Expression of 55304 in various cells and tissues.
PHASE 1.3.3 EXPRESSION OF 55304.1

| TISSUE TYPE | RELATIVE EX-PRESSION |
|---|---|
| 1 Artery normal | 0 |
| 2 Vein normal | 0 |
| 3 Aortic SMC (Smooth Muscle Cell) EARLY | 1.1981 |
| 4 Coronary SMC | 2.022 |
| 5 Static HUVEC (Human Umbilical Vein Endothelial Cell) | 1.4497 |
| 6 Shear HUVEC | 0.6465 |
| 7 Heart normal | 0.2366 |
| 8 Heart CHF (Chronic Heart Failure) | 1.736 |
| 9 Kidney | 38.8754 |
| 10 Skeletal Muscle | 0.1922 |
| 11 Adipose normal | 0 |
| 12 Pancreas | 1.1613 |
| 13 Primary Osteoblasts | 0.0619 |
| 14 Osteoclasts (differentiated) | 0.0143 |
| 15 Skin normal | 0.4192 |
| 16 Spinal cord normal | 3.1619 |
| 17 Brain Cortex normal | 22.5614 |
| 18 Brain Hypothalamus normal | 11.8415 |
| 19 Nerve | 1.1063 |
| 20 DRG (Dorsal Root Ganglion) | 3.472 |
| 21 Glial Cells (Astrocytes) | 3.2395 |
| 22 Glioblastoma | 0.2814 |
| 23 Breast normal | 0.0458 |
| 24 Breast tumor | 0.3818 |
| 25 Ovary normal | 5.3546 |
| 26 Ovary Tumor | 1.1735 |
| 27 Prostate Normal | 0.5003 |
| 28 Prostate Tumor | 0.1529 |
| 29 Epithelial Cells (Prostate) | 40.2463 |
| 30 Colon normal | 0.1002 |
| 31 Colon Tumor | 8.6385 |
| 32 Lung normal | 0 |
| 33 Lung tumor | 4.9444 |
| 34 Lung COPD (Chronic Obstructive Pulmonary Disorder) | 0.0954 |
| 35 Colon IBD (Inflammatory Bowel Disease) | 0.0903 |
| 36 Liver normal | 0.309 |
| 37 Liver fibrosis | 0.4733 |
| 38 Dermal Cells- fibroblasts | 0.2416 |
| 39 Spleen normal | 0.059 |
| 40 Tonsil normal | 0.6159 |
| 41 Lymph node | 0.4684 |
| 42 Small Intestine | 0.1299 |
| 43 Skin-Decubitus | 0.5108 |
| 44 Synovium | 0.0287 |
| 45 BM-MNC (Bone Marrow Mononuclear Cell) | 0.6095 |
| 46 Activated PBMC (Peripheral Blood Mononuclear Cell) | 0.0125 |

Expression levels were determined as described in Example 12.

Example 13

Identification and Characterization of Human 52999 cDNAs

The human 52999 sequence (SEQ ID NO:29), which is approximately 2566 nucleotides long including untranslated regions, contains a predicted methionine-initiated coding sequence of about 2277 nucleotides (nucleotides 194–2470 of SEQ ID NO:29; SEQ ID NO:31). The coding sequence encodes a 758 amino acid protein (SEQ ID NO:30).

Example 14

Identification and Characterization of 21999 Human ADP-Ribosyltransferase cDNAs The human ADP-ribosyltransferase sequence (SEQ ID NO:36), which is approximately 1485 nucleotides long including untranslated regions, contains a predicted methionine-initiated coding sequence of about 876 nucleotides (nucleotides 255–1133 of SEQ ID NO:36). The coding sequence encodes a 292 amino acid protein (SEQ ID NO:37).

Example 15

Distribution of Human 21999 in Various Cells and Tissues

Human 21999 showed elevated levels of expression in skeletal muscle and ovary tissue. See Table 5.

TABLE 5

Expression 21999 in various cells and tissues.
PHASE 1.6.5 OF 21999

| | TISSUE TYPE | RELATIVE EXPRESSION |
|---|---|---|
| 1 | Artery normal | 0 |
| 2 | Aorta diseased | 0 |
| 3 | Vein normal | 0 |
| 4 | Coronary SMC (Smooth Muscle Cell) | 0 |
| 5 | HUVEC (Human Umbilical Vein Endothelial Cell) | 0 |
| 6 | Hemangioma | 0 |
| 7 | Heart normal | 0 |
| 8 | Heart CHF (Chronic Heart Failure) | 0.1044 |
| 9 | Kidney | 0 |
| 10 | Skeletal Muscle | 1.5218 |
| 11 | Adipose normal | 0 |
| 12 | Pancreas | 0 |
| 13 | Primary Osteoblasts | 0 |
| 14 | Osteoclasts (differentiated) | 0 |
| 15 | Skin normal | 0 |
| 16 | Spinal cord normal | 0 |
| 17 | Brain Cortex normal | 0 |
| 18 | Brain Hypothalamus normal | 0 |
| 19 | Nerve | 0 |
| 20 | DRG (Dorsal Root Ganglion) | 0 |
| 21 | Breast normal | 0.1482 |
| 22 | Breast tumor | 0 |
| 23 | Ovary normal | 1.2191 |
| 24 | Ovary Tumor | 0.0332 |
| 25 | Prostate Normal | 0.0641 |
| 26 | Prostate Tumor | 0 |
| 27 | Salivary glands | 0 |
| 28 | Colon normal | 0 |
| 29 | Colon Tumor | 0 |
| 30 | Lung normal | 0.0202 |
| 31 | Lung tumor | 0.871 |
| 32 | Lung COPD (Chronic Obstructive Pulmonary Disease) | 0 |
| 33 | Colon IBD (Inflammatory Bowel Disease) | 0 |
| 34 | Liver normal | 0 |
| 35 | Liver fibrosis | 0 |
| 36 | Spleen normal | 0 |
| 37 | Tonsil normal | 0 |
| 38 | Lymph node normal | 0 |
| 39 | Small intestine normal | 0 |
| 40 | Macrophages | 0 |
| 41 | Synovium | 0 |
| 42 | BM-MNC (Bone-Marrow Mononuclear Cells) | 0 |
| 43 | Activated PBMC (Peripheral Blood Mononuclear Cells) | 0 |
| 44 | Neutrophils | 0 |
| 45 | Megakaryocytes | 0 |
| 46 | Erythroid | 0 |
| 47 | Positive Control | 10.5253 |

Expression levels of 21999 were observed to be higher in tumors of the lung and colon, as well as in metastatic liver, relative to normal tissue. See Table 6, rows 22, 26, 30, 34, and 35. 21999 expression was also elevated in both normoxic and hypoxic colon tumor cell lines (HCT116). Table 6, rows 42 and 43.

TABLE 6

Expression of 21999 in various cells and tissues.
21999.1 ONCOLOGY PHASE II PANEL

| | TISSUE TYPE | RELATIVE EXPRESSION |
|---|---|---|
| 1 | PIT 400 Breast Normal | 0.00 |
| 2 | PIT 372 Breast Normal | 3.15 |
| 3 | CHT 1228 Breast Normal | 1.31 |
| 4 | MDA 304 Breast Tumor: MD-IDC (Moderately Differentiated-Invasive Ductal Carcinoma) | 0.00 |
| 5 | CHT 2002 Breast Tumor: IDC | 0.00 |
| 6 | MDA 236-Breast Tumor: PD-IDC(ILC?) (Poorly Differentiated-IDC(Invasive Lobular Carcinoma?)) | 0.00 |
| 7 | CHT 562 Breast Tumor: IDC | 0.00 |
| 8 | NDR 138 Breast Tumor ILC (LG) | 0.00 |
| 9 | CHT 1841 Lymph node (Breast metastases) | 0.00 |
| 10 | PIT 58 Lung (Breast metastases) | 0.00 |
| 11 | CHT 620 Ovary Normal | 14.38 |
| 12 | PIT 208 Ovary Normal | 6.39 |
| 13 | CLN 012 Ovary Tumor | 96.05 |
| 14 | CLN 07 Ovary Tumor | 0.07 |
| 15 | CLN 17 Ovary Tumor | 9.82 |
| 16 | MDA 25 Ovary Tumor | 0.35 |
| 17 | CLN 08 Ovary Tumor | 0.48 |
| 18 | PIT 298 Lung Normal | 0.05 |
| 19 | MDA 185 Lung Normal | 0.00 |
| 20 | CLN 930 Lung Normal | 0.57 |
| 21 | MPI 215 Lung Tumor--SmC | 0.00 |
| 22 | MDA 259 Lung Tumor-PDNSCCL | 32.13 |
| 23 | CHT 832 Lung Tumor-PDNSCCL | 0.00 |
| 24 | MDA 262 Lung Tumor-SCC (Squamous Cell Carcinoma) | 1.01 |
| 25 | CHT 793 Lung Tumor-ACA | 0.00 |
| 26 | CHT 331 Lung Tumor-ACA | 14.63 |
| 27 | CHT 405 Colon Normal | 0.00 |
| 28 | CHT 523 Colon Normal | 0.20 |
| 29 | CHT 371 Colon Normal | 0.00 |
| 30 | CHT 382 Colon Tumor: MD | 8.46 |
| 31 | CHT 528 Colon Tumor: MD | 0.17 |
| 32 | CLN 609 Colon Tumor | 0.13 |
| 33 | NDR 210 Colon Tumor: MD-PD | 0.00 |
| 34 | CHT 340 Colon-Liver Metastases | 6.19 |
| 35 | CHT 1637 Colon-Liver Metastases | 2.14 |

TABLE 6-continued

Expression of 21999 in various cells and tissues.
21999.1 ONCOLOGY PHASE II PANEL

| TISSUE TYPE | RELATIVE EXPRESSION |
|---|---|
| 36 PIT 260 Liver Normal (female) | 0.00 |
| 37 CHT 1653 Cervix Squamous CC | 0.00 |
| 38 CHT 569 Cervix Squamous CC | 0.00 |
| 39 A24 HMVEC (Human Microvessel Endothelial Cell)-Arresting | 0.00 |
| 40 C48 HMVEC-Proliferating | 0.00 |
| 41 Pooled Hemangiomas | 0.00 |
| 42 HCT116N22 Normoxic | 51.30 |
| 43 HCT116H22 Hypoxic | 47.37 |

Expression levels were determined as described in Example 12.

Example 16

Tissue Distribution of 8035, 84242, 55304, 52999, or 21999 mRNA

Northern blot hybridizations with various RNA samples can be performed under standard conditions and washed under stringent conditions, i.e., 0.2×SSC at 65° C. A DNA probe corresponding to all or a portion of the 8035, 84242, 55304, 52999, or 21999 cDNA (SEQ ID NO:18, SEQ ID NO:22, SEQ ID NO:26, SEQ ID NO:29, or SEQ ID NO:36) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 17

Identification and Characterization of Human 52020 cDNAs

The human 52020 sequence (SEQ ID NO:40), which is approximately 2183 nucleotides long including untranslated regions, contains a predicted methionine-initiated coding sequence of about 912 nucleotides, not including the stop codon (nucleotides 782–1693 of SEQ ID NO:40; nucleotides 1–912 of SEQ ID NO:42). The coding sequence encodes a 304 amino acid protein (SEQ ID NO:41).

Example 18

Tissue Distribution of 52020 mRNA

Northern blot hybridizations with various RNA samples can be performed under standard conditions and washed under stringent conditions, i.e., 0.2×SSC at 65° C. A DNA probe corresponding to all or a portion of the 52020 cDNA (SEQ ID NO:40) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 19

Recombinant Expression of 22406, acyltransferase, 7716, 25233, 8035, 84242, 55304, 52999, 21999, or 52020 in Bacterial Cells In this example, 22406, acyltransferase, 7716, 25233, 8035, 84242, 55304, 52999, 21999, or 52020 is expressed as a recombinant glutathione-S-transferase (GST) fusion polypeptide in E. coli and the fusion polypeptide is isolated and characterized. Specifically, 22406, acyltransferase, 7716, 25233, 8035, 84242, 55304, 52999, 21999, or 52020 is fused to GST and this fusion polypeptide is expressed in E. coli, e.g., strain PEB199. Expression of the GST-22406, acyltransferase, 7716, 25233, 8035, 84242, 55304, 52999, 21999, or 52020 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 20

Expression of Recombinant 22406, Acyltransferase, 7716, 25233, 8035, 84242, 55304, 52999, 21999, or 52020 Protein in COS Cells To express the 22406, acyltransferase, 7716, 25233, 8035, 84242, 55304, 52999, 21999, or 52020 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire 22406, acyltransferase, 7716, 25233, 8035, 84242, 55304, 52999, 21999, or 52020 protein and an HA tag (Wilson et al. (1984) Cell 37:767) or a FLAG tag fused in-frame to its 3' end of the fragment is cloned into the polylinker region of the vector, thereby placing the expression of the recombinant protein under the control of the CMV promoter.

To construct the plasmid, the 22406, acyltransferase, 7716, 25233, 8035, 84242, 55304, 52999, 21999, or 52020 DNA sequence is amplified by PCR using two primers. The 5' primer contains the restriction site of interest followed by approximately twenty nucleotides of the 22406, acyltransferase, 7716, 25233, 8035, 84242, 55304, 52999, 21999, or 52020 coding sequence starting from the initiation codon; the 3' end sequence contains complementary sequences to the other restriction site of interest, a translation stop codon, the HA tag or FLAG tag and the last 20 nucleotides of the 22406, acyltransferase, 7716, 25233, 8035, 84242, 55304, 52999, 21999, or 52020 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 22406, acyltransferase, 7716, 25233, 8035, 84242, 55304, 52999, 21999, or 52020 gene is inserted in the correct orientation. The ligation mixture is transformed into E. coli cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 22406, acyltransferase, 7716, 25233, 8035, 84242, 55304, 52999, 21999, or 52020-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual.* 2nd, ed., *Cold Spring Harbor Laboratory*, Cold Spring Harbor Laboratory Press, Cold Spring Harbor, N.Y., 1989. The expression of the 22406, acyltransferase, 7716, 25233, 8035, 84242, 55304, 52999, 21999, or 52020 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 22406, acyltransferase, 7716, 25233, 8035, 84242, 55304, 52999, 21999, or 52020 coding sequence is cloned directly into the polylinker of the pCDNA/Amp vector using the appropriate restriction sites. The resulting plasmid is transfected into COS cells in the manner described above, and the expression of the 22406, acyltransferase, 7716, 25233, 8035, 84242, 55304, 52999, 21999, or 52020 polypeptide is detected by radiolabelling and immunoprecipitation using a 22406, acyltransferase, 7716, 25233, 8035, 84242, 55304, 52999, 21999, or 52020 specific monoclonal antibody.

EQUIVALENTS

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 43

<210> SEQ ID NO 1
<211> LENGTH: 1770
<212> TYPE: DNA
<213> ORGANISM: Homo sapiens
<220> FEATURE:
<221> NAME/KEY: CDS
<222> LOCATION: (69)...(1091)

<400> SEQUENCE: 1
cacgcgtccg ggccggggag gcgcgcggag gctggagctg gaggcgcggc gccggtgagc      60 tgagaacc atg tgt gct cag tat tgc atc tcc ttt gct gat gtt gaa aaa     110
         Met Cys Ala Gln Tyr Cys Ile Ser Phe Ala Asp Val Glu Lys
           1               5                  10 gct cat atc aac att cga gat tct atc cac ctc aca cca gtg cta aca       158
Ala His Ile Asn Ile Arg Asp Ser Ile His Leu Thr Pro Val Leu Thr
 15                  20                  25                  30 agc tcc att ttg aat caa cta aca ggg cgc aat ctt ttc ttc aaa tgt       206
Ser Ser Ile Leu Asn Gln Leu Thr Gly Arg Asn Leu Phe Phe Lys Cys
                 35                  40                  45 gaa ctc ttc cag aaa aca gga tct ttt aag att cgt ggt gct ctc aat       254
Glu Leu Phe Gln Lys Thr Gly Ser Phe Lys Ile Arg Gly Ala Leu Asn
             50                  55                  60 gcc gtc aga agc ttg gtt cct gat gct tta gaa agg aag ccg aaa gct       302
Ala Val Arg Ser Leu Val Pro Asp Ala Leu Glu Arg Lys Pro Lys Ala
         65                  70                  75 gtt gtt act cac agc agt gga aac cat ggc cag gct ctc acc tat gct       350
Val Val Thr His Ser Ser Gly Asn His Gly Gln Ala Leu Thr Tyr Ala
     80                  85                  90 gcc aaa ttg gaa gga att cct gct tat att gtg gtg ccc cag aca gct       398
Ala Lys Leu Glu Gly Ile Pro Ala Tyr Ile Val Val Pro Gln Thr Ala
 95                  100                 105                 110
```

```
cca gac tgt aaa aaa ctt gca ata caa gcc tac gga gcg tca att gta      446
Pro Asp Cys Lys Lys Leu Ala Ile Gln Ala Tyr Gly Ala Ser Ile Val
            115                 120                 125 tac tgt gaa cct agt gat gag tcc aga gaa aat gtt gca aaa aga gtt      494
Tyr Cys Glu Pro Ser Asp Glu Ser Arg Glu Asn Val Ala Lys Arg Val
            130                 135                 140 aca gaa gaa aca gaa ggc atc atg gta cat ccc aac cag gag cct gca      542
Thr Glu Glu Thr Glu Gly Ile Met Val His Pro Asn Gln Glu Pro Ala
            145                 150                 155 gtg ata gct gga caa ggg aca att gcc ctg gaa gtg ctg aac cag gtt      590
Val Ile Ala Gly Gln Gly Thr Ile Ala Leu Glu Val Leu Asn Gln Val
160                 165                 170 cct ttg gtg gat gca ctg gtg gta cct gta ggt gga gga atg ctt          638
Pro Leu Val Asp Ala Leu Val Val Pro Val Gly Gly Gly Gly Met Leu
175                 180                 185                 190 gct gga ata gca att aca gtt aag gct ctg aaa cct agt gtg aag gta      686
Ala Gly Ile Ala Ile Thr Val Lys Ala Leu Lys Pro Ser Val Lys Val
                195                 200                 205 tat gct gct gaa ccc tca aat gca gat gac tgc tac cag tcc aag ctg      734
Tyr Ala Ala Glu Pro Ser Asn Ala Asp Asp Cys Tyr Gln Ser Lys Leu
                210                 215                 220 aag ggg aaa ctg atg ccc aat ctt tat cct cca gaa acc ata gca gat      782
Lys Gly Lys Leu Met Pro Asn Leu Tyr Pro Pro Glu Thr Ile Ala Asp
                225                 230                 235 ggt gtc aaa tcc agc att ggc ttg aac acc tgg cct att atc agg gac      830
Gly Val Lys Ser Ser Ile Gly Leu Asn Thr Trp Pro Ile Ile Arg Asp
            240                 245                 250 ctt gtg gat gat atc ttc act gtc aca gag gat gaa att aag tgt gca      878
Leu Val Asp Asp Ile Phe Thr Val Thr Glu Asp Glu Ile Lys Cys Ala
255                 260                 265                 270 acc cag ctg gtg tgg gag agg atg aaa cta ctc att gaa cct aca gct      926
Thr Gln Leu Val Trp Glu Arg Met Lys Leu Leu Ile Glu Pro Thr Ala
                275                 280                 285 ggt gtt gga gtg gct gct gtg ctg tct caa cat ttt caa act gtt tcc      974
Gly Val Gly Val Ala Ala Val Leu Ser Gln His Phe Gln Thr Val Ser
                290                 295                 300 cca gaa gta aag aac att tgt att gtg ctc agt ggt gga aat gta gac     1022
Pro Glu Val Lys Asn Ile Cys Ile Val Leu Ser Gly Gly Asn Val Asp
            305                 310                 315 tta acc tcc tcc ata act tgg gtg aag cag gct gaa agg cca gct tct     1070
Leu Thr Ser Ser Ile Thr Trp Val Lys Gln Ala Glu Arg Pro Ala Ser
320                 325                 330 tat cag tct gtt tct gtt taa tttacagaaa aggaaatggt gggaattcag        1121
Tyr Gln Ser Val Ser Val *
335                 340 tgtctttaga tactgaagac attttgtttc ctagtattgt caactcttag ttatcagatt   1181
cttaatggag agtggctatt tcattaagat ttaatagttt ttttggact aagtagtgga   1241 aaaactttta tacttaactg agacattttg tcaaggctaa aaaaaagtct tgcaaaatgg   1301
ggcagtggac tgacaggctg acatagaaaa taaacttttgc ccaatcacaa cttgtgcctc  1361
ccatccctgg agtactgact ggcaccggta agacagaatc tctttgaatc cattactcca  1421
tgcccccttg aggcactgtt gaagaaatct cactttcag ccagggtact ggttctggta   1481
catatggatc ataagtccat ttggggaaga ctcgtttata caggttcatc agtactgtgt  1541
cttgagattt tagcttccca tcaaagctgc atttcatgtg ccatgggta cctagaaaga   1601 catcagaaca agtcggtcaa attaaaagta gaaaattttta aagcaatgac ttccaaccca  1661
```

```
acagtcattt agcaacactg cagaaatgca gacatggtct caaatcccgt gtttccttac    1721
ctaaaggttc cttgatatgt cctctccggc ccccacttcg ttctcagtt               1770
```

<210> SEQ ID NO 2
<211> LENGTH: 340
<212> TYPE: PRT
<213> ORGANISM: Homo sapiens

<400> SEQUENCE: 2

```
Met Cys Ala Gln Tyr Cys Ile Ser Phe Ala Asp Val Glu Lys Ala His
 1               5                  10                  15

Ile Asn Ile Arg Asp Ser Ile His Leu Thr Pro Val Leu Thr Ser Ser
                20                  25                  30

Ile Leu Asn Gln Leu Thr Gly Arg Asn Leu Phe Phe Lys Cys Glu Leu
            35                  40                  45

Phe Gln Lys Thr Gly Ser Phe Lys Ile Arg Gly Ala Leu Asn Ala Val
        50                  55                  60

Arg Ser Leu Val Pro Asp Ala Leu Glu Arg Lys Pro Lys Ala Val Val
65                  70                  75                  80

Thr His Ser Ser Gly Asn His Gly Gln Ala Leu Thr Tyr Ala Ala Lys
                85                  90                  95

Leu Glu Gly Ile Pro Ala Tyr Ile Val Val Pro Gln Thr Ala Pro Asp
            100                 105                 110

Cys Lys Lys Leu Ala Ile Gln Ala Tyr Gly Ala Ser Ile Val Tyr Cys
        115                 120                 125

Glu Pro Ser Asp Glu Ser Arg Glu Asn Val Ala Lys Arg Val Thr Glu
    130                 135                 140

Glu Thr Glu Gly Ile Met Val His Pro Asn Gln Glu Pro Ala Val Ile
145                 150                 155                 160

Ala Gly Gln Gly Thr Ile Ala Leu Glu Val Leu Asn Gln Val Pro Leu
                165                 170                 175

Val Asp Ala Leu Val Val Pro Val Gly Gly Gly Met Leu Ala Gly
            180                 185                 190

Ile Ala Ile Thr Val Lys Ala Leu Lys Pro Ser Val Lys Val Tyr Ala
        195                 200                 205

Ala Glu Pro Ser Asn Ala Asp Asp Cys Tyr Gln Ser Lys Leu Lys Gly
    210                 215                 220

Lys Leu Met Pro Asn Leu Tyr Pro Pro Glu Thr Ile Ala Asp Gly Val
225                 230                 235                 240

Lys Ser Ser Ile Gly Leu Asn Thr Trp Pro Ile Ile Arg Asp Leu Val
                245                 250                 255

Asp Asp Ile Phe Thr Val Thr Glu Asp Glu Ile Lys Cys Ala Thr Gln
            260                 265                 270

Leu Val Trp Glu Arg Met Lys Leu Leu Ile Glu Pro Thr Ala Gly Val
        275                 280                 285

Gly Val Ala Ala Val Leu Ser Gln His Phe Gln Thr Val Ser Pro Glu
    290                 295                 300

Val Lys Asn Ile Cys Ile Val Leu Ser Gly Gly Asn Val Asp Leu Thr
305                 310                 315                 320

Ser Ser Ile Thr Trp Val Lys Gln Ala Glu Arg Pro Ala Ser Tyr Gln
                325                 330                 335

Ser Val Ser Val
            340
```

-continued

```
<210> SEQ ID NO 3
<211> LENGTH: 1020
<212> TYPE: DNA
<213> ORGANISM: Homo sapiens

<400> SEQUENCE: 3
atgtgtgctc agtattgcat ctcctttgct gatgttgaaa aagctcatat caacattcga      60
gattctatcc acctcacacc agtgctaaca agctccattt tgaatcaact aacagggcgc     120
aatcttttct tcaaatgtga actcttccag aaaacaggat cttttaagat tcgtggtgct     180
ctcaatgccg tcagaagctt ggttcctgat gctttagaaa ggaagccgaa agctgttgtt     240
actcacagca gtggaaacca tggccaggct ctcacctatg ctgccaaatt ggaaggaatt     300
cctgcttata ttgtggtgcc ccagacagct ccagactgta aaaaacttgc aatacaagcc     360
tacggagcgt caattgtata ctgtgaacct agtgatgagt ccagagaaaa tgttgcaaaa     420
agagttacag aagaaacaga aggcatcatg gtacatccca accaggagcc tgcagtgata     480
gctggacaag ggacaattgc cctggaagtg ctgaaccagg ttcctttggt ggatgcactg     540
gtggtacctg taggtggagg aggaatgctt gctggaatag caattacagt taaggctctg     600
aaacctagtg tgaaggtata tgctgctgaa ccctcaaatg cagatgactg ctaccagtcc     660
aagctgaagg ggaaactgat gcccaatctt tatcctccag aaaccatagc agatggtgtc     720
aaatccagca ttggcttgaa cacctggcct attatcaggg accttgtgga tgatatcttc     780
actgtcacag aggatgaaat taagtgtgca acccagctgg tgtgggagag atgaaaacta     840
ctcattgaac ctacagctgg tgttggagtg gctgctgtgc tgtctcaaca ttttcaaact     900
gtttccccag aagtaaagaa catttgtatt gtgctcagtg gtggaaatgt agacttaacc     960
tcctccataa cttgggtgaa gcaggctgaa aggccagctt cttatcagtc tgtttctgtt    1020

<210> SEQ ID NO 4
<211> LENGTH: 378
<212> TYPE: PRT
<213> ORGANISM: Artificial Sequence
<220> FEATURE:
<223> OTHER INFORMATION: Pyridoxal-Phosphate Dependent Enzyme Family
      Domain Sequence

<400> SEQUENCE: 4

Val Thr Glu Leu Ile Gly Asn Thr Pro Leu Val Arg Leu Asn Arg Leu
  1               5                  10                  15

Ser Lys Glu Leu Gly Glu Gly Leu Gly Ala Asn Ala Ala Val Glu Ile
                 20                  25                  30

Tyr Leu Lys Leu Glu Asp Leu Asn Gly Pro Thr Gly Ser Phe Lys Asp
             35                  40                  45

Arg Gly Leu Ala Leu Asn Met Ile Leu Leu Ala Glu Lys Leu Gly Lys
         50                  55                  60

Lys Gly Gly Ile Val Pro Gly Thr Val Gln Val Glu Ser Lys Thr Thr
 65                  70                  75                  80

Ile Ile Glu Pro Thr Ser Gly Asn Thr Gly Ile Ala Leu Ala Leu Ala
                 85                  90                  95

Ala Ala Leu Leu Gly Leu Lys Cys Thr Ile Val Met Pro Ala Thr Asp
                100                 105                 110

Thr Ser Arg Glu Lys Arg Ala Gln Leu Arg Ala Leu Gly Ala Glu Leu
            115                 120                 125

Val Val Val Pro Val Ala Gly Gly Ser Asp Asp Leu Ala Asp Ala
        130                 135                 140
```

```
Ile Ala Lys Ala Glu Glu Leu Ala Glu Asn Pro Glu Asn Ala Tyr
145                 150                 155                 160

Leu Leu Asn Gln Ala Ala Gly Pro Phe Asp Asn Pro Ala Asn Pro Glu
            165                 170                 175

Ile Ala Gly Gln Lys Thr Ile Gly Pro Glu Ile Trp Glu Gln Leu Gly
        180                 185                 190

Gly Lys Glu Ile Ser Leu Gly Arg Leu Pro Asp Ala Val Val Ala Pro
    195                 200                 205

Val Gly Gly Gly Gly Thr Ile Thr Gly Ile Ala Arg Tyr Leu Lys Glu
210                 215                 220

Leu Asn Pro Asp Gly Lys Ile Asp Val Leu Glu Leu Pro Val Lys Val
225                 230                 235                 240

Ile Gly Val Glu Pro Glu Gly Ser Ala Val Leu Ser Gly Ser Leu Lys
            245                 250                 255

Ala Thr Leu Thr Leu Ala Gly Lys Pro Gly Pro Leu His Gly Arg Asp
        260                 265                 270

Ser Lys Tyr Leu Leu Gln Asp Glu Pro Val Thr Leu Pro Glu Thr Lys
    275                 280                 285

Ser Ile Gly Ile Gly Leu Gly Val Pro Arg Val Gly Glu Phe Val Pro
290                 295                 300

Pro Ile Leu Asp Glu Leu Leu Asp Arg Arg Gln Gly Ile Asp Glu Val
305                 310                 315                 320

Val Thr Val Thr Asp Glu Glu Ala Leu Glu Ala Ala Arg Leu Leu Ala
            325                 330                 335

Arg Glu Glu Gly Ile Leu Val Gly Pro Ser Ser Gly Ala Ala Val Ala
        340                 345                 350

Ala Ala Leu Lys Leu Ala Lys Glu Gly Lys Pro Leu Asn Lys Gly
    355                 360                 365

Lys Thr Ile Val Val Ile Leu Ser Gly Gly
    370                 375

<210> SEQ ID NO 5
<211> LENGTH: 14
<212> TYPE: PRT
<213> ORGANISM: Artificial Sequence
<220> FEATURE:
<223> OTHER INFORMATION: Pyridoxal-Phosphate Attachment Site Consensus
      Sequence
<220> FEATURE:
<221> NAME/KEY: misc_feature
<222> LOCATION: 2, 3, 4, 5, 7
<223> OTHER INFORMATION: Xaa = Any amino acid

<400> SEQUENCE: 5

Asp Xaa Xaa Xaa Xaa Ser Xaa Ala Phe Lys Asp Arg Gly Leu
1               5                   10

<210> SEQ ID NO 6
<211> LENGTH: 2299
<212> TYPE: DNA
<213> ORGANISM: Homo sapiens
<220> FEATURE:
<221> NAME/KEY: CDS
<222> LOCATION: (495)...(2129)

<400> SEQUENCE: 6
agtggttgct caatggcatt actggatcca ggttaggatt atctgagaat acatttatct    60
gcattttacg gaaggcaacc gaggttcata gagatagtga tttggccagc gtcacagkcc   120
cagtaaaagg gattgaaaat ccaggtccgt ccgaccctaa agcagggaac tctgcctagt   180
```

-continued

```
gtctcgctgt ggaatgttag ggatcctggg gtacccttca gggtcttggc tcggaaggaa      240
aacattcccc tccgagggga tggactatat taccaagggg gtggagccag atgcctgagg      300
gggtgtggcc agagcctggg gcgtgtcaca gccgaagggg cagggcggca gcagcaggcg      360
tctaagtaac ttcagcgcct gcgcagaggc tccccagcgt cgccctaggc tgggactcta      420
gtaggtcttc ggctcagttt tggctgcagc gcccgcgtag atcgcttcgg ccgggttcta      480
cgcccggctc aact atg agc cgg tgc gcc cag gcg gcg gaa gtg gcg gcc        530
               Met Ser Arg Cys Ala Gln Ala Ala Glu Val Ala Ala
                 1               5                  10 aca gtg cca ggt gcc ggc gtc ggg aac gtg ggg ctg cgg ccg ccc atg        578
Thr Val Pro Gly Ala Gly Val Gly Asn Val Gly Leu Arg Pro Pro Met
             15                  20                  25 gtg ccc cgt cag gcg tcc ttc ttc ccg ccg ccg gtg ccg aac ccc ttc        626
Val Pro Arg Gln Ala Ser Phe Phe Pro Pro Pro Val Pro Asn Pro Phe
 30                  35                  40 gtg cag cag acg cag atc ggc tcc gcg agg cgg gtc cag att gtc ctt        674
Val Gln Gln Thr Gln Ile Gly Ser Ala Arg Arg Val Gln Ile Val Leu
 45                  50                  55                  60 ctt ggg att atc ttg ctt cca att cgt gtc tta ttg gtt gcg tta att        722
Leu Gly Ile Ile Leu Leu Pro Ile Arg Val Leu Leu Val Ala Leu Ile
             65                  70                  75 tta tta ctt gca tgg cca ttt gct gca att tca aca gta tgc tgt cct        770
Leu Leu Leu Ala Trp Pro Phe Ala Ala Ile Ser Thr Val Cys Cys Pro
         80                  85                  90 gaa aag ctg acc cac cca ata act ggt tgg agg agg aaa att act caa        818
Glu Lys Leu Thr His Pro Ile Thr Gly Trp Arg Arg Lys Ile Thr Gln
             95                 100                 105 aca gct ttg aaa ttt ctg ggt cgt gct atg ttc ttt tca atg gga ttt        866
Thr Ala Leu Lys Phe Leu Gly Arg Ala Met Phe Phe Ser Met Gly Phe
        110                 115                 120 ata gtt gct gta aaa gga aag att gca agt cct ttg gaa gca cca gtt        914
Ile Val Ala Val Lys Gly Lys Ile Ala Ser Pro Leu Glu Ala Pro Val
125                 130                 135                 140 ttt gtt gct gcc cct cat tca aca ttc ttt gat gga att gcc tgt gtt        962
Phe Val Ala Ala Pro His Ser Thr Phe Phe Asp Gly Ile Ala Cys Val
                145                 150                 155 gta gct ggg tta cct tct ata gta tct cga aat gag aat gca caa gtc       1010
Val Ala Gly Leu Pro Ser Ile Val Ser Arg Asn Glu Asn Ala Gln Val
            160                 165                 170 cct ctg att ggc aga ctg tta cgg gct gtg caa cca gtt ttg gtg tcc       1058
Pro Leu Ile Gly Arg Leu Leu Arg Ala Val Gln Pro Val Leu Val Ser
        175                 180                 185 cgt gta gat ccg gat tcc cga aaa aac aca ata aat gaa ata ata aag       1106
Arg Val Asp Pro Asp Ser Arg Lys Asn Thr Ile Asn Glu Ile Ile Lys
    190                 195                 200 cga aca aca tca gga gga gaa tgg ccc cag ata cta gtt ttc cca gaa       1154
Arg Thr Thr Ser Gly Gly Glu Trp Pro Gln Ile Leu Val Phe Pro Glu
205                 210                 215                 220 ggt act tgt act aat cgt tcc tgt ttg att act ttt aaa cca gga gcc       1202
Gly Thr Cys Thr Asn Arg Ser Cys Leu Ile Thr Phe Lys Pro Gly Ala
                225                 230                 235 ttc att cca gga gtt cca gtg cag cca gtc ctc ctc aga tac cca aac       1250
Phe Ile Pro Gly Val Pro Val Gln Pro Val Leu Leu Arg Tyr Pro Asn
            240                 245                 250 aag ctg gat act gtg acc tgg aca tgg caa gga tat aca ttc att cag       1298
Lys Leu Asp Thr Val Thr Trp Thr Trp Gln Gly Tyr Thr Phe Ile Gln
        255                 260                 265
```

```
ctt tgt atg ctt act ttc tgc cag ctc ttc aca aag gta gaa gtt gag    1346
Leu Cys Met Leu Thr Phe Cys Gln Leu Phe Thr Lys Val Glu Val Glu
    270                 275                 280 ttt atg cca gtt caa gta cca aat gat gaa gaa aaa aat gat cct gtc    1394
Phe Met Pro Val Gln Val Pro Asn Asp Glu Glu Lys Asn Asp Pro Val
285                 290                 295                 300 ctt ttt gcc aat aaa gtc cgg aat tta atg gca gaa gct ctg gga ata    1442
Leu Phe Ala Asn Lys Val Arg Asn Leu Met Ala Glu Ala Leu Gly Ile
                305                 310                 315 cca gta aca gat cat acc tat gaa gac tgc aga ttg atg att tca gca    1490
Pro Val Thr Asp His Thr Tyr Glu Asp Cys Arg Leu Met Ile Ser Ala
            320                 325                 330 gga cag cta aca ttg cct atg gaa gct ggg ctg gtg gaa ttt act aaa    1538
Gly Gln Leu Thr Leu Pro Met Glu Ala Gly Leu Val Glu Phe Thr Lys
        335                 340                 345 att agc cga aaa ttg aaa tta gat tgg gat ggt gtt cgt aag cat ttg    1586
Ile Ser Arg Lys Leu Lys Leu Asp Trp Asp Gly Val Arg Lys His Leu
    350                 355                 360 gat gaa tat gca tct att gcg agt tcc tca aaa gga gga aga att gga    1634
Asp Glu Tyr Ala Ser Ile Ala Ser Ser Ser Lys Gly Gly Arg Ile Gly
365                 370                 375                 380 att gaa gaa ttc gcc aag tat tta aag ttg cct gtt tca gat gtc ttg    1682
Ile Glu Glu Phe Ala Lys Tyr Leu Lys Leu Pro Val Ser Asp Val Leu
                385                 390                 395 aga caa ctt ttt gca ctc ttt gac agg aac cat gat ggc agc att gac    1730
Arg Gln Leu Phe Ala Leu Phe Asp Arg Asn His Asp Gly Ser Ile Asp
            400                 405                 410 ttc cga gag tat gtg att ggc ctg gct gtc ttg tgc aac cct tcc aac    1778
Phe Arg Glu Tyr Val Ile Gly Leu Ala Val Leu Cys Asn Pro Ser Asn
        415                 420                 425 aca gag gag atc atc cag gtg gca ttt aag ctg ttt gac gtt gat gag    1826
Thr Glu Glu Ile Ile Gln Val Ala Phe Lys Leu Phe Asp Val Asp Glu
    430                 435                 440 gat ggc tac ata acg gag gaa gag ttc tcc acc att cta cag gct tcc    1874
Asp Gly Tyr Ile Thr Glu Glu Glu Phe Ser Thr Ile Leu Gln Ala Ser
445                 450                 455                 460 ctt gga gtg cct gac ctt gat gtt tct ggt ctc ttc aag gaa ata gcc    1922
Leu Gly Val Pro Asp Leu Asp Val Ser Gly Leu Phe Lys Glu Ile Ala
                465                 470                 475 caa ggg gac tca att tcc tat gag gaa ttt aaa agt ttt gcc tta aag    1970
Gln Gly Asp Ser Ile Ser Tyr Glu Glu Phe Lys Ser Phe Ala Leu Lys
            480                 485                 490 cat cca gaa tat gct aag ata ttt aca aca tac cta gac ctc cag acg    2018
His Pro Glu Tyr Ala Lys Ile Phe Thr Thr Tyr Leu Asp Leu Gln Thr
        495                 500                 505 tgc cat gtg ttt tca tta cca aaa gaa gtc cag aca acc ccc tcc acc    2066
Cys His Val Phe Ser Leu Pro Lys Glu Val Gln Thr Thr Pro Ser Thr
    510                 515                 520 gcc agt aat aaa gtc agc cct gaa aag cat gaa gag agt acc tca gac    2114
Ala Ser Asn Lys Val Ser Pro Glu Lys His Glu Glu Ser Thr Ser Asp
525                 530                 535                 540 aaa aaa gat gac tga aagcagtatt tccataagg aaaacacagt agcttttgct    2169
Lys Lys Asp Asp * tgaaattgta aaggcactta ttgataatac ttttaatgtg ttggtaatga tgtttaaaat    2229
tgaaagattt ttaaaataaa aatgatagat tttcttacta aaaaaaaaaa aaaaaaaaa    2289 aaaaaaaaaa                                                           2299

<210> SEQ ID NO 7
```

```
<211> LENGTH: 544
<212> TYPE: PRT
<213> ORGANISM: Homo sapiens

<400> SEQUENCE: 7
```

| | | | | | | | | | | | | | | | |
|---|---|---|---|---|---|---|---|---|---|---|---|---|---|---|---|
|Met|Ser|Arg|Cys|Ala|Gln|Ala|Ala|Glu|Val|Ala|Ala|Thr|Val|Pro|Gly|
|1| | | |5| | | | |10| | | | |15| |
|Ala|Gly|Val|Gly|Asn|Val|Gly|Leu|Arg|Pro|Pro|Met|Val|Pro|Arg|Gln|
| | | |20| | | | |25| | | | |30| | |
|Ala|Ser|Phe|Phe|Pro|Pro|Val|Pro|Asn|Pro|Phe|Val|Gln|Gln|Thr| |
| | | |35| | | | |40| | | | |45| | |
|Gln|Ile|Gly|Ser|Ala|Arg|Arg|Val|Gln|Ile|Val|Leu|Leu|Gly|Ile|Ile|
| |50| | | | |55| | | | |60| | | | |
|Leu|Leu|Pro|Ile|Arg|Val|Leu|Val|Ala|Leu|Ile|Leu|Leu|Leu|Ala| |
|65| | | | |70| | | | |75| | | | |80|
|Trp|Pro|Phe|Ala|Ala|Ile|Ser|Thr|Val|Cys|Cys|Pro|Glu|Lys|Leu|Thr|
| | | | |85| | | | |90| | | | |95| |
|His|Pro|Ile|Thr|Gly|Trp|Arg|Lys|Ile|Thr|Gln|Thr|Ala|Leu|Lys| |
| | | |100| | | | |105| | | | |110| | |
|Phe|Leu|Gly|Arg|Ala|Met|Phe|Ser|Met|Gly|Phe|Ile|Val|Ala|Val| |
| | | |115| | | | |120| | | | |125| | |
|Lys|Gly|Lys|Ile|Ala|Ser|Pro|Leu|Glu|Ala|Pro|Val|Phe|Val|Ala|Ala|
| |130| | | | |135| | | | |140| | | | |
|Pro|His|Ser|Thr|Phe|Phe|Asp|Gly|Ile|Ala|Cys|Val|Val|Ala|Gly|Leu|
|145| | | | |150| | | | |155| | | | |160|
|Pro|Ser|Ile|Val|Ser|Arg|Asn|Glu|Asn|Ala|Gln|Val|Pro|Leu|Ile|Gly|
| | | | |165| | | | |170| | | | |175| |
|Arg|Leu|Leu|Arg|Ala|Val|Gln|Pro|Val|Leu|Val|Ser|Arg|Val|Asp|Pro|
| | | |180| | | | |185| | | | |190| | |
|Asp|Ser|Arg|Lys|Asn|Thr|Ile|Asn|Glu|Ile|Ile|Lys|Arg|Thr|Thr|Ser|
| | | |195| | | | |200| | | | |205| | |
|Gly|Gly|Glu|Trp|Pro|Gln|Ile|Leu|Val|Phe|Pro|Glu|Gly|Thr|Cys|Thr|
| |210| | | | |215| | | | |220| | | | |
|Asn|Arg|Ser|Cys|Leu|Ile|Thr|Phe|Lys|Pro|Gly|Ala|Phe|Ile|Pro|Gly|
|225| | | | |230| | | | |235| | | | |240|
|Val|Pro|Val|Gln|Pro|Val|Leu|Leu|Arg|Tyr|Pro|Asn|Lys|Leu|Asp|Thr|
| | | | |245| | | | |250| | | | |255| |
|Val|Thr|Trp|Thr|Trp|Gln|Gly|Tyr|Thr|Phe|Ile|Gln|Leu|Cys|Met|Leu|
| | | | |260| | | | |265| | | | |270| |
|Thr|Phe|Cys|Gln|Leu|Phe|Thr|Lys|Val|Glu|Val|Glu|Phe|Met|Pro|Val|
| | | |275| | | | |280| | | | |285| | |
|Gln|Val|Pro|Asn|Asp|Glu|Glu|Lys|Asn|Asp|Pro|Val|Leu|Phe|Ala|Asn|
| |290| | | | |295| | | | |300| | | | |
|Lys|Val|Arg|Asn|Leu|Met|Ala|Glu|Ala|Leu|Gly|Ile|Pro|Val|Thr|Asp|
|305| | | | |310| | | | |315| | | | |320|
|His|Thr|Tyr|Glu|Asp|Cys|Arg|Leu|Met|Ile|Ser|Ala|Gly|Gln|Leu|Thr|
| | | | |325| | | | |330| | | | |335| |
|Leu|Pro|Met|Glu|Ala|Gly|Leu|Val|Glu|Phe|Thr|Lys|Ile|Ser|Arg|Lys|
| | | |340| | | | |345| | | | |350| | |
|Leu|Lys|Leu|Asp|Trp|Asp|Gly|Val|Arg|Lys|His|Leu|Asp|Glu|Tyr|Ala|
| | | |355| | | | |360| | | | |365| | |
|Ser|Ile|Ala|Ser|Ser|Ser|Lys|Gly|Gly|Arg|Ile|Gly|Ile|Glu|Glu|Phe|
| |370| | | | |375| | | | |380| | | | |
|Ala|Lys|Tyr|Leu|Lys|Leu|Pro|Val|Ser|Asp|Val|Leu|Arg|Gln|Leu|Phe|

-continued

```
            385                 390                 395                 400
    Ala Leu Phe Asp Arg Asn His Asp Gly Ser Ile Asp Phe Arg Glu Tyr
                    405                 410                 415

Val Ile Gly Leu Ala Val Leu Cys Asn Pro Ser Asn Thr Glu Glu Ile
                420                 425                 430

Ile Gln Val Ala Phe Lys Leu Phe Asp Val Asp Glu Asp Gly Tyr Ile
                435                 440                 445

Thr Glu Glu Phe Ser Thr Ile Leu Gln Ala Ser Leu Gly Val Pro
                450                 455                 460

Asp Leu Asp Val Ser Gly Leu Phe Lys Glu Ile Ala Gln Gly Asp Ser
    465                 470                 475                 480

Ile Ser Tyr Glu Glu Phe Lys Ser Phe Ala Leu Lys His Pro Glu Tyr
                    485                 490                 495

Ala Lys Ile Phe Thr Thr Tyr Leu Asp Leu Gln Thr Cys His Val Phe
                500                 505                 510

Ser Leu Pro Lys Glu Val Gln Thr Thr Pro Ser Thr Ala Ser Asn Lys
                515                 520                 525

Val Ser Pro Glu Lys His Glu Glu Ser Thr Ser Asp Lys Lys Asp Asp
                530                 535                 540

<210> SEQ ID NO 8
<211> LENGTH: 1632
<212> TYPE: DNA
<213> ORGANISM: Homo sapiens
<220> FEATURE:
<221> NAME/KEY: CDS
<222> LOCATION: (1)...(1632)

<400> SEQUENCE: 8 atg agc cgg tgc gcc cag gcg gcg gaa gtg gcg gcc aca gtg cca ggt      48
Met Ser Arg Cys Ala Gln Ala Ala Glu Val Ala Ala Thr Val Pro Gly
 1               5                  10                  15 gcc ggc gtc ggg aac gtg ggg ctg cgg ccg ccc atg gtg ccc cgt cag      96
Ala Gly Val Gly Asn Val Gly Leu Arg Pro Pro Met Val Pro Arg Gln
             20                  25                  30 gcg tcc ttc ttc ccg ccg ccg gtg ccg aac ccc ttc gtg cag cag acg     144
Ala Ser Phe Phe Pro Pro Pro Val Pro Asn Pro Phe Val Gln Gln Thr
         35                  40                  45 cag atc ggc tcc gcg agg cgg gtc cag att gtc ctt ctt ggg att atc     192
Gln Ile Gly Ser Ala Arg Arg Val Gln Ile Val Leu Leu Gly Ile Ile
     50                  55                  60 ttg ctt cca att cgt gtc tta ttg gtt gcg tta att tta tta ctt gca     240
Leu Leu Pro Ile Arg Val Leu Leu Val Ala Leu Ile Leu Leu Leu Ala
 65                  70                  75                  80 tgg cca ttt gct gca att tca aca gta tgc tgt cct gaa aag ctg acc     288
Trp Pro Phe Ala Ala Ile Ser Thr Val Cys Cys Pro Glu Lys Leu Thr
                 85                  90                  95 cac cca ata act ggt tgg agg agg aaa att act caa aca gct ttg aaa     336
His Pro Ile Thr Gly Trp Arg Arg Lys Ile Thr Gln Thr Ala Leu Lys
            100                 105                 110 ttt ctg ggt cgt gct atg ttc ttt tca atg gga ttt ata gtt gct gta     384
Phe Leu Gly Arg Ala Met Phe Phe Ser Met Gly Phe Ile Val Ala Val
        115                 120                 125 aaa gga aag att gca agt cct ttg gaa gca cca gtt ttt gtt gct gcc     432
Lys Gly Lys Ile Ala Ser Pro Leu Glu Ala Pro Val Phe Val Ala Ala
    130                 135                 140 cct cat tca aca ttc ttt gat gga att gcc tgt gtt gta gct ggg tta     480
Pro His Ser Thr Phe Phe Asp Gly Ile Ala Cys Val Val Ala Gly Leu
145                 150                 155                 160
```

-continued

| | |
|---|---|
| cct tct ata gta tct cga aat gag aat gca caa gtc cct ctg att ggc<br>Pro Ser Ile Val Ser Arg Asn Glu Asn Ala Gln Val Pro Leu Ile Gly<br>                  165                        170                      175 | 528 |
| aga ctg tta cgg gct gtg caa cca gtt ttg gtg tcc cgt gta gat ccg<br>Arg Leu Leu Arg Ala Val Gln Pro Val Leu Val Ser Arg Val Asp Pro<br>                  180                        185                      190 | 576 |
| gat tcc cga aaa aac aca ata aat gaa ata ata aag cga aca aca tca<br>Asp Ser Arg Lys Asn Thr Ile Asn Glu Ile Ile Lys Arg Thr Thr Ser<br>                195                        200                      205 | 624 |
| gga gga gaa tgg ccc cag ata cta gtt ttc cca gaa ggt act tgt act<br>Gly Gly Glu Trp Pro Gln Ile Leu Val Phe Pro Glu Gly Thr Cys Thr<br>210                      215                        220 | 672 |
| aat cgt tcc tgt ttg att act ttt aaa cca gga gcc ttc att cca gga<br>Asn Arg Ser Cys Leu Ile Thr Phe Lys Pro Gly Ala Phe Ile Pro Gly<br>225                      230                        235                      240 | 720 |
| gtt cca gtg cag cca gtc ctc ctc aga tac cca aac aag ctg gat act<br>Val Pro Val Gln Pro Val Leu Leu Arg Tyr Pro Asn Lys Leu Asp Thr<br>                        245                        250                      255 | 768 |
| gtg acc tgg aca tgg caa gga tat aca ttc att cag ctt tgt atg ctt<br>Val Thr Trp Thr Trp Gln Gly Tyr Thr Phe Ile Gln Leu Cys Met Leu<br>                  260                        265                      270 | 816 |
| act ttc tgc cag ctc ttc aca aag gta gaa gtt gag ttt atg cca gtt<br>Thr Phe Cys Gln Leu Phe Thr Lys Val Glu Val Glu Phe Met Pro Val<br>              275                        280                      285 | 864 |
| caa gta cca aat gat gaa gaa aaa aat gat cct gtc ctt ttt gcc aat<br>Gln Val Pro Asn Asp Glu Glu Lys Asn Asp Pro Val Leu Phe Ala Asn<br>290                      295                        300 | 912 |
| aaa gtc cgg aat tta atg gca gaa gct ctg gga ata cca gta aca gat<br>Lys Val Arg Asn Leu Met Ala Glu Ala Leu Gly Ile Pro Val Thr Asp<br>305                      310                        315                      320 | 960 |
| cat acc tat gaa gac tgc aga ttg atg att tca gca gga cag cta aca<br>His Thr Tyr Glu Asp Cys Arg Leu Met Ile Ser Ala Gly Gln Leu Thr<br>                        325                        330                      335 | 1008 |
| ttg cct atg gaa gct ggg ctg gtg gaa ttt act aaa att agc cga aaa<br>Leu Pro Met Glu Ala Gly Leu Val Glu Phe Thr Lys Ile Ser Arg Lys<br>                  340                        345                      350 | 1056 |
| ttg aaa tta gat tgg gat ggt gtt cgt aag cat ttg gat gaa tat gca<br>Leu Lys Leu Asp Trp Asp Gly Val Arg Lys His Leu Asp Glu Tyr Ala<br>              355                        360                      365 | 1104 |
| tct att gcg agt tcc tca aaa gga gga aga att gga att gaa gaa ttc<br>Ser Ile Ala Ser Ser Ser Lys Gly Gly Arg Ile Gly Ile Glu Glu Phe<br>370                      375                        380 | 1152 |
| gcc aag tat tta aag ttg cct gtt tca gat gtc ttg aga caa ctt ttt<br>Ala Lys Tyr Leu Lys Leu Pro Val Ser Asp Val Leu Arg Gln Leu Phe<br>385                      390                        395                      400 | 1200 |
| gca ctc ttt gac agg aac cat gat ggc agc att gac ttc cga gag tat<br>Ala Leu Phe Asp Arg Asn His Asp Gly Ser Ile Asp Phe Arg Glu Tyr<br>                        405                        410                      415 | 1248 |
| gtg att ggc ctg gct gtc ttg tgc aac cct tcc aac aca gag gag atc<br>Val Ile Gly Leu Ala Val Leu Cys Asn Pro Ser Asn Thr Glu Glu Ile<br>                  420                        425                      430 | 1296 |
| atc cag gtg gca ttt aag ctg ttt gac gtt gat gag gat ggc tac ata<br>Ile Gln Val Ala Phe Lys Leu Phe Asp Val Asp Glu Asp Gly Tyr Ile<br>              435                        440                      445 | 1344 |
| acg gag gaa gag ttc tcc acc att cta cag gct tcc ctt gga gtg cct<br>Thr Glu Glu Glu Phe Ser Thr Ile Leu Gln Ala Ser Leu Gly Val Pro<br>450                      455                        460 | 1392 |
| gac ctt gat gtt tct ggt ctc ttc aag gaa ata gcc caa ggg gac tca<br>Asp Leu Asp Val Ser Gly Leu Phe Lys Glu Ile Ala Gln Gly Asp Ser | 1440 |

```
                465                 470                 475                 480
att tcc tat gag gaa ttt aaa agt ttt gcc tta aag cat cca gaa tat          1488
Ile Ser Tyr Glu Glu Phe Lys Ser Phe Ala Leu Lys His Pro Glu Tyr
                        485                 490                 495 gct aag ata ttt aca aca tac cta gac ctc cag acg tgc cat gtg ttt          1536
Ala Lys Ile Phe Thr Thr Tyr Leu Asp Leu Gln Thr Cys His Val Phe
                500                 505                 510 tca tta cca aaa gaa gtc cag aca acc ccc tcc acc gcc agt aat aaa          1584
Ser Leu Pro Lys Glu Val Gln Thr Thr Pro Ser Thr Ala Ser Asn Lys
            515                 520                 525 gtc agc cct gaa aag cat gaa gag agt acc tca gac aaa aaa gat gac          1632
Val Ser Pro Glu Lys His Glu Glu Ser Thr Ser Asp Lys Lys Asp Asp
        530                 535                 540
```

<210> SEQ ID NO 9
<211> LENGTH: 195
<212> TYPE: PRT
<213> ORGANISM: Artificial Sequence
<220> FEATURE:
<223> OTHER INFORMATION: Prodom consensus sequence for Acyltransferase

<400> SEQUENCE: 9

```
Leu Glu Asn Leu Pro Lys Lys Gly Pro Ala Ile Val Val Ser Asn His
 1               5                  10                  15

Arg Ser Tyr Leu Asp Ile Leu Val Leu Ser Ala Ala Leu Pro Arg Arg
            20                  25                  30

Gly Pro Trp Leu Val Arg Arg Leu Val Phe Ile Ala Lys Lys Glu Leu
        35                  40                  45

Leu Lys Val Pro Leu Leu Phe Gly Trp Leu Met Arg Leu Ala Gly Ala
    50                  55                  60

Ile Phe Ile Asp Arg Asn Asn Arg Ala Lys Asp Ala Leu Ala Ala Ala
65                  70                  75                  80

Asp Glu Leu Val Arg Val Leu Glu Leu Leu Arg Lys Gly Arg Ser Val
                85                  90                  95

Leu Ile Phe Pro Glu Gly Thr Arg Ser Arg Ser Gly Glu Leu Leu Pro
            100                 105                 110

Pro Phe Lys Lys Gly Ile Ala Ala Phe Arg Leu Ala Leu Lys Ala Gly
        115                 120                 125

Val Pro Ile Val Pro Val Val Ile Val Ser Gly Thr Glu Glu Leu Glu
    130                 135                 140

Pro Lys Asn Glu Ala Gly Lys Leu Leu Arg Leu Ala Arg Lys Lys Gly
145                 150                 155                 160

Pro Val Thr Val Arg Val Leu Pro Pro Ile Pro Leu Asp Pro Glu Asp
                165                 170                 175

Ile Lys Glu Leu Ala Glu Arg Leu Arg Asp Ile Leu Val Gln Ala Leu
            180                 185                 190

Glu Glu Leu
        195
```

<210> SEQ ID NO 10
<211> LENGTH: 2547
<212> TYPE: DNA
<213> ORGANISM: Homo sapiens
<220> FEATURE:
<221> NAME/KEY: CDS
<222> LOCATION: (63)...(2324)

<400> SEQUENCE: 10 gcttttgtg ggccgggtgg gtttcctaat ctggtttcgt ctgcttggtt catctgtgtg     60

-continued

| | |
|---|---|
| cg atg gct ccg gac tcg gat ccc ttc cct gaa ggg ccg ctc tta aag<br>   Met Ala Pro Asp Ser Asp Pro Phe Pro Glu Gly Pro Leu Leu Lys<br>    1              5                   10                15 | 107 |
| ctg cta ccc tta gac gct aga gac cgg ggc acc cag cgc tgc cgc ctg<br>Leu Leu Pro Leu Asp Ala Arg Asp Arg Gly Thr Gln Arg Cys Arg Leu<br>                    20                   25                30 | 155 |
| ggc ccg gcc gcc ctc cac gcc ctg ggc gcg cgc ttg ggc tcg gca gtg<br>Gly Pro Ala Ala Leu His Ala Leu Gly Ala Arg Leu Gly Ser Ala Val<br>              35                   40                 45 | 203 |
| aag atc tcg cta ccc gac ggc ggc tcc tgc ctc tgc act gcc tgg cct<br>Lys Ile Ser Leu Pro Asp Gly Gly Ser Cys Leu Cys Thr Ala Trp Pro<br>      50                   55                   60 | 251 |
| cgg cgg gac gga gcg gac ggc ttt gtg cag ctg gac ccg ctg tgc gcg<br>Arg Arg Asp Gly Ala Asp Gly Phe Val Gln Leu Asp Pro Leu Cys Ala<br>     65                   70                  75 | 299 |
| agc ccc ggg gcg gcg gtc ggg gcg tcg aga tcc cgg agg agt ctc agc<br>Ser Pro Gly Ala Ala Val Gly Ala Ser Arg Ser Arg Arg Ser Leu Ser<br>80                   85                   90                95 | 347 |
| ctg aat cgc ctc ctc cta gtg ccc tgt ccg ccc ctg cgg cgc gtc gcc<br>Leu Asn Arg Leu Leu Leu Val Pro Cys Pro Pro Leu Arg Arg Val Ala<br>                   100                105             110 | 395 |
| gtg tgg ccg gtg ttg cga gag cgg gca ggc gcg ccc ggt gcc cgg aat<br>Val Trp Pro Val Leu Arg Glu Arg Ala Gly Ala Pro Gly Ala Arg Asn<br>              115                 120             125 | 443 |
| aca gcc gcg gtg ctg gag gcg gca cag gag ctg ctg aga aac cga ccg<br>Thr Ala Ala Val Leu Glu Ala Ala Gln Glu Leu Leu Arg Asn Arg Pro<br>       130                 135               140 | 491 |
| atc tcc ctg ggc cac gtg gtg gtc gct ccg cca ggc gct cct ggc ctg<br>Ile Ser Leu Gly His Val Val Val Ala Pro Pro Gly Ala Pro Gly Leu<br>145                  150                 155 | 539 |
| gtg gct gcc ttg cac atc gtc ggc ggg acg ccc agt ccc gat ccc gct<br>Val Ala Ala Leu His Ile Val Gly Gly Thr Pro Ser Pro Asp Pro Ala<br>160                  165                170             175 | 587 |
| ggg ctg gtc acc cct cgt acc cgc gtc agc ctt ggc ggg gag cct ccg<br>Gly Leu Val Thr Pro Arg Thr Arg Val Ser Leu Gly Gly Glu Pro Pro<br>              180                 185             190 | 635 |
| tcg gaa gcc cag ccg cag ccc gag gtg ccc ctg gga ggt ctt tcg gag<br>Ser Glu Ala Gln Pro Gln Pro Glu Val Pro Leu Gly Gly Leu Ser Glu<br>            195                200                205 | 683 |
| gcg gcc gac tcg ctg cgg gag ctc ctc cgc ctc ccg ctc cgc tac ccg<br>Ala Ala Asp Ser Leu Arg Glu Leu Leu Arg Leu Pro Leu Arg Tyr Pro<br>       210                 215               220 | 731 |
| cgc gcc ctg acc gcg ctg ggc tta gcg gtg cct cgc ggg gtg ctc ctg<br>Arg Ala Leu Thr Ala Leu Gly Leu Ala Val Pro Arg Gly Val Leu Leu<br>225                  230                 235 | 779 |
| gcg ggg ccc ccc gga gtg ggc aag acc cag ctg gtg cag gcc gtg gcg<br>Ala Gly Pro Pro Gly Val Gly Lys Thr Gln Leu Val Gln Ala Val Ala<br>240                  245                250             255 | 827 |
| cgc gag gcg ggc gcg gag ctg ctg gca gtc agc gcc ccg gcg ctg cag<br>Arg Glu Ala Gly Ala Glu Leu Leu Ala Val Ser Ala Pro Ala Leu Gln<br>              260                 265             270 | 875 |
| ggt tcc cgg cct ggg gag acc gag gag aac gtg cgg cgg gtc ttc cag<br>Gly Ser Arg Pro Gly Glu Thr Glu Glu Asn Val Arg Arg Val Phe Gln<br>       275                 280               285 | 923 |
| cgc gcc cgg gaa ctg gcc agc cgc gga ccc agc ctc ctc ttc ctg gac<br>Arg Ala Arg Glu Leu Ala Ser Arg Gly Pro Ser Leu Leu Phe Leu Asp<br>290                  295                300 | 971 |
| gag atg gac gcc ttg tgt ccc cag cgg ggc agt cga gca ccc gag agc<br>Glu Met Asp Ala Leu Cys Pro Gln Arg Gly Ser Arg Ala Pro Glu Ser | 1019 |

```
                305                 310                 315
cgc gta gtg gcc cag gtg ttg acg ctg ctg gac ggc gcc agt ggg gac    1067
Arg Val Val Ala Gln Val Leu Thr Leu Leu Asp Gly Ala Ser Gly Asp
320                 325                 330                 335 cgc gag gtc gtg gtt gtg gga gcc act aac cgg ccg gac gct cta gac    1115
Arg Glu Val Val Val Val Gly Ala Thr Asn Arg Pro Asp Ala Leu Asp
                340                 345                 350 cca gcg ctg cgt aga ccc ggg aga ttt gac cga gag gtg gtc att ggg    1163
Pro Ala Leu Arg Arg Pro Gly Arg Phe Asp Arg Glu Val Val Ile Gly
            355                 360                 365 act ccc aca ctt aaa caa aga aag gaa att ctg caa gtg att acc tcg    1211
Thr Pro Thr Leu Lys Gln Arg Lys Glu Ile Leu Gln Val Ile Thr Ser
        370                 375                 380 aag atg ccc atc tcc agt cat gtt gat ttg ggc ctt ctt gca gaa atg    1259
Lys Met Pro Ile Ser Ser His Val Asp Leu Gly Leu Leu Ala Glu Met
    385                 390                 395 aca gtt ggc tat gtt ggt gcc gac ctg aca gca ctc tgt agg gag gct    1307
Thr Val Gly Tyr Val Gly Ala Asp Leu Thr Ala Leu Cys Arg Glu Ala
400                 405                 410                 415 gcc atg cat gcc ctc ctt cat agt gag aag aac cag gac aat cct gtg    1355
Ala Met His Ala Leu Leu His Ser Glu Lys Asn Gln Asp Asn Pro Val
                420                 425                 430 att gat gaa ata gac ttc ctt gaa gct ttt aaa aat att cag ccc tca    1403
Ile Asp Glu Ile Asp Phe Leu Glu Ala Phe Lys Asn Ile Gln Pro Ser
            435                 440                 445 tcg ttt cga agc gtc att gga tta atg gat atc aag cct gtt gac tgg    1451
Ser Phe Arg Ser Val Ile Gly Leu Met Asp Ile Lys Pro Val Asp Trp
        450                 455                 460 gag gag att ggt ggc ctt gaa gat gta aaa ctg aag tta aaa cag agc    1499
Glu Glu Ile Gly Gly Leu Glu Asp Val Lys Leu Lys Leu Lys Gln Ser
    465                 470                 475 att gag tgg cct ctg aaa ttc cct tgg gaa ttt gtt aga atg ggc ctg    1547
Ile Glu Trp Pro Leu Lys Phe Pro Trp Glu Phe Val Arg Met Gly Leu
480                 485                 490                 495 aca caa cca aag gga gtt ctc ctc tat ggg ccc cct gga tgt gct aaa    1595
Thr Gln Pro Lys Gly Val Leu Leu Tyr Gly Pro Pro Gly Cys Ala Lys
                500                 505                 510 acc act ctg gtg agg gcc ctg gcc aca agc tgt cac tgc tct ttc gtt    1643
Thr Thr Leu Val Arg Ala Leu Ala Thr Ser Cys His Cys Ser Phe Val
            515                 520                 525 tca gtg agt gga gct gat ctg ttt tca ccg ttt gtt gga gat tca gaa    1691
Ser Val Ser Gly Ala Asp Leu Phe Ser Pro Phe Val Gly Asp Ser Glu
        530                 535                 540 aaa gtg ttg tct cag ata ttt cga caa gca aga gca agc act cca gca    1739
Lys Val Leu Ser Gln Ile Phe Arg Gln Ala Arg Ala Ser Thr Pro Ala
    545                 550                 555 att ttg ttt ttg gat gaa att gat tca atc ttg gga gct cgc tca gcc    1787
Ile Leu Phe Leu Asp Glu Ile Asp Ser Ile Leu Gly Ala Arg Ser Ala
560                 565                 570                 575 agc aag aca gga tgt gat gtt caa gaa cga gtt ctt tct gtt ctc ctg    1835
Ser Lys Thr Gly Cys Asp Val Gln Glu Arg Val Leu Ser Val Leu Leu
                580                 585                 590 aat gaa tta gat ggt gtt gga ctt aag aca ata gag aga aga gga agt    1883
Asn Glu Leu Asp Gly Val Gly Leu Lys Thr Ile Glu Arg Arg Gly Ser
            595                 600                 605 aaa tca agt caa cag gag ttt caa gaa gtt ttt aac cga agt gtc atg    1931
Lys Ser Ser Gln Gln Glu Phe Gln Glu Val Phe Asn Arg Ser Val Met
        610                 615                 620 att att gca gca aca aat aga cct gat gtg tta gat act gct ttg tta    1979
```

```
                                                 -continued

Ile Ile Ala Ala Thr Asn Arg Pro Asp Val Leu Asp Thr Ala Leu Leu
    625                 630                 635 cga cct gga aga tta gat aag atc atc tat atc cca cct cca gat cac      2027
Arg Pro Gly Arg Leu Asp Lys Ile Ile Tyr Ile Pro Pro Pro Asp His
640                 645                 650                 655 aag ggc agg ctt tct att tta aaa gtc tgt aca aaa acc atg cca ata      2075
Lys Gly Arg Leu Ser Ile Leu Lys Val Cys Thr Lys Thr Met Pro Ile
                    660                 665                 670 ggg cct gat gtc tcc tta gaa aac ctc gca gca gaa acc tgt ttt ttt      2123
Gly Pro Asp Val Ser Leu Glu Asn Leu Ala Ala Glu Thr Cys Phe Phe
                675                 680                 685 tct gga gct gat ctt aga aac ctc tgc aca gaa gct gct ttg ctg gct      2171
Ser Gly Ala Asp Leu Arg Asn Leu Cys Thr Glu Ala Ala Leu Leu Ala
            690                 695                 700 ctg caa gaa aat gga cta gac gca act aca gtg aaa caa gag cac ttt      2219
Leu Gln Glu Asn Gly Leu Asp Ala Thr Thr Val Lys Gln Glu His Phe
    705                 710                 715 cta aaa tca ctt aag act gta aaa ccg tcg tta agt tgc aag gac ttg      2267
Leu Lys Ser Leu Lys Thr Val Lys Pro Ser Leu Ser Cys Lys Asp Leu
720                 725                 730                 735 gct tta tat gaa aac tta ttt aag aaa gaa gga ttt tct aac gtg gaa      2315
Ala Leu Tyr Glu Asn Leu Phe Lys Lys Glu Gly Phe Ser Asn Val Glu
                    740                 745                 750 ggt att taa aaatcacctt aaactcttgt tcagttcaca ttaattgaaa              2364
Gly Ile * tgtgaacttg cctgtcgttt gcaacttcac acttttagaa tttgtgttta tatttcctgt    2424
aagtgaataa ataaaacaaa acaaaacaaa aaaaacttgt gcctgataag ctaaggctca    2484 tttatttta aaaggcatat taaataaaat actgtaattt aggaagaaaa aaaaaaaaaa     2544
aaa                                                                   2547

<210> SEQ ID NO 11
<211> LENGTH: 753
<212> TYPE: PRT
<213> ORGANISM: Homo sapiens

<400> SEQUENCE: 11

Met Ala Pro Asp Ser Asp Pro Phe Pro Glu Gly Pro Leu Leu Lys Leu
1               5                   10                  15

Leu Pro Leu Asp Ala Arg Asp Arg Gly Thr Gln Arg Cys Arg Leu Gly
            20                  25                  30

Pro Ala Ala Leu His Ala Leu Gly Ala Arg Leu Gly Ser Ala Val Lys
        35                  40                  45

Ile Ser Leu Pro Asp Gly Gly Ser Cys Leu Cys Thr Ala Trp Pro Arg
    50                  55                  60

Arg Asp Gly Ala Asp Gly Phe Val Gln Leu Asp Pro Leu Cys Ala Ser
65                  70                  75                  80

Pro Gly Ala Ala Val Gly Ala Ser Arg Ser Arg Ser Leu Ser Leu
                85                  90                  95

Asn Arg Leu Leu Leu Val Pro Cys Pro Pro Leu Arg Arg Val Ala Val
                100                 105                 110

Trp Pro Val Leu Arg Glu Arg Ala Gly Ala Pro Gly Ala Arg Asn Thr
            115                 120                 125

Ala Ala Val Leu Glu Ala Ala Gln Glu Leu Leu Arg Asn Arg Pro Ile
        130                 135                 140

Ser Leu Gly His Val Val Val Ala Pro Pro Gly Ala Pro Gly Leu Val
145                 150                 155                 160
```

-continued

```
Ala Ala Leu His Ile Val Gly Gly Thr Pro Ser Pro Asp Pro Ala Gly
            165                 170                 175
Leu Val Thr Pro Arg Thr Arg Val Ser Leu Gly Gly Glu Pro Pro Ser
        180                 185                 190
Glu Ala Gln Pro Gln Pro Glu Val Pro Leu Gly Gly Leu Ser Glu Ala
    195                 200                 205
Ala Asp Ser Leu Arg Glu Leu Leu Arg Leu Pro Leu Arg Tyr Pro Arg
210                 215                 220
Ala Leu Thr Ala Leu Gly Leu Ala Val Pro Arg Gly Val Leu Leu Ala
225                 230                 235                 240
Gly Pro Pro Gly Val Gly Lys Thr Gln Leu Val Gln Ala Val Ala Arg
                245                 250                 255
Glu Ala Gly Ala Glu Leu Leu Ala Val Ser Ala Pro Ala Leu Gln Gly
            260                 265                 270
Ser Arg Pro Gly Glu Thr Glu Asn Val Arg Arg Val Phe Gln Arg
        275                 280                 285
Ala Arg Glu Leu Ala Ser Arg Gly Pro Ser Leu Leu Phe Leu Asp Glu
    290                 295                 300
Met Asp Ala Leu Cys Pro Gln Arg Gly Ser Arg Ala Pro Glu Ser Arg
305                 310                 315                 320
Val Val Ala Gln Val Leu Thr Leu Leu Asp Gly Ala Ser Gly Asp Arg
                325                 330                 335
Glu Val Val Val Val Gly Ala Thr Asn Arg Pro Asp Ala Leu Asp Pro
            340                 345                 350
Ala Leu Arg Arg Pro Gly Arg Phe Asp Arg Glu Val Val Ile Gly Thr
        355                 360                 365
Pro Thr Leu Lys Gln Arg Lys Glu Ile Leu Gln Val Ile Thr Ser Lys
    370                 375                 380
Met Pro Ile Ser Ser His Val Asp Leu Gly Leu Leu Ala Glu Met Thr
385                 390                 395                 400
Val Gly Tyr Val Gly Ala Asp Leu Thr Ala Leu Cys Arg Glu Ala Ala
                405                 410                 415
Met His Ala Leu Leu His Ser Glu Lys Asn Gln Asp Asn Pro Val Ile
            420                 425                 430
Asp Glu Ile Asp Phe Leu Glu Ala Phe Lys Asn Ile Gln Pro Ser Ser
        435                 440                 445
Phe Arg Ser Val Ile Gly Leu Met Asp Ile Lys Pro Val Asp Trp Glu
    450                 455                 460
Glu Ile Gly Gly Leu Glu Asp Val Lys Leu Lys Leu Lys Gln Ser Ile
465                 470                 475                 480
Glu Trp Pro Leu Lys Phe Pro Trp Glu Phe Val Arg Met Gly Leu Thr
                485                 490                 495
Gln Pro Lys Gly Val Leu Leu Tyr Gly Pro Pro Gly Cys Ala Lys Thr
            500                 505                 510
Thr Leu Val Arg Ala Leu Ala Thr Ser Cys His Cys Ser Phe Val Ser
        515                 520                 525
Val Ser Gly Ala Asp Leu Phe Ser Pro Phe Val Gly Asp Ser Glu Lys
    530                 535                 540
Val Leu Ser Gln Ile Phe Arg Gln Ala Arg Ala Ser Thr Pro Ala Ile
545                 550                 555                 560
Leu Phe Leu Asp Glu Ile Asp Ser Ile Leu Gly Ala Arg Ser Ala Ser
                565                 570                 575
```

-continued

```
Lys Thr Gly Cys Asp Val Gln Glu Arg Val Leu Ser Val Leu Leu Asn
            580                 585                 590
Glu Leu Asp Gly Val Gly Leu Lys Thr Ile Glu Arg Gly Ser Lys
        595                 600                 605
Ser Ser Gln Gln Glu Phe Gln Glu Val Phe Asn Arg Ser Val Met Ile
    610                 615                 620
Ile Ala Ala Thr Asn Arg Pro Asp Val Leu Asp Thr Ala Leu Leu Arg
625                 630                 635                 640
Pro Gly Arg Leu Asp Lys Ile Ile Tyr Ile Pro Pro Asp His Lys
            645                 650                 655
Gly Arg Leu Ser Ile Leu Lys Val Cys Thr Lys Thr Met Pro Ile Gly
            660                 665                 670
Pro Asp Val Ser Leu Glu Asn Leu Ala Ala Glu Thr Cys Phe Phe Ser
            675                 680                 685
Gly Ala Asp Leu Arg Asn Leu Cys Thr Glu Ala Ala Leu Leu Ala Leu
        690                 695                 700
Gln Glu Asn Gly Leu Asp Ala Thr Thr Val Lys Gln Glu His Phe Leu
705                 710                 715                 720
Lys Ser Leu Lys Thr Val Lys Pro Ser Leu Ser Cys Lys Asp Leu Ala
            725                 730                 735
Leu Tyr Glu Asn Leu Phe Lys Lys Glu Gly Phe Ser Asn Val Glu Gly
            740                 745                 750
Ile
```

```
<210> SEQ ID NO 12
<211> LENGTH: 2262
<212> TYPE: DNA
<213> ORGANISM: Homo sapiens

<400> SEQUENCE: 12
atggctccgg actcggatcc cttccctgaa gggccgctct taaagctgct acccttagac      60
gctagagacc ggggcaccca gcgctgccgc ctgggcccgg ccgccctcca cgccctgggc     120
gcgcgcttgg gctcggcagt gaagatctcg ctacccgacg gcggctcctg cctctgcact     180
gcctggcctc ggcgggacgg agcggacggc tttgtgcagc tggacccgct gtgcgcgagc     240
cccgggggcgg cggtcgggggc gtcgagatcc ggaggagtc tcagcctgaa tcgcctcctc     300
ctagtgccct gtccgcccct gcggcgcgtc gccgtgtggc cggtgttgcg agagcgggca     360
ggcgcgcccg tgcccggaa tacagccgcg tgctgagg cggcacagga gctgctgaga      420
aaccgaccga tctccctggg ccacgtggtg gtcgctccgc caggcgctcc tggcctggtg     480
gctgccttgc acatcgtcgg cgggacgccc agtcccgatc ccgctgggct ggtcaccccct     540
cgtacccgcg tcagccttgg cggggagcct ccgtcggaag cccagccgca gcccgaggtg     600
cccctgggag tctttcgga ggcggccgac tcgctgcggg agctcctccg cctcccgctc     660
cgctacccgc gcgccctgac cgcgctgggc ttagcggtgc ctcgcgggggt gctcctggcg     720
gggccccccg gagtgggcaa gacccagctg gtgcaggccg tggcgcgcga ggcgggcgcg     780
gagctgctgg cagtcagcgc cccggcgctg cagggttccc ggcctgggga gaccgaggag     840
aacgtgcggc gggtcttcca gcgcgcccgg gaactggcca gcgcggacc cagcctcctc     900
ttcctggacg agatggacgc cttgtgtccc agcggggca gtcgagcacc cgagagccgc     960
gtagtggccc aggtgttgac gctgctggac ggcgccagtg gggaccgcga ggtcgtggtt    1020
gtgggagcca ctaaccggcc ggacgctcta gacccagcgc tgcgtagacc cgggagattt    1080
```

```
gaccgagagg tggtcattgg gactcccaca cttaaacaaa gaaaggaaat tctgcaagtg    1140
attacctcga agatgcccat ctccagtcat gttgatttgg gccttcttgc agaaatgaca    1200
gttggctatg ttggtgccga cctgacagca ctctgtaggg aggctgccat gcatgccctc    1260
cttcatagtg agaagaacca ggacaatcct gtgattgatg aaatagactt ccttgaagct    1320
tttaaaaata ttcagccctc atcgtttcga agcgtcattg gattaatgga tatcaagcct    1380
gttgactggg aggagattgg tggccttgaa gatgtaaaac tgaagttaaa acagagcatt    1440
gagtggcctc tgaaattccc ttgggaattt gttagaatgg gcctgacaca accaaaggga    1500
gttctcctct atgggccccc tggatgtgct aaaaccactc tggtgagggc cctggccaca    1560
agctgtcact gctctttcgt ttcagtgagt ggagctgatc tgttttcacc gtttgttgga    1620
gattcagaaa agtgttgtc tcagatattt cgacaagcaa gagcaagcac tccagcaatt    1680 ttgttttgg atgaaattga ttcaatcttg ggagctcgct cagccagcaa gacaggatgt    1740
gatgttcaag aacgagttct ttctgttctc ctgaatgaat tagatggtgt tggacttaag    1800
acaatagaga gaagaggaag taaatcaagt caacaggagt ttcaagaagt ttttaaccga    1860
agtgtcatga ttattgcagc aacaaataga cctgatgtgt tagatactgc tttgttacga    1920
cctggaagat tagataagat catctatatc ccacctccag atcacaaggg caggctttct    1980
attttaaaag tctgtacaaa aaccatgcca ataggggctg atgtctcctt agaaaacctc    2040
gcagcagaaa cctgtttttt tctggagct gatcttagaa acctctgcac agaagctgct    2100
ttgctggctc tgcaagaaaa tggactagac gcaactacag tgaaacaaga gcactttcta    2160
aaatcactta agactgtaaa accgtcgtta agttgcaagg acttggcttt atatgaaaac    2220
ttatttaaga agaaggatt ttctaacgtg gaaggtattt aa    2262
```

<210> SEQ ID NO 13
<211> LENGTH: 216
<212> TYPE: PRT
<213> ORGANISM: Artificial Sequence
<220> FEATURE:
<223> OTHER INFORMATION: Consensus for AAA ATPase domain

<400> SEQUENCE: 13

```
Gly Val Leu Leu Tyr Gly Pro Pro Gly Thr Gly Lys Thr Leu Leu Ala
  1               5                  10                  15

Lys Ala Val Ala Lys Glu Leu Gly Val Pro Phe Ile Ser Ile Ser Gly
             20                  25                  30

Ser Glu Leu Val Ser Lys Tyr Val Gly Glu Ser Glu Lys Arg Val Arg
         35                  40                  45

Ala Leu Phe Glu Leu Ala Arg Lys Ser Leu Lys Lys Ala Ala Pro Ser
     50                  55                  60

Pro Ile Ile Phe Ile Asp Glu Ile Asp Ala Leu Ala Pro Lys Arg Gly
 65                  70                  75                  80

Asp Glu Gly Asp Val Ser Glu Arg Val Val Asn Gln Leu Leu Thr Glu
                 85                  90                  95

Met Asp Leu Glu Arg Ile Gly Phe Glu Lys His Tyr Leu Arg Val Ser
            100                 105                 110

Asp Val Val Asp Leu Ser Gly Val Ile Val Ile Ala Ala Thr Asn Arg
        115                 120                 125

Pro Asp Leu Leu Asp Pro Ala Leu Leu Arg Pro Gly Arg Phe Asp Arg
    130                 135                 140

Arg Ile Glu Val Pro Leu Pro Asp Glu Glu Arg Leu Glu Ile Leu
145                 150                 155                 160
```

```
Lys Ile His Leu Lys Lys Met Pro Leu Ala Leu Cys Gln Glu Arg Ser
            165                 170                 175

Glu Leu Ala Lys Asp Val Asp Leu Asp Glu Leu Ala Lys Glu Leu Ala
            180                 185                 190

Arg Arg Thr Pro Gly Phe Ser Gly Ala Asp Leu Ala Ala Leu Cys Arg
            195                 200                 205

Glu Ala Ala Leu Arg Ala Leu Arg
            210                 215

<210> SEQ ID NO 14
<211> LENGTH: 2127
<212> TYPE: DNA
<213> ORGANISM: Homo sapiens
<220> FEATURE:
<221> NAME/KEY: CDS
<222> LOCATION: (94)...(1665)
<220> FEATURE:
<221> NAME/KEY: misc_feature
<222> LOCATION: 1895
<223> OTHER INFORMATION: n = A,T,C or G

<400> SEQUENCE: 14
cgccggggcc gggtagctgc tccaggcgcg cgagctaacc gagtgcggcg agggcctacc      60
aggggcgaca gggtttctct ccgcaagcgc gcg atg cag cgg gcg gcg acg ctg     114
                                     Met Gln Arg Ala Ala Thr Leu
                                       1               5 gtc cgg cgg ggc tgt ggt ccc cgg acc ccc agc tcc tgg ggc cgc agc      162
Val Arg Arg Gly Cys Gly Pro Arg Thr Pro Ser Ser Trp Gly Arg Ser
         10                  15                  20 cag agc agc gcg gcc gcc gag gcc tcg gcg gtg ctc aag gtg cgg ccc      210
Gln Ser Ser Ala Ala Ala Glu Ala Ser Ala Val Leu Lys Val Arg Pro
     25                  30                  35 gag cgc agc cgg cgc gag cgc atc ctc acg ctg gag tcc atg aac ccg      258
Glu Arg Ser Arg Arg Glu Arg Ile Leu Thr Leu Glu Ser Met Asn Pro
 40                  45                  50                  55 cag gtg aag gcg gtg gag tac gcc gtg cgg gga ccc atc gtg ctc aag      306
Gln Val Lys Ala Val Glu Tyr Ala Val Arg Gly Pro Ile Val Leu Lys
                 60                  65                  70 gcc ggc gag atc gag ctc gag ctg cag cgg ggt atc aaa aag cca ttc      354
Ala Gly Glu Ile Glu Leu Glu Leu Gln Arg Gly Ile Lys Lys Pro Phe
             75                  80                  85 aca gag gtc atc cga gcc aac atc ggg gac gcc cag gct atg ggg cag      402
Thr Glu Val Ile Arg Ala Asn Ile Gly Asp Ala Gln Ala Met Gly Gln
         90                  95                 100 cag cca atc acc ttc ctc cgg cag gtg atg gca cta tgc acc tac cca      450
Gln Pro Ile Thr Phe Leu Arg Gln Val Met Ala Leu Cys Thr Tyr Pro
     105                 110                 115 aac ctg ctg gac agc ccc agc ttc cca gaa gat gct aag aaa cgt gcc      498
Asn Leu Leu Asp Ser Pro Ser Phe Pro Glu Asp Ala Lys Lys Arg Ala
120                 125                 130                 135 cgg cgg atc ctg cag gct tgt ggc ggg aac agc ctg ggg tcc tac agt      546
Arg Arg Ile Leu Gln Ala Cys Gly Gly Asn Ser Leu Gly Ser Tyr Ser
                 140                 145                 150 gct agc cag ggt gtc aac tgc atc cgt gaa gat gtg gct gcc tac atc      594
Ala Ser Gln Gly Val Asn Cys Ile Arg Glu Asp Val Ala Ala Tyr Ile
             155                 160                 165 acc agg agg gat ggc ggt gtg cct gcg gac ccc gac aac atc tac ctg      642
Thr Arg Arg Asp Gly Gly Val Pro Ala Asp Pro Asp Asn Ile Tyr Leu
         170                 175                 180 acc acg gga gct agt gac ggc att tct acg atc ctg aag atc ctc gtc      690
```

```
                                                         -continued

Thr Thr Gly Ala Ser Asp Gly Ile Ser Thr Ile Leu Lys Ile Leu Val
    185             190             195 tcc ggg ggc ggc aag tca cgg aca ggt gtg atg atc ccc atc cca caa    738
Ser Gly Gly Gly Lys Ser Arg Thr Gly Val Met Ile Pro Ile Pro Gln
200             205             210             215 tat ccc ctc tat tca gct gtc atc tct gag ctc gac gcc atc cag gtg    786
Tyr Pro Leu Tyr Ser Ala Val Ile Ser Glu Leu Asp Ala Ile Gln Val
                220             225             230 aat tac tac ctg gac gag gag aac tgc tgg gcg ctg aat gtg aat gag    834
Asn Tyr Tyr Leu Asp Glu Glu Asn Cys Trp Ala Leu Asn Val Asn Glu
            235             240             245 ctc cgg cgg gcg gtg cag gag gcc aaa gac cac tgt gat cct aag gtg    882
Leu Arg Arg Ala Val Gln Glu Ala Lys Asp His Cys Asp Pro Lys Val
        250             255             260 ctc tgc ata atc aac cct ggg aac ccc aca ggc cag gta caa agc aga    930
Leu Cys Ile Ile Asn Pro Gly Asn Pro Thr Gly Gln Val Gln Ser Arg
    265             270             275 aag tgc ata gaa gat gtg atc cac ttt gcc tgg gaa gag aag ctc ttt    978
Lys Cys Ile Glu Asp Val Ile His Phe Ala Trp Glu Glu Lys Leu Phe
280             285             290             295 ctc ctg gct gat gag gtg tac cag gac aac gtg tac tct cca gat tgc    1026
Leu Leu Ala Asp Glu Val Tyr Gln Asp Asn Val Tyr Ser Pro Asp Cys
                300             305             310 aga ttc cac tcc ttc aag aag gtg ctg tac gag atg ggg ccc gag tac    1074
Arg Phe His Ser Phe Lys Lys Val Leu Tyr Glu Met Gly Pro Glu Tyr
            315             320             325 tcc agc aac gtg gag ctc gcc tcc ttc cac tcc acc tcc aag ggc tac    1122
Ser Ser Asn Val Glu Leu Ala Ser Phe His Ser Thr Ser Lys Gly Tyr
        330             335             340 atg ggc gag tgt ggt tac aga gga ggc tac atg gag gtg atc aac ctg    1170
Met Gly Glu Cys Gly Tyr Arg Gly Gly Tyr Met Glu Val Ile Asn Leu
    345             350             355 cac cct gag atc aag ggc cag ctg gtg aag ctg ctg tcg gtg cgc ctg    1218
His Pro Glu Ile Lys Gly Gln Leu Val Lys Leu Leu Ser Val Arg Leu
360             365             370             375 tgc ccc cca gtg tct ggg cag gcc gcc atg gac att gtc gtg aac ccc    1266
Cys Pro Pro Val Ser Gly Gln Ala Ala Met Asp Ile Val Val Asn Pro
                380             385             390 ccg gtg gca gga gag gag tcc ttt gag caa ttc agc cga gag aag gag    1314
Pro Val Ala Gly Glu Glu Ser Phe Glu Gln Phe Ser Arg Glu Lys Glu
            395             400             405 tcg gtc ctg ggt aat ctg gcc aaa aaa gca aag ctg acg gaa gac ctg    1362
Ser Val Leu Gly Asn Leu Ala Lys Lys Ala Lys Leu Thr Glu Asp Leu
        410             415             420 ttt aac caa gtc cca gga att cac tgc aac ccc ttg cag ggg gcc atg    1410
Phe Asn Gln Val Pro Gly Ile His Cys Asn Pro Leu Gln Gly Ala Met
    425             430             435 tac gcc ttc cct cgg atc ttc att cct gcc aaa gct gtg gag gct gct    1458
Tyr Ala Phe Pro Arg Ile Phe Ile Pro Ala Lys Ala Val Glu Ala Ala
440             445             450             455 cag gcc cat caa atg gct cca gac atg ttc tac tgc atg aag ctc ctg    1506
Gln Ala His Gln Met Ala Pro Asp Met Phe Tyr Cys Met Lys Leu Leu
                460             465             470 gag gag act ggc atc tgt gtc gtg ccc ggc agt ggc ttt ggg cag agg    1554
Glu Glu Thr Gly Ile Cys Val Val Pro Gly Ser Gly Phe Gly Gln Arg
            475             480             485 gaa ggc act tac cac ttc agg atg act atc ctc cct cca gtg gag aag    1602
Glu Gly Thr Tyr His Phe Arg Met Thr Ile Leu Pro Pro Val Glu Lys
        490             495             500
```

-continued

| | | |
|---|---|---|
| ctg aaa acg gtg ctg cag aag gtg aaa gac ttc cac atc aac ttc ctg<br>Leu Lys Thr Val Leu Gln Lys Val Lys Asp Phe His Ile Asn Phe Leu<br>505                           510                        515 | 1650 |
| gag aag tac gcg tga ggacgcctga gccccagcgg agacctgtc cttggctctt<br>Glu Lys Tyr Ala *<br>520 | 1705 |
| cctcccaatg cccgtcaggc tgaactcgcc tcccccgtga ctytgcctcg ggcctcgcag | 1765 |
| aggccgctgg tcacttygtc atcattttgc ccctggagac gtctttcttt gtgccttgat | 1825 |
| gttgagagcg cctctctttt gagcaaacaa gcattctata tgcaaccaga gtagagggga | 1885 |
| cctgctcagn caggtgtgac cagggttctc tgaatctgtt attgttttg cttctggaaa | 1945 |
| gttcatttgg ggtttacaac aactaggatg tgttgggtga gatgtttcag atctggagaa | 2005 |
| atgagcaggt gtcgggaaat gtgtgactta accgtggtga gggctggaaa tccaaactcc | 2065 |
| cccccatgat ctgtgaaata aagcccttag cggtgaaaaa aaaaaaaaaa aaaaaaaarr | 2125 |
| cg | 2127 |

<210> SEQ ID NO 15
<211> LENGTH: 523
<212> TYPE: PRT
<213> ORGANISM: Homo sapiens

<400> SEQUENCE: 15

Met Gln Arg Ala Ala Thr Leu Val Arg Arg Gly Cys Gly Pro Arg Thr
1               5                      10                 15

Pro Ser Ser Trp Gly Arg Ser Gln Ser Ser Ala Ala Glu Ala Ser
             20                      25                      30

Ala Val Leu Lys Val Arg Pro Glu Arg Ser Arg Arg Glu Arg Ile Leu
           35                      40                  45

Thr Leu Glu Ser Met Asn Pro Gln Val Lys Ala Val Glu Tyr Ala Val
   50                   55                    60

Arg Gly Pro Ile Val Leu Lys Ala Gly Glu Ile Glu Leu Glu Leu Gln
65                     70                 75                  80

Arg Gly Ile Lys Lys Pro Phe Thr Glu Val Ile Arg Ala Asn Ile Gly
               85                      90                  95

Asp Ala Gln Ala Met Gly Gln Gln Pro Ile Thr Phe Leu Arg Gln Val
           100                    105                110

Met Ala Leu Cys Thr Tyr Pro Asn Leu Leu Asp Ser Pro Ser Phe Pro
           115                    120                125

Glu Asp Ala Lys Lys Arg Ala Arg Arg Ile Leu Gln Ala Cys Gly Gly
     130                    135                    140

Asn Ser Leu Gly Ser Tyr Ser Ala Ser Gln Gly Val Asn Cys Ile Arg
145                  150                  155               160

Glu Asp Val Ala Ala Tyr Ile Thr Arg Arg Asp Gly Gly Val Pro Ala
               165                    170                175

Asp Pro Asp Asn Ile Tyr Leu Thr Thr Gly Ala Ser Asp Gly Ile Ser
             180                    185                190

Thr Ile Leu Lys Ile Leu Val Ser Gly Gly Gly Lys Ser Arg Thr Gly
         195                    200                205

Val Met Ile Pro Ile Pro Gln Tyr Pro Leu Tyr Ser Ala Val Ile Ser
     210                    215                    220

Glu Leu Asp Ala Ile Gln Val Asn Tyr Tyr Leu Asp Glu Glu Asn Cys
225                  230                  235               240

Trp Ala Leu Asn Val Asn Glu Leu Arg Arg Ala Val Gln Glu Ala Lys
               245                    250                255

```
Asp His Cys Asp Pro Lys Val Leu Cys Ile Ile Asn Pro Gly Asn Pro
            260                 265                 270

Thr Gly Gln Val Gln Ser Arg Lys Cys Ile Glu Asp Val Ile His Phe
        275                 280                 285

Ala Trp Glu Glu Lys Leu Phe Leu Ala Asp Glu Val Tyr Gln Asp
    290                 295                 300

Asn Val Tyr Ser Pro Asp Cys Arg Phe His Ser Phe Lys Lys Val Leu
305                 310                 315                 320

Tyr Glu Met Gly Pro Glu Tyr Ser Ser Asn Val Glu Leu Ala Ser Phe
                325                 330                 335

His Ser Thr Ser Lys Gly Tyr Met Gly Glu Cys Gly Tyr Arg Gly Gly
            340                 345                 350

Tyr Met Glu Val Ile Asn Leu His Pro Glu Ile Lys Gly Gln Leu Val
        355                 360                 365

Lys Leu Leu Ser Val Arg Leu Cys Pro Pro Val Ser Gly Gln Ala Ala
370                 375                 380

Met Asp Ile Val Val Asn Pro Pro Val Ala Gly Glu Glu Ser Phe Glu
385                 390                 395                 400

Gln Phe Ser Arg Glu Lys Glu Ser Val Leu Gly Asn Leu Ala Lys Lys
                405                 410                 415

Ala Lys Leu Thr Glu Asp Leu Phe Asn Gln Val Pro Gly Ile His Cys
            420                 425                 430

Asn Pro Leu Gln Gly Ala Met Tyr Ala Phe Pro Arg Ile Phe Ile Pro
        435                 440                 445

Ala Lys Ala Val Glu Ala Ala Gln Ala His Gln Met Ala Pro Asp Met
    450                 455                 460

Phe Tyr Cys Met Lys Leu Leu Glu Glu Thr Gly Ile Cys Val Val Pro
465                 470                 475                 480

Gly Ser Gly Phe Gly Gln Arg Glu Gly Thr Tyr His Phe Arg Met Thr
                485                 490                 495

Ile Leu Pro Pro Val Glu Lys Leu Lys Thr Val Leu Gln Lys Val Lys
            500                 505                 510

Asp Phe His Ile Asn Phe Leu Glu Lys Tyr Ala
        515                 520

<210> SEQ ID NO 16
<211> LENGTH: 1572
<212> TYPE: DNA
<213> ORGANISM: Homo sapiens
<220> FEATURE:
<221> NAME/KEY: CDS
<222> LOCATION: (1)...(1572)

<400> SEQUENCE: 16 atg cag cgg gcg gcg acg ctg gtc cgg cgg ggc tgt ggt ccc cgg acc    48
Met Gln Arg Ala Ala Thr Leu Val Arg Arg Gly Cys Gly Pro Arg Thr
 1               5                  10                  15 ccc agc tcc tgg ggc cgc agc cag agc agc gcg gcc gcc gag gcc tcg    96
Pro Ser Ser Trp Gly Arg Ser Gln Ser Ser Ala Ala Ala Glu Ala Ser
                 20                  25                  30 gcg gtg ctc aag gtg cgg ccc gag cgc agc cgg cgc gag cgc atc ctc   144
Ala Val Leu Lys Val Arg Pro Glu Arg Ser Arg Arg Glu Arg Ile Leu
             35                  40                  45 acg ctg gag tcc atg aac ccg cag gtg aag gcg gtg gag tac gcc gtg   192
Thr Leu Glu Ser Met Asn Pro Gln Val Lys Ala Val Glu Tyr Ala Val
         50                  55                  60
```

-continued

| | |
|---|---|
| cgg gga ccc atc gtg ctc aag gcc ggc gag atc gag ctc gag ctg cag<br>Arg Gly Pro Ile Val Leu Lys Ala Gly Glu Ile Glu Leu Glu Leu Gln<br>65                        70                      75                      80 | 240 |
| cgg ggt atc aaa aag cca ttc aca gag gtc atc cga gcc aac atc ggg<br>Arg Gly Ile Lys Lys Pro Phe Thr Glu Val Ile Arg Ala Asn Ile Gly<br>                      85                      90                      95 | 288 |
| gac gcc cag gct atg ggg cag cag cca atc acc ttc ctc cgg cag gtg<br>Asp Ala Gln Ala Met Gly Gln Gln Pro Ile Thr Phe Leu Arg Gln Val<br>                  100                    105                    110 | 336 |
| atg gca cta tgc acc tac cca aac ctg ctg gac agc ccc agc ttc cca<br>Met Ala Leu Cys Thr Tyr Pro Asn Leu Leu Asp Ser Pro Ser Phe Pro<br>       115                    120                    125 | 384 |
| gaa gat gct aag aaa cgt gcc cgg cgg atc ctg cag gct tgt ggc ggg<br>Glu Asp Ala Lys Lys Arg Ala Arg Arg Ile Leu Gln Ala Cys Gly Gly<br>130                        135                    140 | 432 |
| aac agc ctg ggg tcc tac agt gct agc cag ggt gtc aac tgc atc cgt<br>Asn Ser Leu Gly Ser Tyr Ser Ala Ser Gln Gly Val Asn Cys Ile Arg<br>145                        150                    155                    160 | 480 |
| gaa gat gtg gct gcc tac atc acc agg agg gat ggc ggt gtg cct gcg<br>Glu Asp Val Ala Ala Tyr Ile Thr Arg Arg Asp Gly Gly Val Pro Ala<br>                  165                    170                    175 | 528 |
| gac ccc gac aac atc tac ctg acc acg gga gct agt gac ggc att tct<br>Asp Pro Asp Asn Ile Tyr Leu Thr Thr Gly Ala Ser Asp Gly Ile Ser<br>                  180                    185                    190 | 576 |
| acg atc ctg aag atc ctc gtc tcc ggg ggc ggc aag tca cgg aca ggt<br>Thr Ile Leu Lys Ile Leu Val Ser Gly Gly Gly Lys Ser Arg Thr Gly<br>       195                    200                    205 | 624 |
| gtg atg atc ccc atc cca caa tat ccc ctc tat tca gct gtc atc tct<br>Val Met Ile Pro Ile Pro Gln Tyr Pro Leu Tyr Ser Ala Val Ile Ser<br>210                        215                    220 | 672 |
| gag ctc gac gcc atc cag gtg aat tac tac ctg gac gag gag aac tgc<br>Glu Leu Asp Ala Ile Gln Val Asn Tyr Tyr Leu Asp Glu Glu Asn Cys<br>225                        230                    235                    240 | 720 |
| tgg gcg ctg aat gtg aat gag ctc cgg cgg gcg gtg cag gag gcc aaa<br>Trp Ala Leu Asn Val Asn Glu Leu Arg Arg Ala Val Gln Glu Ala Lys<br>                  245                    250                    255 | 768 |
| gac cac tgt gat cct aag gtg ctc tgc ata atc aac cct ggg aac ccc<br>Asp His Cys Asp Pro Lys Val Leu Cys Ile Ile Asn Pro Gly Asn Pro<br>                  260                    265                    270 | 816 |
| aca ggc cag gta caa agc aga aag tgc ata gaa gat gtg atc cac ttt<br>Thr Gly Gln Val Gln Ser Arg Lys Cys Ile Glu Asp Val Ile His Phe<br>       275                    280                    285 | 864 |
| gcc tgg gaa gag aag ctc ttt ctc ctg gct gat gag gtg tac cag gac<br>Ala Trp Glu Glu Lys Leu Phe Leu Leu Ala Asp Glu Val Tyr Gln Asp<br>290                        295                    300 | 912 |
| aac gtg tac tct cca gat tgc aga ttc cac tcc ttc aag aag gtg ctg<br>Asn Val Tyr Ser Pro Asp Cys Arg Phe His Ser Phe Lys Lys Val Leu<br>305                        310                    315                    320 | 960 |
| tac gag atg ggg ccc gag tac tcc agc aac gtg gag ctc gcc tcc ttc<br>Tyr Glu Met Gly Pro Glu Tyr Ser Ser Asn Val Glu Leu Ala Ser Phe<br>                  325                    330                    335 | 1008 |
| cac tcc acc tcc aag ggc tac atg ggc gag tgt ggt tac aga gga ggc<br>His Ser Thr Ser Lys Gly Tyr Met Gly Glu Cys Gly Tyr Arg Gly Gly<br>                  340                    345                    350 | 1056 |
| tac atg gag gtg atc aac ctg cac cct gag atc aag ggc cag ctg gtg<br>Tyr Met Glu Val Ile Asn Leu His Pro Glu Ile Lys Gly Gln Leu Val<br>       355                    360                    365 | 1104 |
| aag ctg ctg tcg gtg cgc ctg tgc ccc cca gtg tct ggg cag gcc gcc<br>Lys Leu Leu Ser Val Arg Leu Cys Pro Pro Val Ser Gly Gln Ala Ala<br>370                        375                    380 | 1152 |

```
atg gac att gtc gtg aac ccc ccg gtg gca gga gag gag tcc ttt gag    1200
Met Asp Ile Val Val Asn Pro Pro Val Ala Gly Glu Glu Ser Phe Glu
385                 390                 395                 400 caa ttc agc cga gag aag gag tcg gtc ctg ggt aat ctg gcc aaa aaa    1248
Gln Phe Ser Arg Glu Lys Glu Ser Val Leu Gly Asn Leu Ala Lys Lys
                405                 410                 415 gca aag ctg acg gaa gac ctg ttt aac caa gtc cca gga att cac tgc    1296
Ala Lys Leu Thr Glu Asp Leu Phe Asn Gln Val Pro Gly Ile His Cys
            420                 425                 430 aac ccc ttg cag ggg gcc atg tac gcc ttc cct cgg atc ttc att cct    1344
Asn Pro Leu Gln Gly Ala Met Tyr Ala Phe Pro Arg Ile Phe Ile Pro
        435                 440                 445 gcc aaa gct gtg gag gct gct cag gcc cat caa atg gct cca gac atg    1392
Ala Lys Ala Val Glu Ala Ala Gln Ala His Gln Met Ala Pro Asp Met
    450                 455                 460 ttc tac tgc atg aag ctc ctg gag gag act ggc atc tgt gtc gtg ccc    1440
Phe Tyr Cys Met Lys Leu Leu Glu Glu Thr Gly Ile Cys Val Val Pro
465                 470                 475                 480 ggc agt ggc ttt ggg cag agg gaa ggc act tac cac ttc agg atg act    1488
Gly Ser Gly Phe Gly Gln Arg Glu Gly Thr Tyr His Phe Arg Met Thr
                485                 490                 495 atc ctc cct cca gtg gag aag ctg aaa acg gtg ctg cag aag gtg aaa    1536
Ile Leu Pro Pro Val Glu Lys Leu Lys Thr Val Leu Gln Lys Val Lys
            500                 505                 510 gac ttc cac atc aac ttc ctg gag aag tac gcg tga                    1572
Asp Phe His Ile Asn Phe Leu Glu Lys Tyr Ala *
        515                 520

<210> SEQ ID NO 17
<211> LENGTH: 447
<212> TYPE: PRT
<213> ORGANISM: Artificial Sequence
<220> FEATURE:
<223> OTHER INFORMATION: Pfam Aminotransferase family model

<400> SEQUENCE: 17

Leu Ser Ser Met Ala Ala Asn Val Ser His Gly Pro Gly Asp Pro Ile
1               5                   10                  15

Leu Gly Val Trp Glu Ala Phe Lys Glu Asp Pro Arg Pro Gly Lys Asp
                20                  25                  30

Asn Pro Asn Gly Val Ile Gly Val Gly Ala Tyr Glu Pro Gln Leu Gly
            35                  40                  45

Lys Asp Leu Val Leu Pro Ala Val Lys Lys Ala Glu Lys Arg Leu Ala
    50                  55                  60

Leu Asp Arg Glu Gly Asn Ile Glu Phe Arg Glu Ile Lys Glu Tyr Leu
65                  70                  75                  80

Pro Ile His Gly Leu Pro Glu Phe Arg Glu Ala Ile Ala Lys Leu Leu
                85                  90                  95

Phe Gly Ala Arg Ser Pro Lys Leu Lys Phe Lys Arg Val Arg Val Val
                100                 105                 110

Gln Thr Leu Gly Gly Thr Gly Ala Leu Arg Leu Ala Ala Asp Phe Leu
            115                 120                 125

Ala Asn Pro Gly Asp Gly Ser Arg Gly Arg Glu Val Leu Val Pro Thr
    130                 135                 140

Pro Thr Trp Pro Asn Tyr Lys Arg Asp Ile Phe Trp Ala Ala Gly Val
145                 150                 155                 160

Glu Val Ile Val Pro Tyr His Tyr Tyr Lys Asp Glu Asn Asn Phe Gly
                165                 170                 175
```

-continued

```
Leu Asp Phe Glu Ala Leu Glu Ala Ala Ile Glu Lys Ala Pro Glu Lys
            180                 185                 190

Asn Ile Lys Thr Lys Val Leu Leu His Asn Asn Pro His Asn Pro Thr
        195                 200                 205

Gly Thr Asp Pro Thr Arg Glu Gln Leu Lys Lys Ile Ala Asp Val Val
    210                 215                 220

Lys Glu Lys Asn Ile Leu Leu Ser Asp Ala Tyr Gln Gly Phe
225                 230                 235                 240

Val Phe Gly Ser Leu Asp Glu Asp Ala Ala Ser Val Ala Glu Phe Ala
                245                 250                 255

Glu Glu Val Lys Glu Glu Met Glu Cys Asn Gly Asp Glu Leu Leu Val
            260                 265                 270

Val Gln Ser Phe Ser Lys Asn Phe Gly Leu Tyr Gly Trp Arg Val Gly
        275                 280                 285

Ala Ile Tyr Val Val Asn Pro Arg Ile Gly Asp Ala Val Ile Ser Ala
    290                 295                 300

Ala Ala Lys Met Ser Ser Ala Gly Arg Val Ser Ser Gln Leu Gln Ala
305                 310                 315                 320

Leu Ala Arg Ala Met Tyr Ser Asn Pro Asp Phe Pro Asp His Gly
                325                 330                 335

Ala Glu Ile Val Ala Arg Ile Leu Glu Arg Arg Asp Leu Phe Thr Ser
            340                 345                 350

Trp Leu Glu Glu Val Lys Gly Met Ala Cys Arg Ile Pro Asn Gly Arg
        355                 360                 365

Leu Tyr Leu Trp Met Asp Leu Arg Lys Leu Leu Lys Glu Glu Asp Asp
    370                 375                 380

Trp Ser His Ile Ile Glu Gln Glu Gly Met Phe Ser Phe Thr Trp Leu
385                 390                 395                 400

Leu Asn Glu Glu Gln Val Asn Val Ser Pro Gly Ser Glu Phe His Ile
                405                 410                 415

Tyr Glu Pro Gly Trp Gly Arg Ile Ser Leu Ala Gly Leu Ser Glu Ala
            420                 425                 430

Asn Val Glu Glu Ala Ala Glu Arg Ile Arg Ala Phe Val Lys Arg
        435                 440                 445

<210> SEQ ID NO 18
<211> LENGTH: 2876
<212> TYPE: DNA
<213> ORGANISM: Homo sapiens
<220> FEATURE:
<221> NAME/KEY: CDS
<222> LOCATION: (613)...(1914)

<400> SEQUENCE: 18
gtcaccacgc gtccgcggac gcgcgtccgg cgcccagcgg agtagggget gegcttgggg      60 tttgctgaag ctggctgcct ctcccactcc ccttttgggt gcaaagcgcc gctagcggga     120 agacggggc cgggcgggga caggggcacc tgcgtagctg gactgagagc ctgcgcccag     180
cttacatcga ccccacccgg ccccggcccg accgacgcg accegatccg atccgatccc     240 attccatccg ttcctcgtct cctcccggtc tgacccgttg cccggccgtg gttcgccaca     300
ccaggcatcc aaagctgagg tcgctcctac ggcctggget cgccttcgct ttagagatgt     360
ttggcctctt ccctcccaaa cagcccatct tcaaaacctg gactcttgga ctggcacctg     420
gccacctttc cctctaccaa gactccactt ccgtcttacc cacttcttcc tcagattctt     480
```

```
ggtacccct gggttggaga ctgctcattt tccttccaaa ttaatcccag accccctaaa    540
atattgacaa ccttgacaac cccccaaccg aggagccaga ctttgttttg gactaacttc    600
catagccctg tc atg gag gca gtg tac ctg gta gtg aat ggg ttg ggc ctg    651
              Met Glu Ala Val Tyr Leu Val Val Asn Gly Leu Gly Leu
                1               5                  10 gtg ctg gac gtg ctg acc ttg gtg ttg gac ctc aac ttc ctg ctg gtg    699
Val Leu Asp Val Leu Thr Leu Val Leu Asp Leu Asn Phe Leu Leu Val
 15                  20                  25 tcc tcc ctc ctg gct tcc ctg gcc tgg ctc ctg gcc ttc gtc tac aac    747
Ser Ser Leu Leu Ala Ser Leu Ala Trp Leu Leu Ala Phe Val Tyr Asn
 30                  35                  40                  45 ctg ccg cac acg gta ctg act agt ctt ctg cac ttg ggc cgc gga gtc    795
Leu Pro His Thr Val Leu Thr Ser Leu Leu His Leu Gly Arg Gly Val
                 50                  55                  60 ttg ctt tca ttg ctg gcc ttg atc gaa gcc gtg gtc cgg ttc aca tgt    843
Leu Leu Ser Leu Leu Ala Leu Ile Glu Ala Val Val Arg Phe Thr Cys
             65                  70                  75 ggg ggc ttg cag gcc ttg tgt act ctg ctg tat agc tgc tgc tct ggc    891
Gly Gly Leu Gln Ala Leu Cys Thr Leu Leu Tyr Ser Cys Cys Ser Gly
         80                  85                  90 cta gag agc cta aag ctc ctg ggg cac ctg gcc tct cat ggg gca ctg    939
Leu Glu Ser Leu Lys Leu Leu Gly His Leu Ala Ser His Gly Ala Leu
     95                  100                 105 cgg agc agg gag ata ctg cac cgg ggc gtc ctc aat gtg gtc tcc agt    987
Arg Ser Arg Glu Ile Leu His Arg Gly Val Leu Asn Val Val Ser Ser
110                 115                 120                 125 ggc cat gct ttg ctg cgc cag gcc tgt gac atc tgt gcc att gcc atg   1035
Gly His Ala Leu Leu Arg Gln Ala Cys Asp Ile Cys Ala Ile Ala Met
                 130                 135                 140 agc ctg gtg gct tat gtg atc aac agc ctg gtc aac atc tgc ctc atc   1083
Ser Leu Val Ala Tyr Val Ile Asn Ser Leu Val Asn Ile Cys Leu Ile
             145                 150                 155 ggc act cag aac ctc ttt tcc ctg gtg ctg gcc ctg tgg gat gca gtg   1131
Gly Thr Gln Asn Leu Phe Ser Leu Val Leu Ala Leu Trp Asp Ala Val
         160                 165                 170 acc ggg cct ctg tgg agg atg aca gac gta gtg gct gcc ttc cta gcc   1179
Thr Gly Pro Leu Trp Arg Met Thr Asp Val Val Ala Ala Phe Leu Ala
     175                 180                 185 cac att tcc agc agt gct gtg gcc atg gcc atc ctc ctt tgg aca ccc   1227
His Ile Ser Ser Ser Ala Val Ala Met Ala Ile Leu Leu Trp Thr Pro
190                 195                 200                 205 tgc caa cta gcc ctg gag ctg ctg gcc tca gct gcc cgc ctc ctg gcc   1275
Cys Gln Leu Ala Leu Glu Leu Leu Ala Ser Ala Ala Arg Leu Leu Ala
                 210                 215                 220 agc ttt gtg ctt gtc aat ctc act ggc ttg gtg ttg cta gct tgt gtg   1323
Ser Phe Val Leu Val Asn Leu Thr Gly Leu Val Leu Leu Ala Cys Val
             225                 230                 235 ctg gca gtg acg gtg act gtg ttg cat ccg gac ttc acc ctg agg ctg   1371
Leu Ala Val Thr Val Thr Val Leu His Pro Asp Phe Thr Leu Arg Leu
         240                 245                 250 gct acc cag gca ctc agc cag ctc cat gcc cgg cca tcc tac cac cgt   1419
Ala Thr Gln Ala Leu Ser Gln Leu His Ala Arg Pro Ser Tyr His Arg
     255                 260                 265 ctt cga gag gat gtc atg cgg ctc tct cgc cta gca ctg ggc tca gag   1467
Leu Arg Glu Asp Val Met Arg Leu Ser Arg Leu Ala Leu Gly Ser Glu
270                 275                 280                 285 gcc tgg cgc cga gtc tgg agc cgc agt ctg cag ctg gcg agt tgg cca   1515
Ala Trp Arg Arg Val Trp Ser Arg Ser Leu Gln Leu Ala Ser Trp Pro
                 290                 295                 300
```

```
aac cgg gga ggg gca cct gga gct ccc cag ggt gac cct atg agg gta    1563
Asn Arg Gly Gly Ala Pro Gly Ala Pro Gln Gly Asp Pro Met Arg Val
            305                 310                 315 ttc tca gtt agg acc cgg aga cag gac act ctt cct gaa gcg ggg cgc    1611
Phe Ser Val Arg Thr Arg Arg Gln Asp Thr Leu Pro Glu Ala Gly Arg
        320                 325                 330 aga tca gag gca gaa gag gag gag gcc agg acc atc aga gtg aca cct    1659
Arg Ser Glu Ala Glu Glu Glu Glu Ala Arg Thr Ile Arg Val Thr Pro
    335                 340                 345 gtc agg ggc cga gag agg ctc aat gag gag gag cct cca ggt ggg caa    1707
Val Arg Gly Arg Glu Arg Leu Asn Glu Glu Glu Pro Pro Gly Gly Gln
350                 355                 360                 365 gac cct tgg aaa ttg ctg aag gag caa gag gag cgg aag aag tgt gtc    1755
Asp Pro Trp Lys Leu Leu Lys Glu Gln Glu Glu Arg Lys Lys Cys Val
                370                 375                 380 atc tgc cag gac cag agc aag aca gtg ttg ctc ctg ccc tgc cgg cat    1803
Ile Cys Gln Asp Gln Ser Lys Thr Val Leu Leu Leu Pro Cys Arg His
            385                 390                 395 ctg tgc ctg tgc cag gcc tgc act gaa atc ctg atg cgc cac ccc gtc    1851
Leu Cys Leu Cys Gln Ala Cys Thr Glu Ile Leu Met Arg His Pro Val
        400                 405                 410 tac cac cgc aat tgc ccg ctc tgc cgc cgg ggc atc ctg cag acc ctc    1899
Tyr His Arg Asn Cys Pro Leu Cys Arg Arg Gly Ile Leu Gln Thr Leu
    415                 420                 425 aat gtc tac ctc tga agcctccttc cctgcctgcc caccoctcca tgctccacgc    1954
Asn Val Tyr Leu *
430 aggcactcac gctaggacag cattaacacc tcatctccgg gtcctggtct gaatcccctc   2014 ctaccoctgt ggccatcctg ccatacatcc aggacattga gttggaagac tatgatctgg   2074 gtgggggcag gataacatgg cttctctta cccagtgggt cccttcgatg ctgagggtgg    2134 tgagtatgtc actatgcaag ggccctgaga ctatttgctg tgggctctcc tccagcctgc   2194 ccagggccca cccagatgcc tctggggtta cccctgtctg cttctggttt ttctgttgga   2254 gatctatagg tcctttttcct gcctccttca catttcctcc ccagcttttg cggccacaac   2314 acatcagtgt catttgggtg ttttggcaac tcaggggcct tcggatgatc ttaaaccttt   2374 gtgttcagcc agagcccctg tgccctggta ggcgttgggg ttagtatctc tcgggtgccc   2434 tcagagccac ctctgcctgt gatcgtctga tgaggctccc tcccaacctg atccaaaagc   2494 cagtctcagg agtttacccc tgggatgggg gatgcatctg cacctgactt tggggccacg   2554 tgccctgtgg caccccagct cactgggagt ctcaggaggg ataaccggat ttctgctctt   2614 tccoctgtca ctcccacatc acacagaaaa atggcattcc tctctgtctc tccctggcat   2674 ggagagggca gactgtgcac atttcactag gtccaaata cagaagggcc cagggcccag    2734 gggcttgcag cttcgtgagg ggtctctggc ccagtttcca atgaataaag ttctcttgac   2794 agctcaaaaa aaaaaaaaaa aaaaaaaaaa aaaaaaggc cgcaagctta tcaatttcga    2854 cctatactgg gtcgtattac aa                                           2876

<210> SEQ ID NO 19
<211> LENGTH: 433
<212> TYPE: PRT
<213> ORGANISM: Homo sapiens

<400> SEQUENCE: 19

Met Glu Ala Val Tyr Leu Val Val Asn Gly Leu Gly Leu Val Leu Asp
1               5                   10                  15
```

-continued

```
Val Leu Thr Leu Val Leu Asp Leu Asn Phe Leu Leu Val Ser Ser Leu
             20                  25                  30

Leu Ala Ser Leu Ala Trp Leu Leu Ala Phe Val Tyr Asn Leu Pro His
         35                  40                  45

Thr Val Leu Thr Ser Leu Leu His Leu Gly Arg Gly Val Leu Leu Ser
     50                  55                  60

Leu Leu Ala Leu Ile Glu Ala Val Val Arg Phe Thr Cys Gly Gly Leu
 65                  70                  75                  80

Gln Ala Leu Cys Thr Leu Leu Tyr Ser Cys Cys Ser Gly Leu Glu Ser
                 85                  90                  95

Leu Lys Leu Leu Gly His Leu Ala Ser His Gly Ala Leu Arg Ser Arg
             100                 105                 110

Glu Ile Leu His Arg Gly Val Leu Asn Val Val Ser Ser Gly His Ala
         115                 120                 125

Leu Leu Arg Gln Ala Cys Asp Ile Cys Ala Ile Ala Met Ser Leu Val
     130                 135                 140

Ala Tyr Val Ile Asn Ser Leu Val Asn Ile Cys Leu Ile Gly Thr Gln
145                 150                 155                 160

Asn Leu Phe Ser Leu Val Leu Ala Leu Trp Asp Ala Val Thr Gly Pro
                 165                 170                 175

Leu Trp Arg Met Thr Asp Val Val Ala Ala Phe Leu Ala His Ile Ser
             180                 185                 190

Ser Ser Ala Val Ala Met Ala Ile Leu Leu Trp Thr Pro Cys Gln Leu
         195                 200                 205

Ala Leu Glu Leu Leu Ala Ser Ala Ala Arg Leu Leu Ala Ser Phe Val
     210                 215                 220

Leu Val Asn Leu Thr Gly Leu Val Leu Leu Ala Cys Val Leu Ala Val
225                 230                 235                 240

Thr Val Thr Val Leu His Pro Asp Phe Thr Leu Arg Leu Ala Thr Gln
                 245                 250                 255

Ala Leu Ser Gln Leu His Ala Arg Pro Ser Tyr His Arg Leu Arg Glu
             260                 265                 270

Asp Val Met Arg Leu Ser Arg Leu Ala Leu Gly Ser Glu Ala Trp Arg
     275                 280                 285

Arg Val Trp Ser Arg Ser Leu Gln Leu Ala Ser Trp Pro Asn Arg Gly
         290                 295                 300

Gly Ala Pro Gly Ala Pro Gln Gly Asp Pro Met Arg Val Phe Ser Val
305                 310                 315                 320

Arg Thr Arg Arg Gln Asp Thr Leu Pro Glu Ala Gly Arg Arg Ser Glu
                 325                 330                 335

Ala Glu Glu Glu Ala Arg Thr Ile Arg Val Thr Pro Val Arg Gly
             340                 345                 350

Arg Glu Arg Leu Asn Glu Glu Pro Pro Gly Gly Gln Asp Pro Trp
     355                 360                 365

Lys Leu Leu Lys Glu Gln Glu Glu Arg Lys Lys Cys Val Ile Cys Gln
     370                 375                 380

Asp Gln Ser Lys Thr Val Leu Leu Pro Cys Arg His Leu Cys Leu
385                 390                 395                 400

Cys Gln Ala Cys Thr Glu Ile Leu Met Arg His Pro Val Tyr His Arg
                 405                 410                 415

Asn Cys Pro Leu Cys Arg Arg Gly Ile Leu Gln Thr Leu Asn Val Tyr
             420                 425                 430
```

Leu

<210> SEQ ID NO 20
<211> LENGTH: 1302
<212> TYPE: DNA
<213> ORGANISM: Homo sapiens
<220> FEATURE:
<221> NAME/KEY: CDS
<222> LOCATION: (1)...(1302)

<400> SEQUENCE: 20

| | | | | | | | | | | | | | | | | |
|---|---|---|---|---|---|---|---|---|---|---|---|---|---|---|---|---|
| atg | gag | gca | gtg | tac | ctg | gta | gtg | aat | ggg | ttg | ggc | ctg | gtg | ctg | gac | 48 |
| Met | Glu | Ala | Val | Tyr | Leu | Val | Val | Asn | Gly | Leu | Gly | Leu | Val | Leu | Asp | |
| 1 | | | | 5 | | | | | 10 | | | | | 15 | | |
| gtg | ctg | acc | ttg | gtg | ttg | gac | ctc | aac | ttc | ctg | ctg | gtg | tcc | tcc | ctc | 96 |
| Val | Leu | Thr | Leu | Val | Leu | Asp | Leu | Asn | Phe | Leu | Leu | Val | Ser | Ser | Leu | |
| | | | 20 | | | | | 25 | | | | | 30 | | | |
| ctg | gct | tcc | ctg | gcc | tgg | ctc | ctg | gcc | ttc | gtc | tac | aac | ctg | ccg | cac | 144 |
| Leu | Ala | Ser | Leu | Ala | Trp | Leu | Leu | Ala | Phe | Val | Tyr | Asn | Leu | Pro | His | |
| | | 35 | | | | | 40 | | | | | 45 | | | | |
| acg | gta | ctg | act | agt | ctt | ctg | cac | ttg | ggc | cgc | gga | gtc | ttg | ctt | tca | 192 |
| Thr | Val | Leu | Thr | Ser | Leu | Leu | His | Leu | Gly | Arg | Gly | Val | Leu | Leu | Ser | |
| | 50 | | | | | 55 | | | | | 60 | | | | | |
| ttg | ctg | gcc | ttg | atc | gaa | gcc | gtg | gtc | cgg | ttc | aca | tgt | ggg | ggc | ttg | 240 |
| Leu | Leu | Ala | Leu | Ile | Glu | Ala | Val | Val | Arg | Phe | Thr | Cys | Gly | Gly | Leu | |
| 65 | | | | | 70 | | | | | 75 | | | | | 80 | |
| cag | gcc | ttg | tgt | act | ctg | ctg | tat | agc | tgc | tgc | tct | ggc | cta | gag | agc | 288 |
| Gln | Ala | Leu | Cys | Thr | Leu | Leu | Tyr | Ser | Cys | Cys | Ser | Gly | Leu | Glu | Ser | |
| | | | | 85 | | | | | 90 | | | | | 95 | | |
| cta | aag | ctc | ctg | ggg | cac | ctg | gcc | tct | cat | ggg | gca | ctg | cgg | agc | agg | 336 |
| Leu | Lys | Leu | Leu | Gly | His | Leu | Ala | Ser | His | Gly | Ala | Leu | Arg | Ser | Arg | |
| | | | 100 | | | | | 105 | | | | | 110 | | | |
| gag | ata | ctg | cac | cgg | ggc | gtc | ctc | aat | gtg | gtc | tcc | agt | ggc | cat | gct | 384 |
| Glu | Ile | Leu | His | Arg | Gly | Val | Leu | Asn | Val | Val | Ser | Ser | Gly | His | Ala | |
| | | 115 | | | | | 120 | | | | | 125 | | | | |
| ttg | ctg | cgc | cag | gcc | tgt | gac | atc | tgt | gcc | att | gcc | atg | agc | ctg | gtg | 432 |
| Leu | Leu | Arg | Gln | Ala | Cys | Asp | Ile | Cys | Ala | Ile | Ala | Met | Ser | Leu | Val | |
| | 130 | | | | | 135 | | | | | 140 | | | | | |
| gct | tat | gtg | atc | aac | agc | ctg | gtc | aac | atc | tgc | ctc | atc | ggc | act | cag | 480 |
| Ala | Tyr | Val | Ile | Asn | Ser | Leu | Val | Asn | Ile | Cys | Leu | Ile | Gly | Thr | Gln | |
| 145 | | | | | 150 | | | | | 155 | | | | | 160 | |
| aac | ctc | ttt | tcc | ctg | gtg | ctg | gcc | ctg | tgg | gat | gca | gtg | acc | ggg | cct | 528 |
| Asn | Leu | Phe | Ser | Leu | Val | Leu | Ala | Leu | Trp | Asp | Ala | Val | Thr | Gly | Pro | |
| | | | | 165 | | | | | 170 | | | | | 175 | | |
| ctg | tgg | agg | atg | aca | gac | gta | gtg | gct | gcc | ttc | cta | gcc | cac | att | tcc | 576 |
| Leu | Trp | Arg | Met | Thr | Asp | Val | Val | Ala | Ala | Phe | Leu | Ala | His | Ile | Ser | |
| | | | 180 | | | | | 185 | | | | | 190 | | | |
| agc | agt | gct | gtg | gcc | atg | gcc | atc | ctc | ctt | tgg | aca | ccc | tgc | caa | cta | 624 |
| Ser | Ser | Ala | Val | Ala | Met | Ala | Ile | Leu | Leu | Trp | Thr | Pro | Cys | Gln | Leu | |
| | | 195 | | | | | 200 | | | | | 205 | | | | |
| gcc | ctg | gag | ctg | ctg | gcc | tca | gct | gcc | cgc | ctc | ctg | gcc | agc | ttt | gtg | 672 |
| Ala | Leu | Glu | Leu | Leu | Ala | Ser | Ala | Ala | Arg | Leu | Leu | Ala | Ser | Phe | Val | |
| | 210 | | | | | 215 | | | | | 220 | | | | | |
| ctt | gtc | aat | ctc | act | ggc | ttg | gtg | ttg | cta | gct | tgt | gtg | ctg | gca | gtg | 720 |
| Leu | Val | Asn | Leu | Thr | Gly | Leu | Val | Leu | Leu | Ala | Cys | Val | Leu | Ala | Val | |
| 225 | | | | | 230 | | | | | 235 | | | | | 240 | |
| acg | gtg | act | gtg | ttg | cat | ccg | gac | ttc | acc | ctg | agg | ctg | gct | acc | cag | 768 |
| Thr | Val | Thr | Val | Leu | His | Pro | Asp | Phe | Thr | Leu | Arg | Leu | Ala | Thr | Gln | |
| | | | | 245 | | | | | 250 | | | | | 255 | | |
| gca | ctc | agc | cag | ctc | cat | gcc | cgg | cca | tcc | tac | cac | cgt | ctt | cga | gag | 816 |
| Ala | Leu | Ser | Gln | Leu | His | Ala | Arg | Pro | Ser | Tyr | His | Arg | Leu | Arg | Glu | |

-continued

```
             260                 265                 270
gat gtc atg cgg ctc tct cgc cta gca ctg ggc tca gag gcc tgg cgc      864
Asp Val Met Arg Leu Ser Arg Leu Ala Leu Gly Ser Glu Ala Trp Arg
            275                 280                 285 cga gtc tgg agc cgc agt ctg cag ctg gcg agt tgg cca aac cgg gga      912
Arg Val Trp Ser Arg Ser Leu Gln Leu Ala Ser Trp Pro Asn Arg Gly
        290                 295                 300 ggg gca cct gga gct ccc cag ggt gac cct atg agg gta ttc tca gtt      960
Gly Ala Pro Gly Ala Pro Gln Gly Asp Pro Met Arg Val Phe Ser Val
305                 310                 315                 320 agg acc cgg aga cag gac act ctt cct gaa gcg ggg cgc aga tca gag     1008
Arg Thr Arg Arg Gln Asp Thr Leu Pro Glu Ala Gly Arg Arg Ser Glu
                325                 330                 335 gca gaa gag gag gag gcc agg acc atc aga gtg aca cct gtc agg ggc     1056
Ala Glu Glu Glu Glu Ala Arg Thr Ile Arg Val Thr Pro Val Arg Gly
            340                 345                 350 cga gag agg ctc aat gag gag gag cct cca ggt ggg caa gac cct tgg     1104
Arg Glu Arg Leu Asn Glu Glu Glu Pro Pro Gly Gly Gln Asp Pro Trp
        355                 360                 365 aaa ttg ctg aag gag caa gag gag cgg aag aag tgt gtc atc tgc cag     1152
Lys Leu Leu Lys Glu Gln Glu Glu Arg Lys Lys Cys Val Ile Cys Gln
    370                 375                 380 gac cag agc aag aca gtg ttg ctc ctg ccc tgc cgg cat ctg tgc ctg     1200
Asp Gln Ser Lys Thr Val Leu Leu Leu Pro Cys Arg His Leu Cys Leu
385                 390                 395                 400 tgc cag gcc tgc act gaa atc ctg atg cgc cac ccc gtc tac cac cgc     1248
Cys Gln Ala Cys Thr Glu Ile Leu Met Arg His Pro Val Tyr His Arg
                405                 410                 415 aat tgc ccg ctc tgc cgc cgg ggc atc ctg cag acc ctc aat gtc tac     1296
Asn Cys Pro Leu Cys Arg Arg Gly Ile Leu Gln Thr Leu Asn Val Tyr
            420                 425                 430 ctc tga                                                             1302
Leu *
```

<210> SEQ ID NO 21
<211> LENGTH: 54
<212> TYPE: PRT
<213> ORGANISM: Artificial Sequence
<220> FEATURE:
<223> OTHER INFORMATION: Pfam consensus sequence

<400> SEQUENCE: 21

```
Cys Pro Ile Cys Leu Thr Thr Phe Asp Leu Asp Glu Pro Lys Pro Phe
1               5                   10                  15

Lys Glu Pro Val Leu Leu Pro Cys Gly His Ser Phe Cys Ser Lys Cys
            20                  25                  30

Ile Val Glu Leu Leu Arg Leu Ser Gln Asn Ser Lys Asn Asn Ser Val
        35                  40                  45

Tyr Lys Cys Pro Leu Cys
    50
```

<210> SEQ ID NO 22
<211> LENGTH: 2810
<212> TYPE: DNA
<213> ORGANISM: Homo sapiens
<220> FEATURE:
<221> NAME/KEY: CDS
<222> LOCATION: (744)...(1955)
<220> FEATURE:
<221> NAME/KEY: misc_feature
<222> LOCATION: 344, 345, 346, 347, 348, 349, 350, 351, 352, 353, 354,
       355, 356, 357, 358, 359, 360, 361, 362, 363, 364, 365, 366, 367, -continued

```
      368, 369, 370, 371, 372, 373, 374, 375, 376, 377, 378, 379,
      380, 381, 382, 383, 384, 385, 386, 387, 388, 389, 390
<223> OTHER INFORMATION: n = A,T,C or G
<220> FEATURE:
<221> NAME/KEY: misc_feature
<222> LOCATION: 391, 392, 393, 394, 395, 396, 397, 398, 399, 400, 401,
      402, 403, 404, 405, 406, 407, 408, 409, 410, 411, 412, 413, 414,
      415, 416, 417, 418, 419, 420, 421, 422, 423, 424, 425, 426,
      427, 428, 429, 430, 431, 432, 433, 434, 435, 436, 437
<223> OTHER INFORMATION: n = A,T,C or G
<220> FEATURE:
<221> NAME/KEY: misc_feature
<222> LOCATION: 438, 439, 440, 441, 442, 443, 444, 445, 446, 447, 448,
      449, 450, 451
<223> OTHER INFORMATION: n = A,T,C or G

<400> SEQUENCE: 22
```

```
cgcctgcgca gggcagcggc ccgcggggcg gaggctttat aatcacttcg tcgttgccgc      60
tcggcttcta tcgccgggag ggcggttgag gcggtggtgg cggcgtcggc ggcggccggc     120
gctggctgag gggcgctgag gcgggagctg tggcgctggg cgcccctggc tcctcggcct     180
ctgccggcca tgggctccga aaggactcc gagtcgccgc gctccacatc gctacatgcg      240
gccgcacccg accctaagtg ccgcagcggg ggccggcgcc ggcgcctcac cttgcacagc     300
gtcttttttg cctcggcccg cggccgccgc gcccgggcca agcnnnnnnn nnnnnnnnn      360 nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn ncgcaggccg agccgccgcc ccggcggcgg     480
cggagcctgg gttcgacgat gaggaggcgg cggaggcgg tggcccgggc gcggaggagg      540
tggagtgtcc gctgtgcctg gtgcggctgc cgcctgagcg ggccccgcgc ctcctcagct     600
gtccgcaccg ctcgtgccgg gactgcctcc gccactacct cgcctggag ataagcgaga      660 gcagggtgcc catcagctgc cccgagtgca gcagcgact caacccgcac gacatccgct      720
tgctgctcgc cgaccgccg ctt atg cac aag tac gag gag ttc atg ctg cgc    773
                          Met His Lys Tyr Glu Glu Phe Met Leu Arg
                            1               5                  10 cgc tac cta gcc tcg gac ccc gac tgc cgc tgg tgc ccg gcc ccg gac       821
Arg Tyr Leu Ala Ser Asp Pro Asp Cys Arg Trp Cys Pro Ala Pro Asp
              15                  20                  25 tgc ggt tat gct gtt att gcc tat ggc tgt gcc agc tgc ccg aag cta       869
Cys Gly Tyr Ala Val Ile Ala Tyr Gly Cys Ala Ser Cys Pro Lys Leu
          30                  35                  40 act tgt gag agg gaa ggt tgc cag act gag ttc tgc tac cac tgc aag       917
Thr Cys Glu Arg Glu Gly Cys Gln Thr Glu Phe Cys Tyr His Cys Lys
      45                  50                  55 cag ata tgg cat cca aat cag aca tgc gat atg gcc gtt caa cag agg       965
Gln Ile Trp His Pro Asn Gln Thr Cys Asp Met Ala Arg Gln Gln Arg
  60                  65                  70 gcc cag act tta cga gtt cgg acc aaa cac act tca ggt ctc agt tat      1013
Ala Gln Thr Leu Arg Val Arg Thr Lys His Thr Ser Gly Leu Ser Tyr
 75                  80                  85                  90 ggg caa gaa tct gga cca gat gac atc aag cca tgc cca cga tgc agt      1061
Gly Gln Glu Ser Gly Pro Asp Asp Ile Lys Pro Cys Pro Arg Cys Ser
                  95                 100                 105 gca tac att atc aag atg aat gat gga agc tgt aat cac atg acc tgt      1109
Ala Tyr Ile Ile Lys Met Asn Asp Gly Ser Cys Asn His Met Thr Cys
             110                 115                 120 gca gtg tgt ggc tgt gaa ttc tgt tgg ctt tgt atg aaa gag atc tca      1157
Ala Val Cys Gly Cys Glu Phe Cys Trp Leu Cys Met Lys Glu Ile Ser
         125                 130                 135 gac ttg cat tac ctc agc ccc tct ggc tgt aca ttc tgg ggc aag aag      1205
```

-continued

```
          Asp Leu His Tyr Leu Ser Pro Ser Gly Cys Thr Phe Trp Gly Lys Lys
          140                 145                 150 cca tgg agc cgt aag aag aaa att ctt tgg cag ctg ggc acg ttg att      1253
Pro Trp Ser Arg Lys Lys Lys Ile Leu Trp Gln Leu Gly Thr Leu Ile
155                 160                 165                 170 ggt gct cca gtg ggg att tct ctc att gat ggc att gcc att cct gcc      1301
Gly Ala Pro Val Gly Ile Ser Leu Ile Asp Gly Ile Ala Ile Pro Ala
                175                 180                 185 atg gtc att ggc att cct gtt tat gtt gga agg aag att cac agc agg      1349
Met Val Ile Gly Ile Pro Val Tyr Val Gly Arg Lys Ile His Ser Arg
            190                 195                 200 tat gag gga agg aaa acc tcc aaa cac aag agg aat ttg gct atc act      1397
Tyr Glu Gly Arg Lys Thr Ser Lys His Lys Arg Asn Leu Ala Ile Thr
        205                 210                 215 gga gga gtg act ttg tcg gtc att gca tcc cca gtt att gct gca gtt      1445
Gly Gly Val Thr Leu Ser Val Ile Ala Ser Pro Val Ile Ala Ala Val
    220                 225                 230 agt gtt ggt att ggt gtc ccc att atg ctg gca tat gtt tat ggg gtt      1493
Ser Val Gly Ile Gly Val Pro Ile Met Leu Ala Tyr Val Tyr Gly Val
235                 240                 245                 250 gtg ccc att tct ctt tgt cgt gga ggt ggc tgt gga gtt agc aca gcc      1541
Val Pro Ile Ser Leu Cys Arg Gly Gly Gly Cys Gly Val Ser Thr Ala
                255                 260                 265 aac gga aaa gga gtg aaa att gaa ttt gat gaa gat gat ggt cca atc      1589
Asn Gly Lys Gly Val Lys Ile Glu Phe Asp Glu Asp Asp Gly Pro Ile
            270                 275                 280 aca gtg gca gat gcc tgg aga gcc ctc aag aat ccc agc att ggg gaa      1637
Thr Val Ala Asp Ala Trp Arg Ala Leu Lys Asn Pro Ser Ile Gly Glu
        285                 290                 295 agc agc att gaa ggc ctg act agt gta ttg agc act agt gga agc cct      1685
Ser Ser Ile Glu Gly Leu Thr Ser Val Leu Ser Thr Ser Gly Ser Pro
    300                 305                 310 aca gat gga ctt agt gtt atg caa ggt cct tac agc gaa acg gcc agc      1733
Thr Asp Gly Leu Ser Val Met Gln Gly Pro Tyr Ser Glu Thr Ala Ser
315                 320                 325                 330 ttt gca gcc ctc tca ggg ggc acg ctg agt ggc ggc att ctc tcc agt      1781
Phe Ala Ala Leu Ser Gly Gly Thr Leu Ser Gly Gly Ile Leu Ser Ser
                335                 340                 345 ggc aag gga aaa tat agc agg tta gaa gtt caa gcc gat gtc caa aag      1829
Gly Lys Gly Lys Tyr Ser Arg Leu Glu Val Gln Ala Asp Val Gln Lys
            350                 355                 360 gaa att ttc ccc aaa gac aca gcc agt ctt ggt gca att agt gac aac      1877
Glu Ile Phe Pro Lys Asp Thr Ala Ser Leu Gly Ala Ile Ser Asp Asn
        365                 370                 375 gca agc act cgt gct atg gcc ggt tcc ata atc agt tcc tac aac cca      1925
Ala Ser Thr Arg Ala Met Ala Gly Ser Ile Ile Ser Ser Tyr Asn Pro
    380                 385                 390 cag gac agg ttt agc atg atc cat gca tga ctcagcaaag tggattttgt        1975
Gln Asp Arg Phe Ser Met Ile His Ala *
395                 400 ctccacagag aatgcaacaa tatggaaatc caagtggaca ttgaagccaa accaagccac    2035
tatcagctgg tgagtggaag cagcacggag gactcgctcc atgttcatgc tcagatggca    2095
gagaatgaag aagaaggtag tggtggcgga ggcagtgaag aggatccccc ctgcagacac    2155
caaagctgtg aacagaaaga ctgcctggcc agcaaacctt gggacatcag cctggcccag    2215
cctgaaagca tccgcagtga cctagagagt tctgatgcac agtcagacga tgtgccagac    2275
atcacctcag atgagtgtgg ctccccccgc tcccatactg cagcctgccc ctcgacccccc   2335
```

-continued

```
agagcccaag gtgcaccgag cccaagtgcc catatgaacc tctctgccct agccgaggga    2395
caaactgtct tgaagccaga aggtggagaa gccagagtat gaagtggaat gaatgctcct    2455
gttctgagaa gcacacttgt aactgcatct tttggaattt ttttttttt ttttccaagg    2515 ggtagagatt tatgtatttt atttcacaga ttctctggtc acaggttttt gcccagggaa    2575
attctgagaa attcacaatt tcttaccaga taaaacatga aaagtttgcc gttagttccc    2635
ctcccctccc ctccctcttt ttagttttaa tttattggtt aaactgatgg cagcaatcca    2695
tgaggtgtgt caaagagtgt acatatgtat gtgtgtatat tgaatgctaa acatattact    2755
gaaagacaca ttttaataaa gatttctgtc ataattcaaa aaaaaaaaaa aaaaa         2810
```

<210> SEQ ID NO 23
<211> LENGTH: 403
<212> TYPE: PRT
<213> ORGANISM: Homo sapiens

<400> SEQUENCE: 23

```
Met His Lys Tyr Glu Glu Phe Met Leu Arg Arg Tyr Leu Ala Ser Asp
  1               5                  10                  15

Pro Asp Cys Arg Trp Cys Pro Ala Pro Asp Cys Gly Tyr Ala Val Ile
             20                  25                  30

Ala Tyr Gly Cys Ala Ser Cys Pro Lys Leu Thr Cys Glu Arg Glu Gly
         35                  40                  45

Cys Gln Thr Glu Phe Cys Tyr His Cys Lys Gln Ile Trp His Pro Asn
     50                  55                  60

Gln Thr Cys Asp Met Ala Arg Gln Gln Arg Ala Gln Thr Leu Arg Val
 65                  70                  75                  80

Arg Thr Lys His Thr Ser Gly Leu Ser Tyr Gly Gln Glu Ser Gly Pro
                 85                  90                  95

Asp Asp Ile Lys Pro Cys Pro Arg Cys Ser Ala Tyr Ile Ile Lys Met
            100                 105                 110

Asn Asp Gly Ser Cys Asn His Met Thr Cys Ala Val Cys Gly Cys Glu
        115                 120                 125

Phe Cys Trp Leu Cys Met Lys Glu Ile Ser Asp Leu His Tyr Leu Ser
    130                 135                 140

Pro Ser Gly Cys Thr Phe Trp Gly Lys Lys Pro Trp Ser Arg Lys Lys
145                 150                 155                 160

Lys Ile Leu Trp Gln Leu Gly Thr Leu Ile Gly Ala Pro Val Gly Ile
                165                 170                 175

Ser Leu Ile Asp Gly Ile Ala Ile Pro Ala Met Val Ile Gly Ile Pro
            180                 185                 190

Val Tyr Val Gly Arg Lys Ile His Ser Arg Tyr Glu Gly Arg Lys Thr
        195                 200                 205

Ser Lys His Lys Arg Asn Leu Ala Ile Thr Gly Gly Val Thr Leu Ser
    210                 215                 220

Val Ile Ala Ser Pro Val Ile Ala Ala Val Ser Val Gly Ile Gly Val
225                 230                 235                 240

Pro Ile Met Leu Ala Tyr Val Tyr Gly Val Val Pro Ile Ser Leu Cys
                245                 250                 255

Arg Gly Gly Gly Cys Gly Val Ser Thr Ala Asn Gly Lys Gly Val Lys
            260                 265                 270

Ile Glu Phe Asp Glu Asp Asp Gly Pro Ile Thr Val Ala Asp Ala Trp
        275                 280                 285

Arg Ala Leu Lys Asn Pro Ser Ile Gly Glu Ser Ser Ile Glu Gly Leu
```

```
            290                 295                 300
Thr Ser Val Leu Ser Thr Ser Gly Ser Pro Thr Asp Gly Leu Ser Val
305                 310                 315                 320

Met Gln Gly Pro Tyr Ser Glu Thr Ala Ser Phe Ala Ala Leu Ser Gly
                325                 330                 335

Gly Thr Leu Ser Gly Gly Ile Leu Ser Ser Gly Lys Gly Lys Tyr Ser
            340                 345                 350

Arg Leu Glu Val Gln Ala Asp Val Gln Lys Glu Ile Phe Pro Lys Asp
        355                 360                 365

Thr Ala Ser Leu Gly Ala Ile Ser Asp Asn Ala Ser Thr Arg Ala Met
    370                 375                 380

Ala Gly Ser Ile Ile Ser Ser Tyr Asn Pro Gln Asp Arg Phe Ser Met
385                 390                 395                 400

Ile His Ala

<210> SEQ ID NO 24
<211> LENGTH: 1212
<212> TYPE: DNA
<213> ORGANISM: Homo sapiens
<220> FEATURE:
<221> NAME/KEY: CDS
<222> LOCATION: (1)...(1212)

<400> SEQUENCE: 24 atg cac aag tac gag gag ttc atg ctg cgc cgc tac cta gcc tcg gac    48
Met His Lys Tyr Glu Glu Phe Met Leu Arg Arg Tyr Leu Ala Ser Asp
  1               5                  10                  15 ccc gac tgc cgc tgg tgc ccg gcc ccg gac tgc ggt tat gct gtt att    96
Pro Asp Cys Arg Trp Cys Pro Ala Pro Asp Cys Gly Tyr Ala Val Ile
                 20                  25                  30 gcc tat ggc tgt gcc agc tgc ccg aag cta act tgt gag agg gaa ggt   144
Ala Tyr Gly Cys Ala Ser Cys Pro Lys Leu Thr Cys Glu Arg Glu Gly
             35                  40                  45 tgc cag act gag ttc tgc tac cac tgc aag cag ata tgg cat cca aat   192
Cys Gln Thr Glu Phe Cys Tyr His Cys Lys Gln Ile Trp His Pro Asn
         50                  55                  60 cag aca tgc gat atg gcc cgt caa cag agg gcc cag act tta cga gtt   240
Gln Thr Cys Asp Met Ala Arg Gln Gln Arg Ala Gln Thr Leu Arg Val
 65                  70                  75                  80 cgg acc aaa cac act tca ggt ctc agt tat ggg caa gaa tct gga cca   288
Arg Thr Lys His Thr Ser Gly Leu Ser Tyr Gly Gln Glu Ser Gly Pro
                 85                  90                  95 gat gac atc aag cca tgc cca cga tgc agt gca tac att atc aag atg   336
Asp Asp Ile Lys Pro Cys Pro Arg Cys Ser Ala Tyr Ile Ile Lys Met
                100                 105                 110 aat gat gga agc tgt aat cac atg acc tgt gca gtg tgt ggc tgt gaa   384
Asn Asp Gly Ser Cys Asn His Met Thr Cys Ala Val Cys Gly Cys Glu
            115                 120                 125 ttc tgt tgg ctt tgt atg aaa gag atc tca gac ttg cat tac ctc agc   432
Phe Cys Trp Leu Cys Met Lys Glu Ile Ser Asp Leu His Tyr Leu Ser
        130                 135                 140 ccc tct ggc tgt aca ttc tgg ggc aag aag cca tgg agc cgt aag aag   480
Pro Ser Gly Cys Thr Phe Trp Gly Lys Lys Pro Trp Ser Arg Lys Lys
145                 150                 155                 160 aaa att ctt tgg cag ctg ggc acg ttg att ggt gct cca gtg ggg att   528
Lys Ile Leu Trp Gln Leu Gly Thr Leu Ile Gly Ala Pro Val Gly Ile
                165                 170                 175 tct ctc att gat ggc att gcc att cct gcc atg gtc att ggc att cct   576
Ser Leu Ile Asp Gly Ile Ala Ile Pro Ala Met Val Ile Gly Ile Pro
```

```
                180                 185                 190
gtt tat gtt gga agg aag att cac agc agg tat gag gga agg aaa acc    624
Val Tyr Val Gly Arg Lys Ile His Ser Arg Tyr Glu Gly Arg Lys Thr
        195                 200                 205 tcc aaa cac aag agg aat ttg gct atc act gga gga gtg act ttg tcg    672
Ser Lys His Lys Arg Asn Leu Ala Ile Thr Gly Gly Val Thr Leu Ser
    210                 215                 220 gtc att gca tcc cca gtt att gct gca gtt agt gtt ggt att ggt gtc    720
Val Ile Ala Ser Pro Val Ile Ala Ala Val Ser Val Gly Ile Gly Val
225                 230                 235                 240 ccc att atg ctg gca tat gtt tat ggg gtt gtg ccc att tct ctt tgt    768
Pro Ile Met Leu Ala Tyr Val Tyr Gly Val Val Pro Ile Ser Leu Cys
                245                 250                 255 cgt gga ggt ggc tgt gga gtt agc aca gcc aac gga aaa gga gtg aaa    816
Arg Gly Gly Gly Cys Gly Val Ser Thr Ala Asn Gly Lys Gly Val Lys
            260                 265                 270 att gaa ttt gat gaa gat gat ggt cca atc aca gtg gca gat gcc tgg    864
Ile Glu Phe Asp Glu Asp Asp Gly Pro Ile Thr Val Ala Asp Ala Trp
        275                 280                 285 aga gcc ctc aag aat ccc agc att ggg gaa agc agc att gaa ggc ctg    912
Arg Ala Leu Lys Asn Pro Ser Ile Gly Glu Ser Ser Ile Glu Gly Leu
    290                 295                 300 act agt gta ttg agc act agt gga agc cct aca gat gga ctt agt gtt    960
Thr Ser Val Leu Ser Thr Ser Gly Ser Pro Thr Asp Gly Leu Ser Val
305                 310                 315                 320 atg caa ggt cct tac agc gaa acg gcc agc ttt gca gcc ctc tca ggg   1008
Met Gln Gly Pro Tyr Ser Glu Thr Ala Ser Phe Ala Ala Leu Ser Gly
                325                 330                 335 ggc acg ctg agt ggc ggc att ctc tcc agt ggc aag gga aaa tat agc   1056
Gly Thr Leu Ser Gly Gly Ile Leu Ser Ser Gly Lys Gly Lys Tyr Ser
            340                 345                 350 agg tta gaa gtt caa gcc gat gtc caa aag gaa att ttc ccc aaa gac   1104
Arg Leu Glu Val Gln Ala Asp Val Gln Lys Glu Ile Phe Pro Lys Asp
        355                 360                 365 aca gcc agt ctt ggt gca att agt gac aac gca agc act cgt gct atg   1152
Thr Ala Ser Leu Gly Ala Ile Ser Asp Asn Ala Ser Thr Arg Ala Met
    370                 375                 380 gcc ggt tcc ata atc agt tcc tac aac cca cag gac agg ttt agc atg   1200
Ala Gly Ser Ile Ile Ser Ser Tyr Asn Pro Gln Asp Arg Phe Ser Met
385                 390                 395                 400 atc cat gca tga                                                    1212
Ile His Ala *
```

<210> SEQ ID NO 25
<211> LENGTH: 72
<212> TYPE: PRT
<213> ORGANISM: Artificial Sequence
<220> FEATURE:
<223> OTHER INFORMATION: Pfam consensus sequence

<400> SEQUENCE: 25

```
Glu Lys Tyr Glu Lys Phe Met Val Arg Ser Tyr Val Glu Lys Asn Pro
1               5                   10                  15

Asp Leu Lys Trp Cys Pro Gly Pro Asp Cys Ser Tyr Ala Val Arg Leu
            20                  25                  30

Thr Glu Val Ser Ser Ser Thr Glu Leu Ala Glu Pro Pro Arg Val Glu
        35                  40                  45

Cys Lys Lys Pro Ala Cys Gly Thr Ser Phe Cys Phe Lys Cys Gly Ala
    50                  55                  60
```

```
Glu Trp His Ala Pro Val Ser Cys
65              70

<210> SEQ ID NO 26
<211> LENGTH: 5502
<212> TYPE: DNA
<213> ORGANISM: Homo sapiens
<220> FEATURE:
<221> NAME/KEY: CDS
<222> LOCATION: (803)...(2845)

<400> SEQUENCE: 26
ttaaactccc atgtgtgagg agtgtgcctc cctgygccct ctcagctctg aggctggycg     60
tctttcgggg tgttcctttt ggcaaatata cactgtaatc ttgagtctaa atttatatgt    120
tgaaatgcta cctttttaa agtaagaagc taaataaaat tattttacta tcagtatcag    180
taaaaaaaaa aaaaaaaggg cggccgcgcc accgccggag agggaggccc gagcgcagga    240
gcctctggtg gatgggtgca gcggcggcgg gaggacgcgg aagaggagcc ccggggtag    300 cggcggcgcg agcaggggcg cggggaccgg gctgtctgag gtgcgcgccg cgctggggct    360
cgcgctctac ctgatcgcgc tgcggacgct ggtgcagctc tcgctgcagc agctcgtgct    420
acgcggggcc gctggacacc gcggggagtt cgacgcgctc caagccaggg attatcttga    480
acacataacc tccattggcc ccaggactac aggaagtcca gaaatgaaa ttctgaccgt    540 gcactacctt ttggaacaga ttaaactgat tgaagtgcaa agcaacagcc ttcataagat    600
ttcagtagat gtacaacggc ccacaggctc ttttagcatt gatttcttgg gaggttttac    660
aagctattat gacaacatca ccaatgttgt ggtaaagctg gaacccagag atggagccca    720
gcatgctgtc ttggctaatt gtcatttga ctcagtagca aactcaccag gtgccagtga    780
tgatgcagtt agctgctcag tg atg ctg gaa gtc ctt cgc gtc ttg tca aca    832
                         Met Leu Glu Val Leu Arg Val Leu Ser Thr
                         1               5                   10 tct tca gaa gcc ttg cat cat gct gtc ata ttt ctc ttt aat ggt gct       880
Ser Ser Glu Ala Leu His His Ala Val Ile Phe Leu Phe Asn Gly Ala
            15                  20                  25 gag gaa aat gtc ttg caa gcc agt cat ggt ttc att act cag cac ccc       928
Glu Glu Asn Val Leu Gln Ala Ser His Gly Phe Ile Thr Gln His Pro
        30                  35                  40 tgg gct agc ttg att cgt gca ttc att aac cta gag gca gca ggt gta       976
Trp Ala Ser Leu Ile Arg Ala Phe Ile Asn Leu Glu Ala Ala Gly Val
    45                  50                  55 gga ggg aaa gaa ctt gta ttc caa aca ggt cct gaa aat cct tgg ttg      1024
Gly Gly Lys Glu Leu Val Phe Gln Thr Gly Pro Glu Asn Pro Trp Leu
60                  65                  70 gtt caa gct tat gtt tca gca gct aaa cac cct ttt gct tct gtg gtg      1072
Val Gln Ala Tyr Val Ser Ala Ala Lys His Pro Phe Ala Ser Val Val
    75                  80                  85                  90 gct cag gag gtt ttt cag agt gga atc att cct tca gat act gac ttt      1120
Ala Gln Glu Val Phe Gln Ser Gly Ile Ile Pro Ser Asp Thr Asp Phe
            95                  100                 105 cgt atc tac agg gat ttt ggg aac att cca gga ata gac tta gct ttt      1168
Arg Ile Tyr Arg Asp Phe Gly Asn Ile Pro Gly Ile Asp Leu Ala Phe
        110                 115                 120 att gag aat gga tac att tat cac acc aag tat gac aca gcg gac aga      1216
Ile Glu Asn Gly Tyr Ile Tyr His Thr Lys Tyr Asp Thr Ala Asp Arg
    125                 130                 135 att cta aca gat tcc att cag aga gca ggt gac aac att tta gca gtt      1264
Ile Leu Thr Asp Ser Ile Gln Arg Ala Gly Asp Asn Ile Leu Ala Val
140                 145                 150
```

-continued

```
ctt aag cat cta gct aca tct gat atg ctg gct gct gct tct aag tat      1312
Leu Lys His Leu Ala Thr Ser Asp Met Leu Ala Ala Ala Ser Lys Tyr
155                 160                 165                 170 cga cat gga aac atg gtc ttc ttt gat gtg ctg ggc ctg ttt gtc att      1360
Arg His Gly Asn Met Val Phe Phe Asp Val Leu Gly Leu Phe Val Ile
                175                 180                 185 gcc tac ccc tct cgt att ggc tca atc ata aac tac atg gtg gta atg      1408
Ala Tyr Pro Ser Arg Ile Gly Ser Ile Ile Asn Tyr Met Val Val Met
            190                 195                 200 ggt gtt gtt ttg tac ctg ggc aaa aaa ttt ttg cag ccc aaa cat aag      1456
Gly Val Val Leu Tyr Leu Gly Lys Lys Phe Leu Gln Pro Lys His Lys
        205                 210                 215 act ggt aac tac aag aag gac ttc ttg tgt gga ctt ggc atc act ttg      1504
Thr Gly Asn Tyr Lys Lys Asp Phe Leu Cys Gly Leu Gly Ile Thr Leu
    220                 225                 230 atc agc tgg ttc act agc ctt gtt acc gtt ctc att ata gca gtg ttc      1552
Ile Ser Trp Phe Thr Ser Leu Val Thr Val Leu Ile Ile Ala Val Phe
235                 240                 245                 250 atc tct ctt att gga cag tct ctc tca tgg tat aac cac ttc tat gtc      1600
Ile Ser Leu Ile Gly Gln Ser Leu Ser Trp Tyr Asn His Phe Tyr Val
                255                 260                 265 tcc gtt tgt ctg tat gga act gca act gta gcc aaa ata ata ctt ata      1648
Ser Val Cys Leu Tyr Gly Thr Ala Thr Val Ala Lys Ile Ile Leu Ile
            270                 275                 280 cat act ctt gcg aaa aga ttt tat tac atg aat gcc agt gcc cag tat      1696
His Thr Leu Ala Lys Arg Phe Tyr Tyr Met Asn Ala Ser Ala Gln Tyr
        285                 290                 295 ctg gga gaa gta ttt ttt gac att tcg ctg ttt gtc cat tgc tgt ttt      1744
Leu Gly Glu Val Phe Phe Asp Ile Ser Leu Phe Val His Cys Cys Phe
    300                 305                 310 ctt gtt acc ctc act tac caa gga ctt tgc tcg gcg ttt att agt gct      1792
Leu Val Thr Leu Thr Tyr Gln Gly Leu Cys Ser Ala Phe Ile Ser Ala
315                 320                 325                 330 gtc tgg gta gca ttc cca ttg ctc aca aag ctc tgt gtg cat aag gac      1840
Val Trp Val Ala Phe Pro Leu Leu Thr Lys Leu Cys Val His Lys Asp
                335                 340                 345 ttc aag cag cat ggt gcc caa gga aaa ttt att gct ttt tac ctt ttg      1888
Phe Lys Gln His Gly Ala Gln Gly Lys Phe Ile Ala Phe Tyr Leu Leu
            350                 355                 360 ggg atg ttt att cct tat ctt tat gca ttg tac ctc atc tgg gca gta      1936
Gly Met Phe Ile Pro Tyr Leu Tyr Ala Leu Tyr Leu Ile Trp Ala Val
        365                 370                 375 ttt gag atg ttt acc cct atc ctc ggg aga agt ggt tct gaa atc cca      1984
Phe Glu Met Phe Thr Pro Ile Leu Gly Arg Ser Gly Ser Glu Ile Pro
    380                 385                 390 cct gat gtt gtg ctg gca tcc att ttg gct ggc tgt aca atg att ctc      2032
Pro Asp Val Val Leu Ala Ser Ile Leu Ala Gly Cys Thr Met Ile Leu
395                 400                 405                 410 tcg tcc tat ttt att aac ttc atc tac ctt gcc aag agc aca aaa aaa      2080
Ser Ser Tyr Phe Ile Asn Phe Ile Tyr Leu Ala Lys Ser Thr Lys Lys
                415                 420                 425 acc atg cta act tta act ttg gta tgt gca att aca ttc ctc ctt gtt      2128
Thr Met Leu Thr Leu Thr Leu Val Cys Ala Ile Thr Phe Leu Leu Val
            430                 435                 440 tgc agt gga aca ttt ttt cca tat agc tcc aat cct gct aat ccg aag      2176
Cys Ser Gly Thr Phe Phe Pro Tyr Ser Ser Asn Pro Ala Asn Pro Lys
        445                 450                 455 cca aag aga gtg ttt ctt cag cat atg act aga aca ttc cat gac ttg      2224
Pro Lys Arg Val Phe Leu Gln His Met Thr Arg Thr Phe His Asp Leu
```

```
                460                 465                 470
gaa gga aat gca gtt aaa cgg gac tct gga ata tgg atc aat ggg ttt      2272
Glu Gly Asn Ala Val Lys Arg Asp Ser Gly Ile Trp Ile Asn Gly Phe
475                 480                 485                 490 gat tat act gga att tct cac ata acc cct cac att cct gag atc aat      2320
Asp Tyr Thr Gly Ile Ser His Ile Thr Pro His Ile Pro Glu Ile Asn
                495                 500                 505 gat agt atc cga gct cac tgt gag gag aat gca cct ctt tgt ggt ttt      2368
Asp Ser Ile Arg Ala His Cys Glu Glu Asn Ala Pro Leu Cys Gly Phe
            510                 515                 520 cct tgg tat ctt cca gtg cac ttt ctg atc agg aaa aac tgg tat ctt      2416
Pro Trp Tyr Leu Pro Val His Phe Leu Ile Arg Lys Asn Trp Tyr Leu
        525                 530                 535 cct gcc cca gaa gtt tct cca aga aat cct cct cat ttc cga ctc ata      2464
Pro Ala Pro Glu Val Ser Pro Arg Asn Pro Pro His Phe Arg Leu Ile
    540                 545                 550 tcc aaa gaa cag aca cct tgg gat tct ata aaa ttg act ttt gaa gca      2512
Ser Lys Glu Gln Thr Pro Trp Asp Ser Ile Lys Leu Thr Phe Glu Ala
555                 560                 565                 570 aca gga cca agc cat atg tcc ttc tat gtt cga gcc cac aaa ggg tca      2560
Thr Gly Pro Ser His Met Ser Phe Tyr Val Arg Ala His Lys Gly Ser
                575                 580                 585 aca ctt tct cag tgg tct ctt ggc aat ggc acc cca gtc aca agt aaa      2608
Thr Leu Ser Gln Trp Ser Leu Gly Asn Gly Thr Pro Val Thr Ser Lys
            590                 595                 600 gga gga gac tac ttt gtc ttt tac tcc cat gga ctc cag gcc tct gca      2656
Gly Gly Asp Tyr Phe Val Phe Tyr Ser His Gly Leu Gln Ala Ser Ala
        605                 610                 615 tgg cag ttc tgg ata gaa gtg cag gtt tca gaa gaa cat cct gaa gga      2704
Trp Gln Phe Trp Ile Glu Val Gln Val Ser Glu Glu His Pro Glu Gly
    620                 625                 630 atg gtc acc gtg gcc att gct gcc cac tat ctg tct ggg gaa gac aag      2752
Met Val Thr Val Ala Ile Ala Ala His Tyr Leu Ser Gly Glu Asp Lys
635                 640                 645                 650 aga tcc cct caa ctg gat gct ctg aag gaa aag ttc cca gat tgg aca      2800
Arg Ser Pro Gln Leu Asp Ala Leu Lys Glu Lys Phe Pro Asp Trp Thr
                655                 660                 665 ttt ccc tct gcc tgg gtg tgc acc tac gat ctc ttt gta ttt taa          2845
Phe Pro Ser Ala Trp Val Cys Thr Tyr Asp Leu Phe Val Phe  *
            670                 675                 680 tcttgtggat gagctctaag tacatgccca gtggatactc catgtgacat ggtttctccc   2905
tatgttacgt ggatgtttgt aacgtaagtc aatgaatttt aatgatcata tgttcaaaga   2965
gctttctggg ttaacgcttt tcagggccaa gcactataag ggtttagctg tggcgcagtg   3025
atgcatggcc tgttgacact tgaaaatgcc agtcttttgg cacttcagca catgtgggta   3085
ctgccactac acacacgtca ttttatatga ccttaaggac aaagccaaca atccacttca   3145
atagctgccc ctttaggatc aagaaagatg tacactgtca gagcattgtt aatgagacaa   3205
aagttgtttc caatttaagc cccaaaacca tttgttgtat tagtggatgg tgggtaaaat   3265
atcattcact gaggtaatga ttccccttga gaatataact ctgtgtaggt cactggaaag   3325
tgattgccat agggctggga gagaagcatt gcactcttga ggctgtagcc tgtgtcaagc   3385
tgtttcttca ggcagcctct caaatgtgct ttgtctctct gtgctgaggc ctggaccctg   3445
tgctgagctg gtgactcact gtcctgacaa gtggacacac agatgcactg ctgtgctgct   3505
ttcctgaggt ggttttctat gcctgttttc ctctgaaaca tgtctgttac ccctctccat   3565
cttaccaagt tgaaaagggg aatatttggc cacataccccc tctggttttc gtaggttctt   3625
```

-continued

```
ttggttcaga atattgtttg tgccagtaca tgaccttaac ttccttcctc agagcactga    3685
gctgccatct gggctattct ggggtagaag gaaggctggg agtggtggga attttataaa    3745
tatttattct cttttctttg tttcatagga gtcttgtgtt atacaaggtt agtccttcat    3805
ggtataatct tactgatgca ctgggcctat cttttttgttt tccagccagt tgaatagatt   3865 agttttttctc agtaacttac tatccagcag actggctttc ctgagacttg aggttgtggc   3925
ttatactgga atgagaccac tgtacgtgta ggtggttcag atcctgcgta atggcagcat    3985
gaggacttaa aaggtggttt tcattttgaa gatggctatg tagcttgtaa ggtgtatcac    4045
agcagtacct ctcatggctt tttggttcca gcagtgaggg cattggtgag atcaatggta    4105
aactgtgcaa gctttctttt tatcattagg aaatgtgaaa cgttggacaa attttgagtt    4165
ttaacaagga caaaaagttg aaagaaaagg cacagttaac aaaaaagggt ggctagattt    4225
atcttgggtg atggaggaaa tgagagagga atgctcttga aggtggtct gtggatctgt     4285 ctgaatagaa agagcacagt aagtatgcat tgccggagaa acgtccttg aagctgcttg      4345 tctcatgtgt atgatgtgct ttttaaatca tgcccctcgt tgcctgccta atctgtgact    4405
ccctaaaaac taactgggcc catgtagatg gggctgcaac cagagctgaa taacatgtta    4465
ggctcacaca tgcatcagca ctgcacactg gaatcattgc tcttcctgga ctttgtagaa    4525
atcagtctca agtgcttcaa gagtctggct cctgctactt ttatctgtca ggtagcacat    4585
aaggtttgca gggtttatat tttgtataga atcacagttg tggagaaaaa gtaataattt    4645
ctcaatgaat tttaaaaatg ggcctatttt ctatccccgt ggttcatctg atataattag    4705
tgttccctgt gaattccccc cctctatggg aaggatgcct ttactctttta tcagtaataa   4765 attatgactg ttttcatatt gccttagggt tatttccctg tgtaaaccat tgtcttttgt    4825
tttggttttc tttagcatta tgaagctttg gtattgtaca aggtcagtag taagatgctc    4885
actagtctca gggcttgtgt aatattctgg gaggtcattt aaatgccaga atggtcaag     4945 caattataca cagtatttat gactctgtta agcataccgt ttgtctgtca cattagtaga    5005
ttctgagatt aaaaaaaatt tttaaagagt gatcatttaa ataatttcta aaagggtctt    5065
ttcaagctct aacaaagtca ctaacaaatg cattattttc tacagaatta gatgttagta    5125
gtacagtact gcatattcag ggaaaaagtg tgaggaattg atttcaaaat agttcgttct    5185
tgtgtttgac ctaagaatga ttgtcgcatg aagtgtttgt ttttacagtt tagcatatat    5245
aaacaaacat gataggattc cttaagatgt taccacccag ggggccacaa gccagcctgc    5305
tgtctcagga agctgtagaa ggagtgtttg tcaatttctt gtcactggtt tgctgactta    5365
ctgaggatta attgttgcct tacaatgtta ctgaaataaa ctgtttaata aaaaaaaaa     5425 aaaaaaaaaa aaaaaaaaa aaaaaaaaa aaaaaaaaa aaaaaaaaa aaaaacaaa         5485 aaaaaaggg cggccgc                                                   5502
```

<210> SEQ ID NO 27
<211> LENGTH: 680
<212> TYPE: PRT
<213> ORGANISM: Homo sapiens

<400> SEQUENCE: 27

Met Leu Glu Val Leu Arg Val Leu Ser Thr Ser Ser Glu Ala Leu His
 1               5                   10                  15

His Ala Val Ile Phe Leu Phe Asn Gly Ala Glu Glu Asn Val Leu Gln
             20                  25                  30

```
Ala Ser His Gly Phe Ile Thr Gln His Pro Trp Ala Ser Leu Ile Arg
        35                  40                  45

Ala Phe Ile Asn Leu Glu Ala Ala Gly Val Gly Gly Lys Glu Leu Val
        50                  55                  60

Phe Gln Thr Gly Pro Glu Asn Pro Trp Leu Val Gln Ala Tyr Val Ser
65                  70                  75                  80

Ala Ala Lys His Pro Phe Ala Ser Val Val Ala Gln Glu Val Phe Gln
                85                  90                  95

Ser Gly Ile Ile Pro Ser Asp Thr Asp Phe Arg Ile Tyr Arg Asp Phe
                100                 105                 110

Gly Asn Ile Pro Gly Ile Asp Leu Ala Phe Ile Glu Asn Gly Tyr Ile
            115                 120                 125

Tyr His Thr Lys Tyr Asp Thr Ala Asp Arg Ile Leu Thr Asp Ser Ile
    130                 135                 140

Gln Arg Ala Gly Asp Asn Ile Leu Ala Val Leu Lys His Leu Ala Thr
145                 150                 155                 160

Ser Asp Met Leu Ala Ala Ala Ser Lys Tyr Arg His Gly Asn Met Val
                165                 170                 175

Phe Phe Asp Val Leu Gly Leu Phe Val Ile Ala Tyr Pro Ser Arg Ile
                180                 185                 190

Gly Ser Ile Ile Asn Tyr Met Val Met Gly Val Val Leu Tyr Leu
            195                 200                 205

Gly Lys Lys Phe Leu Gln Pro Lys His Lys Thr Gly Asn Tyr Lys Lys
        210                 215                 220

Asp Phe Leu Cys Gly Leu Gly Ile Thr Leu Ile Ser Trp Phe Thr Ser
225                 230                 235                 240

Leu Val Thr Val Leu Ile Ile Ala Val Phe Ile Ser Leu Ile Gly Gln
                245                 250                 255

Ser Leu Ser Trp Tyr Asn His Phe Tyr Val Ser Val Cys Leu Tyr Gly
            260                 265                 270

Thr Ala Thr Val Ala Lys Ile Ile Leu Ile His Thr Leu Ala Lys Arg
        275                 280                 285

Phe Tyr Tyr Met Asn Ala Ser Ala Gln Tyr Leu Gly Glu Val Phe Phe
    290                 295                 300

Asp Ile Ser Leu Phe Val His Cys Cys Phe Leu Val Thr Leu Thr Tyr
305                 310                 315                 320

Gln Gly Leu Cys Ser Ala Phe Ile Ser Ala Val Trp Val Ala Phe Pro
                325                 330                 335

Leu Leu Thr Lys Leu Cys Val His Lys Asp Phe Lys Gln His Gly Ala
            340                 345                 350

Gln Gly Lys Phe Ile Ala Phe Tyr Leu Leu Gly Met Phe Ile Pro Tyr
        355                 360                 365

Leu Tyr Ala Leu Tyr Leu Ile Trp Ala Val Phe Glu Met Phe Thr Pro
    370                 375                 380

Ile Leu Gly Arg Ser Gly Ser Glu Ile Pro Pro Asp Val Val Leu Ala
385                 390                 395                 400

Ser Ile Leu Ala Gly Cys Thr Met Ile Leu Ser Ser Tyr Phe Ile Asn
                405                 410                 415

Phe Ile Tyr Leu Ala Lys Ser Thr Lys Lys Thr Met Leu Thr Leu Thr
            420                 425                 430

Leu Val Cys Ala Ile Thr Phe Leu Leu Val Cys Ser Gly Thr Phe Phe
        435                 440                 445

Pro Tyr Ser Ser Asn Pro Ala Asn Pro Lys Pro Lys Arg Val Phe Leu
```

```
                450             455             460
Gln His Met Thr Arg Thr Phe His Asp Leu Glu Gly Asn Ala Val Lys
465                     470                 475                 480

Arg Asp Ser Gly Ile Trp Ile Asn Gly Phe Asp Tyr Thr Gly Ile Ser
                485                 490                 495

His Ile Thr Pro His Ile Pro Glu Ile Asn Asp Ser Ile Arg Ala His
            500                 505                 510

Cys Glu Glu Asn Ala Pro Leu Cys Gly Phe Pro Trp Tyr Leu Pro Val
            515                 520                 525

His Phe Leu Ile Arg Lys Asn Trp Tyr Leu Pro Ala Pro Glu Val Ser
530                 535                 540

Pro Arg Asn Pro Pro His Phe Arg Leu Ile Ser Lys Glu Gln Thr Pro
545                 550                 555                 560

Trp Asp Ser Ile Lys Leu Thr Phe Glu Ala Thr Gly Pro Ser His Met
                565                 570                 575

Ser Phe Tyr Val Arg Ala His Lys Gly Ser Thr Leu Ser Gln Trp Ser
            580                 585                 590

Leu Gly Asn Gly Thr Pro Val Thr Ser Lys Gly Gly Asp Tyr Phe Val
            595                 600                 605

Phe Tyr Ser His Gly Leu Gln Ala Ser Ala Trp Gln Phe Trp Ile Glu
            610                 615                 620

Val Gln Val Ser Glu Glu His Pro Glu Gly Met Val Thr Val Ala Ile
625                 630                 635                 640

Ala Ala His Tyr Leu Ser Gly Glu Asp Lys Arg Ser Pro Gln Leu Asp
                645                 650                 655

Ala Leu Lys Glu Lys Phe Pro Asp Trp Thr Phe Pro Ser Ala Trp Val
                660                 665                 670

Cys Thr Tyr Asp Leu Phe Val Phe
            675                 680

<210> SEQ ID NO 28
<211> LENGTH: 2043
<212> TYPE: DNA
<213> ORGANISM: Homo sapiens
<220> FEATURE:
<221> NAME/KEY: CDS
<222> LOCATION: (1)...(2043)

<400> SEQUENCE: 28 atg ctg gaa gtc ctt cgc gtc ttg tca aca tct tca gaa gcc ttg cat     48
Met Leu Glu Val Leu Arg Val Leu Ser Thr Ser Ser Glu Ala Leu His
 1               5                  10                  15 cat gct gtc ata ttt ctc ttt aat ggt gct gag gaa aat gtc ttg caa     96
His Ala Val Ile Phe Leu Phe Asn Gly Ala Glu Glu Asn Val Leu Gln
                20                  25                  30 gcc agt cat ggt ttc att act cag cac ccc tgg gct agc ttg att cgt    144
Ala Ser His Gly Phe Ile Thr Gln His Pro Trp Ala Ser Leu Ile Arg
            35                  40                  45 gca ttc att aac cta gag gca gca ggt gta gga ggg aaa gaa ctt gta    192
Ala Phe Ile Asn Leu Glu Ala Ala Gly Val Gly Gly Lys Glu Leu Val
        50                  55                  60 ttc caa aca ggt cct gaa aat cct tgg ttg gtt caa gct tat gtt tca    240
Phe Gln Thr Gly Pro Glu Asn Pro Trp Leu Val Gln Ala Tyr Val Ser
65                  70                  75                  80 gca gct aaa cac cct ttt gct tct gtg gtg gct cag gag gtt ttt cag    288
Ala Ala Lys His Pro Phe Ala Ser Val Val Ala Gln Glu Val Phe Gln
                85                  90                  95
```

-continued

```
agt gga atc att cct tca gat act gac ttt cgt atc tac agg gat ttt      336
Ser Gly Ile Ile Pro Ser Asp Thr Asp Phe Arg Ile Tyr Arg Asp Phe
        100                 105                 110 ggg aac att cca gga ata gac tta gct ttt att gag aat gga tac att      384
Gly Asn Ile Pro Gly Ile Asp Leu Ala Phe Ile Glu Asn Gly Tyr Ile
    115                 120                 125 tat cac acc aag tat gac aca gcg gac aga att cta aca gat tcc att      432
Tyr His Thr Lys Tyr Asp Thr Ala Asp Arg Ile Leu Thr Asp Ser Ile
130                 135                 140 cag aga gca ggt gac aac att tta gca gtt ctt aag cat cta gct aca      480
Gln Arg Ala Gly Asp Asn Ile Leu Ala Val Leu Lys His Leu Ala Thr
145                 150                 155                 160 tct gat atg ctg gct gct gct tct aag tat cga cat gga aac atg gtc      528
Ser Asp Met Leu Ala Ala Ala Ser Lys Tyr Arg His Gly Asn Met Val
            165                 170                 175 ttc ttt gat gtg ctg ggc ctg ttt gtc att gcc tac ccc tct cgt att      576
Phe Phe Asp Val Leu Gly Leu Phe Val Ile Ala Tyr Pro Ser Arg Ile
        180                 185                 190 ggc tca atc ata aac tac atg gtg gta atg ggt gtt gtt ttg tac ctg      624
Gly Ser Ile Ile Asn Tyr Met Val Val Met Gly Val Val Leu Tyr Leu
    195                 200                 205 ggc aaa aaa ttt ttg cag ccc aaa cat aag act ggt aac tac aag aag      672
Gly Lys Lys Phe Leu Gln Pro Lys His Lys Thr Gly Asn Tyr Lys Lys
210                 215                 220 gac ttc ttg tgt gga ctt ggc atc act ttg atc agc tgg ttc act agc      720
Asp Phe Leu Cys Gly Leu Gly Ile Thr Leu Ile Ser Trp Phe Thr Ser
225                 230                 235                 240 ctt gtt acc gtt ctc att ata gca gtg ttc atc tct ctt att gga cag      768
Leu Val Thr Val Leu Ile Ile Ala Val Phe Ile Ser Leu Ile Gly Gln
            245                 250                 255 tct ctc tca tgg tat aac cac ttc tat gtc tcc gtt tgt ctg tat gga      816
Ser Leu Ser Trp Tyr Asn His Phe Tyr Val Ser Val Cys Leu Tyr Gly
        260                 265                 270 act gca act gta gcc aaa ata ata ctt ata cat act ctt gcg aaa aga      864
Thr Ala Thr Val Ala Lys Ile Ile Leu Ile His Thr Leu Ala Lys Arg
    275                 280                 285 ttt tat tac atg aat gcc agt gcc cag tat ctg gga gaa gta ttt ttt      912
Phe Tyr Tyr Met Asn Ala Ser Ala Gln Tyr Leu Gly Glu Val Phe Phe
290                 295                 300 gac att tcg ctg ttt gtc cat tgc tgt ttt ctt gtt acc ctc act tac      960
Asp Ile Ser Leu Phe Val His Cys Cys Phe Leu Val Thr Leu Thr Tyr
305                 310                 315                 320 caa gga ctt tgc tcg gcg ttt att agt gct gtc tgg gta gca ttc cca     1008
Gln Gly Leu Cys Ser Ala Phe Ile Ser Ala Val Trp Val Ala Phe Pro
            325                 330                 335 ttg ctc aca aag ctc tgt gtg cat aag gac ttc aag cag cat ggt gcc     1056
Leu Leu Thr Lys Leu Cys Val His Lys Asp Phe Lys Gln His Gly Ala
        340                 345                 350 caa gga aaa ttt att gct ttt tac ctt ttg ggg atg ttt att cct tat     1104
Gln Gly Lys Phe Ile Ala Phe Tyr Leu Leu Gly Met Phe Ile Pro Tyr
    355                 360                 365 ctt tat gca ttg tac ctc atc tgg gca gta ttt gag atg ttt acc cct     1152
Leu Tyr Ala Leu Tyr Leu Ile Trp Ala Val Phe Glu Met Phe Thr Pro
370                 375                 380 atc ctc ggg aga agt ggt tct gaa atc cca cct gat gtt gtg ctg gca     1200
Ile Leu Gly Arg Ser Gly Ser Glu Ile Pro Pro Asp Val Val Leu Ala
385                 390                 395                 400 tcc att ttg gct ggc tgt aca atg att ctc tcg tcc tat ttt att aac     1248
Ser Ile Leu Ala Gly Cys Thr Met Ile Leu Ser Ser Tyr Phe Ile Asn
            405                 410                 415
```

```
ttc atc tac ctt gcc aag agc aca aaa aaa acc atg cta act tta act    1296
Phe Ile Tyr Leu Ala Lys Ser Thr Lys Lys Thr Met Leu Thr Leu Thr
        420                 425                 430 ttg gta tgt gca att aca ttc ctc ctt gtt tgc agt gga aca ttt ttt    1344
Leu Val Cys Ala Ile Thr Phe Leu Leu Val Cys Ser Gly Thr Phe Phe
            435                 440                 445 cca tat agc tcc aat cct gct aat ccg aag cca aag aga gtg ttt ctt    1392
Pro Tyr Ser Ser Asn Pro Ala Asn Pro Lys Pro Lys Arg Val Phe Leu
450                 455                 460 cag cat atg act aga aca ttc cat gac ttg gaa gga aat gca gtt aaa    1440
Gln His Met Thr Arg Thr Phe His Asp Leu Glu Gly Asn Ala Val Lys
465                 470                 475                 480 cgg gac tct gga ata tgg atc aat ggg ttt gat tat act gga att tct    1488
Arg Asp Ser Gly Ile Trp Ile Asn Gly Phe Asp Tyr Thr Gly Ile Ser
                485                 490                 495 cac ata acc cct cac att cct gag atc aat gat agt atc cga gct cac    1536
His Ile Thr Pro His Ile Pro Glu Ile Asn Asp Ser Ile Arg Ala His
            500                 505                 510 tgt gag gag aat gca cct ctt tgt ggt ttt cct tgg tat ctt cca gtg    1584
Cys Glu Glu Asn Ala Pro Leu Cys Gly Phe Pro Trp Tyr Leu Pro Val
        515                 520                 525 cac ttt ctg atc agg aaa aac tgg tat ctt cct gcc cca gaa gtt tct    1632
His Phe Leu Ile Arg Lys Asn Trp Tyr Leu Pro Ala Pro Glu Val Ser
    530                 535                 540 cca aga aat cct cct cat ttc cga ctc ata tcc aaa gaa cag aca cct    1680
Pro Arg Asn Pro Pro His Phe Arg Leu Ile Ser Lys Glu Gln Thr Pro
545                 550                 555                 560 tgg gat tct ata aaa ttg act ttt gaa gca aca gga cca agc cat atg    1728
Trp Asp Ser Ile Lys Leu Thr Phe Glu Ala Thr Gly Pro Ser His Met
                565                 570                 575 tcc ttc tat gtt cga gcc cac aaa ggg tca aca ctt tct cag tgg tct    1776
Ser Phe Tyr Val Arg Ala His Lys Gly Ser Thr Leu Ser Gln Trp Ser
            580                 585                 590 ctt ggc aat ggc acc cca gtc aca agt aaa gga gga gac tac ttt gtc    1824
Leu Gly Asn Gly Thr Pro Val Thr Ser Lys Gly Gly Asp Tyr Phe Val
        595                 600                 605 ttt tac tcc cat gga ctc cag gcc tct gca tgg cag ttc tgg ata gaa    1872
Phe Tyr Ser His Gly Leu Gln Ala Ser Ala Trp Gln Phe Trp Ile Glu
    610                 615                 620 gtg cag gtt tca gaa gaa cat cct gaa gga atg gtc acc gtg gcc att    1920
Val Gln Val Ser Glu Glu His Pro Glu Gly Met Val Thr Val Ala Ile
625                 630                 635                 640 gct gcc cac tat ctg tct ggg gaa gac aag aga tcc cct caa ctg gat    1968
Ala Ala His Tyr Leu Ser Gly Glu Asp Lys Arg Ser Pro Gln Leu Asp
                645                 650                 655 gct ctg aag gaa aag ttc cca gat tgg aca ttt ccc tct gcc tgg gtg    2016
Ala Leu Lys Glu Lys Phe Pro Asp Trp Thr Phe Pro Ser Ala Trp Val
            660                 665                 670 tgc acc tac gat ctc ttt gta ttt taa                                2043
Cys Thr Tyr Asp Leu Phe Val Phe *
        675                 680
```

<210> SEQ ID NO 29
<211> LENGTH: 2566
<212> TYPE: DNA
<213> ORGANISM: Homo sapiens
<220> FEATURE:
<221> NAME/KEY: CDS
<222> LOCATION: (194)...(2470)

<400> SEQUENCE: 29

-continued

```
raaggggacta gtcctgcaag tttaaacgaa tttcactcct cttactacac tataggggctc      60 gagcggccgc ccgggcaggt gggggggcata ggtgaaaaat agtaaagaga ggaaagccag      120
aaacagtgag ccaggggaaca agggggacgga agacaggggatc caggctgtat ctacggagag    180
acacagaagg gag atg ctg ctg ctg ccg ctg ctg ctg ctg ctg ccg cca          229
            Met Leu Leu Leu Pro Leu Leu Leu Leu Leu Pro Pro
              1               5                  10 cta gtc ctc agg gtt gct gca agc cga tgt cta cat gat gag aca cag         277
Leu Val Leu Arg Val Ala Ala Ser Arg Cys Leu His Asp Glu Thr Gln
         15                  20                  25 aag tct gtg agc ctt ctc agg ccc cct ttc tcc caa ctc ccc tca aaa         325
Lys Ser Val Ser Leu Leu Arg Pro Pro Phe Ser Gln Leu Pro Ser Lys
     30                  35                  40 tct cgc tct tcc tcc ctc acc ctc cct agc tcc cgt gat cct caa ccc         373
Ser Arg Ser Ser Ser Leu Thr Leu Pro Ser Ser Arg Asp Pro Gln Pro
 45                  50                  55                  60 cta cga atc caa agc tgc tat cta gga gat cat ata tca gat gga gct         421
Leu Arg Ile Gln Ser Cys Tyr Leu Gly Asp His Ile Ser Asp Gly Ala
             65                  70                  75 tgg gat cct gag gga gaa ggg atg aga ggg gga tcc cga gcc ctg gcc         469
Trp Asp Pro Glu Gly Glu Gly Met Arg Gly Gly Ser Arg Ala Leu Ala
         80                  85                  90 gca gtg aga gag gcc act cag cga atc cag gct gtt cta gca gtc cct         517
Ala Val Arg Glu Ala Thr Gln Arg Ile Gln Ala Val Leu Ala Val Pro
     95                  100                 105 cca gtg caa gga ccc ctg ctt ctg agt cga gac cct gca cag tat tgc         565
Pro Val Gln Gly Pro Leu Leu Leu Ser Arg Asp Pro Ala Gln Tyr Cys
 110                 115                 120 cac gct gtc tgg gga gac cca gat agc cca aac tac cac agg tgc agc         613
His Ala Val Trp Gly Asp Pro Asp Ser Pro Asn Tyr His Arg Cys Ser
 125                 130                 135                 140 ctc ttg aac cca gga tac aaa gga gag agt tgc ctg ggg gca aag att         661
Leu Leu Asn Pro Gly Tyr Lys Gly Glu Ser Cys Leu Gly Ala Lys Ile
             145                 150                 155 cct gac acc cat ctt cgc ggt tat gcc ttg tgg ccg gag cag ggt ccc         709
Pro Asp Thr His Leu Arg Gly Tyr Ala Leu Trp Pro Glu Gln Gly Pro
         160                 165                 170 cca caa ctg gtc cag cca gat ggg cct ggg gtc caa aac act gat ttt         757
Pro Gln Leu Val Gln Pro Asp Gly Pro Gly Val Gln Asn Thr Asp Phe
     175                 180                 185 ctc ctg tat gtg cga gtt gct cac act tcc aag tgc cac caa gag aca         805
Leu Leu Tyr Val Arg Val Ala His Thr Ser Lys Cys His Gln Glu Thr
 190                 195                 200 gtc tca ctc tgt tgc cca ggc tgg agt aca gcg gcc caa tca cag ctc         853
Val Ser Leu Cys Cys Pro Gly Trp Ser Thr Ala Ala Gln Ser Gln Leu
205                  210                 215                 220 acc gca gcc ttg acc tcc tgg gct cag ccc tct gtc ata gcc tat gct         901
Thr Ala Ala Leu Thr Ser Trp Ala Gln Pro Ser Val Ile Ala Tyr Ala
             225                 230                 235 gcc tgc tgc cag ctg gac tca gaa gac agg ccc ctc gct ggt acc att         949
Ala Cys Cys Gln Leu Asp Ser Glu Asp Arg Pro Leu Ala Gly Thr Ile
         240                 245                 250 gtc tac tgt gcc caa cat ctc acc agc ccc agc ctc agc cac agt gac         997
Val Tyr Cys Ala Gln His Leu Thr Ser Pro Ser Leu Ser His Ser Asp
     255                 260                 265 atc gtc atg gcc aca tta cat gaa ttg ctc cat gcc ttg ggt ttc tct        1045
Ile Val Met Ala Thr Leu His Glu Leu Leu His Ala Leu Gly Phe Ser
 270                 275                 280
```

```
gga cag ctc ttc aag aaa tgg cga gac tgc ccc tca gga ttc agt gtt    1093
Gly Gln Leu Phe Lys Lys Trp Arg Asp Cys Pro Ser Gly Phe Ser Val
285             290                 295                 300 aga gag aac tgt tct aca agg caa caa gtg aca agg caa gat gag tgg    1141
Arg Glu Asn Cys Ser Thr Arg Gln Gln Val Thr Arg Gln Asp Glu Trp
                305                 310                 315 gga caa ctg ctt ctc acc acc cca gct gtt agc ctc agc ctg gcc aaa    1189
Gly Gln Leu Leu Leu Thr Thr Pro Ala Val Ser Leu Ser Leu Ala Lys
320                 325                 330 cac ttg gga gtg tcg ggg gct tcc ctg ggt gtt ccc ttg gaa gaa gag    1237
His Leu Gly Val Ser Gly Ala Ser Leu Gly Val Pro Leu Glu Glu Glu
            335                 340                 345 gag ggc ctt ctg tcc tcg cac tgg gag gcc aga cta ctc cag ggt tct    1285
Glu Gly Leu Leu Ser Ser His Trp Glu Ala Arg Leu Leu Gln Gly Ser
350                 355                 360 tta atg act gct acc ttt gat gga gcc cag cgc act cga ctc gac cca    1333
Leu Met Thr Ala Thr Phe Asp Gly Ala Gln Arg Thr Arg Leu Asp Pro
365             370                 375                 380 atc acc ctc gct gcc ttc aaa gac tca ggc tgg tac cag gtc aac cac    1381
Ile Thr Leu Ala Ala Phe Lys Asp Ser Gly Trp Tyr Gln Val Asn His
            385                 390                 395 agc gct gca gag gag ctg ttg tgg ggc cag gga tct ggc cca gaa ttt    1429
Ser Ala Ala Glu Glu Leu Leu Trp Gly Gln Gly Ser Gly Pro Glu Phe
                400                 405                 410 ggc ttg gtg acc aca tgt ggg act ggc tcc tca gac ttc ttc tgt act    1477
Gly Leu Val Thr Thr Cys Gly Thr Gly Ser Ser Asp Phe Phe Cys Thr
            415                 420                 425 ggc agt ggg ctg ggc tgc cac tac ctg cac ctg gac aag gga agc tgc    1525
Gly Ser Gly Leu Gly Cys His Tyr Leu His Leu Asp Lys Gly Ser Cys
430                 435                 440 tcc tca gac ccc atg ctg gaa ggc tgc cgc atg tac aag ccc tta gcc    1573
Ser Ser Asp Pro Met Leu Glu Gly Cys Arg Met Tyr Lys Pro Leu Ala
445                 450                 455                 460 aat ggg agt gaa tgc tgg aag aag gaa aac gga ttc cct gct ggg gtg    1621
Asn Gly Ser Glu Cys Trp Lys Lys Glu Asn Gly Phe Pro Ala Gly Val
                465                 470                 475 gat aat ccc cat ggg gag atc tac cat ccc cag agc cgt tgc ttc ttt    1669
Asp Asn Pro His Gly Glu Ile Tyr His Pro Gln Ser Arg Cys Phe Phe
            480                 485                 490 gcc aac ctc act tca cag ctg ctc cct ggg gat aag ccc agg cat cct    1717
Ala Asn Leu Thr Ser Gln Leu Leu Pro Gly Asp Lys Pro Arg His Pro
            495                 500                 505 tct ctt acc cca cac ctc aag gaa gca gag ctc atg ggc cgc tgc tac    1765
Ser Leu Thr Pro His Leu Lys Glu Ala Glu Leu Met Gly Arg Cys Tyr
510                 515                 520 tta cat caa tgc aca ggg agg gga gct tac aag gtg cag gtg gag ggc    1813
Leu His Gln Cys Thr Gly Arg Gly Ala Tyr Lys Val Gln Val Glu Gly
525                 530                 535                 540 tcg cct tgg gtc cca tgc ctt cct gga aag gtt ata cag ata cct ggg    1861
Ser Pro Trp Val Pro Cys Leu Pro Gly Lys Val Ile Gln Ile Pro Gly
                545                 550                 555 tac tat ggt ctt ctc ttc tgt ccc cgg ggt cgg ctg tgt cag act aat    1909
Tyr Tyr Gly Leu Leu Phe Cys Pro Arg Gly Arg Leu Cys Gln Thr Asn
            560                 565                 570 gaa ggt atc aat gct gtt act tcc cca cct gtg agt ctt tca acc cca    1957
Glu Gly Ile Asn Ala Val Thr Ser Pro Pro Val Ser Leu Ser Thr Pro
575                 580                 585 gat cca cta ttc cag ctc tct tta gaa tta gct ggg cct cca gga cac    2005
Asp Pro Leu Phe Gln Leu Ser Leu Glu Leu Ala Gly Pro Pro Gly His
590                 595                 600
```

```
tct ctg ggg aag gaa cag caa gaa ggg cta gct gaa gca gta ctg gag      2053
Ser Leu Gly Lys Glu Gln Gln Glu Gly Leu Ala Glu Ala Val Leu Glu
605                 610                 615                 620 gct ttg gcg agc aga ggc ggc act ggc agg tgc tat ttc cat ggc cca      2101
Ala Leu Ala Ser Arg Gly Gly Thr Gly Arg Cys Tyr Phe His Gly Pro
                625                 630                 635 tca att acc act agc ttg gtg ttt act gtg cat atg tgg aag tcc cct      2149
Ser Ile Thr Thr Ser Leu Val Phe Thr Val His Met Trp Lys Ser Pro
            640                 645                 650 ggc tgc caa ggg cct tca gtt gct aca ctg cac aag gcc ctg act ctg      2197
Gly Cys Gln Gly Pro Ser Val Ala Thr Leu His Lys Ala Leu Thr Leu
        655                 660                 665 act ctc cag aaa aaa ccc cta gaa gtg tat cat gga gga gcc aac ttt      2245
Thr Leu Gln Lys Lys Pro Leu Glu Val Tyr His Gly Gly Ala Asn Phe
    670                 675                 680 acc aca caa ccc agc aag ttg ctg gtt act tca gac cat aat ccc tcc      2293
Thr Thr Gln Pro Ser Lys Leu Leu Val Thr Ser Asp His Asn Pro Ser
685                 690                 695                 700 atg acc cac cta agg ctg tcc atg gga ctc tgc cta atg ctg cta atc      2341
Met Thr His Leu Arg Leu Ser Met Gly Leu Cys Leu Met Leu Leu Ile
                705                 710                 715 ctg gtg ggt gta atg gga acc aca gcc tac cag aaa aga gcc act ctt      2389
Leu Val Gly Val Met Gly Thr Thr Ala Tyr Gln Lys Arg Ala Thr Leu
            720                 725                 730 cct gtg aga cca tct gcc tct tac cat tca cca gag ctc cac agc aca      2437
Pro Val Arg Pro Ser Ala Ser Tyr His Ser Pro Glu Leu His Ser Thr
        735                 740                 745 agg gtc cca gtt aga gga ata agg gag gtg tga tgttgcccag aacatgacag    2490
Arg Val Pro Val Arg Gly Ile Arg Glu Val *
    750                 755 ggggtaagga agagaataat ttcttgtgag acgactggat ggaaaatcta ttgggtatac    2550
ttaatttcta ctttct                                                    2566

<210> SEQ ID NO 30
<211> LENGTH: 758
<212> TYPE: PRT
<213> ORGANISM: Homo sapiens

<400> SEQUENCE: 30

Met Leu Leu Leu Pro Leu Leu Leu Leu Pro Pro Leu Val Leu Arg
 1               5                  10                  15

Val Ala Ala Ser Arg Cys Leu His Asp Glu Thr Gln Lys Ser Val Ser
                20                  25                  30

Leu Leu Arg Pro Pro Phe Ser Gln Leu Pro Ser Lys Ser Arg Ser Ser
            35                  40                  45

Ser Leu Thr Leu Pro Ser Ser Arg Asp Pro Gln Pro Leu Arg Ile Gln
    50                  55                  60

Ser Cys Tyr Leu Gly Asp His Ile Ser Asp Gly Ala Trp Asp Pro Glu
65                  70                  75                  80

Gly Glu Gly Met Arg Gly Gly Ser Arg Ala Leu Ala Ala Val Arg Glu
                85                  90                  95

Ala Thr Gln Arg Ile Gln Ala Val Leu Ala Val Pro Pro Val Gln Gly
                100                 105                 110

Pro Leu Leu Leu Ser Arg Asp Pro Ala Gln Tyr Cys His Ala Val Trp
            115                 120                 125

Gly Asp Pro Asp Ser Pro Asn Tyr His Arg Cys Ser Leu Leu Asn Pro
    130                 135                 140
```

```
Gly Tyr Lys Gly Glu Ser Cys Leu Gly Ala Lys Ile Pro Asp Thr His
145                 150                 155                 160

Leu Arg Gly Tyr Ala Leu Trp Pro Glu Gln Gly Pro Pro Gln Leu Val
            165                 170                 175

Gln Pro Asp Gly Pro Gly Val Gln Asn Thr Asp Phe Leu Leu Tyr Val
        180                 185                 190

Arg Val Ala His Thr Ser Lys Cys His Gln Glu Thr Val Ser Leu Cys
        195                 200                 205

Cys Pro Gly Trp Ser Thr Ala Ala Gln Ser Gln Leu Thr Ala Ala Leu
        210                 215                 220

Thr Ser Trp Ala Gln Pro Ser Val Ile Ala Tyr Ala Ala Cys Cys Gln
225                 230                 235                 240

Leu Asp Ser Glu Asp Arg Pro Leu Ala Gly Thr Ile Val Tyr Cys Ala
            245                 250                 255

Gln His Leu Thr Ser Pro Ser Leu Ser His Ser Asp Ile Val Met Ala
        260                 265                 270

Thr Leu His Glu Leu Leu His Ala Leu Gly Phe Ser Gly Gln Leu Phe
275                 280                 285

Lys Lys Trp Arg Asp Cys Pro Ser Gly Phe Ser Val Arg Glu Asn Cys
290                 295                 300

Ser Thr Arg Gln Gln Val Thr Arg Gln Asp Glu Trp Gly Gln Leu Leu
305                 310                 315                 320

Leu Thr Thr Pro Ala Val Ser Leu Ser Leu Ala Lys His Leu Gly Val
            325                 330                 335

Ser Gly Ala Ser Leu Gly Val Pro Leu Glu Glu Glu Gly Leu Leu
        340                 345                 350

Ser Ser His Trp Glu Ala Arg Leu Leu Gln Gly Ser Leu Met Thr Ala
        355                 360                 365

Thr Phe Asp Gly Ala Gln Arg Thr Arg Leu Asp Pro Ile Thr Leu Ala
370                 375                 380

Ala Phe Lys Asp Ser Gly Trp Tyr Gln Val Asn His Ser Ala Ala Glu
385                 390                 395                 400

Glu Leu Leu Trp Gly Gln Gly Ser Gly Pro Glu Phe Gly Leu Val Thr
            405                 410                 415

Thr Cys Gly Thr Gly Ser Ser Asp Phe Phe Cys Thr Gly Ser Gly Leu
        420                 425                 430

Gly Cys His Tyr Leu His Leu Asp Lys Gly Ser Cys Ser Ser Asp Pro
        435                 440                 445

Met Leu Glu Gly Cys Arg Met Tyr Lys Pro Leu Ala Asn Gly Ser Glu
450                 455                 460

Cys Trp Lys Lys Glu Asn Gly Phe Pro Ala Gly Val Asp Asn Pro His
465                 470                 475                 480

Gly Glu Ile Tyr His Pro Gln Ser Arg Cys Phe Phe Ala Asn Leu Thr
            485                 490                 495

Ser Gln Leu Leu Pro Gly Asp Lys Pro Arg His Pro Ser Leu Thr Pro
        500                 505                 510

His Leu Lys Glu Ala Glu Leu Met Gly Arg Cys Tyr Leu His Gln Cys
        515                 520                 525

Thr Gly Arg Gly Ala Tyr Lys Val Gln Val Glu Gly Ser Pro Trp Val
530                 535                 540

Pro Cys Leu Pro Gly Lys Val Ile Gln Ile Pro Gly Tyr Tyr Gly Leu
545                 550                 555                 560
```

```
Leu Phe Cys Pro Arg Gly Arg Leu Cys Gln Thr Asn Glu Gly Ile Asn
                565                 570                 575

Ala Val Thr Ser Pro Pro Val Ser Leu Ser Thr Pro Asp Pro Leu Phe
            580                 585                 590

Gln Leu Ser Leu Glu Leu Ala Gly Pro Pro Gly His Ser Leu Gly Lys
        595                 600                 605

Glu Gln Gln Glu Gly Leu Ala Glu Ala Val Leu Glu Ala Leu Ala Ser
    610                 615                 620

Arg Gly Gly Thr Gly Arg Cys Tyr Phe His Gly Pro Ser Ile Thr Thr
625                 630                 635                 640

Ser Leu Val Phe Thr Val His Met Trp Lys Ser Pro Gly Cys Gln Gly
                645                 650                 655

Pro Ser Val Ala Thr Leu His Lys Ala Leu Thr Leu Thr Leu Gln Lys
            660                 665                 670

Lys Pro Leu Glu Val Tyr His Gly Gly Ala Asn Phe Thr Thr Gln Pro
        675                 680                 685

Ser Lys Leu Leu Val Thr Ser Asp His Asn Pro Ser Met Thr His Leu
    690                 695                 700

Arg Leu Ser Met Gly Leu Cys Leu Met Leu Leu Ile Leu Val Gly Val
705                 710                 715                 720

Met Gly Thr Thr Ala Tyr Gln Lys Arg Ala Thr Leu Pro Val Arg Pro
                725                 730                 735

Ser Ala Ser Tyr His Ser Pro Glu Leu His Ser Thr Arg Val Pro Val
            740                 745                 750

Arg Gly Ile Arg Glu Val
        755

<210> SEQ ID NO 31
<211> LENGTH: 2277
<212> TYPE: DNA
<213> ORGANISM: Homo sapiens
<220> FEATURE:
<221> NAME/KEY: CDS
<222> LOCATION: (1)...(2277)

<400> SEQUENCE: 31 atg ctg ctg ctg ccg ctg ctg ctg ctg ctg ccg cca cta gtc ctc agg     48
Met Leu Leu Leu Pro Leu Leu Leu Leu Leu Pro Pro Leu Val Leu Arg
 1               5                   10                  15 gtt gct gca agc cga tgt cta cat gat gag aca cag aag tct gtg agc     96
Val Ala Ala Ser Arg Cys Leu His Asp Glu Thr Gln Lys Ser Val Ser
            20                  25                  30 ctt ctc agg ccc cct ttc tcc caa ctc ccc tca aaa tct cgc tct tcc    144
Leu Leu Arg Pro Pro Phe Ser Gln Leu Pro Ser Lys Ser Arg Ser Ser
        35                  40                  45 tcc ctc acc ctc cct agc tcc cgt gat cct caa ccc cta cga atc caa    192
Ser Leu Thr Leu Pro Ser Ser Arg Asp Pro Gln Pro Leu Arg Ile Gln
    50                  55                  60 agc tgc tat cta gga gat cat ata tca gat gga gct tgg gat cct gag    240
Ser Cys Tyr Leu Gly Asp His Ile Ser Asp Gly Ala Trp Asp Pro Glu
65                  70                  75                  80 gga gaa ggg atg aga ggg gga tcc cga gcc ctg gcc gca gtg aga gag    288
Gly Glu Gly Met Arg Gly Gly Ser Arg Ala Leu Ala Ala Val Arg Glu
                85                  90                  95 gcc act cag cga atc cag gct gtt cta gca gtc cct cca gtg caa gga    336
Ala Thr Gln Arg Ile Gln Ala Val Leu Ala Val Pro Pro Val Gln Gly
            100                 105                 110 ccc ctg ctt ctg agt cga gac cct gca cag tat tgc cac gct gtc tgg    384
```

-continued

```
            Pro Leu Leu Leu Ser Arg Asp Pro Ala Gln Tyr Cys His Ala Val Trp
                    115                 120                 125 gga gac cca gat agc cca aac tac cac agg tgc agc ctc ttg aac cca      432
Gly Asp Pro Asp Ser Pro Asn Tyr His Arg Cys Ser Leu Leu Asn Pro
130                 135                 140 gga tac aaa gga gag agt tgc ctg ggg gca aag att cct gac acc cat      480
Gly Tyr Lys Gly Glu Ser Cys Leu Gly Ala Lys Ile Pro Asp Thr His
145                 150                 155                 160 ctt cgc ggt tat gcc ttg tgg ccg gag cag ggt ccc cca caa ctg gtc      528
Leu Arg Gly Tyr Ala Leu Trp Pro Glu Gln Gly Pro Pro Gln Leu Val
                165                 170                 175 cag cca gat ggg cct ggg gtc caa aac act gat ttt ctc ctg tat gtg      576
Gln Pro Asp Gly Pro Gly Val Gln Asn Thr Asp Phe Leu Leu Tyr Val
            180                 185                 190 cga gtt gct cac act tcc aag tgc cac caa gag aca gtc tca ctc tgt      624
Arg Val Ala His Thr Ser Lys Cys His Gln Glu Thr Val Ser Leu Cys
        195                 200                 205 tgc cca ggc tgg agt aca gcg gcc caa tca cag ctc acc gca gcc ttg      672
Cys Pro Gly Trp Ser Thr Ala Ala Gln Ser Gln Leu Thr Ala Ala Leu
    210                 215                 220 acc tcc tgg gct cag ccc tct gtc ata gcc tat gct gcc tgc tgc cag      720
Thr Ser Trp Ala Gln Pro Ser Val Ile Ala Tyr Ala Ala Cys Cys Gln
225                 230                 235                 240 ctg gac tca gaa gac agg ccc ctc gct ggt acc att gtc tac tgt gcc      768
Leu Asp Ser Glu Asp Arg Pro Leu Ala Gly Thr Ile Val Tyr Cys Ala
                245                 250                 255 caa cat ctc acc agc ccc agc ctc agc cac agt gac atc gtc atg gcc      816
Gln His Leu Thr Ser Pro Ser Leu Ser His Ser Asp Ile Val Met Ala
            260                 265                 270 aca tta cat gaa ttg ctc cat gcc ttg ggt ttc tct gga cag ctc ttc      864
Thr Leu His Glu Leu Leu His Ala Leu Gly Phe Ser Gly Gln Leu Phe
        275                 280                 285 aag aaa tgg cga gac tgc ccc tca gga ttc agt gtt aga gag aac tgt      912
Lys Lys Trp Arg Asp Cys Pro Ser Gly Phe Ser Val Arg Glu Asn Cys
    290                 295                 300 tct aca agg caa caa gtg aca agg caa gat gag tgg gga caa ctg ctt      960
Ser Thr Arg Gln Gln Val Thr Arg Gln Asp Glu Trp Gly Gln Leu Leu
305                 310                 315                 320 ctc acc acc cca gct gtt agc ctc agc ctg gcc aaa cac ttg gga gtg     1008
Leu Thr Thr Pro Ala Val Ser Leu Ser Leu Ala Lys His Leu Gly Val
                325                 330                 335 tcg ggg gct tcc ctg ggt gtt ccc ttg gaa gaa gag gag ggc ctt ctg     1056
Ser Gly Ala Ser Leu Gly Val Pro Leu Glu Glu Glu Glu Gly Leu Leu
            340                 345                 350 tcc tcg cac tgg gag gcc aga cta ctc cag ggt tct tta atg act gct     1104
Ser Ser His Trp Glu Ala Arg Leu Leu Gln Gly Ser Leu Met Thr Ala
        355                 360                 365 acc ttt gat gga gcc cag cgc act cga ctc gac cca atc acc ctc gct     1152
Thr Phe Asp Gly Ala Gln Arg Thr Arg Leu Asp Pro Ile Thr Leu Ala
    370                 375                 380 gcc ttc aaa gac tca ggc tgg tac cag gtc aac cac agc gct gca gag     1200
Ala Phe Lys Asp Ser Gly Trp Tyr Gln Val Asn His Ser Ala Ala Glu
385                 390                 395                 400 gag ctg ttg tgg ggc cag gga tct ggc cca gaa ttt ggc ttg gtg acc     1248
Glu Leu Leu Trp Gly Gln Gly Ser Gly Pro Glu Phe Gly Leu Val Thr
                405                 410                 415 aca tgt ggg act ggc tcc tca gac ttc ttc tgt act ggc agt ggg ctg     1296
Thr Cys Gly Thr Gly Ser Ser Asp Phe Phe Cys Thr Gly Ser Gly Leu
            420                 425                 430
```

-continued

| | |
|---|---|
| ggc tgc cac tac ctg cac ctg gac aag gga agc tgc tcc tca gac ccc<br>Gly Cys His Tyr Leu His Leu Asp Lys Gly Ser Cys Ser Ser Asp Pro<br>435                    440                    445 | 1344 |
| atg ctg gaa ggc tgc cgc atg tac aag ccc tta gcc aat ggg agt gaa<br>Met Leu Glu Gly Cys Arg Met Tyr Lys Pro Leu Ala Asn Gly Ser Glu<br>450                    455                    460 | 1392 |
| tgc tgg aag aag gaa aac gga ttc cct gct ggg gtg gat aat ccc cat<br>Cys Trp Lys Lys Glu Asn Gly Phe Pro Ala Gly Val Asp Asn Pro His<br>465                    470                    475                    480 | 1440 |
| ggg gag atc tac cat ccc cag agc cgt tgc ttc ttt gcc aac ctc act<br>Gly Glu Ile Tyr His Pro Gln Ser Arg Cys Phe Phe Ala Asn Leu Thr<br>                    485                    490                    495 | 1488 |
| tca cag ctg ctc cct ggg gat aag ccc agg cat cct tct ctt acc cca<br>Ser Gln Leu Leu Pro Gly Asp Lys Pro Arg His Pro Ser Leu Thr Pro<br>          500                    505                    510 | 1536 |
| cac ctc aag gaa gca gag ctc atg ggc cgc tgc tac tta cat caa tgc<br>His Leu Lys Glu Ala Glu Leu Met Gly Arg Cys Tyr Leu His Gln Cys<br>          515                    520                    525 | 1584 |
| aca ggg agg gga gct tac aag gtg cag gtg gag ggc tcg cct tgg gtc<br>Thr Gly Arg Gly Ala Tyr Lys Val Gln Val Glu Gly Ser Pro Trp Val<br>530                    535                    540 | 1632 |
| cca tgc ctt cct gga aag gtt ata cag ata cct ggg tac tat ggt ctt<br>Pro Cys Leu Pro Gly Lys Val Ile Gln Ile Pro Gly Tyr Tyr Gly Leu<br>545                    550                    555                    560 | 1680 |
| ctc ttc tgt ccc cgg ggt cgg ctg tgt cag act aat gaa ggt atc aat<br>Leu Phe Cys Pro Arg Gly Arg Leu Cys Gln Thr Asn Glu Gly Ile Asn<br>                    565                    570                    575 | 1728 |
| gct gtt act tcc cca cct gtg agt ctt tca acc cca gat cca cta ttc<br>Ala Val Thr Ser Pro Pro Val Ser Leu Ser Thr Pro Asp Pro Leu Phe<br>          580                    585                    590 | 1776 |
| cag ctc tct tta gaa tta gct ggg cct cca gga cac tct ctg ggg aag<br>Gln Leu Ser Leu Glu Leu Ala Gly Pro Pro Gly His Ser Leu Gly Lys<br>          595                    600                    605 | 1824 |
| gaa cag caa gaa ggg cta gct gaa gca gta ctg gag gct ttg gcg agc<br>Glu Gln Gln Glu Gly Leu Ala Glu Ala Val Leu Glu Ala Leu Ala Ser<br>610                    615                    620 | 1872 |
| aga ggc ggc act ggc agg tgc tat ttc cat ggc cca tca att acc act<br>Arg Gly Gly Thr Gly Arg Cys Tyr Phe His Gly Pro Ser Ile Thr Thr<br>625                    630                    635                    640 | 1920 |
| agc ttg gtg ttt act gtg cat atg tgg aag tcc cct ggc tgc caa ggg<br>Ser Leu Val Phe Thr Val His Met Trp Lys Ser Pro Gly Cys Gln Gly<br>                    645                    650                    655 | 1968 |
| cct tca gtt gct aca ctg cac aag gcc ctg act ctg act ctc cag aaa<br>Pro Ser Val Ala Thr Leu His Lys Ala Leu Thr Leu Thr Leu Gln Lys<br>          660                    665                    670 | 2016 |
| aaa ccc cta gaa gtg tat cat gga gga gcc aac ttt acc aca caa ccc<br>Lys Pro Leu Glu Val Tyr His Gly Gly Ala Asn Phe Thr Thr Gln Pro<br>          675                    680                    685 | 2064 |
| agc aag ttg ctg gtt act tca gac cat aat ccc tcc atg acc cac cta<br>Ser Lys Leu Leu Val Thr Ser Asp His Asn Pro Ser Met Thr His Leu<br>          690                    695                    700 | 2112 |
| agg ctg tcc atg gga ctc tgc cta atg ctg atc ctg gtg ggt gta<br>Arg Leu Ser Met Gly Leu Cys Leu Met Leu Ile Leu Val Gly Val<br>705                    710                    715                    720 | 2160 |
| atg gga acc aca gcc tac cag aaa aga gcc act ctt cct gtg aga cca<br>Met Gly Thr Thr Ala Tyr Gln Lys Arg Ala Thr Leu Pro Val Arg Pro<br>                    725                    730                    735 | 2208 |
| tct gcc tct tac cat tca cca gag ctc cac agc aca agg gtc cca gtt<br>Ser Ala Ser Tyr His Ser Pro Glu Leu His Ser Thr Arg Val Pro Val<br>          740                    745                    750 | 2256 |

```
aga gga ata agg gag gtg tga                                          2277
Arg Gly Ile Arg Glu Val *
        755
```

<210> SEQ ID NO 32
<211> LENGTH: 13
<212> TYPE: PRT
<213> ORGANISM: Artificial Sequence
<220> FEATURE:
<223> OTHER INFORMATION: Pfam consensus sequence

<400> SEQUENCE: 32

Gly Glu Gly Val Ser Asn Thr Asp Phe Val Leu Tyr Val
1               5                   10

<210> SEQ ID NO 33
<211> LENGTH: 65
<212> TYPE: PRT
<213> ORGANISM: Artificial Sequence
<220> FEATURE:
<223> OTHER INFORMATION: Pfam consensus sequence

<400> SEQUENCE: 33

Pro Gly Val Leu Ala Trp Ala Thr Thr Cys Gln Val Phe Ser Asp Phe
1               5                   10                  15

Gly Arg Pro Ala Val Gly Val Ile Asn Ile Pro Ala Ala Asn Ile Thr
            20                  25                  30

Ser Arg Asn His Tyr Asp Gln Leu Val Thr Arg Val Val Thr His Glu
        35                  40                  45

Ile Ala His Ala Leu Gly Phe Ser Val Gly Leu Tyr Thr Phe Phe Glu
    50                  55                  60

Glu
65

<210> SEQ ID NO 34
<211> LENGTH: 55
<212> TYPE: PRT
<213> ORGANISM: Artificial Sequence
<220> FEATURE:
<223> OTHER INFORMATION: Pfam consensus sequence

<400> SEQUENCE: 34

Ser His Trp Lys Lys Arg Asn Ala Lys Asp Glu Leu Met Ala Gly Ala
1               5                   10                  15

Ala Gly Ser Asp Ala Gly Tyr Tyr Ser Ala Leu Thr Met Ala Val Phe
            20                  25                  30

Glu Asp Leu Gly Phe Tyr Lys Ala Asp Phe Ser Lys Ala Glu Asp Met
        35                  40                  45

Pro Trp Gly Lys Asn Ala Gly
    50                  55

<210> SEQ ID NO 35
<211> LENGTH: 37
<212> TYPE: PRT
<213> ORGANISM: Artificial Sequence
<220> FEATURE:
<223> OTHER INFORMATION: Pfam consensus sequence

<400> SEQUENCE: 35

Ala Ala Leu Cys Ala Asn Val Lys Cys Asp Thr Ala Thr Arg Thr Tyr
1               5                   10                  15

Ser Val Gln Val Tyr Gly Ser Ser Gly Tyr Tyr Pro Cys Thr Pro Gly

-continued

```
                    20                  25                  30
Leu Arg Val Glu Leu
            35

<210> SEQ ID NO 36
<211> LENGTH: 1485
<212> TYPE: DNA
<213> ORGANISM: Homo sapiens
<220> FEATURE:
<221> NAME/KEY: CDS
<222> LOCATION: (255)...(1133)

<400> SEQUENCE: 36
acaggctgta tcttctcaaa atttcattga ttgggctcaa tgaagtcacc tgcaacatrg      60
tagtagagta gggctcccct tcacacgct tttggaagg cttcttcaag tcacatttc      120 cgttcggtct tcctttgccc tgtgtttgcr gtcatcatgt gagggctac ctatgttcag      180 cccaggcaac ccacagggag agagggcaga gcggggagat ggcccctggt gagcactgag      240 gctcccttc aagg atg gcg ctg gcg gct ttg atg atc gcc ctc ggc agc        290
             Met Ala Leu Ala Ala Leu Met Ile Ala Leu Gly Ser
               1               5                  10 ctc ggc ctc cac acc tgg cag gcc cag gct gtt ccc acc atc ctg ccc        338
Leu Gly Leu His Thr Trp Gln Ala Gln Ala Val Pro Thr Ile Leu Pro
        15                  20                  25 ctg ggc ctg gct cca gac acc ttt gac gat acc tat gtg ggt tgt gca        386
Leu Gly Leu Ala Pro Asp Thr Phe Asp Asp Thr Tyr Val Gly Cys Ala
    30                  35                  40 gag gag atg gag gag aag gca gcc ccc ctg cta aag gag gaa atg gcc        434
Glu Glu Met Glu Glu Lys Ala Ala Pro Leu Leu Lys Glu Glu Met Ala
45                  50                  55                  60 cac cat gcc ctg ctg cgg gaa tcc tgg gag gca gcc cag gag acc tgg        482
His His Ala Leu Leu Arg Glu Ser Trp Glu Ala Ala Gln Glu Thr Trp
                65                  70                  75 gag gac aag cgt cga ggg ctt acc ttg ccc cct ggc ttc aaa gcc cag        530
Glu Asp Lys Arg Arg Gly Leu Thr Leu Pro Pro Gly Phe Lys Ala Gln
            80                  85                  90 aat gga ata gcc att atg gtc tac acc aac tca tcg aac acc ttg tac        578
Asn Gly Ile Ala Ile Met Val Tyr Thr Asn Ser Ser Asn Thr Leu Tyr
        95                  100                 105 tgg gag ttg aat cag gcc gtg cgg acg ggc gga ggc tcc cgg gag ctc        626
Trp Glu Leu Asn Gln Ala Val Arg Thr Gly Gly Gly Ser Arg Glu Leu
    110                 115                 120 tac atg agg cac ttt ccc ttc aag gcc ctg cat ttc tac ctg atc cgg        674
Tyr Met Arg His Phe Pro Phe Lys Ala Leu His Phe Tyr Leu Ile Arg
125                 130                 135                 140 gcc ctg cag ctg ctg cga ggc agt ggg ggc tgc agc agg gga cct ggg        722
Ala Leu Gln Leu Leu Arg Gly Ser Gly Gly Cys Ser Arg Gly Pro Gly
                145                 150                 155 gag gtg gtg ttc cga ggt gtg ggc agc ctt cgc ttt gaa ccc aag agg        770
Glu Val Val Phe Arg Gly Val Gly Ser Leu Arg Phe Glu Pro Lys Arg
            160                 165                 170 ctg ggg gac tct gtc cgc ttg ggc cag ttt gcc tcc agc tcc ctg gat        818
Leu Gly Asp Ser Val Arg Leu Gly Gln Phe Ala Ser Ser Ser Leu Asp
        175                 180                 185 aag gca gtg gcc cac aga ttt ggt aat gcc acc ctc ttc tct cta aca        866
Lys Ala Val Ala His Arg Phe Gly Asn Ala Thr Leu Phe Ser Leu Thr
    190                 195                 200 act tgc ttt ggg gcc cct ata cag gcc ttc tct gtc ttt ccc aag gag        914
Thr Cys Phe Gly Ala Pro Ile Gln Ala Phe Ser Val Phe Pro Lys Glu
205                 210                 215                 220
```

-continued

| | |
|---|---|
| cgc gag gtg ctg att ccc ccc cat gaa gtc ttt ttg gtt acc aga ttc<br>Arg Glu Val Leu Ile Pro Pro His Glu Val Phe Leu Val Thr Arg Phe<br>                225                          230                    235 | 962 |
| tct cag gat gga gcc cag agc ttg gtg act ctc tgg agc tat aat cag<br>Ser Gln Asp Gly Ala Gln Ser Leu Val Thr Leu Trp Ser Tyr Asn Gln<br>            240                          245                    250 | 1010 |
| acc tgt agc cat ttt aac tgc gcc tat ctg ggt ggg gag aag agg cgg<br>Thr Cys Ser His Phe Asn Cys Ala Tyr Leu Gly Gly Glu Lys Arg Arg<br>               255                        260                    265 | 1058 |
| ggc tgt gtg tct gcg cca gga gcc ctg gga acg ggt gac ctt cat atg<br>Gly Cys Val Ser Ala Pro Gly Ala Leu Gly Thr Gly Asp Leu His Met<br>    270                          275                    280 | 1106 |
| acg aag agg cac ctc cag cag cct tga gaagcaagaa catggttccg<br>Thr Lys Arg His Leu Gln Gln Pro *<br>285                        290 | 1153 |
| gacccagccc tagcagcctt ctccccaacc aggatgttgg cctggggagg ccacagcagg | 1213 |
| gctgagggaa ctctgctatg tgatggggac ttcctgggac aagcaaggaa agtactgagg | 1273 |
| cagccacttg attgaacggt gttgcaatgt ggagacatgg agttttattg aggtagctac | 1333 |
| gtgattaaat ggtattgcag tgtggadaaa dgrramwwmm wgggacaagc aaggaaagta | 1393 |
| ctgaggcagc cacttgattg aacggtgttg caatgtggag acatggagtt ttattgaggt | 1453 |
| agctacgtga ttaaatggta ttgcagtgtg ga | 1485 |

<210> SEQ ID NO 37
<211> LENGTH: 292
<212> TYPE: PRT
<213> ORGANISM: Homo sapiens

<400> SEQUENCE: 37

Met Ala Leu Ala Ala Leu Met Ile Ala Leu Gly Ser Leu Gly Leu His
1               5                   10                  15

Thr Trp Gln Ala Gln Ala Val Pro Thr Ile Leu Pro Leu Gly Leu Ala
            20                  25                  30

Pro Asp Thr Phe Asp Asp Thr Tyr Val Gly Cys Ala Glu Glu Met Glu
        35                  40                  45

Glu Lys Ala Ala Pro Leu Leu Lys Glu Glu Met Ala His His Ala Leu
    50                  55                  60

Leu Arg Glu Ser Trp Glu Ala Ala Gln Glu Thr Trp Glu Asp Lys Arg
65                  70                  75                  80

Arg Gly Leu Thr Leu Pro Pro Gly Phe Lys Ala Gln Asn Gly Ile Ala
                85                  90                  95

Ile Met Val Tyr Thr Asn Ser Ser Asn Thr Leu Tyr Trp Glu Leu Asn
            100                 105                 110

Gln Ala Val Arg Thr Gly Gly Gly Ser Arg Glu Leu Tyr Met Arg His
        115                 120                 125

Phe Pro Phe Lys Ala Leu His Phe Tyr Leu Ile Arg Ala Leu Gln Leu
    130                 135                 140

Leu Arg Gly Ser Gly Cys Ser Arg Gly Pro Gly Glu Val Val Phe
145                 150                 155                 160

Arg Gly Val Gly Ser Leu Arg Phe Glu Pro Lys Arg Leu Gly Asp Ser
                165                 170                 175

Val Arg Leu Gly Gln Phe Ala Ser Ser Leu Asp Lys Ala Val Ala
            180                 185                 190

His Arg Phe Gly Asn Ala Thr Leu Phe Ser Leu Thr Thr Cys Phe Gly
        195                 200                 205

```
Ala Pro Ile Gln Ala Phe Ser Val Phe Pro Lys Glu Arg Glu Val Leu
    210                 215                 220

Ile Pro Pro His Glu Val Phe Leu Val Thr Arg Phe Ser Gln Asp Gly
225                 230                 235                 240

Ala Gln Ser Leu Val Thr Leu Trp Ser Tyr Asn Gln Thr Cys Ser His
                245                 250                 255

Phe Asn Cys Ala Tyr Leu Gly Gly Glu Lys Arg Arg Gly Cys Val Ser
                260                 265                 270

Ala Pro Gly Ala Leu Gly Thr Gly Asp Leu His Met Thr Lys Arg His
                275                 280                 285

Leu Gln Gln Pro
        290

<210> SEQ ID NO 38
<211> LENGTH: 879
<212> TYPE: DNA
<213> ORGANISM: Homo sapiens
<220> FEATURE:
<221> NAME/KEY: CDS
<222> LOCATION: (1)...(879)

<400> SEQUENCE: 38
```

| | | |
|---|---|---|
| atg gcg ctg gcg gct ttg atg atc gcc ctc ggc agc ctc ggc ctc cac<br>Met Ala Leu Ala Ala Leu Met Ile Ala Leu Gly Ser Leu Gly Leu His<br>1                    5                      10                    15 | | 48 |
| acc tgg cag gcc cag gct gtt ccc acc atc ctg ccc ctg ggc ctg gct<br>Thr Trp Gln Ala Gln Ala Val Pro Thr Ile Leu Pro Leu Gly Leu Ala<br>                  20                    25                    30 | | 96 |
| cca gac acc ttt gac gat acc tat gtg ggt tgt gca gag gag atg gag<br>Pro Asp Thr Phe Asp Asp Thr Tyr Val Gly Cys Ala Glu Glu Met Glu<br>                35                    40                    45 | | 144 |
| gag aag gca gcc ccc cta cta aag gag gaa atg gcc cac cat gcc ctg<br>Glu Lys Ala Ala Pro Leu Leu Lys Glu Glu Met Ala His His Ala Leu<br>      50                    55                    60 | | 192 |
| ctg cgg gaa tcc tgg gag gca gcc cag gag acc tgg gag gac aag cgt<br>Leu Arg Glu Ser Trp Glu Ala Ala Gln Glu Thr Trp Glu Asp Lys Arg<br>65                    70                    75                    80 | | 240 |
| cga ggg ctt acc ttg ccc cct ggc ttc aaa gcc cag aat gga ata gcc<br>Arg Gly Leu Thr Leu Pro Pro Gly Phe Lys Ala Gln Asn Gly Ile Ala<br>                  85                    90                    95 | | 288 |
| att atg gtc tac acc aac tca tcg aac acc ttg tac tgg gag ttg aat<br>Ile Met Val Tyr Thr Asn Ser Ser Asn Thr Leu Tyr Trp Glu Leu Asn<br>                100                    105                    110 | | 336 |
| cag gcc gtg cgg acg ggc gga ggc tcc cgg gag ctc tac atg agg cac<br>Gln Ala Val Arg Thr Gly Gly Gly Ser Arg Glu Leu Tyr Met Arg His<br>            115                    120                    125 | | 384 |
| ttt ccc ttc aag gcc ctg cat ttc tac ctg atc cgg gcc ctg cag ctg<br>Phe Pro Phe Lys Ala Leu His Phe Tyr Leu Ile Arg Ala Leu Gln Leu<br>130                    135                    140 | | 432 |
| ctg cga ggc agt ggg ggc tgc agc agg gga cct ggg gag gtg gtg ttc<br>Leu Arg Gly Ser Gly Gly Cys Ser Arg Gly Pro Gly Glu Val Val Phe<br>145                    150                    155                    160 | | 480 |
| cga ggt gtg ggc agc ctt cgc ttt gaa ccc aag agg ctg ggg gac tct<br>Arg Gly Val Gly Ser Leu Arg Phe Glu Pro Lys Arg Leu Gly Asp Ser<br>                  165                    170                    175 | | 528 |
| gtc cgc ttg ggc cag ttt gcc tcc agc tcc ctg gat aag gca gtg gcc<br>Val Arg Leu Gly Gln Phe Ala Ser Ser Ser Leu Asp Lys Ala Val Ala<br>            180                    185                    190 | | 576 |
| cac aga ttt ggt aat gcc acc ctc ttc tct cta aca act tgc ttt ggg | | 624 |

```
His Arg Phe Gly Asn Ala Thr Leu Phe Ser Leu Thr Thr Cys Phe Gly
        195                 200                 205 gcc cct ata cag gcc ttc tct gtc ttt ccc aag gag cgc gag gtg ctg      672
Ala Pro Ile Gln Ala Phe Ser Val Phe Pro Lys Glu Arg Glu Val Leu
210                 215                 220 att ccc ccc cat gaa gtc ttt ttg gtt acc aga ttc tct cag gat gga      720
Ile Pro Pro His Glu Val Phe Leu Val Thr Arg Phe Ser Gln Asp Gly
225                 230                 235                 240 gcc cag agc ttg gtg act ctc tgg agc tat aat cag acc tgt agc cat      768
Ala Gln Ser Leu Val Thr Leu Trp Ser Tyr Asn Gln Thr Cys Ser His
            245                 250                 255 ttt aac tgc gcc tat ctg ggt ggg gag aag agg cgg ggc tgt gtg tct      816
Phe Asn Cys Ala Tyr Leu Gly Gly Glu Lys Arg Arg Gly Cys Val Ser
            260                 265                 270 gcg cca gga gcc ctg gga acg ggt gac ctt cat atg acg aag agg cac      864
Ala Pro Gly Ala Leu Gly Thr Gly Asp Leu His Met Thr Lys Arg His
            275                 280                 285 ctc cag cag cct tga                                                  879
Leu Gln Gln Pro  *
            290

<210> SEQ ID NO 39
<211> LENGTH: 296
<212> TYPE: PRT
<213> ORGANISM: Artificial Sequence
<220> FEATURE:
<223> OTHER INFORMATION: Pfam consensus sequence

<400> SEQUENCE: 39

Met Pro Ala Leu His Phe Val Leu Leu Leu Ser Val Gly Leu Leu Leu
 1               5                  10                  15

Ser Thr Gln Ala Leu Ser Ser Ala Ile Gln Gln Lys Asp Gly Leu Val
            20                  25                  30

Lys Glu Leu Val Leu Asp Met Ala Pro Asn Ser Phe Asp Asp Gln Tyr
        35                  40                  45

Leu Gly Cys Val Asp Arg Met Glu Ala Lys Tyr Leu Pro Gln Leu Leu
    50                  55                  60

Lys Glu Glu Phe Ala Ala Asn Glu Val Leu Ala Val Gly Trp Glu Ser
65                  70                  75                  80

Ala Lys Ala Lys Trp Gln Glu Arg Lys Ala Arg Gly Ser Val Trp Gly
                85                  90                  95

Ser Leu Pro Tyr Pro Ser Pro Pro Met Gly Phe Lys Asp Glu His Gly
            100                 105                 110

Ile Ala Leu Leu Ala Tyr Thr Ala Ser Ser Gln Glu Gln Thr Pro Leu
        115                 120                 125

Tyr Arg Glu Phe Asn Glu Ala Val Arg Glu Ala Gly Arg Ser Arg Glu
    130                 135                 140

Asp Tyr Leu His His Phe His Phe Lys Ala Leu His Tyr Leu Thr
145                 150                 155                 160

Arg Ala Leu Gln Leu Leu Arg Ser Ser Gly Gly Cys Gln Pro Gly Pro
                165                 170                 175

Cys His Val Val Tyr Arg Gly Val Arg Gly Leu Arg Phe Arg Pro Gln
            180                 185                 190

Gly Gly Gly Ala Ser Val Arg Phe Gly Gln Phe Thr Ser Ser Ser Leu
        195                 200                 205

Lys Lys Lys Val Ala Gln Ser Ser Glu Phe Phe Phe Gly Gln Asp Thr
    210                 215                 220
```

```
Phe Phe Ser Ile Lys Thr Cys Leu Gly Val Pro Ile Lys Ala Phe Ser
225                 230                 235                 240

Phe Phe Pro Ser Glu Glu Val Leu Ile Pro Pro Phe Glu Val Phe
                245                 250                 255

Gln Val Ile Asn Thr Ser Arg Pro Thr Ala Gly Ser Ala Ile Ile Leu
                260                 265                 270

Leu Ser Ser Lys Gly Lys Cys Ser Thr Tyr Asn Cys Glu Tyr Leu Lys
            275                 280                 285

Gly Lys Lys Thr Glu Asn Cys Ile
    290                 295

<210> SEQ ID NO 40
<211> LENGTH: 2183
<212> TYPE: DNA
<213> ORGANISM: Homo sapiens
<220> FEATURE:
<221> NAME/KEY: CDS
<222> LOCATION: (782)...(1696)
<220> FEATURE:
<221> NAME/KEY: misc_feature
<222> LOCATION: 2134, 2147, 2153
<223> OTHER INFORMATION: n = A,T,C or G

<400> SEQUENCE: 40
gccgagctcg aattgcggcc gcatgcatgc ataagcttgc tcgagtctag attttttttt      60
tttttttttt gaggttgatc aaaaacctttt attctggtcc tcatcattca ggaagccact    120
tatgcagaac actttcttca tctctgctct aagcagcagc agctgcatcc aggcttgata    180
tggaagacag acagaaatag tggaagacct tgcagagaag agctaattga tgagatctct    240
gcttatcccg gcataggtga aggcagaaca ggaagagtgt gtgtaagtgc aaagactccg    300
ttcttcaaag ctgaggcctg tgcagagggg tgaactgaag gcttcagatg aaggctcaca    360
aaactgcccc gctcggcaat caatctaaag taccttccag aaaagcaaat tcatccacag    420
cttctattgc attatccaag tctctcctct gaagggtttt ccttttttccc tgctgagcgc    480 aacagtaggc atcttttgca atggtctcca caaacagttc cgcggctcgt gccagaatga    540
agatggcttc ctgtcccgct agcgtcacgt cgggatctgc cttcaccaag gccttcactc    600
gcgccagagg caacctcgag agacgagccc caggcacact cgttgggggcc tggggctgcg    660 aggccgctgc ctccccagca ggtacctcct cctctcgggg cgtcccgctt cctgccgccg    720
ccgccgcgtc gacgcggctg cttgcctacc ggagtgtgcg ccggcacctg ccgccggaga    780 c atg ttg caa aaa ccg agg aac cgg ggc cgc tct ggc ggc cag gcc gag    829
  Met Leu Gln Lys Pro Arg Asn Arg Gly Arg Ser Gly Gly Gln Ala Glu
   1               5                   10                  15 agg gac aga gac tgg agc cat agc gga aac ccc ggg gct tcg cgg gcc      877
Arg Asp Arg Asp Trp Ser His Ser Gly Asn Pro Gly Ala Ser Arg Ala
            20                  25                  30 ggg gaa gac gcc cgg gtt ctc aga gac ggc ttt gcc gag gag gcc ccg      925
Gly Glu Asp Ala Arg Val Leu Arg Asp Gly Phe Ala Glu Glu Ala Pro
        35                  40                  45 agc acg tcc cgc ggg ccg ggc ggc tcg cag ggg tcg cag ggc ccc tcg      973
Ser Thr Ser Arg Gly Pro Gly Gly Ser Gln Gly Ser Gln Gly Pro Ser
    50                  55                  60 cct cag ggc gcc cgc cgg gcc cag gcc gcc ccc gcc gtg ggg ccc agg     1021
Pro Gln Gly Ala Arg Arg Ala Gln Ala Ala Pro Ala Val Gly Pro Arg
65                  70                  75                  80 agc cag aag cag ctg gag ctg aaa gtg tcc gag ctg gtg cag ttc ttg     1069
Ser Gln Lys Gln Leu Glu Leu Lys Val Ser Glu Leu Val Gln Phe Leu
                85                  90                  95
```

```
ctg att aaa gac cag aag aag att ccg atc aag cgg gcc gac ata ctg    1117
Leu Ile Lys Asp Gln Lys Lys Ile Pro Ile Lys Arg Ala Asp Ile Leu
        100                 105                 110 aag cac gtc atc ggg gac tac aag gac atc ttc ccc gac ctc ttc aaa    1165
Lys His Val Ile Gly Asp Tyr Lys Asp Ile Phe Pro Asp Leu Phe Lys
            115                 120                 125 cgg gcc gcc gag cgc ctc cag tac gtc ttc ggg tat aag ctg gtg gaa    1213
Arg Ala Ala Glu Arg Leu Gln Tyr Val Phe Gly Tyr Lys Leu Val Glu
    130                 135                 140 ctt gaa ccc aag agc aac act tac atc ctc atc aac acc ctg gag cct    1261
Leu Glu Pro Lys Ser Asn Thr Tyr Ile Leu Ile Asn Thr Leu Glu Pro
145                 150                 155                 160 gtg gag gag gat gcc gag atg agg ggt gac caa ggc acg ccc act acg    1309
Val Glu Glu Asp Ala Glu Met Arg Gly Asp Gln Gly Thr Pro Thr Thr
                165                 170                 175 ggc ctc ctg atg atc gtc tta ggg ctc atc ttt atg aag ggc aac acc    1357
Gly Leu Leu Met Ile Val Leu Gly Leu Ile Phe Met Lys Gly Asn Thr
        180                 185                 190 atc aag gaa act gaa gcc tgg gac ttt ctg cgg cgc tta ggg gtc tac    1405
Ile Lys Glu Thr Glu Ala Trp Asp Phe Leu Arg Arg Leu Gly Val Tyr
            195                 200                 205 ccc acc aag aag cat tta att ttc gga gat cca aag aaa ctc att act    1453
Pro Thr Lys Lys His Leu Ile Phe Gly Asp Pro Lys Lys Leu Ile Thr
    210                 215                 220 gag gac ttt gtg cga cag cgt tac ctg gaa tac cgg cgg ata ccc cac    1501
Glu Asp Phe Val Arg Gln Arg Tyr Leu Glu Tyr Arg Arg Ile Pro His
225                 230                 235                 240 acc gac ccc gtc gac tac gaa ttc cag tgg ggc ccg cga acc aac ctg    1549
Thr Asp Pro Val Asp Tyr Glu Phe Gln Trp Gly Pro Arg Thr Asn Leu
                245                 250                 255 gaa acc agc aag atg aaa gtt ctt aag ttt gtg gcc aag gtc cat aat    1597
Glu Thr Ser Lys Met Lys Val Leu Lys Phe Val Ala Lys Val His Asn
        260                 265                 270 caa gac ccc aag gac tgg cca gcg cag tac tgt gag gct ttg gca gat    1645
Gln Asp Pro Lys Asp Trp Pro Ala Gln Tyr Cys Glu Ala Leu Ala Asp
            275                 280                 285 gag gag aac agg gcc aga cct cag cct agt ggc cca gct cca tcc tct    1693
Glu Glu Asn Arg Ala Arg Pro Gln Pro Ser Gly Pro Ala Pro Ser Ser
    290                 295                 300 tga aaggtggatt cagagggacc cccgggacaa gggtctgaga cccaaaggca          1746
* cagtttagag gattggggga agggagaacg aacccaggga gcatattgct gtaaacgctt   1806
caatgtgtgt agcttttagga tgtgtttgca aagttttgtt tttttaatgt tgtgttattt  1866
tgctccagat tttcatctat aaacaaagga gcatttgttt tgattttact ctttttggta   1926 taaaaattt tgctagctta rtaaaacgaa ttggaaaact tgmytatkat ctggaacaga    1986
taatgcaaga aggracmcwt aagtaagttg yttttggtgc caagaaaata aaaaagctat   2046
tatcaaggtc tcctaactac cccagtttg taagggaaaa ataaaaaagt ttttattaaa    2106
atttaaaaaa aaaaaaaaar gggccggncg cttagactta ntcttanaga aaaaaacctt   2166 cccacaccttt cccctg                                                  2183

<210> SEQ ID NO 41
<211> LENGTH: 304
<212> TYPE: PRT
<213> ORGANISM: Homo sapiens

<400> SEQUENCE: 41
```

-continued

```
Met Leu Gln Lys Pro Arg Asn Arg Gly Arg Ser Gly Gly Gln Ala Glu
 1               5                  10                 15

Arg Asp Arg Asp Trp Ser His Ser Gly Asn Pro Gly Ala Ser Arg Ala
             20                  25                 30

Gly Glu Asp Ala Arg Val Leu Arg Asp Gly Phe Ala Glu Ala Pro
         35                  40                  45

Ser Thr Ser Arg Gly Pro Gly Ser Gln Gly Ser Gln Gly Pro Ser
 50                  55                  60

Pro Gln Gly Ala Arg Arg Ala Gln Ala Ala Pro Ala Val Gly Pro Arg
 65                  70                  75                  80

Ser Gln Lys Gln Leu Glu Leu Lys Val Ser Glu Leu Val Gln Phe Leu
                 85                  90                  95

Leu Ile Lys Asp Gln Lys Lys Ile Pro Ile Lys Arg Ala Asp Ile Leu
                100                 105                 110

Lys His Val Ile Gly Asp Tyr Lys Asp Ile Phe Pro Asp Leu Phe Lys
            115                 120                 125

Arg Ala Ala Glu Arg Leu Gln Tyr Val Phe Gly Tyr Lys Leu Val Glu
130                 135                 140

Leu Glu Pro Lys Ser Asn Thr Tyr Ile Leu Ile Asn Thr Leu Glu Pro
145                 150                 155                 160

Val Glu Glu Asp Ala Glu Met Arg Gly Asp Gln Gly Thr Pro Thr Thr
                165                 170                 175

Gly Leu Leu Met Ile Val Leu Gly Leu Ile Phe Met Lys Gly Asn Thr
            180                 185                 190

Ile Lys Glu Thr Glu Ala Trp Asp Phe Leu Arg Arg Leu Gly Val Tyr
        195                 200                 205

Pro Thr Lys Lys His Leu Ile Phe Gly Asp Pro Lys Lys Leu Ile Thr
210                 215                 220

Glu Asp Phe Val Arg Gln Arg Tyr Leu Glu Tyr Arg Arg Ile Pro His
225                 230                 235                 240

Thr Asp Pro Val Asp Tyr Glu Phe Gln Trp Gly Pro Arg Thr Asn Leu
                245                 250                 255

Glu Thr Ser Lys Met Lys Val Leu Lys Phe Val Ala Lys Val His Asn
            260                 265                 270

Gln Asp Pro Lys Asp Trp Pro Ala Gln Tyr Cys Glu Ala Leu Ala Asp
        275                 280                 285

Glu Glu Asn Arg Ala Arg Pro Gln Pro Ser Gly Pro Ala Pro Ser Ser
290                 295                 300
```

<210> SEQ ID NO 42
<211> LENGTH: 915
<212> TYPE: DNA
<213> ORGANISM: Homo sapiens

<400> SEQUENCE: 42

```
atgttgcaaa aaccgaggaa ccggggccgc tctggcggcc aggccgagag ggacagagac    60
tggagccata gcgaaacccc ggggcttcg cgggccgggg aagacgcccg ggttctcaga   120
gacggctttg ccgaggaggc cccgagcacg tcccgcgggc cggcggctc gcagggtcg    180
cagggcccct cgcctcaggg cgcccgccgg gccaggccg ccccgccgt ggggcccagg    240
agccagaagc agctggagct gaaagtgtcc gagctggtgc agttcttgct gattaaagac   300
cagaagaaga ttccgatcaa gcgggccgac atactgaagc acgtcatcgg ggactacaag   360
gacatcttcc ccgacctctt caaacgggcc gccgagcgcc tccagtacgt cttcgggtat   420
```

-continued

```
aagctggtgg aacttgaacc caagagcaac acttacatcc tcatcaacac cctggagcct    480
gtggaggagg atgccgagat gagggtgac caaggcacgc ccactacggg cctcctgatg    540
atcgtcttag ggctcatctt tatgaagggc aacaccatca aggaaactga agcctgggac    600
tttctgcggc gcttagggt ctaccccacc aagaagcatt taattttcgg agatccaaag    660
aaactcatta ctgaggactt tgtgcgacag cgttacctgg aataccggcg gatacccac    720 accgaccccg tcgactacga attccagtgg ggcccgcgaa ccaacctgga aaccagcaag    780
atgaaagttc ttaagtttgt ggccaaggtc cataatcaag accccaagga ctggccagcg    840
cagtactgtg aggctttggc agatgaggag aacagggcca gacctcagcc tagtggccca    900
gctccatcct cttga                                                     915
```

<210> SEQ ID NO 43
<211> LENGTH: 260
<212> TYPE: PRT
<213> ORGANISM: Artificial Sequence
<220> FEATURE:
<223> OTHER INFORMATION: MAGE family PFAM consensus domain

<400> SEQUENCE: 43

```
Arg Gly Gln Lys Ser Gln Leu Cys Lys Arg Glu Glu Arg Leu Gln Ala
 1               5                  10                  15

Arg Gly Glu Thr Gln Gly Leu Val Gly Ala Gln Ala Pro Ala Ala Glu
            20                  25                  30

Glu Gln Gln Glu Glu Ala Ser Ser Ser Pro Leu Gln Ser Pro Val
        35                  40                  45

Ser Leu Gly Val Ser Glu Asp Glu Ala Leu Val Leu Gly Thr Leu Glu
    50                  55                  60

Glu Val Pro Ala Ala Gly Gly Ser Pro Ser Pro Pro Gln Ser Pro Gln
65                  70                  75                  80

Gly Ser Pro Pro Glu Ser Pro Leu Ala Ser Ser Thr Ile Ser Ala Val
                85                  90                  95

Ala Ala Lys Thr Ser Trp Thr Gln Ser Asp Glu Gly Ser Ser Ser Gln
            100                 105                 110

Val Val Leu Gln Glu Glu Glu Gly Pro Ser Thr Ser Gln Ala Leu Thr
        115                 120                 125

Ser Thr Glu Ser Leu Phe Arg Asp Ala Leu Asp Glu Lys Val Ala Glu
    130                 135                 140

Leu Val Gln Phe Leu Leu Leu Lys Tyr Gln Met Lys Glu Pro Val Thr
145                 150                 155                 160

Lys Ala Glu Met Leu Lys Ser Val Ile Lys Asn Tyr Lys Asp His Phe
                165                 170                 175

Pro Glu Ile Phe Arg Lys Ala Ser Glu Phe Leu Glu Leu Val Phe Gly
            180                 185                 190

Ile Asp Leu Lys Glu Val Asp Pro Thr Gly His Ser Tyr Val Leu Val
        195                 200                 205

Thr Lys Leu Gly Leu Ser Tyr Asp Gly Leu Leu Ser Asp Asn Gln Gly
    210                 215                 220

Met Pro Lys Thr Gly Leu Leu Ile Ile Val Leu Gly Val Ile Phe Met
225                 230                 235                 240
```

```
Lys Gly Asn Cys Ala Pro Glu Glu Ile Trp Glu Val Leu Ser Val
            245                 250                 255
Leu Gly Val Tyr
            260
```

That invention claimed is:

1. An isolated polypeptide selected from the group consisting of:
   a) a polypeptide which is encoded by a nucleic acid molecule comprising a nucleotide sequence which is at least 95% identical to a nucleic acid comprising the nucleotide sequences of SEQ ID NO:14 or SEQ ID NO:16, wherein the polypeptide has aminotransferase activity;
   b) a polypeptide comprising a variant of the amino acid sequence of SEQ ID NO:15, wherein the variant is encoded by a nucleic acid molecule which hybridizes to a nucleic acid molecule comprising SEQ ID NO:14 or SEQ ID NO:16, or the complement thereof under conditions of 0.5 M sodium phosphate, 7% SDS at 65° C., followed by one or more washes at 0.2×SSC, 1% SDS at 65° C., wherein the variant has aminotransferase activity;
   c) a polypeptide comprising a fragment of the amino acid sequence of SEQ ID NO:15, wherein the fragment comprises at least 200 contiguous amino acids of SEQ ID NO:15, wherein the fragment has aminotransferase activity; and
   d) a polypeptide comprising an amino acid sequence at least 95% identical to SEQ ID NO:15, wherein the polypeptide has aminotransferase activity.

2. The polypeptide of claim 1 further comprising heterologous amino acid sequences.

3. A method for identifying a compound which binds to the polypeptide of claim 1 comprising the steps of:
   a) contacting an assay mixture comprising the polypeptide with a test compound; and
   b) determining whether the polypeptide binds to the test compound.

4. The method of claim 3, wherein the binding of the test compound to the polypeptide is detected by a method selected from the group consisting of:
   a) detection of binding by direct detecting of test compound/polypeptide binding; and,
   b) detection of binding using a competition binding assay.

5. A method for identifying a compound which modulates the activity of a polypeptide selected from the group consisting of:
   i) a polypeptide which is encoded by a nucleic acid molecule comprising a nucleotide sequence which is at least 95% identical to a nucleic acid comprising the nucleotide sequences of SEQ ID NO:14 or SEQ ID NO:16, wherein the polypeptide has aminitansferase activity;
   ii) a polypeptide comprising a variant of the amino acid sequence of SEQ ID NO:15, wherein the variant is encoded by a nucleic acid molecule which hybridizes to a nucleic acid molecule comprising SEQ ID NO:14 or SEQ ID NO:16, or the complement thereof under conditions of 0.5M sodium phosphate, 7% SDS at 65° C., followed by one or more washes at 0.2×SSC, 1% SDS at 65° C., wherein the variant has aminotransferase activity;
   iii) a polypeptide comprising a fragment of the amino acid sequence of SEQ ID NO:15, wherein the fragment comprises at least 200 contiguous amino acids of SEQ ID NO:15, wherein the fragment has aminotransferase activity; and
   iv) a polypeptide comprising an amino acid sequence at least 95% identical to SEQ ID NO:15, wherein the polypeptide has aminotransferase activity; comprising:
      a) contacting the polypeptide or a cell comprising the polyprptide with a test compound; and
      b) determining the effect of the test compound on the activity of the polypeptide to thereby identify a compound which modulates the activity of the polypeptide.

6. The polypeptide of claim 1, wherein the polypeptide comprises amino acid residues 83–517 of SEQ ID NO: 15, wherein the polypeptide has aminotransferase activity.

7. A polypeptide comprising an amino acid sequence selected from the group consisting of:
   a) SEQ ID NO: 15
   b) the amino acid sequence encoded by SEQ ID NO: 14; and
   c) the amino acid sequence encoded by SEQ ID NO: 16.

8. The polypeptide of claim 7, consisting of an amino acid sequence selected from the group consisting of:
   a) SEQ ID NO: 15;
   b) the amino acid sequence encoded by SEQ ID NO: 14; and
   c) the amino acid sequence encoded by SEQ ID NO: 16.

9. The polypeptide of claim 6 further comprising heterologous amino acid sequences.

10. The polypeptide of claim 7 further comprising heterologous amino acid sequences.

11. The method of claim 3, wherein the assay mixture comprises a cell expressing the polypeptide.

12. The method of claim 3, wherein the polypeptide is immobilized.

13. The method of claim 3, wherein the test compound is detectably labeled.

14. The method of claim 4, wherein the detectable label is selected from the group consisting of:
    a) an enzymatic label; and
    b) a radioisotope label.

15. The method of claim 5, wherein the cell is selected from the group consisting of:
    a pancreas cell, a brain cortex cell, a glial cell, a liver cell, a breast tumor cell, an ovary tumor cell, and a lung tumor cell.

* * * * *